US011415571B2

(12) United States Patent
Larsen et al.

(10) Patent No.: US 11,415,571 B2
(45) Date of Patent: Aug. 16, 2022

(54) LARGE SCALE ORGANOID ANALYSIS

(71) Applicant: Tempus Labs, Inc., Chicago, IL (US)

(72) Inventors: Brian M. Larsen, Chicago, IL (US); Michelle M. Stein, Morton Grove, IL (US); Luka A. Karginov, Westmont, IL (US); Ameen Salahudeen, Oak Park, IL (US); Madhavi Kannan, Chicago, IL (US); Aly A. Khan, Chicago, IL (US); Verónica Sánchez Freire, Chicago, IL (US); Yilin Zhang, Wilmette, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 17/114,386

(22) Filed: Dec. 7, 2020

(65) Prior Publication Data
US 2021/0172931 A1   Jun. 10, 2021

Related U.S. Application Data

(60) Provisional application No. 63/012,885, filed on Apr. 20, 2020, provisional application No. 62/944,292, filed on Dec. 5, 2019.

(51) Int. Cl.
*G01N 33/50* (2006.01)
*G01N 33/58* (2006.01)

(52) U.S. Cl.
CPC ....... *G01N 33/5005* (2013.01); *G01N 33/582* (2013.01); *G01N 2800/7028* (2013.01)

(58) Field of Classification Search
CPC ............. G01N 33/5005; G01N 33/582; G01N 2800/7028; G01N 2500/00; G01N 2800/52; G01N 33/5008; C12Q 2600/106
See application file for complete search history.

(56) References Cited

U.S. PATENT DOCUMENTS

| | | |
|---|---|---|
| 2010/0158330 A1 | 6/2010 | Guissin |
| 2012/0200694 A1 | 8/2012 | Garsha |
| 2012/0200695 A1 | 8/2012 | Yamane |
| 2015/0329829 A1 | 11/2015 | Shen et al. |
| 2017/0336392 A1 | 11/2017 | Theodorakis |
| 2019/0065905 A1 | 2/2019 | Raphaeli |
| 2020/0211716 A1 | 7/2020 | Lefkofsky |
| 2020/0365232 A1 | 11/2020 | Jaros |
| 2020/0381087 A1 | 12/2020 | Ozeran |
| 2021/0090694 A1 | 3/2021 | Colley |

FOREIGN PATENT DOCUMENTS

| | | |
|---|---|---|
| EP | 2 412 800 A1 | 2/2012 |
| EP | 2 743 345 A1 | 6/2014 |
| WO | WO 2009/022907 A2 | 2/2009 |
| WO | WO 2010/090513 A2 | 8/2010 |
| WO | WO 2012/014076 A2 | 2/2012 |
| WO | WO 2012/168930 A2 | 12/2012 |
| WO | WO 2013/093812 A2 | 6/2013 |
| WO | WO 2014/159356 A1 | 10/2014 |
| WO | WO 2015/173425 A1 | 11/2015 |
| WO | WO 2016/083612 A1 | 6/2016 |
| WO | WO 2016/083613 A2 | 6/2016 |
| WO | WO 2017/149025 A1 | 9/2017 |
| WO | WO 2017/220586 A1 | 12/2017 |
| WO | WO 2019018693 A2 | 1/2019 |
| WO | WO 2019/035766 A1 | 2/2019 |
| WO | WO 2019094230 A1 | 5/2019 |
| WO | WO 2019/152767 A1 | 8/2019 |

OTHER PUBLICATIONS

Jabs et al. (Molecular Systems Biology, vol. 13 (955), pp. 1-16 published 2017) (Year: 2017).*
Liu et al. ("Automated Counting of Cancer Cells by Ensembling Deep Features," Cells, vol. 8 (1019), pp. 1-14, published Sep. 2, 2019) (Year: 2019).*
Celli et al. ("An imaging-based platform for high-content, quantitative evaluation of therapeutic response in 3D tumour models," Scientific Reports, vol. 4 (3751), pp. 1-10, published Jan. 17, 2014) (Year: 2014).*
Supplementary Information for Li, X. et al, Nature Communications vol. 9, Article No. 2983 (Jul. 30, 2018), online at https://www.nature.com/articles/s41467-018-05190-9#Sec26, 11 printed pages. (Year: 2018).
Supplementary Materials for "Patient-derived organoids model treatment response of metastatic gastrointestinal cancers" (V published Feb. 23, 2018, Science 359, 920) from https ://science .sciencemag.org/content/suppl/2018/02/21 /359. 6378. 920. DC 1 47 pages printed (Year: 2018).
Yancovitz, M. et al. "Intra- and Inter-Tumor Heterogeneity of BRAFV600E Mutations in Primary and Metastatic Melanoma" PLoS ONE, Jan., 2012, vol. 7, issue 1 (Year: 2012).
Ou, S.-H. I. et al. "Liquid Biopsy to Identify Actionable Genomic Alterations" American Society of Clinical Oncology Educational Book 38 (May 23, 2018) 978-997 (Year: 2018).
Bronkhorst, A.J. et al. "Characterization of the cell-free DNA released by cultured cancer cells", Biochimica et Biophysica Acta 1863 (2016) 157-165 (Year: 2016).
Li, X. et al. "Organoid cultures recapitulate esophageal adenocarcinoma heterogeneity providing a model for clonality studies and precision therapeutics" Nature Communications, (2018) 9:2983, pp. 1-11 (Year: 2018).
Eke et al. "Radiobiology goes 3D: How ECM and cell morphology impact on cell survival after irradiation", Radiotherapy and Oncology, vol. 99, pp. 271-278 (2011).
Breslin et al. "Three-dimensional cell culture: the missing link in drug discovery", Drug Discovery Today, vol. 18, Nos. 5/6 (2013).

(Continued)

*Primary Examiner* — Tracy Vivlemore
*Assistant Examiner* — Nam P Nguyen
(74) *Attorney, Agent, or Firm* — Morgan, Lewis & Bockius LLP

(57) ABSTRACT

Methods, systems, and software are provided for using organoid cultures, e.g., patient-derived tumor organoid cultures, to improve treatment predictions and outcomes.

27 Claims, 69 Drawing Sheets

(51 of 69 Drawing Sheet(s) Filed in Color)

(56) References Cited

OTHER PUBLICATIONS

Driehuis et al. "Oral Mucosal Organoids as a Potential Platform for Personalized Cancer Therapy", Cancer Discovery, vol. 9, pp. 852-871 (2019).
Tuveson et al. "Cancer modeling meets human organoid technology", Science, vol. 364, pp. 952-955 (2019).
Eder et al. :3D Hanging Drop Culture to Establish Prostate Cancer Organoids, 3D Cell Culture: Methodsand Protocols, Methods in Molecular Biology, vol. 1612, pp. 167-175.
Andor et al. "Pan-cancer analysis of the extent and consequences of intra-tumor heterogeneity", Nat Med., vol. 22, pp. 105-113 (2016).
Bein et al. "Microfluidic Organ-on-a-Chip models of Human Intestine", Cellular and Molecular Gastroenterology and Heptatology, vol. 5, No. 4, pp. 659-668 (2018).
Ben-David et al. "Genetic and Trascriptional evolution alters cancer cell line drug response", Nature, vol. 560, pp. 325-330 (2018).
Boj et al. "Organoid Models of Human and Mouse Ductal Pancreatic Cancer", Cell, vol. 160, pp. 324-338 (2015).
Bozic et al. "Timing and heterogeneity of mutations associated with drug resistance in metastic cancers" PNAS, vol. 111, No. 45, pp. 15964-15968 (2014).
Brayer et al. "Recurrent Fusions in MYB and MYBL1 Define a Common, Transcription Factor-Driven Oncogenic Pathway in Salivary Gland Adenoid Cystic Carcinoma" Cancer Discov., vol. 6, pp. 176-187 (2016).
Broutier et al. "Human Primary Liver Cancer-derived Organoid Cultures for disease modelling and drug screening" Nat. Med., vol. 23, pp. 1424-1435 (2017).
Pflug et al. "TRUmiCount: correctly counting absolute numbers of molecules using unique molecular identifiers", Bioinformatics, vol. 24, pp. 3137-3144 (2018).
Chomczynski et al. "The single-step method of RNA isolation by acid guanidinium thiocyanate-phenol-chloroform extraction: twenty-something years on", Nature Protocols, vol. 1, No. 2, pp. 581-585 (2006).
Chowell et al. "When (distant) relatives stay too long: implications for cancer medicine", Genome Biology, vol. 17, pp. 1-3 (2016).
Rio et al. "Enrichment of Poly(A) mRNA Using Immobilized Oligo(dT)", Cold Spring Harbor Laboratory Press, vol. 2010, Issue 7, pp. 1-3 (2010).
Mootha et al. "PGC-1α-responsive genes involved in oxidative phosphorylation are coordinately downregulated in human diabetes", Nature genetics, vol. 34, pp. 267-273 (2003).
Burgess et al. "RNA extraction from self-assembling peptide hydrogels to allow qPCR analysis of encapsulated cells" PLOS ONE, pp. 1-19, (2018).
De Lau et al. "The R-spondin protein family", Genome Biology, vol. 13, pp. 1-10 (2012).
Ozsolak et al. "Direct RNA sequencing", Nature, vol. 461, pp. 814-818 (2009).
Finotello et al. "Measuring differential gene expression with RNA-seq: challenges and strategies for data analysis", Briefings in Functional Genomics, vol. 14, pp. 130-142 (2014).
Ganesh et al. "A rectal cancer organoid platform to study individual responses to chemoradiation", Nature Medicine.
Gao et al. "Organoid cultures derived from patients with advanced prostate cancer", Cell, vol. 159, pp. 176-187 (2014).
Goodspeed et al. "Tumor-Derived Cell Lines as Molecular Models of Cancer Pharmacogenomics", Mol. Cancer. Res., vol. 14, pp. 3-13 (2016).
Gramont et al. "Novel TGF-β inhibitors ready for prime time in onco-immunology", Oncoimmunology, vol. 6, pp. e1257453 (2017).
Jabs et al. "Screening drug effects in patient-derived cancer cells links organoid responses to genome alterations", Mol. Systems Biology, vol. 13, pp. 1-16 (2017).
Kivioja et al. "Counting absolute numbers of molecules using unique molecular identifiers", Nature Methods, vol. 9, No. 1, pp. 72-74 (2012).
Landau et al. "Evolution and impact of subclonal mutations in chronic lymphocytic leukemia", Cell, vol. 152, pp. 714-726 (2013).
Lee et al. "Tumor evolution and drug response in patient-derived organoid models of bladder cancer", Cell, vol. 173, pp. 515-528 (2018).
Lin et al. "mRNA/cDNA Library Construction Using RNA-Polymerase Cycling Reaction", Methods in Molecular Biology, vol. 221, pp. 129-143.
Liu et al. "The Cross-contaminated Cell Lines of Adenoid Cystic Carcinoma: A Crucial Concern", Translational Surgery, vol. 2, pp. 10-13 (2017).
Maley et al. "Genetic clonal diversity predicts progression to esophageal adenocarcinoma", Nature Genetics, vol. 38, pp. 468-473 (2006).
McConnell et al. "Construction of a representative cDNA library from mRNA isolated from mouse oocytes", FEBS, vol. 195, pp. 199-202 (1986.
McCune and Grace "Distance Measures", Chapter 6, pp. 45-57 (2002).
Yan et al. "A Comprehensive Human Gastric Cancer Organoid Biobank Captures Tumor Subtype Heterogeneity and Enables Therapeutic Screening", Cell Stem Cell, vol. 23, pp. 882-897 (2018).
Nagalakshmi et al. "The Transcriptional Landscape of the Yeast Genome Defined by RNA Sequencing", Science, vol. 320, pp. 1344-1349 (2008).
Nagle et al. "Patient-derived tumor organoids for prediction of cancer treatment response", Seminars in Cancer Biology, vol. 15, pp. 258-264 (2018).
Shendure et al. "Next-generation DNA sequencing", Nature Biotechnology, vol. 26, pp. 1135-1145 (2008).
Niederst et al. "Bypass Mechanisms of Resistance to Receptor Tyrosine Kinase Inhibition in Lung Cancer", Sci Signal, vol. 6, pp. 1-12 (2014).
Garalde et al. "Highly parallel direct RNA sequencing on an array of nanopores", Nature Methods, vol. 15, pp.
Oh et al. "An improved method for constructing a full-length enriched cDNA library using small amounts of total RNA as a starting material", Experimental and Molecular Medicine, vol. 35, pp. 586-590 (2003).
Ooft et al. "Patient-derived organoids can predict response to chemotherapy in metastatic colorectal cancer patients", Science Translational Medicine, vol. 11, pp. 1-9 (2019).
Pereira et al. "The somatic mutation profiles of 2,433 breast cancers refines their genomic and transcriptomic landscapes", Nature Communications, vol. 7, pp. 1-15 (2016).
Poeckh et al. "Adsorption and elution characteristics of nucleic acids on silica surfaces and their use in designing a miniaturized purification unit", Anal. Biochem., vol. 15, pp. 253-262 (2008).
Puca et al. "Patient derived organoids to model rare prostate cancer phenotypes", Nature Communications, vol. 9, pp. 1-10 (2018).
Duda et al. "Pattern Classification", Second Edition, 735 pages.
Drost et al. "Organoids in cancer research", Nature Reviews, vol. 18, pp. 407-418 (2018).
Sachs et al. "A Living Biobank of Breast Cancer Organoids Captures Disease Heterogeneity", Cell, vol. 172, pp. 373-386 (2018).
Fuji et al. "A Colorectal Tumor Organoid Library Demonstrates Progressive Loss of Niche Factor Requirements during Tumorigenesis", Cell Stem Cell, vol. 18, pp. 827-838 (2016).
Serrati et al. "Next-generation sequencing: advances and applications in cancer diagnosis". OncoTargets and Therapy, vol. 9, pp. 7355-7365 (2016).
Subramanian et al. "Gene set enrichment analysis: A knowledge-based approach for interpreting genome-wide expression profiles", PNAS, vol. 102, No. 43, pp. 15545-15550 (2005).
Islam et al. "Quantitative single-cell RNA-seq with unique molecular identifiers", Nature Methods, vol. 11, No. 2, pp. 163-166 (2014).
Urbischek et al. "Organoid culture media formulated with growth factors of defined cellular activity", Scientific Reports, vol. 9, pp. 1-11 (2019).
Van De Wetering et al. "Prospective derivation of a Living Organoid Biobank of colorectal cancer patients", Cell, vol. 161, pp. 933-945 (2015).

(56) References Cited

OTHER PUBLICATIONS

Vlachogiannis et al. "Patient-derived organoids model treatment response of metastatic gastrointestinal cancers", Science, vol. 359, pp. 920-926 (2018).
Wang et al. "RNA-Seq: a revolutionary tool for transcriptomics", Nat Rev Genet., vol. 10, pp. 57-63 (2009).
Xu et al. "Organoid technology and applications in cancer research", Journal of Hematology & Oncology, vol. 11, pp. 1-15 (2018).
Yao et al. "Patient-Derived Organoids Predict Chemoradiation Responses of Locally Advanced Rectal Cancer", Cell Press, vol. 26, pp. 1-10 (2020).
Zhang et al. "Intra-tumor Heterogeneity in Localized Lung Adenocarcinomas Delineated by Multi-region Sequencing", Science, vol. 346, pp. 256-259 (2014).
Korenchuk et al. "VCaP, A Cell-Based Model System of Human Prostate Cancer", In Vivo, vol. 15, pp. 163-168 (2001).
Cardea's Tech+Bio Infrastructure, Cardea Bio | Graphene-based, Biology-gated Transistor Technology, https://cardeabio.com/technology/, 4 pages.
Ashford, Molika, "Harvard Team Advancing Algorithmic Signature to Improve PARP Inhibitor Patient Selection", genomeweb, Apr. 18, 2019, 3 pages.
Brenan, Lisa, et al. "Phenotypic characterization of a comprehensive set of MAPK1/ERK2 missense mutants", Cell Rep., Oct. 18, 2016, 23 pages.
Dijkstra, Krijn K., et al. "Generation of Tumor-Reactive T Cells by Co-culture of Peripheral Blood Lymphocytes and Tumor Organoids", CellPress, Sep. 6, 2018, Cell 174, pp. 1586-1598.
Findlay, Gregory M., et al. "Saturation Editing of Genomic Regions by Multiplex Homology-Directed Repair", Nature, Sep. 4, 2014, 24 pages.
Findlay, Gregory M., et al. "Accurate classification of BRCA1 variants with saturation genome editing", Nature, Oct. 2018, 32 pages.
Giacomelli, Andrew O., et al. "Mutational processes shape the landscape of TP53 mutations in human cancer", Nat Genet, Oct. 2018, 20 pages.
Gulhan, Doga C., et al. "Detecting the mutational signature of homologous recombination deficiency in clinical samples", Technical Report, Nature Genetics, vol. 51, May 2019, pp. 912-919.
Jenkins, et al. "Ex Vivo Profiling of PD-1 Blockade Using Organotypic Tumor Spheroids", Cancer Discov., Feb. 2018, 36 pages.
Kohsaka, Shinji, et al. "A method of high-throughput functional evaluation of EGFR gene variants of unknown significance in cancer", Science Translational Medicine | Research Resource, Med. 9, Nov. 15, 2017, 12 pages.
Matreyek, Kenneth A., et al. "Multiplex Assessment of Protein Variant Abundance by Massively Parallel Sequencing", Nat Genet., Jun. 2018, 27 pages.
Mighell, Taylor L., et al. "A Saturation Mutagenesis Approach to Understanding PTEN Lipid Phosphatase Activity and Genotype-Phenotype Relationships", The American Journal of Human Genetics 102, May 3, 2018, pp. 943-955.
Sato, Toshiro, et al. "Single Lgr5 stem cells build crypt-villus structures in vitro without a mesenchymal niche", Nature, vol. 459, May 14, 2009, pp. 262-265.
Sato, Toshiro, et al. "Long-term Expansion of Epithelial Organoids From Human Colon, Adenoma, Adenocarcinoma, and Barrett's Epithelium", Gastroenterology, vol. 141, No. 5, Nov. 2011, pp. 1762-1772.
Neal, James T., et al. "Organoid Modeling of the Tumor Immune Microenvironment", Cell 175, 2018, pp. 1972-1988.
Bailo, O. et al. "Red blood cell image generation for data augmentation using conditional generative adversarial networks." Proceedings of the IEEE/CVF Conference on Computer Vision and Pattern Recognition Workshops. 2019.
Brunet, D., et al. "On the mathematical properties of the structural similarity index." IEEE Transactions on Image Processing 21.4 (2012): 1488-1499.
Ihle, S., et al. "UDCT: Unsupervised data to content transformation with histogram-matching cycle-consistent generative adversarial networks." bioRxiv (2019): 563734.
Ouyang, W., et al. "Deep learning massively accelerates super-resolution localization microscopy." Nature biotechnology 36.5 (2018): 460-468.
Renieblas, G. P., et al. "Structural similarity index family for image quality assessment in radiological images." Journal of medical imaging 4.3 (2017): 035501.
Rivenson, Y., et al. "Virtual histological staining of unlabelled tissue-autofluorescence images via deep learning." Nature biomedical engineering 3.6 (2019): 466-477.
Sampat, M. P., et al. "Complex wavelet structural similarity: A new image similarity index." IEEE transactions on image processing 18.11 (2009): 2385-2401.
Tsuda, H. et al. "Cell image segmentation by integrating pix2pixs for each class." Proceedings of the IEEE/CVF Conference on Computer Vision and Pattern Recognition Workshops. 2019.
Wang, Z., et al. "Image quality assessment: from error visibility to structural similarity." IEEE transactions on image processing 13.4 (2004): 600-612.
Zhu, J.-Y., et al. "Unpaired Image-to-Image Translation using Cycle-Consistent Adversarial Networks." arXiv preprint arXiv:1703.10593 (2017).
Business Wire. Recursion Pharmaceuticals Announces Research Agreement With Sanofi Genzyme. Apr. 25, 2016. Version accessed Apr. 26, 2016. Available online at https://www.businesswire.com/news/home/20160425005113/en/Recursion-Pharmaceuticals-Announces-Research-Agreement-Sanofi-Genzyme.
Christiansen, Eric M., et al. "In silico labeling: predicting fluorescent labels in unlabeled images." Cell 173.3 (2018): 792-803.
El-Melegy, M., et al. "Identification of tuberculosis bacilli in ZN-stained sputum smear images: A deep learning approach." Proceedings of the IEEE/CVF Conference on Computer Vision and Pattern Recognition Workshops. 2019.
Fu, C., et al. "Three Dimensional Fluorescence Microscopy Image Synthesis and Segmentation." arXiv preprint arXiv:1801.07198 (2018).
Gilead. Gilead and insitro Announce Strategic Collaboration to Discover and Develop Novel Therapies for Nonalcoholic Steatohepatitis. Press Release. Apr. 16, 2019. Version accessed Jun. 28, 2020. https://web.archive.org/web/20200628202335/https://www.gilead.com/news-and-press/press-room/press-releases/2019/4/gilead-and-insitro-announce-strategic-collaboration-to-discover-and-develop-novel-therapies-for-nonalcoholic-steatohepatitis.
Guo, S.-M., et al. "Revealing architectural order with quantitative label-free imaging and deep neural networks." BioRxiv (2019): 631101.
Han, L. et al. "Transferring microscopy image modalities with conditional generative adversarial networks." Proceedings of the IEEE Conference on Computer Vision and Pattern Recognition Workshops. 2017.
International Searching Authority. International Search Report and Written Opinion for application PCT/US2020/063619. dated Mar. 9, 2021. 11 pages.
Isola, P., et al. "Image-to-Image Translation with Conditional Adversarial Networks." arXiv preprint arXiv:1611.07004 (2016).
Kim, D., et al. "AI-powered transmitted light microscopy for functional analysis of live cells." Scientific reports 9.1 (2019): 1-9.
Lee, H.-C., et al. "Enhancing high-content imaging for studying microtubule networks at large-scale." arXiv preprint arXiv:1910.00662 (2019).
Leopold, G. Intel Adds Memory to Deep Learning for Drug Discovery. May 31, 2018. Version accessed Jun. 20, 2020 at https://web.archive.org/web/20200620144314/https://www.datanami.com/2018/05/31/intel-adds-memory-to-deep-learning-for-drug-discovery/.
Nguyen, T. C., et al. "Virtual organelle self-coding for fluorescence imaging via adversarial learning." Journal of biomedical optics 25.9 (2020): 096009.
Ounkomol, C., et al. "Label-free prediction of three-dimensional fluorescence images from transmitted-light microscopy." Nature methods 15.11 (2018): 917-920.

(56) References Cited

OTHER PUBLICATIONS

U.S. Appl. No. 16/693,117, titled "Tumor Organoid Culture Compositions, Systems, and Methods" and filed Nov. 22, 2019.
U.S. Appl. No. 62/804,724, titled "Therapeutic Suggestion Improvements Gained Through Genomic Biomarker Matching Plus Clinical History", filed Feb. 12, 2019.
U.S. Appl. No. 62/924,515, titled "Artificial Intelligence Assisted Precision Medicine Enhancements to Standardized Laboratory Diagnostic Testing", and filed Oct. 22, 2019.
U.S. Appl. No. 62/924,621, titled "Systems and Methods for Predicting Therapeutic Sensitivity" and filed Oct. 22, 2019.
U.S. Appl. No. 62/944,292, titled "Large Scale Phenotypic Organoid Analysis" and filed Dec. 5, 2019.
Wang, Z. et al. "Multiscale structural similarity for image quality assessment." The Thrity-Seventh Asilomar Conference on Signals, Systems & Computers, 2003. vol. 2. Ieee, 2003.
Zhang, Z., et al. "Label-Free Estimation of Therapeutic Efficacy on 3D Cancer Spheres Using Convolutional Neural Network Image Analysis." Analytical chemistry 91.21 (2019): 14093-14100.
Zhao, H., et al. "Loss functions for image restoration with neural networks." IEEE Transactions on computational imaging 3.1 (2016): 47-57.
Zhao, H., et al. "Loss functions for neural networks for image processing." arXiv preprint arXiv:1511.08861 (2015).
Matsumoto, N. et al. "C3a Enhances the Formation of Intestinal Organoids through C3aR1" Frontiers in Immunology 2017, Sep. 4, vol. 8:1046 (Year 2017).
Nam, M.-O. et al. "Effects of a small molecule R-spondin-1 substitute RS-246204 on a mouse intestinal organoid culture" Oncotarget, 2018, vol. 9, (No. 5), pp. 6356-6368 (Published: Dec. 26, 2017). (Year 2017).

* cited by examiner

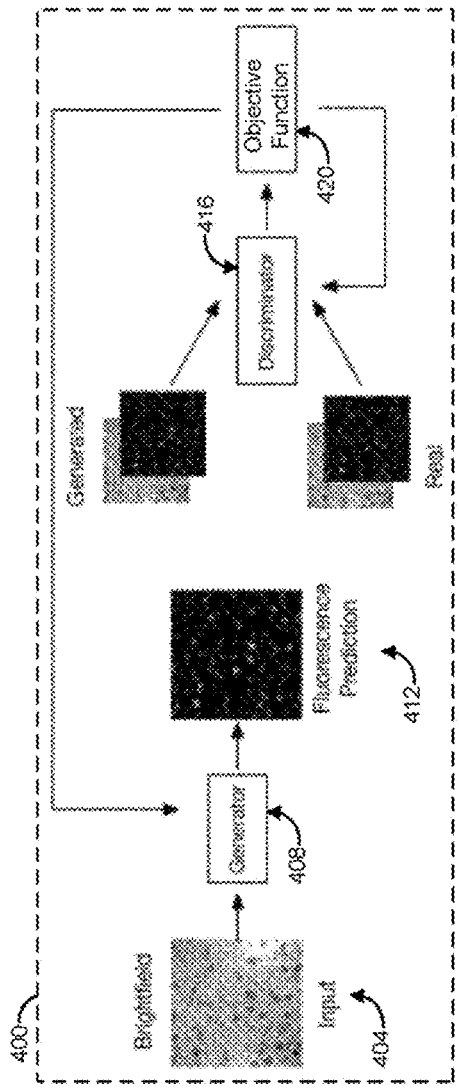
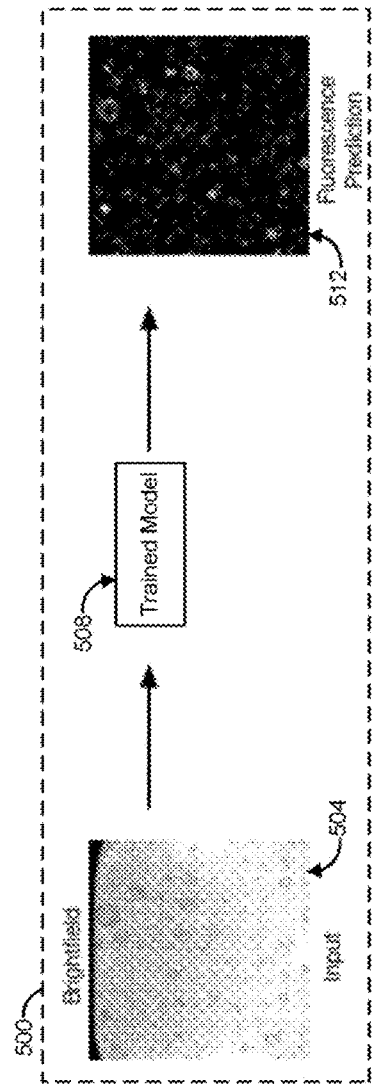
FIG. 36
Fig. 4

FIG. 19E

| Complete Media Components* | Tissue of Origin | References** |
|---|---|---|
| Type E Media<br>Wnt-3A 100ng/mL<br>Noggin 100ng/mL<br>EGF 50ng/mL<br>R-spondin 1 500ng/mL | head and neck<br>lung<br>colon<br>pancreas | Neal et al. 2018<br>Boj et al.<br>Dhietsuis et al.<br>Fujii et al.<br>Sato et al.<br>Van de Wetering et al.<br>Narasimhan et al. |
| Type F Media<br>Wnt-3A 100ng/mL<br>Noggin 100ng/mL<br>EGF 50ng/mL<br>R-spondin 1 500ng/mL<br>FGF-7 25ng/mL<br>FGF-10 100ng/mL | gastric<br>hepatobiliary<br>breast<br>ovarian<br>endometrial<br>genitourinary | Vlachogiannis et al.<br>Saohs et al.<br>Seinen et al.<br>Brossler et al.<br>Hill et al.<br>Boretto et al.<br>Turco et al.<br>Yan et al.<br>Lee et al. |
| Minimal Media B Components* | | |
| Minimal Media C Components*<br>Noggin 100ng/mL<br>EGF 50ng/mL | head and neck<br>lung<br>colon | N/A |
| Minimal Media D Components*<br>Noggin 100ng/mL<br>EGF 50ng/mL<br>FGF-7 25ng/mL<br>FGF-10 100ng/mL | breast<br>ovarian<br>endometrial<br>genitourinary | |

* Base media of Advanced DMEM/F12, 1X B27 Supplement, 10mM nicotinamide, 0.5mM N-Acetylcysteine, 500nM A83-01, 500nM SB202190. ** Studies that overlap with listed media components.

G

F

LARGE SCALE ORGANOID ANALYSIS

CROSS-REFERENCE TO RELATED APPLICATIONS

This application claims the benefit of U.S. Provisional Application No. 62/944,292, filed on Dec. 5, 2019, and U.S. Provisional Application No. 63/012,885, filed on Apr. 20, 2020, which are expressly incorporated by reference in their entireties for all purposes.

TECHNICAL FIELD

The present disclosure relates generally to large scale organoid analysis and use of organoids for predicting patient sensitivity to therapeutic agents.

BACKGROUND

Precision oncology is the practice of tailoring cancer therapy to the unique genomic, epigenetic, and/or transcriptomic profile of an individual tumor. This is in contrast to conventional methods for treating a cancer patient based merely on the type of cancer the patient is afflicted with, e.g., treating all breast cancer patients with a first therapy and all lung cancer patients with a second therapy. Precision oncology was borne out of many observations that different patients diagnosed with the same type of cancer responded very differently to common treatment regimes. Over time, researchers have identified genomic, epigenetic, and transcriptomic markers that facilitate some level of prediction as to how an individual cancer will respond to a particular treatment modality.

Therapy targeted to specific genomic alterations is already the standard of care in several tumor types (e.g., as suggested in the National Comprehensive Cancer Network (NCCN) guidelines for melanoma, colorectal cancer, and non-small cell lung cancer). These few, well known mutations in the NCCN guidelines can be addressed with individual assays or small next generation sequencing (NGS) panels. However, for the largest number of patients to benefit from personalized oncology, molecular alterations that can be targeted with off-label drug indications, combination therapy, or tissue agnostic immunotherapy should be assessed. See Schwaederle et al. 2016 *JAMA Oncol.* 2, 1452-1459; Schwaederle et al. 2015 *J Clin Oncol.* 32, 3817-3825; and Wheler et al. 2016 *Cancer Res.* 76, 3690-3701. Large panel NGS assays also cast a wider net for clinical trial enrollment. See Coyne et al. 2017 *Curr. Probl. Cancer* 41, 182-193; and Markman 2017 *Oncology* 31, 158, 168.

Genomic analysis of tumors is rapidly becoming routine clinical practice to provide tailored patient treatments and improve outcomes. See Fernandes et al. 2017 *Clinics* 72, 588-594. Indeed, recent studies indicate that clinical care is guided by NGS assay results for 30-40% of patients receiving such testing. See Hirshfield et al. 2016 *Oncologist* 21, 1315-1325; Groisberg et al. 2017 *Oncotarget* 8, 39254-39267; Ross et al. *JAMA Oncol.* 1, 40-49; and Ross et al. 2015 *Arch. Pathol. Lab Med.* 139, 642-649. There is growing evidence that patients who receive therapeutic advice guided by genetics have better outcomes. See, for example Wheler et al. who used matching scores (e.g., scores based on the number of therapeutic associations and genomic aberrations per patient) to demonstrate that patients with higher matching scores have a greater frequency of stable disease, longer time to treatment failure, and greater overall survival (2016 *Cancer Res.* 76, 3690-3701). Such methods may be particularly useful for patients who have already failed multiple lines of therapy.

Targeted therapies have shown significant improvements in patient outcomes, especially in terms of progression-free survival. See Radovich et al. 2016 *Oncotarget* 7, 56491-56500. Further, recent evidence reported from the IMPACT trial, which involved genetic testing of advanced stage tumors from 3,743 patients and where approximately 19% of patients received matched targeted therapies based on their tumor biology, showed a response rate of 16.2% in patients with matched treatments versus 5.2% in patients with non-matched treatments. See Bankhead. "IMPACT Trial: Support for Targeted Cancer Tx Approaches." *MedPageToday.* Jun. 5, 2018. The IMPACT study further found that the three-year overall survival for patients given a molecularly matched therapy was more than twice that of non-matched patients (15% vs. 7%). See Id. and ASCO Post. "2018 ASCO: IMPACT Trial Matches Treatment to Genetic Changes in the Tumor to Improve Survival Across Multiple Cancer conditions." The ASCO POST. Jun. 6, 2018. Estimates of the proportion of patients for whom genetic testing changes the trajectory of their care vary widely, from approximately 10% to more than 50%. See Fernandes et al. 2017 *Clinics* 72, 588-594.

SUMMARY

Given the above background, what is needed in the art are improved ways to identify which cancer patients will respond favorably to therapeutic agents. The present disclosure addresses these and other needs by providing systems and methods for using organoid cultures to improve treatment predictions and outcomes. There is also a need for systems and methods for assessing the effectiveness of various drugs on one or more tumor organoid lines. Such systems or methods may be used to determine if a specific drug may be useful in killing cancer cells with specific genetic mutations or phenotypes.

Provided herein is a high-throughput drug screening method and system more applicable for the unique characteristics of tumor organoids (TOs). The systems and methods provided herein are capable of measuring TO therapeutic response with high statistical confidence and exquisite inter-assay reproducibility. This approach can be utilized in research settings to elucidate heterogeneity of therapeutic responses within and among patients, and may be utilized in the clinical laboratory to potentially guide precision oncology treatments. In some embodiments, the platform couples high content fluorescent confocal imaging analysis with a robust statistical analytical approach to measure hundreds of discrete data points of TO viability from as few as $1 \times 10^3$ cells. This approach was validated through evaluating responses to hundreds of small molecule inhibitors as well as a panel of chemotherapeutic agents in TO models derived from different patients.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5A) and caspase 3/7 staining (Caspase 3/7; FIG. 5B), in accordance with some embodiments of the present disclosure.

FIG. 7A shows brighfield, real fluorescence, and generated fluorescence images for colon, lung, ovarian, and breast cancers. FIG. 7B illustrates the correlation between the neural network predictions and fluorescent-based drug responses for the colon, lung, ovarian, and breast cancers.

FIGS. 19A-19E provide a summary of a study disclosed herein for organoid development via a chemically defined pan-cancer approach. A: Illustration of workflow for generating TOs for multiple downstream assays. B: Representative H&E staining of 10 TO histologic types. C: Percent of established and high-proliferation TOs in prevalent histologic cancer types. D: Growth rate ($\log_{10}$ $\mu m^2$/day) of TOs from prevalent cancer types. E: Exemplary media used to culture the tumor organoids described herein.

FIG. 36 shows an exemplary flow for training a generator to generate an artificial fluorescent image based on an input brightfield image of organoid cells.

Like reference numerals refer to corresponding parts throughout the several views of the drawings.

DETAILED DESCRIPTION

Figure 1:
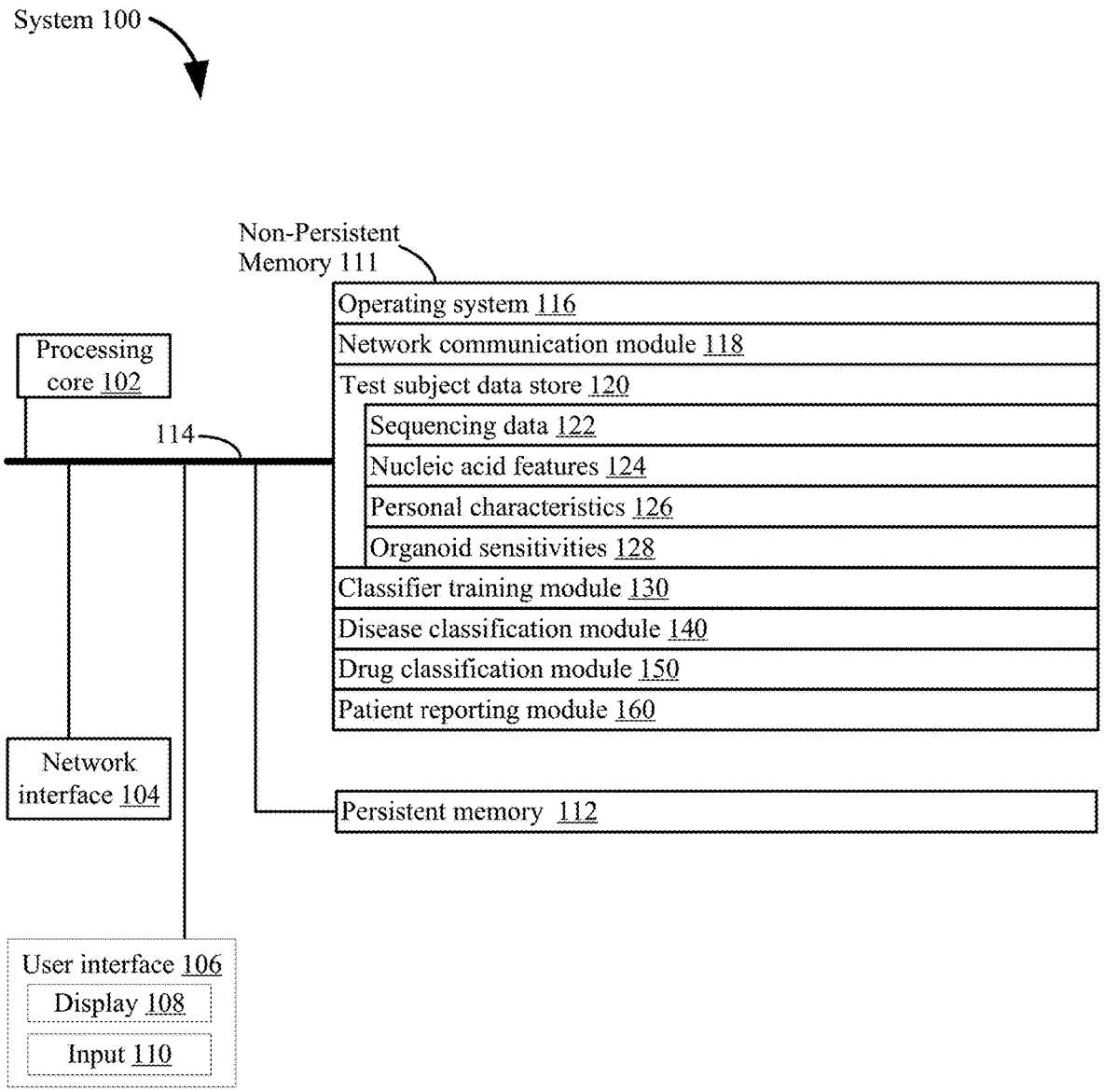
FIG. 1 illustrates a block diagram of an example of a computing device for using information derived from organoid-based assays to improve therapeutic outcomes, in accordance with some embodiments of the present disclosure.

In some embodiments, the present disclosure provides systems and methods for using organoid cultures, e.g., patient-derived tumor organoid cultures, to improve treatment predictions and outcomes.

For instance, in one aspect, the disclosure provides methods and systems for performing methods of training a classifier to discriminate between two or more tumor sensitivities to one or more therapeutic agents. In some embodiments, the method includes obtaining a data set comprising, for each respective tissue sample in a plurality of tissue samples, (i) a corresponding plurality of nucleic acid features of the tissue sample, and (ii) a corresponding indication of the sensitivity of a respective organoid cultured from one or more cells of the tissue sample to the one or more therapeutic agents. The method then includes training an untrained classifier against at least (i) the corresponding plurality of features and (ii) the corresponding indication of the sensitivity of the organoid to the one or more therapeutic agents, across the plurality of tissue samples, thereby obtaining a trained classifier that discriminates between the two or more tumor sensitivities to one or more therapeutic agents.

In another aspect, the disclosure provides method and systems for performing methods of recommending therapy for treating a cancer in a subject. In some embodiments, the method includes obtaining a first test data set comprising a plurality of nucleic acid features of a tumor biopsy from a test subject. The method then includes evaluating the first test data set using a classifier trained to discriminate between two or more tumor sensitivities to a first therapeutic agent. The classifier is trained against, for each respective training tissue sample in a plurality of training tissue samples, at least (i) the plurality of nucleic acid features obtained from the respective training tissue sample, and (ii) a corresponding indication of the sensitivity of a respective organoid cultured from one or more cells of the respective training tissue sample to the first therapeutic agent. In some embodiments, the sensitivity of the training tissue sample is determined in a two-dimensional cell culture, a three-dimensional cell culture prepared in a matrix, a three-dimensional cell culture prepared in suspension culture, a cell culture suspension, or a xenograft model. A first tumor sensitivity in the two or more tumor sensitivities to the first therapeutic agent is associated with a first recommendation, in a plurality of recommendations, to treat the cancer in the subject with the first therapeutic agent. A second tumor sensitivity in the two or more tumor sensitivities to the first therapeutic agent is associated with a second recommendation, in the plurality of recommendations, not to treat the cancer in the subject with the first therapeutic agent. In some embodiments, the method includes providing a respective recommendation, in the plurality of recommendations, for treating the cancer in the test subject based on the results of the evaluation.

In another aspect, the disclosure provides methods and systems for performing methods of treating, or assigning therapy for, a cancer in a test subject. In some embodiments, the methods include determining a probability or likelihood that the cancer will be sensitive to a therapeutic agent, and treating cancer in the subject. When the probability or likelihood that the cancer will be sensitive to the therapeutic agent satisfies a sensitivity threshold, the method includes administering, or communicating, a recommended therapy comprising the therapeutic agent to the test subject. When the probability or likelihood that the cancer will be sensitive to the therapeutic agent does not satisfy a sensitivity threshold, the method includes administering, or communicating, a recommended therapy that does not include the therapeutic agent to the test subject.

In another aspect, the disclosure provides methods and systems for performing methods of providing a clinical report for a cancer patient to a physician. In some embodiments, the methods include obtaining a first test data set comprising features of a transcriptome from a tumor biopsy from the cancer patient. In some embodiments, the methods include evaluating the first test data set using a classifier trained, e.g., as described herein, to discriminate between two or more tumor sensitivities to a first therapeutic agent. The methods then include receiving a recommended therapy for the cancer patient from the classifier, and including the recommended therapy, or sending the recommended therapy to a third party for inclusion, in a clinical report for the cancer patient.

In another aspect, the disclosure provides methods and systems for performing methods of identifying a new use for a pharmaceutical compound of a first pharmaceutical class. In some embodiments, the methods include obtaining a plurality of tissue samples, wherein each respective tissue sample in the plurality of tissue samples is sensitive to a respective class of pharmaceutical agents in a plurality of classes of pharmaceutical agents that excludes the first pharmaceutical class. The methods then includes culturing, for each respective tissue sample in the plurality of tissue samples, one or more respective organoids from one or more cells of the respective tissue sample, thereby generating a plurality of organoid cultures. The methods then include exposing, for each organoid culture in the plurality of organoid cultures, the respective one or more organoids to one or more concentrations of the pharmaceutical agent, and measuring, for each organoid culture in the plurality of organoid cultures, the fitness of cells in the respective one or more organoids following the exposure to the pharmaceutical agent. Reduced fitness of the cells in the respective one or more organoids is indicative that the pharmaceutical molecule shares pharmacological properties with the class of pharmaceutical compounds in the plurality of classes of pharmaceutical classes to which the tissue sample corresponding to the respective one or more organoids is sensitive.

In another aspect, the disclosure provides methods and systems for performing methods of determining the eligibility of a cancer patient for a clinical trial of a candidate cancer pharmaceutical agent. In some embodiments, the methods include obtaining a tumor biopsy from the cancer patient, and culturing one or more tumor organoids from one or more cells of the tumor biopsy. The methods then include exposing the one or more tumor organoids to one or more concentrations of the candidate cancer pharmaceutical agent, and measuring the fitness of cells in the one or more tumor organoids following the exposure to the one or more concentrations of the candidate cancer pharmaceutical agent. The methods then include determining whether the cancer patient is eligible for the clinical trial based on at least the measured fitness of the cells in the one or more tumor organoids, wherein reduced fitness of the cells in the one or more tumor organoids is indicative that the cancer patient is eligible for the clinical trial.

In another aspect, the disclosure provides methods and systems for performing methods of determining the eligibility of a cancer patient for a clinical trial of a candidate cancer pharmaceutical agent. In some embodiments, the methods include obtaining a first test data set comprising a plurality of nucleic acid features of a tumor biopsy from the cancer patient. The methods then include evaluating the first test data set using a classifier trained to discriminate between two or more tumor sensitivities to the candidate cancer pharmaceutical agent. The classifier is trained against, for each respective training tissue sample in a plurality of training tissue samples, at least (i) the plurality of nucleic acid features obtained from the respective training tissue sample, and (ii) a corresponding indication of the sensitivity of a respective organoid cultured from one or more cells of the respective training tissue sample to the candidate cancer pharmaceutical agent. A first tumor sensitivity in the two or more tumor sensitivities to the candidate cancer pharmaceutical agent is associated with an indication that the cancer patient is eligible for the clinical trial. A second tumor sensitivity in the two or more tumor sensitivities to the candidate cancer pharmaceutical agent is associated with an indication that the cancer patient is eligible for the clinical trial. The methods then include determining whether the cancer patient is eligible for the clinical trial based on at least the evaluation.

In another aspect, the disclosure provides methods and systems for performing methods of identifying a resistance to a chemotherapeutic agent in a patient with cancer. In some embodiments, the methods include obtaining a first test data set comprising a plurality of nucleic acid features of a tumor biopsy from the patient with cancer. The methods then include evaluating the first test data set using a classifier trained to discriminate between two or more tumor sensitivities to the chemotherapeutic agent. The classifier is trained against, for each respective training tissue sample in a plurality of training tissue samples, at least (i) the plurality of nucleic acid features obtained from the respective training tissue sample, and (ii) a corresponding indication of the sensitivity of a respective organoid cultured from one or more cells of the respective training tissue sample to the chemotherapeutic agent. A first tumor sensitivity in the two or more tumor sensitivities to the candidate cancer pharmaceutical agent is associated with an indication that the patient's cancer is resistant to the chemotherapeutic agent. A second tumor sensitivity in the two or more tumor sensitivities to the candidate cancer pharmaceutical agent is associated with an indication that the patient's cancer is not resistant to the chemotherapeutic agent. The methods then include providing a report indicating whether the patient's cancer is resistant to the chemotherapeutic agent based on at least the results of the evaluation.

In another aspect, the disclosure provides methods and systems for evaluating an effect of a cancer therapeutic agent. In some embodiments, the method includes providing a plurality of tumor organoids cultured in a tumor organoid culture medium, where the plurality of tumor organoids is divided into a plurality of tumor organoid subsets. The method then includes contacting each subset in the plurality of tumor organoid subsets with a cancer therapeutic agent. The method also includes contacting each subset in the plurality of tumor organoid subsets with one or more cell death detection agents and a total cell detection agent. The method then includes obtaining a tumor organoid profile for each subset in the plurality of subset. In some embodiments, the tumor organoid profile includes a cell viability value for every tumor organoid in the subset. The method then includes assessing the effect of the cancer therapeutic agent based on the tumor organoid profiles.

In another aspect, the disclosure provides methods and systems for assigning a treatment dosage of a cancer therapeutic agent for a subject in need thereof. In some embodiments, the method includes providing a plurality of tumor organoids cultured in a tumor organoid culture medium, where the tumor organoids are derived from a subject, and where the plurality of tumor organoids is divided into a plurality of tumor organoid subsets. The method then includes contacting each subset in the plurality of tumor organoid subsets with a different dosage of a cancer therapeutic agent. The method also includes contacting each subset in the plurality of tumor organoid subsets with one or more cell death detection agents and a total cell detection agent. The method then includes obtaining a tumor organoid profile for each subset in the plurality of subset, where the tumor organoid profile includes a cell viability value for every tumor organoid in the subset. The method then includes determining a therapeutic agent dosage curve from the tumor organoid profiles. The method then includes assigning a treatment dosage of the cancer therapeutic agent to the subject based on the therapeutic agent dosage curve.

A. Definitions

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "including," "includes," "having," "has," "with," or variants thereof are used in either the detailed description and/or the claims, such terms are intended to be inclusive in a manner similar to the term "comprising."

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the term "organoid" refers to an in vitro three-dimensional multicellular construct that is developed from stem cells (e.g., embryonic stem cells, induced pluripotent stem cells, and somatic stem cells or tissue derived progenitor cells) or cancer cells in a specific 3D organoid culture system. Organoids contain multiple cells types of the in vivo counter parts and organize similarly to the primary tissue. In some embodiments, the organoid culture system includes an organoid culture medium and an extracellular matrix or extracellular matrix substitute. An "organoid cell line" refers to a plurality of organoids that are derived and established from the same cell or cell population. A "tumor organoid" refers to an organoid derived from a tumor cell or population of tumor cells.

As used herein, the term "subject" refers to any living or non-living human. In some embodiments, a subject is a male or female of any stage (e.g., a man, a women or a child).

As used herein, the terms "control," "control sample," "reference," "reference sample," "normal," and "normal sample" describe a sample from a subject that does not have a particular condition, or is otherwise healthy. In an example, a method as disclosed herein can be performed on a subject having a tumor, where the reference sample is a sample taken from a healthy tissue of the subject. A reference sample can be obtained from the subject, or from a database. The reference can be, e.g., a reference genome that is used to map sequence reads obtained from sequencing a sample from the subject. A reference genome can refer to a haploid or diploid genome to which sequence reads from the biological sample and a constitutional sample can be aligned and compared. An example of constitutional sample can be DNA of white blood cells obtained from the subject. For a haploid genome, there can be only one nucleotide at each locus. For a diploid genome, heterozygous loci can be identified; each heterozygous locus can have two alleles, where either allele can allow a match for alignment to the locus.

As used herein, the term "locus" refers to a position (e.g., a site) within a genome, e.g., on a particular chromosome. In some embodiments, a locus refers to a single nucleotide position within a genome, i.e., on a particular chromosome. In some embodiments, a locus refers to a small group of nucleotide positions within a genome, e.g., as defined by a mutation (e.g., substitution, insertion, or deletion) of consecutive nucleotides within a cancer genome. Because normal mammalian cells have diploid genomes, a normal mammalian genome (e.g., a human genome) will generally have two copies of every locus in the genome, or at least two copies of every locus located on the autosomal chromosomes, e.g., one copy on the maternal autosomal chromosome and one copy on the paternal autosomal chromosome.

As used herein, the term "allele" refers to a particular sequence of one or more nucleotides at a chromosomal locus.

As used herein, the term "reference allele" refers to the sequence of one or more nucleotides at a chromosomal locus that is either the predominant allele represented at that chromosomal locus within the population of the species (e.g., the "wild-type" sequence), or an allele that is predefined within a reference genome for the species.

As used herein, the term "variant allele" refers to a sequence of one or more nucleotides at a chromosomal locus that is either not the predominant allele represented at that chromosomal locus within the population of the species (e.g., not the "wild-type" sequence), or not an allele that is predefined within a reference genome for the species.

As used herein, the term "single nucleotide variant" or "SNV" refers to a substitution of one nucleotide to a different nucleotide at a position (e.g., site) of a nucleotide sequence, e.g., a sequence read from an individual. A substitution from a first nucleobase X to a second nucleobase Y may be denoted as "X>Y." For example, a cytosine to thymine SNV may be denoted as "C>T."

As used herein, the term "mutation" or "variant" refers to a detectable change in the genetic material of one or more cells. In a particular example, one or more mutations can be found in, and can identify, cancer cells (e.g., driver and passenger mutations). A mutation can be transmitted from apparent cell to a daughter cell. A person having skill in the art will appreciate that a genetic mutation (e.g., a driver mutation) in a parent cell can induce additional, different mutations (e.g., passenger mutations) in a daughter cell. A mutation generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example of a "tissue-specific allele." For example, a tumor can have a mutation that results in an allele at a locus that does not occur in normal cells. Another example of a "tissue-specific allele" is a fetal-specific allele that occurs in the fetal tissue, but not the maternal tissue.

As used herein the term "cancer," "cancerous tissue," or "tumor" refers to an abnormal mass of tissue in which the growth of the mass surpasses and is not coordinated with the growth of normal tissue. A cancer or tumor can be defined as "benign" or "malignant" depending on the following characteristics: degree of cellular differentiation including morphology and functionality, rate of growth, local invasion and metastasis. A "benign" tumor can be well differentiated, have characteristically slower growth than a malignant tumor and remain localized to the site of origin. In addition, in some cases a benign tumor does not have the capacity to infiltrate, invade or metastasize to distant sites. A "malignant" tumor can be a poorly differentiated (anaplasia), have characteristically rapid growth accompanied by progressive infiltration, invasion, and destruction of the surrounding tissue. Furthermore, a malignant tumor can have the capacity to metastasize to distant sites. Accordingly, a cancer cell is a cell found within the abnormal mass of tissue whose growth is not coordinated with the growth of normal tissue. Accordingly, a "tumor sample" refers to a biological sample obtained or derived from a tumor of a subject, as described herein.

As used herein, the terms "sequencing," "sequence determination," and the like as used herein refers generally to any and all biochemical processes that may be used to determine the order of biological macromolecules such as nucleic acids or proteins. For example, sequencing data can include all or a portion of the nucleotide bases in a nucleic acid molecule such as an mRNA transcript or a genomic locus.

As used herein, the term "sequence reads" or "reads" refers to nucleotide sequences produced by any sequencing process described herein or known in the art. Reads can be generated from one end of nucleic acid fragments ("single-end reads"), and sometimes are generated from both ends of nucleic acids (e.g., paired-end reads, double-end reads). The length of the sequence read is often associated with the particular sequencing technology. High-throughput methods, for example, provide sequence reads that can vary in size from tens to hundreds of base pairs (bp). In some embodiments, the sequence reads are of a mean, median or average length of about 15 bp to 900 bp long (e.g., about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. In some embodiments, the sequence reads are of a mean, median or average length of about 1000 bp, 2000 bp, 5000 bp, 10,000 bp, or 50,000 bp or more. Nanopore sequencing, for example, can provide sequence reads that can vary in size from tens to hundreds to thousands of base pairs. Illumina parallel sequencing can provide sequence reads that do not vary as much, for example, most of the sequence reads can be smaller than 200 bp. A sequence read (or sequencing read) can refer to sequence information corresponding to a nucleic acid molecule (e.g., a string of nucleotides). For example, a sequence read can correspond to a string of nucleotides (e.g., about 20 to about 150) from part of a nucleic acid fragment, can correspond to a string of nucleotides at one or both ends of a nucleic acid fragment, or can correspond to nucleotides of the entire nucleic acid fragment. A sequence read can be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

As used herein, the term "read segment" or "read" refers to any nucleotide sequences including sequence reads obtained from an individual and/or nucleotide sequences derived from the initial sequence read from a sample obtained from an individual. For example, a read segment can refer to an aligned sequence read, a collapsed sequence read, or a stitched read. Furthermore, a read segment can refer to an individual nucleotide base, such as a single nucleotide variant.

As used herein, the term, "reference exome" refers to any particular known, sequenced or characterized exome, whether partial or complete, of any tissue from any organism or pathogen that may be used to reference identified sequences from a subject. Example reference exomes used for human subjects as well as many other organisms are provided in the on-line genome browser hosted by the National Center for Biotechnology Information ("NCBI").

As used herein, the term "reference genome" refers to any particular known, sequenced or characterized genome, whether partial or complete, of any organism or pathogen that may be used to reference identified sequences from a subject. Exemplary reference genomes used for human subjects as well as many other organisms are provided in the on-line genome browser hosted by the National Center for Biotechnology Information ("NCBI") or the University of California, Santa Cruz (UCSC). A "genome" refers to the complete genetic information of an organism or pathogen, expressed in nucleic acid sequences. As used herein, a reference sequence or reference genome often is an assembled or partially assembled genomic sequence from an individual or multiple individuals. In some embodiments, a reference genome is an assembled or partially assembled genomic sequence from one or more human individuals. The reference genome can be viewed as a representative example of a species' set of genes. In some embodiments, a reference genome comprises sequences assigned to chromosomes. Exemplary human reference genomes include but are not limited to NCBI build 34 (UCSC equivalent: hg16), NCBI build 35 (UCSC equivalent: hg17), NCBI build 36.1 (UCSC equivalent: hg18), GRCh37 (UCSC equivalent: hg19), and GRCh38 (UCSC equivalent: hg38).

As used herein, the term "assay" refers to a technique for determining a property of a substance, e.g., a nucleic acid, a protein, a cell, a tissue, or an organ. An assay (e.g., a first assay or a second assay) can comprise a technique for determining the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art can be used to detect any of the properties of nucleic acids mentioned herein. Properties of a nucleic acids can include a sequence, genomic identity, copy number, methylation state at one or more nucleotide positions, size of the nucleic acid, presence or absence of a mutation in the nucleic acid at one or more nucleotide positions, and pattern of fragmentation of a nucleic acid (e.g., the nucleotide position(s) at which a nucleic acid fragments). An assay or method can have a particular sensitivity and/or specificity, and their relative usefulness as a diagnostic tool can be measured using ROC-AUC statistics.

The term "classification" can refer to any number(s) or other characters(s) that are associated with a particular property of a sample. For example, in some embodiments, the term "classification" can refer to a type of cancer in a subject or sample, a stage of cancer in a subject or sample, a prognosis for a cancer in a subject or sample, a tumor load in a subject, a presence of tumor metastasis in a subject, and the like. The classification can be binary (e.g., positive or negative) or have more levels of classification (e.g., a scale from 1 to 10 or 0 to 1). The terms "cutoff" and "threshold" can refer to predetermined numbers used in an operation. For example, a cutoff size can refer to a size above which fragments are excluded. A threshold value can be a value above or below which a particular classification applies. Either of these terms can be used in either of these contexts.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

B. Example System Embodiments

Now that an overview of some aspects of the present disclosure and some definitions used in the present disclosure have been provided, details of an exemplary system are now described in conjunction with FIG. 1. FIG. 1 is a block diagram illustrating a system 100 in accordance with some implementations. The device 100 in some implementations includes one or more processing units CPU(s) 102 (also referred to as processors), one or more network interfaces 104, a user interface 106, a non-persistent memory 111, a persistent memory 112, and one or more communication buses 114 for interconnecting these components. The one or more communication buses 114 optionally include circuitry (sometimes called a chipset) that interconnects and controls communications between system components. The non-persistent memory 111 typically includes high-speed random access memory, such as DRAM, SRAM, DDR RAM, ROM, EEPROM, flash memory, whereas the persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, flash memory devices, or other non-volatile solid state storage devices. The persistent memory 112 optionally includes one or more storage devices remotely located from the CPU(s) 102. The persistent memory 112, and the non-volatile memory device(s) within the non-persistent memory 112, comprise non-transitory computer readable storage medium. In some implementations, the non-persistent memory 111 or alternatively the non-transitory computer readable storage medium stores the following programs, modules and data structures, or a subset thereof, sometimes in conjunction with the persistent memory 112:
- an optional operating system 116, which includes procedures for handling various basic system services and for performing hardware dependent tasks;
- an optional network communication module (or instructions) 118 for connecting the system 100 with other devices and/or a communication network;
- a test subject data store 120 for storing datasets containing biological information and/or personal characteristics about test subjects, including sequencing data 122, nucleic acid features 124, personal characteristics 126, and/or organoid sensitivities 128;
- an optional classifier training module 130 for training classifiers, e.g., to distinguish between disease states or predicted treatment outcomes, for example, based on information learned from studies of patient-based organoid cultures;
- an optional disease classification module 130 for classifying the cancer status of a subject based on test subject data, e.g., sequencing data 122, nucleic acid features 124, personal characteristics 126, and/or patient-derived organoid sensitivities 128 stored in test subject data store 120;
- an optional drug classification module 150 for classifying a utility of a therapeutic compound based on organoid-derived sensitivities to the therapeutic compound; and
- an optional patient reporting module 160 for generating reports about the disease (e.g., cancer) status of a test subject.

In various implementations, one or more of the above identified elements are stored in one or more of the previously mentioned memory devices, and correspond to a set of instructions for performing a function described above. The above identified modules, data, or programs (e.g., sets of instructions) need not be implemented as separate software programs, procedures, datasets, or modules, and thus various subsets of these modules and data may be combined or otherwise re-arranged in various implementations.

In some implementations, the non-persistent memory 111 optionally stores a subset of the modules and data structures identified above. Furthermore, in some embodiments, the memory stores additional modules and data structures not described above. In some embodiments, one or more of the above identified elements is stored in a computer system, other than that of system 100, that is addressable by system 100 so that system 100 may retrieve all or a portion of such data when needed.

Although FIG. 1 depicts a "system 100," the figure is intended more as functional description of the various features which may be present in one or more computer systems than as a structural schematic of the implementations described herein. In practice, and as recognized by those of ordinary skill in the art, items shown separately could be combined and some items could be separated. Moreover, although FIG. 1 depicts certain data and modules in non-persistent memory 111, some or all of these data and modules may be in persistent memory 112.

Figure 2:
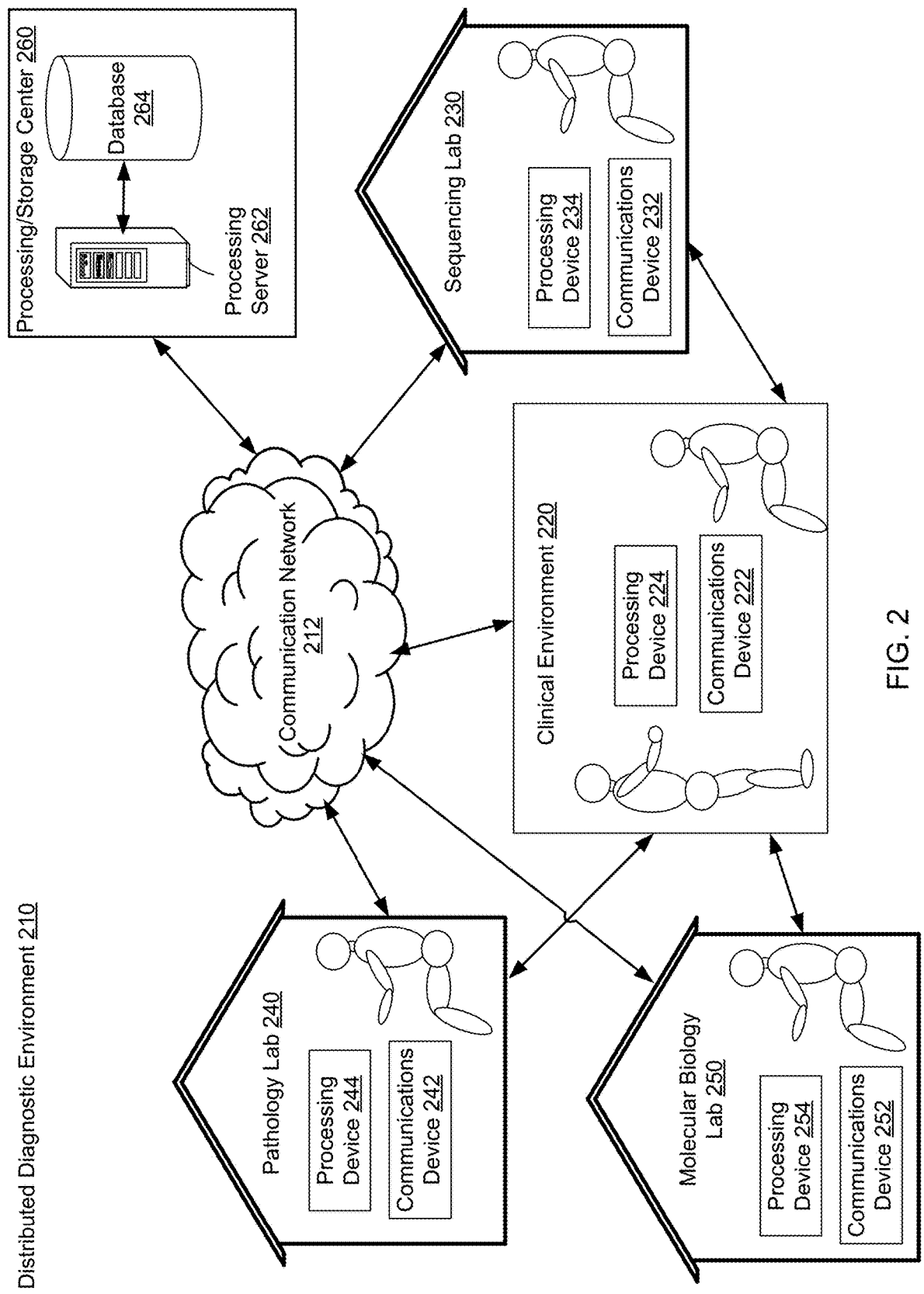
FIG. 2 illustrates an example of a distributed diagnostic environment for evaluating therapeutic regimes using information derived from tumor organoid studies, in accordance with some embodiments of the present disclosure.

For instance, as depicted in FIG. 2, in some embodiments the methods described herein are performed across a distributed diagnostic environment 210, e.g., connected via communication network 212. In some embodiments, one or more biological sample, e.g., one or more tumor biopsy or control sample, is collected from a subject in clinical environment 220, e.g., a doctor's office, hospital, or medical clinic. In some embodiments, a portion of the sample is processed within the clinical environment using a processing device 224, e.g., a nucleic acid sequencer for obtaining sequencing data, a microscope for obtaining pathology data, a mass spectrometer for obtaining proteomic data, etc. In some embodiments, the biological sample or a portion of the biological sample is sent to one or more external environments, e.g., sequencing lab 230, pathology lab 240, and molecular biology lab 250, each of which includes a processing device 234, 244, and 254, respectively, to generate biological data about the subject. Each environment includes a communications device 222, 232, 242, and 252, respectively, for communicating biological data about the subject to a processing server 262 and/or database 264, which may located in yet another environment, e.g., processing/storage center 260. Thus, in some embodiments, different portions of the systems and methods described herein are fulfilled by different processing devices located in different physical environments.

C. Classifiers

In some embodiments, the methods described herein use biological features, e.g., genomic features, of a subject and/or cultured organoid, e.g., a patient-specific tumor organoid, to classify a condition, e.g., cancer, predicted an effect of a particular therapy, etc. Generally, any classifier architecture can be trained for these purposes. Non-limiting examples of classifier types that can be used in conjunction with the methods described herein include a machine learning algorithm, a neural network algorithm, a support vector machine algorithm, a decision tree algorithm, an unsupervised clustering model algorithm, a supervised clustering model algorithm, or a regression model. In some embodiments, the trained classifier is binomial or multinomial.

In some embodiments, the classifier is implemented as an artificial intelligence engine and may include gradient boosting models, random forest models, neural networks (NN), regression models, Naive Bayes models, and/or machine learning algorithms (MLA). MLAs include supervised algorithms (such as algorithms where the features/classifications in the data set are annotated) using linear regression, logistic regression, decision trees, classification and regression trees, naïve Bayes, nearest neighbor clustering; unsupervised algorithms (such as algorithms where no features/classification in the data set are annotated) using apriori, means clustering, principal component analysis, random forest, adaptive boosting; and semi-supervised algorithms (such as algorithms where an incomplete number of features/classifications in the data set are annotated) using generative approach (such as a mixture of Gaussian distributions, mixture of multinomial distributions, hidden Markov models), low density separation, graph-based approaches (such as mincut, harmonic function, manifold regularization), heuristic approaches, or support vector machines.

While MLA and neural networks identify distinct approaches to machine learning, the terms may be used interchangeably herein. Thus, a mention of MLA may include a corresponding NN or a mention of NN may include a corresponding MLA unless explicitly stated otherwise. Training may include providing optimized datasets, labeling these traits as they occur in patient records, and training the MLA to predict or classify based on new inputs. Artificial NNs are efficient computing models which have shown their strengths in solving hard problems in artificial intelligence. They have also been shown to be universal approximators, that is, they can represent a wide variety of functions when given appropriate parameters.

Neural network (NN) algorithms, including convolutional neural network algorithms, that can serve as the classifier for the instant methods are disclosed in See, Vincent et al., 2010, "Stacked denoising autoencoders: Learning useful representations in a deep network with a local denoising criterion," J Mach Learn Res 11, pp. 3371-3408; Larochelle et al., 2009, "Exploring strategies for training deep neural networks," J Mach Learn Res 10, pp. 1-40; and Hassoun, 1995, Fundamentals of Artificial Neural Networks, Massachusetts Institute of Technology, each of which is hereby incorporated by reference. NNs include conditional random fields, convolutional neural networks, attention based neural networks, deep learning, long short term memory networks, or other neural models.

Example logistic regression algorithms are disclosed in Agresti, An Introduction to Categorical Data Analysis, 1996, Chapter 5, pp. 103-144, John Wiley & Son, New York, which is hereby incorporated by reference.

Support vector machine (SVM) algorithms that can serve as the classifier for the instant methods are described in Cristianini and Shawe-Taylor, 2000, "An Introduction to Support Vector Machines," Cambridge University Press, Cambridge; Boser et al., 1992, "A training algorithm for optimal margin classifiers," in Proceedings of the $5^{th}$ Annual ACM Workshop on Computational Learning Theory, ACM Press, Pittsburgh, Pa., pp. 142-152; Vapnik, 1998, Statistical Learning Theory, Wiley, New York; Mount, 2001, Bioinformatics: sequence and genome analysis, Cold Spring Harbor Laboratory Press, Cold Spring Harbor, N.Y.; Duda, Pattern Classification, Second Edition, 2001, John Wiley & Sons, Inc., pp. 259, 262-265; and Hastie, 2001, The Elements of Statistical Learning, Springer, New York; and Furey et al., 2000, Bioinformatics 16, 906-914, each of which is hereby incorporated by reference in its entirety. When used for classification, SVMs separate a given set of binary-labeled data training set with a hyper-plane that is maximally distant from the labeled data. For cases in which no linear separation is possible, SVMs can work in combination with the technique of 'kernels', which automatically realizes a non-linear mapping to a feature space. The hyper-plane found by the SVM in feature space corresponds to a non-linear decision boundary in the input space. Decision trees (e.g., random forest, boosted trees) that can serve as the classifier for the instant methods are described generally by Duda, 2001, Pattern Classification, John Wiley & Sons, Inc., New York, pp. 395-396, which is hereby incorporated by reference. Tree-based methods partition the feature space into a set of rectangles, and then fit a model (like a constant) in each one. In some embodiments, the decision tree is random forest regression. One specific algorithm that can serve as the classifier for the instant methods is a classification and regression tree (CART). Other specific decision tree algorithms that can serve as the classifier for the instant methods include, but are not limited to, ID3, C4.5, MART, and Random Forests. CART, ID3, and C4.5 are described in Duda, 2001, Pattern Classification, John Wiley & Sons, Inc., New York, pp. 396-408 and pp. 411-412, which is hereby incorporated by reference. CART, MART, and C4.5 are described in Hastie et al., 2001, The Elements of Statistical Learning, Springer-Verlag, New York, Chapter 9, which is hereby incorporated by reference in its entirety. Random Forests are described in Breiman, 1999, "Random Forests—Random Features," Technical Report 567, Statistics Department, U. C. Berkeley, September 1999, which is hereby incorporated by reference in its entirety.

D. Biological Samples

In some embodiments, one or more biological samples collected from a subject is a solid tissue sample, e.g., a solid tumor sample or a solid normal tissue sample. Methods for obtaining solid tissue samples, e.g., of cancerous and/or normal tissue are known in the art, and are dependent upon the type of tissue being sampled. For example, bone marrow biopsies and isolation of circulating tumor cells can be used to obtain samples of blood cancers, endoscopic biopsies can be used to obtain samples of cancers of the digestive tract, bladder, and lungs, needle biopsies (e.g., fine-needle aspiration, core needle aspiration, vacuum-assisted biopsy, and image-guided biopsy, can be used to obtain samples of subdermal tumors, skin biopsies, e.g., shave biopsy, punch biopsy, incisional biopsy, and excisional biopsy, can be used to obtain samples of dermal cancers, and surgical biopsies can be used to obtain samples of cancers affecting internal organs of a patient. In some embodiments, a solid tissue sample is a formalin-fixed tissue (FFT). In some embodiments, a solid tissue sample is a macro-dissected formalin fixed paraffin embedded (FFPE) tissue. In some embodiments, a solid tissue sample is a fresh frozen tissue sample.

In some embodiments, one or more of the biological samples collected from a subject is a liquid biological sample, also referred to as a liquid biopsy sample. In some embodiments, one or more of the biological samples obtained from the patient are selected from blood, plasma, serum, urine, vaginal fluid, fluid from a hydrocele (e.g., of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g., thyroid, breast), etc. In some embodiments, the liquid biopsy sample includes blood and/or saliva. In some embodiments, the liquid biopsy sample is peripheral blood. In some embodiments, blood samples are collected from patients in commercial blood collection containers, e.g., using a PAXgene® Blood DNA Tubes. In some embodiments, saliva samples are collected from patients in commercial saliva collection containers, e.g., using an Oragene® DNA Saliva Kit.

Liquid biopsy samples include cell free nucleic acids, including cell-free DNA (cfDNA). As described above, cfDNA isolated from cancer patients includes DNA originating from cancerous cells, also referred to as circulating tumor DNA (ctDNA), cfDNA originating from germline (e.g., healthy or non-cancerous) cells, and cfDNA originating from hematopoietic cells (e.g., white blood cells). The relative proportions of cancerous and non-cancerous cfDNA present in a liquid biopsy sample varies depending on the characteristics (e.g., the type, stage, lineage, genomic profile, etc.) of the patient's cancer.

cfDNA is a particularly useful source of biological data for various implementations of the methods and systems described herein, because it is readily obtained from various body fluids. Advantageously, use of bodily fluids facilitates serial monitoring because of the ease of collection, as these fluids are collectable by non-invasive or minimally-invasive methodologies. This is in contrast to methods that rely upon solid tissue samples, such as biopsies, which often times require invasive surgical procedures. Further, because bodily fluids, such as blood, circulate throughout the body, the cfDNA population represents a sampling of many different tissue types from many different locations.

In some embodiments, a liquid biopsy sample is separated into two different samples. For example in some embodiments, a blood sample is separated into a blood plasma sample, containing cfDNA, and a buffy coat preparation, containing white blood cells.

In some embodiments, a dedicated normal sample is also collected from a subject, for co-processing with a solid or liquid cancer sample. Generally, the normal sample is of a non-cancerous tissue, and can be collected using any tissue collection means described above. In some embodiments, buccal cells collected from the inside of a patient's cheeks are used as a normal sample. Buccal cells can be collected by placing an absorbent material, e.g., a swab, in the subjects mouth and rubbing it against their cheek, e.g., for at least 15 second or for at least 30 seconds. The swab is then removed from the patient's mouth and inserted into a tube, such that the tip of the tube is submerged into a liquid that serves to extract the buccal cells off of the absorbent material. An example of buccal cell recovery and collection devices is provided in U.S. Pat. No. 9,138,205, the content of which is hereby incorporated by reference, in its entirety, for all purposes. In some embodiments, the buccal swab DNA is used as a source of normal DNA in circulating heme malignancies.

The biological samples collected from the patient are, optionally, sent to various analytical environments (e.g., sequencing lab 230, pathology lab 240, and/or molecular biology lab 250) for processing (e.g., data collection) and/or analysis (e.g., feature extraction). Wet lab processing 204 may include cataloguing samples (e.g., accessioning), examining clinical features of one or more samples (e.g., pathology review), and nucleic acid sequence analysis (e.g., extraction, library prep, capture+hybridize, pooling, and sequencing). In some embodiments, the workflow includes clinical analysis of one or more biological samples collected from the subject, e.g., at a pathology lab 240 and/or a molecular and cellular biology lab 250, to generate clinical features such as pathology features 128-3, imaging data 128-3, and/or tissue culture/organoid data 128-3.

E. Feature Extraction

In some embodiments, tissue culture/organoid data includes features identified by evaluation of cultured tissue from the subject. For instance, in some embodiments, tissue samples obtained from the patients (e.g., tumor tissue, normal tissue, or both) are cultured (e.g., in liquid culture, solid-phase culture, and/or organoid culture) and various features, such as cell morphology, growth characteristics, genomic alterations, and/or drug sensitivity, are evaluated. In some embodiments, tissue culture/organoid data 128-3 includes features determined using machine learning algorithms to evaluate tissue culture/organoid data collected as described herein. Genetic sequencing used to generate the features used in the methods described herein may be done on either a tumor organoid, e.g., cultured from cells of a test subject, or the source tissue (patient biopsy used to generate the TO), e.g., to determine the tumor organoid's (e.g., the subject's cancer) BRCA1/2 mutation status, loss of heterozygosity, bi-allelic loss status, etc.

In some embodiments of the methods described herein, nucleic acid sequencing of one or more samples, e.g., a biological sample from a subject and/or a tissue culture/organoid sample, is performed. Briefly, nucleic acids, e.g., RNA and/or DNA are extracted (304) from the one or more biological samples. Methods for isolating nucleic acids from biological samples are known in the art, and are dependent upon the type of nucleic acid being isolated (e.g., cfDNA, DNA, and/or RNA) and the type of sample from which the nucleic acids are being isolated (e.g., liquid biopsy samples, white blood cell buffy coat preparations, formalin-fixed paraffin-embedded (FFPE) solid tissue samples, and fresh frozen solid tissue samples). The selection of any particular nucleic acid isolation technique for use in conjunction with the embodiments described herein is well within the skill of the person having ordinary skill in the art, who will consider the sample type, the state of the sample, the type of nucleic acid being sequenced and the sequencing technology being used.

For instance, many techniques for DNA isolation, e.g., genomic DNA isolation, from a tissue sample are known in the art, such as organic extraction, silica adsorption, and anion exchange chromatography. Likewise, many techniques for RNA isolation, e.g., mRNA isolation, from a tissue sample are known in the art. For example, acid guanidinium thiocyanate-phenol-chloroform extraction (see, for example, Chomczynski and Sacchi, 2006, Nat Protoc, 1(2):581-85, which is hereby incorporated by reference herein), and silica bead/glass fiber adsorption (see, for example, Poeckh, T. et al., 2008, Anal Biochem., 373(2): 253-62, which is hereby incorporated by reference herein). The selection of any particular DNA or RNA isolation technique for use in conjunction with the embodiments described herein is well within the skill of the person having ordinary skill in the art, who will consider the tissue type, the state of the tissue, e.g., fresh, frozen, formalin-fixed, paraffin-embedded (FFPE), and the type of nucleic acid analysis that is to be performed.

In some embodiments, a nucleic acid library is prepared from the isolated nucleic acids (e.g., cfDNA, DNA, and/or RNA). For example, in some embodiments, DNA libraries (e.g., gDNA and/or cfDNA libraries) are prepared from isolated DNA from the one or more biological samples. In some embodiments, the DNA libraries are prepared using a commercial library preparation kit, e.g., the KAPA Hyper Prep Kit, a New England Biolabs (NEB) kit, or a similar kit.

In some embodiments, during library preparation, adapters (e.g., UDI adapters, such as Roche SeqCap dual end adapters, or UMI adapters such as full length or stubby Y adapters) are ligated onto the nucleic acid molecules. In some embodiments, the adapters include unique molecular identifiers (UMIs), which are short nucleic acid sequences (e.g., 3-10 base pairs) that are added to ends of DNA fragments during adapter ligation. In some embodiments, UMIs are degenerate base pairs that serve as a unique tag that can be used to identify sequence reads originating from a specific DNA fragment. In some embodiments, e.g., when multiplex sequencing will be used to sequence DNA from a plurality of samples (e.g., from the same or different subjects) in a single sequencing reaction, a patient-specific index is also added to the nucleic acid molecules. In some embodiments, the patient specific index is a short nucleic acid sequence (e.g., 3-20 nucleotides) that are added to ends of DNA fragments during library construction, that serve as a unique tag that can be used to identify sequence reads originating from a specific patient sample. Examples of identifier sequences are described, for example, in Kivioja et al., Nat. Methods 9(1):72-74 (2011) and Islam et al., Nat. Methods 11(2):163-66 (2014), the contents of which are hereby incorporated by reference, in their entireties, for all purposes.

In some embodiments, an adapter includes a PCR primer landing site, designed for efficient binding of a PCR or second-strand synthesis primer used during the sequencing reaction. In some embodiments, an adapter includes an anchor binding site, to facilitate binding of the DNA molecule to anchor oligonucleotide molecules on a sequencer flow cell, serving as a seed for the sequencing process by providing a starting point for the sequencing reaction. During PCR amplification following adapter ligation, the UMIs, patient indexes, and binding sites are replicated along with the attached DNA fragment. This provides a way to identify sequence reads that came from the same original fragment in downstream analysis.

In some embodiments, a sequencing library, or pool of sequencing libraries, is enriched for target nucleic acids, e.g., nucleic acids encompassing loci that are informative for precision oncology and/or used as internal controls for sequencing or bioinformatics processes. In some embodiments, enrichment is achieved by hybridizing target nucleic acids in the sequencing library to probes that hybridize to the target sequences, and then isolating the captured nucleic acids away from off-target nucleic acids that are not bound by the capture probes.

In some embodiments, e.g., where a whole genome sequencing method will be used, nucleic acid sequencing libraries are not target-enriched prior to sequencing, in order to obtain sequencing data on substantially all of the competent nucleic acids in the sequencing library. Similarly, in some embodiments, e.g., where a whole genome sequencing method will be used, nucleic acid sequencing libraries are not mixed, because of bandwidth limitations related to obtaining significant sequencing depth across an entire genome. However, in other embodiments, e.g., where a low pass whole genome sequencing (LPWGS) methodology will be used, nucleic acid sequencing libraries can still be pooled, because very low average sequencing coverage is achieved across a respective genome, e.g., between about 0.5× and about 5×.

In some embodiments, the probe set includes probes targeting one or more gene loci, e.g., exon or intron loci. In some embodiments, the probe set includes probes targeting one or more loci not encoding a protein, e.g., regulatory loci, miRNA loci, and other non-coding loci, e.g., that have been found to be associated with cancer. In some embodiments, the plurality of loci include at least 25, 50, 100, 150, 200, 250, 300, 350, 400, 500, 750, 1000, 2500, 5000, or more human genomic loci. In some embodiments, the gene panel is a whole-exome panel that analyzes the exomes of a biological sample. In some embodiments, the gene panel is a whole-genome panel that analyzes the genome of a specimen.

Sequence reads are then generated from the sequencing library or pool of sequencing libraries. Sequencing data may be acquired by any methodology known in the art. For example, next generation sequencing (NGS) techniques such as sequencing-by-synthesis technology (Illumina), pyrosequencing (454 Life Sciences), ion semiconductor technology (Ion Torrent sequencing), single-molecule real-time sequencing (Pacific Biosciences), sequencing by ligation (SOLiD sequencing), nanopore sequencing (Oxford Nanopore Technologies), or paired-end sequencing. In some embodiments, massively parallel sequencing is performed using sequencing-by-synthesis with reversible dye terminators. In some embodiments, sequencing is performed using next generation sequencing technologies, such as short-read technologies. In other embodiments, long-read sequencing or another sequencing method known in the art is used.

In some embodiments, the methods described herein include one or more of obtaining a biological sample, extracting nucleic acids from the biological sample, and sequencing the isolated nucleic acids. In other embodiments, sequencing data or feature data sets obtained therefrom used in the improved systems and methods described herein are obtained by receiving previously generated sequence reads or feature data sets, in electronic form.

In some embodiments, the methods and systems described herein use additional features to perform the various classifications provided herein. Non-limiting examples of other characteristics that may be used for these purposes include tumor organoid histology, and baseline histology (H&E image; features; see also Patent Application Nos. 62/787,047 and 62/824,039); clinical data (gender, age, family medical history, personal history of cancer, treatment history of cancer, diagnosis, subtype, IHC markers, DNA/RNA sequence); methylation sequence; radiology images/features; comorbidities, geographic location, ancestry, ethnic features, diet, gut microbiome, substance usage, alcohol use, physical exam findings, baseline vitals, vaccination history, religious or cultural beliefs, marital status, sexual orientation, nocturnal/diurnal rhythm, sleep schedule, travel history (including airplane travel), travel to certain regions, presence/absence of parasitic organisms, infectious disease history (including parasitic organisms, viruses, bacteria), germline DNA sequence, biometric features (like distance between eyes, bones), skull shape, physical profile, occupational history, living with pets (including birds), mental health; tumor organoid morphology; viability; and smoking status.

F. Training a Classifier to Evaluate Sensitivity to a Therapeutic Agent

In one aspect, the disclosure provides methods and systems for performing methods of training a classifier to discriminate between two or more tumor sensitivities to a therapeutic agent. In some embodiments, the method includes obtaining a data set comprising, for each respective tissue sample in a plurality of tissue samples, (i) a corresponding plurality of nucleic acid features of the tissue sample, and (ii) a corresponding indication of the sensitivity of a respective organoid cultured from one or more cells of the tissue sample to the therapeutic agent. The method then includes training an untrained classifier against at least (i) the corresponding plurality of features and (ii) the corresponding indication of the sensitivity of the organoid to the therapeutic agent, across the plurality of tissue samples, thereby obtaining a trained classifier that discriminates between the two or more tumor sensitivities to a therapeutic agent.

In some embodiments, the two or more tumor sensitivities include a first level of sensitivity to a first therapeutic agent and a second level of sensitivity to the first therapeutic agent. In some embodiments, the two or more tumor sensitivities include a first sensitivity to a first therapeutic agent and a second sensitivity to a second therapeutic agent.

In some embodiments, the classifier is further trained to discriminate between the two or more tumor sensitivities to a therapeutic agent and one or more tumor sensitivity to a chemotherapeutic drug that is not the therapeutic agent.

In some embodiments, each tissue sample in the plurality of tissue samples was obtained from a subject that had not received treatment for cancer prior to the tissue sample being obtained. In some embodiments, each tissue sample in the plurality of tissue samples is a breast cancer biopsy. In some embodiments, each tissue sample in the plurality of tissue samples is an ovarian cancer biopsy. In some embodiments, each tissue sample in the plurality of tissue samples is a biopsy of a homologous recombination deficient (HRD) cancer. In some embodiments, each tissue sample in the plurality of tissue samples is a biopsy from a cancer other than breast cancer or ovarian cancer.

In some embodiments, the plurality of nucleic acid features of the tissue sample includes one or more of support for a single nucleotide variant at a genomic location, a methylation status at a genomic location, a relative copy number for a genomic location, an allelic ratio for a genomic location, a relative expression level of a gene, and mathematical combinations thereof. In some embodiments, at least a sub-plurality of the plurality of nucleic acid features of the tissue sample are measured from a tumor organoid cultured from one or more cells of the tissue sample.

In some embodiments, the indication of the sensitivity of the respective organoid to the therapeutic agent is based at least in part on one or more cellular fitness measurements obtained by: i) culturing one or more organoids, each respective organoid in the one or more organoids from one or more cells of the respective tissue sample, ii) exposing the one or more organoids cultured in i) to one or more amounts of the therapeutic agent, and iii) measuring the fitness of cells, e.g., using a cellular viability assay or cell death assay, in the one or more organoids following the exposure to the one or more amounts of the therapeutic agent, thereby obtaining the one or more cellular fitness measurements.

In some embodiments, the one or more cellular fitness measurements are one or more measurements of cellular apoptosis following exposure to the therapeutic agent.

In some embodiments, for at least one respective tissue sample in the plurality of tissue samples, the one or more cultured organoids are exposed to a sensitizing therapy, e.g., radiation or a different chemotherapeutic drug, before being exposed to the therapeutic agent.

In some embodiments, the untrained classifier is further trained against, for each respective tissue sample in the plurality of tissue samples, a corresponding cancer classification of the tissue sample in a plurality of cancer classifications. In some embodiments, the plurality of cancer classifications includes cancerous tissue and non-cancerous tissue. In some embodiments, the plurality of cancer classifications includes a plurality of types of cancer. In some embodiments, the plurality of cancer classifications includes a plurality of stages of cancer.

In some embodiments, the plurality of tissue samples includes a plurality of tumor biopsies, and the classifier training includes identifying a plurality of genes that are differentially expressed between (i) organoids, cultured from one or more cells of a respective tumor biopsy in the plurality of tumor biopsies, that have a first sensitivity to the therapeutic agent, e.g., organoids that experience at least a threshold level of cell death upon exposure of the organoid to the therapeutic agent, and (ii) organoids, cultured from one or more cells of a respective tumor biopsy in the plurality of tumor biopsies, that have a second sensitivity to the therapeutic agent, e.g., organoids that experience less than a threshold level of cell death upon exposure of the organoid to the therapeutic agent.

In some embodiments, the classifier is further trained against, for each respective tissue sample in the plurality of tissue samples, one or more phenotypic characteristics of the tissue sample. In some embodiments, the one or more phenotypic characteristics of the tissue sample include a histologic feature of the tissue sample.

In some embodiments, the classifier is further trained against, for each respective tissue sample in the plurality of tissue samples, one or more characteristics of the subject from which the tissue sample was obtained, e.g., as described above.

In some embodiments, the classifier is a multinomial classifier that is trained to provide a plurality of likelihoods, wherein each respective likelihood in the plurality of likelihoods is a likelihood that tumor cells from a test subject with cancer will have a different respective sensitivity in the two or more tumor sensitivities to a therapeutic agent. In some embodiments, the classifier is a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, or a clustering algorithm.

G. Diagnosing Therapeutic Agent Sensitivity

In some embodiments, the disclosure provides method and systems for performing methods of recommending therapy for treating a cancer in a subject. In some embodiments, the method includes obtaining a first test data set comprising a plurality of nucleic acid features of a tumor biopsy from the test subject. The method then includes evaluating the first test data set using a classifier trained to discriminate between two or more tumor sensitivities to a first therapeutic agent. The classifier is trained against, for each respective training tissue sample in a plurality of training tissue samples, at least (i) the plurality of nucleic acid features obtained from the respective training tissue sample, and (ii) a corresponding indication of the sensitivity of a respective organoid cultured from one or more cells of the respective training tissue sample to the first therapeutic agent. In some embodiments, the sensitivity of the training tissue sample is determined in a two-dimensional cell culture, a three-dimensional cell culture prepared in a matrix, a three-dimensional cell culture prepared in suspension culture, a cell culture suspension, or a xenograft model. A first tumor sensitivity in the two or more tumor sensitivities to the first therapeutic agent is associated with a first recommendation, in a plurality of recommendations, to treat the cancer in the subject with the first therapeutic agent. A second tumor sensitivity in the two or more tumor sensitivities to the first therapeutic agent is associated with a second recommendation, in the plurality of recommendations, not to treat the cancer in the subject with the first therapeutic agent. In some embodiments, the method includes providing a respective recommendation, in the plurality of recommendations, for treating the cancer in the test subject based on the results of the evaluation.

In some embodiments, the cancer is a breast cancer. In some embodiments, the cancer is an ovarian cancer. In some embodiments, the cancer is not breast cancer or ovarian cancer. In some embodiments, the test subject has not previously been treated for cancer. That is, in some embodiments, the therapeutic agent is administered as a first-line therapy. In some embodiments, the test subject has been previously treated for the cancer. That is, in some embodiments, the therapeutic agent is administered as a second-line therapy.

In some embodiments, the plurality of nucleic acid features of the tumor biopsy comprise one or more of support for a single nucleotide variant at a genomic location, a methylation status at a genomic location, a relative copy number for a genomic location, an allelic ratio for a genomic location, a relative expression level of a gene, and mathematical combinations thereof.

In some embodiments, the first test data set further comprises a cancer status of the test subject in a plurality of cancer statuses, the classifier was further trained against, for each respective training tissue sample in a plurality of training tissue samples, a cancer status of the respective training tissue sample in the plurality of cancer statuses.

In some embodiments, the plurality of cancer statuses comprises a plurality of types of cancer. In some embodiments, the plurality of cancer statuses comprises a plurality of stages of cancer.

In some embodiments, the first test data set further comprises one or more phenotypic characteristics of the tumor biopsy, and the classifier was further trained against, for each respective training tissue sample in a plurality of training tissue samples, the one or more phenotypic characteristics of the respective training tissue sample. In some embodiments, the one or more phenotypic characteristics of the tumor biopsy comprise a histologic feature of the tumor biopsy.

In some embodiments, the first test data set further comprises one or more characteristics of the subject, as described in the feature selection section above, and the classifier was further trained against, for each respective training tissue sample in a plurality of training tissue samples, the one or more characteristics of the subject from which the respective training tissue sample was obtained.

In some embodiments, the method also includes obtaining a second test data set comprising the plurality of nucleic acid features of a tumor biopsy from the test subject, and evaluating the second test data set using the classifier trained to discriminate between two or more tumor sensitivities to a first therapeutic agent, where the plurality of nucleic acid features in the first test data set are from a first tumor biopsy from the test subject and the second test data set are from a second tumor biopsy from the test subject that is different from the first tumor biopsy. In some embodiments, the first tumor biopsy and the second tumor biopsy are from different sections of a same tumor of the subject. In some embodiments, the first tumor biopsy and the second tumor biopsy are from different tumors of the subject.

In some embodiments, the classifier is a multinomial classifier that is trained to provide a plurality of likelihoods, wherein each respective likelihood in the plurality of likelihoods is a likelihood that a different respective treatment regime, in a plurality of treatment regimes, for the cancer in the subject will be more effective than the other treatment regimes in the plurality of treatment regimes.

In some embodiments, the classifier is a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, or a clustering algorithm.

In some embodiments, the classifier is trained to further discriminate between two or more tumor sensitivities to a second therapeutic agent, wherein the second therapeutic agent is different than the first therapeutic agent In some embodiments, the classifier is trained to further discriminate between two or more tumor sensitivities to a chemotherapeutic drug that is not in the same class of agents as the therapeutic agent.

In some embodiments, the first recommendation is a recommendation to treat the cancer in the subject with the first therapeutic agent as a first-line therapy. In some embodiments, the first recommendation is a recommendation to treat the cancer in the subject with the first therapeutic agent as a second-line therapy.

In some embodiments, the first recommendation is a recommendation to treat the cancer in the subject with the first therapeutic agent and without any other chemotherapeutic drug. In some embodiments, after providing, or instead of providing, the first recommendation for treating the cancer in the subject, the method includes administering the first therapeutic agent to the test subject.

In some embodiments, the first recommendation is a recommendation to treat the cancer in the subject with the first therapeutic agent and with a second cancer therapy, e.g., radiation, surgery, a second therapeutic agent, or a chemotherapeutic drug that is not in the same class as first therapeutic agent. In some embodiments, after providing, or instead of providing, the first recommendation for treating the cancer in the subject, the method includes co-administering the first therapeutic agent and the second cancer therapy to the test subject. In some embodiments, the second cancer therapy is administration of a chemotherapeutic drug that is not in the same class as the first therapeutic agent.

In some embodiments, the second recommendation is a recommendation to treat the cancer in the subject with a second therapeutic agent. In some embodiments, after providing, or instead of providing, the second recommendation for treating the cancer in the subject, the method includes administering the second therapeutic agent to the test subject.

In some embodiments, the plurality of recommendations further comprises a third recommendation to treat the cancer in the subject with a chemotherapeutic drug that is not in the same class as the first or second therapeutic agent. In some embodiments, after providing, or instead of providing, the third recommendation for treating the cancer in the subject, the method includes administering the chemotherapeutic drug that is not in the same class as the first or second therapeutic agent to the test subject.

In some embodiments, prior to providing the respective recommendation, the method includes identifying at least two recommendations, in the plurality of recommendations, based on the results of the evaluation, e.g., that are associated with better likelihoods that their associated treatment regimens will be more effective than treatment regimens associated with other recommendations, and determining a sensitivity of the cancer in the subject to each respective therapy regimen, in a plurality of therapy regimens, associated with the at least two recommendations by: a) culturing a plurality of tumor organoids, each respective tumor organoid in the plurality of tumor organoids from one or more cells of a tumor biopsy from the subject, b) exposing the one or more organoids cultured in a) to one or more amounts of a therapeutic agent associated with the respective therapy regimen, and c) measuring the fitness of cells, e.g., using a cellular viability assay or cell death assay, in the one or more organoids following the exposure to the one or more amounts of the therapeutic agent, thereby obtaining one or more cellular fitness measurements for each respective therapy regimen associated with the two or more recommendations. In this embodiments, the therapeutic recommendation and/or treatment is selected from the two or more recommendations and is based on the one or more cellular fitness measurements obtained for each respective therapy regimen associated with the two or more recommendations.

In some embodiments, the methods described herein include administering the recommended therapy for treating cancer to the test subject.

H. Treatment of Cancers with Therapeutic Agents

In some embodiments, the disclosure provides methods and systems for performing methods of treating a cancer in a test subject. In some embodiments, the methods include determining a probability or likelihood that the cancer will be sensitive to a therapeutic agent, and treating cancer in the subject. When the probability or likelihood that the cancer will be sensitive to the therapeutic agent satisfies a threshold likelihood, the method includes administering, or communicating, a recommended therapy comprising the therapeutic agent to the test subject. When the probability or likelihood that the cancer will be sensitive to the therapeutic agent does not satisfy a threshold likelihood, the method includes administrating, or communicating, a recommended therapy that does not include the therapeutic agent to the test subject.

In some embodiments, the cancer is a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer. In some embodiments, the test subject has been previously treated for the cancer. That is, in some embodiments, the therapeutic agent is administered as a second-line therapy.

In some embodiments, the probability or likelihood that the cancer will be sensitive to the therapeutic agent is determined by: 1) culturing a plurality of tumor organoids, each respective tumor organoid in the plurality of tumor organoids from one or more cells of a tumor biopsy from the test subject, 2) exposing the one or more organoids cultured in a) to one or more amounts of the therapeutic agent, 3) measuring the fitness of cells, e.g., using a cellular viability assay or cell death assay, in the one or more tumor organoids following the exposure to the one or more amounts of the therapeutic agent, and 4) correlating the measured fitness of the cells with a probability or likelihood that the cancer will be sensitive to the therapeutic agent.

In some embodiments, the probability or likelihood that the cancer will be sensitive to the therapeutic agent is determined by: 1) obtaining a first test data set comprising a plurality of nucleic acid features of a tumor biopsy from the test subject, 2) evaluating the first test data set using a classifier trained to discriminate between two or more tumor sensitivities to the therapeutic agent, where the classifier was trained against, for each respective training tissue sample in a plurality of training tissue samples, at least (i) the plurality of nucleic acid features obtained from the respective training tissue sample, and (ii) a corresponding indication of the sensitivity of a respective organoid cultured from one or more cells of the respective training tissue sample to the therapeutic agent.

In some embodiments, the plurality of nucleic acid features of the tumor biopsy comprise one or more of support for a single nucleotide variant at a genomic location, a methylation status at a genomic location, a relative copy number for a genomic location, an allelic ratio for a genomic location, a relative expression level of a gene, and mathematical combinations thereof.

In some embodiments, the first test data set further comprises a cancer status of the test subject in a plurality of cancer statuses, and the classifier was further trained against, for each respective training tissue sample in a plurality of training tissue samples, a cancer status of the respective training tissue sample in the plurality of cancer statuses. In some embodiments, the plurality of cancer statuses comprises a plurality of types of cancer. In some embodiments, the plurality of cancer statuses comprises a plurality of stages of cancer.

In some embodiments, the first test data set further comprises one or more phenotypic characteristics of the tumor biopsy, and the classifier was further trained against, for each respective training tissue sample in a plurality of training tissue samples, the one or more phenotypic characteristics of the respective training tissue sample. In some embodiments, the one or more phenotypic characteristics of the tumor biopsy comprise a histologic feature of the tumor biopsy.

In some embodiments, the first test data set further comprises one or more characteristics of the subject, as described in the feature selection section above, and the classifier was further trained against, for each respective training tissue sample in a plurality of training tissue samples, the one or more characteristics of the subject from which the respective training tissue sample was obtained.

In some embodiments, the method also includes obtaining a second test data set comprising the plurality of nucleic acid features of a tumor biopsy from the test subject, and evaluating the second test data set using the classifier trained to discriminate between the two or more tumor sensitivities to the therapeutic agent, where the plurality of nucleic acid features in the first test data set are from a first tumor biopsy from the test subject and the second test data set are from a second tumor biopsy from the test subject that is different from the first tumor biopsy. Ins some embodiments, the first tumor biopsy and the second tumor biopsy are from different sections of a same tumor of the subject. In some embodiments, the first tumor biopsy and the second tumor biopsy are from different tumors of the subject.

In some embodiments, the classifier is a multinomial classifier that is trained to provide a plurality of likelihoods, wherein each respective likelihood in the plurality of likelihoods is a likelihood that a different respective treatment regime, in a plurality of treatment regimes, for the cancer in the subject will be more effective than the other treatment regimes in the plurality of treatment regimes.

In some embodiments, the classifier is a neural network algorithm, a support vector machine algorithm, a Naive Bayes algorithm, a nearest neighbor algorithm, a boosted trees algorithm, a random forest algorithm, a convolutional neural network algorithm, a decision tree algorithm, a regression algorithm, or a clustering algorithm.

In some embodiments, the methods described herein also include administering the recommended therapy for treating cancer to the test subject.

I. Providing Therapeutic Agent Info on a Clinical Report

In some embodiments, the disclosure provides methods and systems for performing methods of providing a clinical report for a cancer patient to a physician. In some embodiments, the methods include obtaining a first test data set comprising features of a transcriptome from a tumor biopsy from the cancer patient. In some embodiments, the methods include evaluating the first test data set using a classifier trained, e.g., as described herein, to discriminate between two or more tumor sensitivities to a first therapeutic agent. The methods then include receiving a recommended therapy for the cancer patient from the classifier, and including the recommended therapy, or sending the recommended therapy to a third party for inclusion, in a clinical report for the cancer patient.

In some embodiments, the recommended therapy for the cancer patient comprises administration of the therapeutic agent.

In some embodiments, the patient has a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer. In some embodiments, the patient has a breast cancer. In some embodiments, the patient has an ovarian cancer. In some embodiments, the patient does not have has breast cancer or ovarian cancer. In some embodiments, the patient has a colorectal cancer. In some embodiments, the patient has a lung cancer. In some embodiments, the patient has a non-small cell lung cancer. In some embodiments, the patient has an endometrial cancer. In some embodiments, the patient has not previously been treated for cancer. In some embodiments, the patient has previously been treated for the cancer.

J. Research Tool for Repurposing Drugs

In some embodiments, the disclosure provides methods and systems for performing methods of identifying a new use for a pharmaceutical compound of a first pharmaceutical class. In some embodiments, the methods include obtaining a plurality of tissue samples, wherein each respective tissue sample in the plurality of tissue samples is sensitive to a respective class of pharmaceutical agents in a plurality of classes of pharmaceutical agents that excludes the first pharmaceutical class. The methods then includes culturing, for each respective tissue sample in the plurality of tissue samples, one or more respective organoids from one or more cells of the respective tissue sample, thereby generating a plurality of organoid cultures. The methods then include exposing, for each organoid culture in the plurality of organoid cultures, the respective one or more organoids to one or more concentrations of the pharmaceutical agent, and measuring, for each organoid culture in the plurality of organoid cultures, the fitness of cells in the respective one or more organoids following the exposure to the pharmaceutical agent. Reduced fitness of the cells in the respective one or more organoids is indicative that the pharmaceutical molecule shares pharmacological properties with the class of pharmaceutical compounds in the plurality of classes of pharmaceutical classes to which the tissue sample corresponding to the respective one or more organoids is sensitive.

In some embodiments, the plurality of tissue samples comprises cells from at least 3 different types of cancers. In some embodiments, the plurality of tissue samples comprises cells from at least 4, 5, 6, 7, 8, 9, 10, 11, 12, 13, 14, 15, or more different types of cancers.

K. Selecting Patients for Clinical Trials with an Organoid Assay

In some embodiments, the disclosure provides methods and systems for performing methods of determining the eligibility of a cancer patient for a clinical trial of a candidate cancer pharmaceutical agent. In some embodiments, the methods include obtaining a tumor biopsy from the cancer patient, and culturing one or more tumor organoids from one or more cells of the tumor biopsy. The methods then include exposing the one or more tumor organoids to one or more concentrations of the candidate cancer pharmaceutical agent, and measuring the fitness of cells in the one or more tumor organoids following the exposure to the one or more concentrations of the candidate cancer pharmaceutical agent. The methods then include determining whether the cancer patient is eligible for the clinical trial based on at least the measured fitness of the cells in the one or more tumor organoids, wherein reduced fitness of the cells in the one or more tumor organoids is indicative that the cancer patient is eligible for the clinical trial.

In some embodiments, the clinical trial is for the treatment of a breast cancer. In some embodiments, the clinical trial is for the treatment of an ovarian cancer. In some embodiments, the clinical trial is for the treatment of a breast cancer or ovarian cancer. In some embodiments, the clinical trial is for the treatment of a colorectal cancer. In some embodiments, the clinical trial is for the treatment of a lung cancer. In some embodiments, the clinical trial is for the treatment of a non-small cell lung cancer. In some embodiments, the clinical trial is for the treatment of an endometrial cancer. In some embodiments, the clinical trial is for the treatment of a patient that has not previously been treated for cancer. In some embodiments, the clinical trial is for the treatment of a patient that has previously been treated for the cancer.

L. Selecting Patients for Clinical Trials with a Classifier

In some embodiments, the disclosure provides methods and systems for performing methods of determining the eligibility of a cancer patient for a clinical trial of a candidate cancer pharmaceutical agent. In some embodiments, the methods include obtaining a first test data set comprising a plurality of nucleic acid features of a tumor biopsy from the cancer patient. The methods then include evaluating the first test data set using a classifier trained to discriminate between two or more tumor sensitivities to the candidate cancer pharmaceutical agent. The classifier is trained against, for each respective training tissue sample in a plurality of training tissue samples, at least (i) the plurality of nucleic acid features obtained from the respective training tissue sample, and (ii) a corresponding indication of the sensitivity of a respective organoid cultured from one or more cells of the respective training tissue sample to the candidate cancer pharmaceutical agent. A first tumor sensitivity in the two or more tumor sensitivities to the candidate cancer pharmaceutical agent is associated with an indication that the cancer patient is eligible for the clinical trial. A second tumor sensitivity in the two or more tumor sensitivities to the candidate cancer pharmaceutical agent is associated with an indication that the cancer patient is eligible for the clinical trial. The methods then include determining whether the cancer patient is eligible for the clinical trial based on at least the evaluation.

In some embodiments, the clinical trial is for the treatment of a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer. In some embodiments, the clinical trial is for the treatment of a patient that has not previously been treated for cancer.

In some embodiments, the clinical trial is for the treatment of a patient that has previously been treated for the cancer.

In some embodiments, the candidate cancer pharmaceutical agent has previously been found to be effective for the treatment of a cancer having a first clinical marker and the clinical trial is for the treatment of a cancer that does not have the first clinical marker.

In some embodiments, the plurality of nucleic acid features of the tumor biopsy include one or more of support for a single nucleotide variant at a genomic location, a methylation status at a genomic location, a relative copy number for a genomic location, an allelic ratio for a genomic location, a relative expression level of a gene, and a mathematical combination thereof.

In some embodiments, the first test data set also includes a cancer status of the test subject in a plurality of cancer statuses, and the classifier was further trained against, for each respective training tissue sample in a plurality of the training tissue samples, a cancer status of the respective training tissue sample in the plurality of cancer statuses. In some embodiments, the plurality of cancer statuses comprises a plurality of types of cancer. In some embodiments, the plurality of cancer statuses comprises a plurality of stages of cancer.

In some embodiments, the first test data set further comprises one or more phenotypic characteristics of the tumor biopsy, and the classifier was further trained against, for each respective training tissue sample in a plurality of training tissue samples, the one or more phenotypic characteristics of the respective training tissue sample. In some embodiments, the one or more phenotypic characteristics of the tumor biopsy comprise a histologic feature of the tumor biopsy.

In some embodiments, the first test data set also includes one or more characteristics of the subject, as described in the feature selection section above, and the classifier was further trained against, for each respective training tissue sample in a plurality of training tissue samples, the one or more characteristics of the subject from which the respective training tissue sample was obtained.

M. Detecting Drug Resistance with a Classifier

In some embodiments, the disclosure provides methods and systems for performing methods of identifying a resistance to a chemotherapeutic agent in a patient with cancer. In some embodiments, the methods include obtaining a first test data set comprising a plurality of nucleic acid features of a tumor biopsy from the patient with cancer. The methods then include evaluating the first test data set using a classifier trained to discriminate between two or more tumor sensitivities to the chemotherapeutic agent. The classifier is trained against, for each respective training tissue sample in a plurality of training tissue samples, at least (i) the plurality of nucleic acid features obtained from the respective training tissue sample, and (ii) a corresponding indication of the sensitivity of a respective organoid cultured from one or more cells of the respective training tissue sample to the chemotherapeutic agent. A first tumor sensitivity in the two or more tumor sensitivities to the candidate cancer pharmaceutical agent is associated with an indication that the patient's cancer is resistant to the chemotherapeutic agent. A second tumor sensitivity in the two or more tumor sensitivities to the candidate cancer pharmaceutical agent is associated with an indication that the patient's cancer is not resistant to the chemotherapeutic agent. The methods then include providing a report indicating whether the patient's cancer is resistant to the chemotherapeutic agent based on at least the results of the evaluation.

In some embodiments, the patient has a has a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer. In some embodiments, the patient has not previously been treated for cancer. In some embodiments, the patient has previously been treated for the cancer.

In some embodiments, the chemotherapeutic agent has been previously associated with a clinical marker and the cancer has the clinical marker.

In some embodiments, the plurality of nucleic acid features includes one or more of support for a single nucleotide variant at a genomic location, a methylation status at a genomic location, a relative copy number for a genomic location, an allelic ratio for a genomic location, a relative expression level of a gene, and a mathematical combination thereof.

In some embodiments, the first test data set also includes one or more phenotypic characteristics of the tumor biopsy, and the classifier was further trained against, for each respective training tissue sample in a plurality of training tissue samples, the one or more phenotypic characteristics of the respective training tissue sample. In some embodiments, the one or more phenotypic characteristics of the tumor biopsy comprise a histologic feature of the tumor biopsy.

In some embodiments, the first test data set also includes one or more characteristics of the subject, as described in the feature selection section above, and the classifier was further trained against, for each respective training tissue sample in a plurality of training tissue samples, the one or more characteristics of the subject from which the respective training tissue sample was obtained.

N. Evaluating Effect of Cancer Drug Using Tumor Organoid Assay and Assigning Cancer Treatment Based on Tumor Organoid Assay In some aspects, the present disclosure provides systems and methods for large scale analysis of therapeutic responses using tumor organoids (TOs).

In certain aspects, a drug screening platform may be utilized to assess the effectiveness of drugs or other agents on tumor organoids. In one embodiment, tumor organoids are first dissociated into single cells, which are then seeded into individual partitions in the presence of tumor organoid culture media. Tumor organoids used in the methods provided herein can be derived from cells from any suitable cancer including, but not limited to, an anal cancer, a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, a rectal cancer.

Tumor organoids that subsequently form from the individual cells in each partition exhibit tumor organoid heterogeneity. In some embodiments, the single cells are seeded in a multi-well plate (e.g., 24-, 48-, 96-, 384-well). Preferably, individual cells are seeded at a density to allow sufficient number of TOs to form while not overcrowding the plate so that TOs do not overlap or touch allowing for easy identification of individual TOs.

Any suitable tumor organoid medium can be used to culture the tumor organoids. In some embodiments, the tumor organoid medium includes one or more tumor organoid growth factors. Organoid growth factors include an epidermal growth factor (EGF), a fibroblast growth factor (FGF), a hepatocyte growth factor (HGF), a Wnt, Noggin, an R-spondin, Gastrin, Prostaglandin, and Neuregulin. Organoid growth factors include ligands (natural, semi-synthetic, or synthetic, agonist or antagonist) of EGF family receptors, HGF family of receptors, Wnt family receptors, NOTCH family receptors, LRP receptor, Frizzled receptor, LGRS receptor, insulin receptor, neuregulin family of receptors, or any growth factor receptor tyrosine kinase family member. Exemplary organoid culture media are summarized below in Table 1. In particular embodiments, the organoid culture medium is free of R-spondins. In some embodiments, the organoid culture medium is free of Wnt. An example of systems and methods for culturing tumor organoids may be found in U.S. patent application Ser. No. 16/693,117, titled "Tumor Organoid Culture Compositions, Systems, and Methods" and filed Nov. 22, 2019, which is incorporated by reference herein in its entirety and in relevant parts related to systems and methods for culturing tumor organoids.

TABLE 1

| Organoid Culture Medium | Growth Factors | Molecular Inhibitors | Additional Components |
|---|---|---|---|
| B | Noggin | Rho kinase inhibitor, transforming growth factor-beta inhibitor, and MAP kinase inhibitor | a chemically-defined, minimal culture medium; L-glutamine; a serum replacement supplement; N-acetyl-L-cysteine; and nicotinamide |
| C | EGF and Noggin | Rho kinase inhibitor, transforming growth factor-beta inhibitor, and MAP kinase inhibitor | a chemically-defined, minimal culture medium; L-glutamine; a serum replacement supplement; N-acetyl-L-cysteine; and nicotinamide |
| D | EGF, Noggin, FGF7 and FGF10 | Rho kinase inhibitor, transforming growth factor-beta inhibitor, and MAP kinase inhibitor | a chemically-defined, minimal culture medium; L-glutamine; a serum replacement supplement; N-acetyl-L-cysteine; and nicotinamide |

In one example, the TOs are also cultured in the presence of one or more extracellular matrix (ECM) components that function as a substrate for culturing the TO. In particular embodiments, the substrate is a Matrigel.

In one example, one or more therapeutic agents are applied to the TOs in the partitions. Exemplary therapeutic agents include, but are not limited to, a molecular inhibitors, antibodies, recombinant nucleic acids (e.g., antisense oligonucleotides) and engineered immune cells (e.g., CAR T-cells and NK cells). Exemplary therapeutic agents include, but are not limited to, Paclitaxel, Gemcitabine, Cisplatin, Carboplatin, Oxaliplatin, Capecitabine, SN-38 (CPT-11), 5-FU, MTX (methotrexate), Docetaxel, Bortezomib, Everolimus, Ulixertinib, Dasatinib, Vinblastine, Nelarabine, Epirubicin, Afatinib, Lapatinib, Cytarabine, Cladribine, Doxorubicin, Azacitidine, and Staurosporine. Other examples include classes of drugs including but not limited to: taxanes, platinating agents, *vinca* alkaloids, alkylating agents, and anthracyclines. One or more molecular inhibitors may be applied to the TOs in the well plates. Molecular inhibitors may be selected by name, target, pathway, formula, or other known characterizations.

In some embodiments, the one or more therapeutic agents include one or more of the following: an inhibitor of SUV4-20 (SUV420H1 or SUV420H2), a tyrosine kinase inhibitor, a retinoid-like compound, a wee1 kinase inhibitor, an anaplastic lymphoma kinase inhibitor, an aurora A kinase inhibitor, an aurora B kinase inhibitor, a reversible inhibitor of eukaryotic nuclear DNA replication, an antimetabolite antineoplastic agent, an ataxia telangiectasia and Rad3-related protein (ATR) kinase inhibitor, an ATM kinase inhibitor, a checkpoint kinase inhibitor, a GSK-3a/b inhibitor, a proteasome inhibitor, an AXL or RET inhibitor, a c-Met or VEGFR2 inhibitor, an alkylating antineoplastic agent, a DNA-PK and/or mTOR inhibitor, an inhibitor of mammalian target of rapamycin (mTOR), a checkpoint kinase 1 (CHK1) inhibitor, a retinoic acid receptor β (RARβ) or RARγ antagonist, a retinoic acid receptor (RAR) γ-selective agonist, RARγ-selective retinoid, inducer of apoptosis, CDK2 a RAR agonist, a chemotherapy, a tyrosine kinase inhibitor antineoplastic agent, an antimicrotubular antineoplastic agent, a topoisomerase inhibitor antineoplastic agent, a sodium-glucose cotransporter-2/SGLT2 inhibitor, an inhibitor of the tropomyosin receptor kinases A, B and C, C-ros oncogene 1 and anaplastic lymphoma kinase, a topoisomerase inhibitor antineoplastic agent, an inhibitor of mTOR, an inhibitor of phosphatidylinositol 3-kinase (PI3K), an inhibitor of RIP3K, an analog of cyclophosphamide, an SGLT2 inhibitor, aWnt/β-catenin inhibitor, a tyrosine kinase inhibitor that interrupts the HER2/neu and epidermal growth factor receptor/EGFR pathways, an inhibitor of tropomyosin kinase receptors TrkA, TrkB, and TrkC, a cyclin-dependent kinase (CDK) inhibitor, a CDK7 inhibitor, an inhibitor of VEGFR1, VEGFR2 and VEGFR3 kinases, a DNA-PK/PI3K/mTOR inhibitor, a poly ADP ribose polymerase (PARP) inhibitor, an inhibitor of Rac GTPase, a taxane, a Bromodomain And PHD Finger Containing 1 (BRPF1) bromodomain inhibitor, a mitogen-activated protein kinase-activated protein kinase 2 (MAPK2) inhibitor, a RAF inhibitor, a histone deacetylase (HDAC) inhibitor, a CDK1 inhibitor, aTGF-beta/Smad inhibitor, a Pim kinase inhibitor, a DNA topoisomerase I inhibitor, active metabolite of CPT-11/Irinotecan, an atypical retinoid, apoptosis inducer, a multi-kinase inhibitor, a fms-like tyrosine kinase-3 (FLT3) inhibitor, a MEK inhibitor, an inhibitor of extracellular signal-regulated kinase (ERK) 1 and/or 2, or a DNA-dependent protein kinase/DNA-PK inhibitor.

In some embodiments, the one or more therapeutic agents include one or more for the following: A-196 (inhibitor of SUV4-20 or SUV420H1 and SUV420H2), Afatinib (tyrosine kinase inhibitor), Adapalene (retinoid-like compound), Adavosertib (MK-1775, wee1 kinase inhibitor), Alectinib (CH5424802, anaplastic lymphoma kinase inhibitor), Alisertib (MLN8237, aurora A kinase inhibitor), Aphidicolin (reversible inhibitor of eukaryotic nuclear DNA replication, antimitotic), Azacitidine (an antimetabolite antineoplastic agent, a chemotherapy), AZ20 (ataxia telangiectasia and Rad3-related protein/ATR kinase inhibitor), AZ31 (ataxia-telangiectasia mutated/ATM kinase inhibitor), AZD6738 (ataxia telangiectasia and Rad3-related protein/ATR kinase inhibitor), AZD7762 (checkpoint kinase inhibitor), Barasertib (AZD1152-HQPA, aurora B kinase inhibitor), BAY-1895344 (ATR and ATM kinase inhibitor), Berzosertib (ATR and ATM kinase inhibitor), BIO-acetoxime (GSK-3a/b inhibitor), Bortezomib (proteasome inhibitor), Cabozantinib (kinase inhibitor, inhibitor of AXL, RET, and tyrosine kinases c-Met and VEGFR2), Capecitabine (an antimetabolite antineoplastic agent, a chemotherapy), Carboplatin (an alkylating antineoplastic agent, a chemotherapy), CC-115 (DNA-PK and mTOR inhibitor), CC-223 (inhibitor of mammalian target of rapamycin/mTOR), CCT-245737 (checkpoint kinase 1/CHK1 inhibitor), CD-2665 (retinoic acid receptor β (RARβ)/RARγ antagonist), CD-437 (retinoic acid receptor (RAR)γ-selective agonist, γ-selective retinoid; inducer of apoptosis), CDK2 inhibitor II, CH-55 (RAR agonist), Cisplatin (an alkylating antineoplastic agent, a chemotherapy), Cladribine (an antimetabolite antineoplastic agent, a chemotherapy), Cytarabine (an antimetabolite antineoplastic agent, a chemotherapy), Dasatinib (a tyrosine kinase inhibitor antineoplastic agent, a chemotherapy), Docetaxel (an antimicrotubular antineoplastic agent, a chemotherapy), Doxorubicin (Adriamycin, a topoisomerase inhibitor antineoplastic agent, a chemotherapy), Empagliflozin (BI 10773, a sodium-glucose cotransporter-2/SGLT2 inhibitor), Entrectinib (RXDX-101, tyrosine kinase inhibitor, inhibitor of the tropomyosin receptor kinases A, B and C, C-ros oncogene 1 and anaplastic lymphoma kinase), Epirubicin (a topoisomerase inhibitor antineoplastic agent, a chemotherapy), Etoposide (a topoisomerase inhibitor antineoplastic agent, a chemotherapy), Everolimus (inhibitor of mTOR), Fluorouracil/5-FU (an antimetabolite antineoplastic agent, a chemotherapy), GDC-0349 (inhibitor of mTOR), GDC-0575 (ARRY-575, CHK1 inhibitor), Gemcitabine (an antimetabolite antineoplastic agent, a chemotherapy), GSK2292767 (inhibitor of phosphatidylinositol 3-kinase/PI3K), GSK-872 (GSK2399872A, kinase inhibitor, inhibitor of RIP3K), Hesperadin (aurora kinase inhibitor), Hydroxyurea (an antimetabolite antineoplastic agent, a chemotherapy), Ifosfamide (an analog of cyclophosphamide, an alkylating antineoplastic agent, a chemotherapy), Ipragliflozin (ASP1941, an SGLT2 inhibitor), KYA1797K (Wnt/β-catenin inhibitor), Lapatinib (tyrosine kinase inhibitor that interrupts the HER2/neu and epidermal growth factor receptor/EGFR pathways, an antineoplastic agent, a chemotherapy), Larotrectinib (inhibitor of tropomyosin kinase receptors TrkA, TrkB, and TrkC), LDC 4297 (Cyclin-dependent kinase/CDK inhibitor, CDK7 inhibitor), Lenvatinib (multiple kinase inhibitor, inhibitor of VEGFR1, VEGFR2 and VEGFR3 kinases), LY3023414 (DNA-PK/PI3K/mTOR Inhibitor), Methotrexate (an antimetabolite antineoplastic agent, a chemotherapy), Nelarabine (an antimetabolite antineoplastic agent, a chemotherapy), Niraparib (MK-4827, a poly ADP ribose polymerase/PARP inhibitor), NSC 23766 (inhibitor of Rac GTPase), Olaparib (PARP inhibitor), Oxaliplatin (an alkylating antineoplastic agent, a chemotherapy), Paclitaxel (a taxane, an antimicrotubular antineoplastic agent, a chemotherapy), Pamiparib (BGB-290, PARP inhibitor), PFI-4 (Bromodomain And PHD Finger Containing 1/BRPF1 bromodomain inhibitor), PHA-767491 HCl (Mitogen-activated protein kinase-activated protein kinase 2/MK2 and CDK inhibitor), PLX7904 (RAF inhibitor), Pracinostat (histone deacetylase/HDAC inhibitor), Pralatrexate (an antimetabolite antineoplastic agent, a chemotherapy), Prexasertib HCl (checkpoint kinase 1/CHK1 inhibitor), RO-3306 (CDK1 inhibitor), Rucaparib (PARP inhibitor), Selpercatinib (LOXO-292, ARRY-192, a tyrosine kinase inhibitor), SIS3 HCl (TGF-beta/Smad inhibitor), SMI-4a (Pim kinase inhibitor), SN-38 (inhibitor of DNA topoisomerase I, active metabolite of CPT-11/Irinotecan), ST-1926 (Adarotene, atypical retinoid, apoptosis inducer), Staurosporine (multi-kinase inhibitor used as a positive control), Talazoparib (BMN-673, PARP inhibitor), TCS 359 (fms-like tyrosine kinase-3/FLT3 inhibitor), Tenalisib (RP6530, a PI3K δ/γ inhibitor), Tozasertib (VX-680, MK-0457, an Aurora Kinase inhibitor), Trametinib (GSK1120212, a MEK inhibitor), Ulixertinib (inhibitor of extracellular signal-regulated kinase/ERK 1 and 2, with potential antineoplastic activity), Veliparib (ABT-888, PARP inhibitor), Vinblastine (an antimicrotubular antineoplastic agent, a chemotherapy), or VX-984 (DNA-dependent protein kinase/DNA-PK inhibitor).

In some embodiments, the one or more therapeutic agents include one or the follow therapeutic agents or combination therapeutic: afatinib plus MET inhibitor (for example, tivantinib, cabozantinib, crizotinib, etc.), AZ31 plus SN-38, bevacizumab (anti-VEGF monoclonal IgG1 antibody), cetuximab (epidermal growth factor receptor/EGFR inhibitor), crizotinib (a tyrosine kinase inhibitor antineoplastic agent), cyclophosphamide (an alkylating antineoplastic agent), erlotinib (epidermal growth factor receptor inhibitor antineoplastic agent), FOLFIRI, bevacizumab plus FOLFIRI, FOLFOX, gefitinib (EGFR inhibitor), gemcitabine plus docetaxel, pemtrexed (an antimetabolite antineoplastic agent), ramucirumab (Vascular Endothelial Growth Factor Receptor 2/VEGFR2 Inhibitor), or topotecan (a topoisomerase inhibitor).

Additional exemplary therapeutic agents that can be used with the methods described herein are provided in Table 2.

TABLE 2

| Agent | Target | Pathway | Formula |
|---|---|---|---|
| Veliparib (ABT-888) | PARP | DNA Damage | $C_{13}H_{16}N_4O$ |
| Selumetinib (AZD6244) | MEK | MAPK | $C_{17}H_{15}BrClFN_4O_3$ |
| PD184352 (CI-1040) | MEK | MAPK | $C_{17}H_{14}ClF_2IN_2O_2$ |
| PD0325901 | MEK | MAPK | $C_{16}H_{14}F_3IN_2O_4$ |
| Tozasertib (VX-680, MK-0457) | Aurora Kinase | Cell Cycle | $C_{23}H_{28}N_8OS$ |
| Y-27632 2HCl | Autophagy, ROCK | Cell Cycle | $C_{14}H_{23}C_{l2}N_3O$ |
| Olaparib (AZD2281, Ku-0059436) | PARP | DNA Damage | $C_{24}H_{23}FN_4O_3$ |
| SL-327 | MEK | MAPK | $C_{16}H_{12}F_3N_3S$ |
| SB431542 | TGF-beta/Smad | TGF-beta/Smad | $C_{22}H_{16}N_4O_3$ |
| MK-2206 2HCl | Akt | PI3K/Akt/mTOR | $C_{25}H_{23}C_{l2}N_5O$ |
| Refametinib (RDEA119, Bay 86-9766) | MEK | MAPK | $C_{19}H_{20}F_3IN_2O_5S$ |
| KU-55933 (ATM Kinase Inhibitor) | ATM/ATR | DNA Damage | $C_{21}H_{17}NO_3S_2$ |
| GSK1904529A | IGF-1R | Protein Tyrosine Kinase | $C_{44}H_{47}F_2N_9O_5S$ |
| PF-04217903 | c-Met | Protein Tyrosine Kinase | $C_{19}H_{16}N_8O$ |
| U0126-EtOH | MEK | MAPK | $C_{20}H_{22}N_6OS_2$ |
| BI 2536 | PLK | Cell Cycle | C28H39N7O3 |
| JNJ-38877605 | c-Met | Protein Tyrosine Kinase | C19H13F2N7 |
| Odanacatib (MK-0822) | Cysteine Protease | Proteases | $C_{25}H_{27}F_4N_3O_3S$ |
| Alisertib (MLN8237) | Aurora Kinase | Cell Cycle | C27H20ClFN4O4 |
| Barasertib (AZD1152-HQPA) | Aurora Kinase | Cell Cycle | C26H30FN7O3 |
| CP-724714 | EGFR, HER2 | Protein Tyrosine Kinase | C27H27N5O3 |
| TGX-221 | PI3K | PI3K/Akt/mTOR | C21H24N4O2 |
| WZ4002 | EGFR | Protein Tyrosine Kinase | C25H27ClN6O3 |
| BIBR 1532 | Telomerase | DNA Damage | C21H17NO3 |
| Anastrozole | Aromatase | Endocrinology & Hormones | C17H19N5 |
| Aprepitant | Substance P | Others | C23H21F7N4O3 |
| TAK-700 (Orteronel) | P450 (e.g. CYP17) | Metabolism | C18H17N3O2 |
| PFI-1 (PF-6405761) | Epigenetic Reader Domain | Epigenetics | C16H17N3O4S |
| KU-0063794 | mTOR | PI3K/Akt/mTOR | C25H31N5O4 |
| CHIR-99021 (CT99021) | GSK-3 | PI3K/Akt/mTOR | C22H18Cl2N8 |
| WYE-354 | mTOR | PI3K/Akt/mTOR | C24H29N7O5 |
| TG100-115 | PI3K | PI3K/Akt/mTOR | C18H14N6O2 |
| Aurora A Inhibitor I | Aurora Kinase | Cell Cycle | C31H31ClFN7O2 |
| Ispinesib (SB-715992) | Kinesin | Cytoskeletal Signaling | C30H33ClN4O2 |
| Zibotentan (ZD4054) | Endothelin Receptor | GPCR & G Protein | C19H16N6O4S |

TABLE 2-continued

| Agent | Target | Pathway | Formula |
|---|---|---|---|
| Safinamide Mesylate | MAO | Metabolism | C18H23FN2O5S |
| GSK429286A | ROCK | Cell Cycle | C21H16F4N4O2 |
| Pimasertib (AS-703026) | MEK | MAPK | C15H15FIN3O3 |
| Tadalafil | PDE | Metabolism | C22H19N3O4 |
| Adavosertib (MK-1775) | Wee1 | Cell Cycle | C27H32N8O2 |
| CP-673451 | PDGFR | Protein Tyrosine Kinase | C24H27N5O2 |
| Selisistat (EX 527) | Sirtuin | Epigenetics | C13H13ClN2O |
| Dapagliflozin | SGLT | GPCR & G Protein | C21H25ClO6 |
| Nebivolol HCl | Adrenergic Receptor | Neuronal Signaling | C22H26ClF2NO4 |
| Pimobendan | PDE | Metabolism | C19H18N4O2 |
| AZD8055 | mTOR | PI3K/Akt/mTOR | C25H31N5O4 |
| KU-60019 | ATM/ATR | DNA Damage | C30H33N3O5S |
| Tie2 kinase inhibitor | Tie-2 | ProteinTyrosine Kinase | C26H21N3O2S |
| Apixaban | Factor Xa | Metabolism | C25H25N5O4 |
| Raltegravir (MK-0518) | Integrase | Microbiology | C20H21FN6O5 |
| PCI-34051 | HDAC | Epigenetics | C17H16N2O3 |
| Ambrisentan | Endothelin Receptor | GPCR & G Protein | C22H22N2O4 |
| SB743921 HCl | Kinesin | Cytoskeletal Signaling | C31H34Cl2N2O3 |
| AST-1306 | EGFR | Protein Tyrosine Kinase | $C_{31}H_{26}ClFN_4O_5S$ |
| Sapitinib (AZD8931) | EGFR, HER2 | Protein Tyrosine Kinase | C23H25ClFN5O3 |
| GSK461364 | PLK | Cell Cycle | C27H28F3N5O2S |
| Mubritinib (TAK 165) | HER2 | Protein Tyrosine Kinase | C25H23F3N4O2 |
| UK 383367 | Procollagen C Proteinase | Metabolism | C15H24N4O4 |
| Cryptotanshinone | STAT | JAK/STAT | C19H20O3 |
| Icariin | PDE | Metabolism | C33H40O15 |
| OSI-027 | mTOR | PI3K/Akt/mTOR | C21H22N6O3 |
| Rabusertib (LY2603618) | Chk | Cell Cycle | C18H22BrN5O3 |
| URB597 | FAAH | Metabolism | C20H22N2O3 |
| A66 | PI3K | PI3K/Akt/mTOR | C17H23N5O2S2 |
| ICG-001 | Wnt/beta-catenin | Stem Cells & Wnt | C33H32N4O4 |
| PF-3845 | FAAH | Metabolism | C24H23F3N4O2 |
| Trametinib (GSK1120212) | MEK | MAPK | C26H23FIN5O4 |
| Ibrutinib (PCI-32765) | BTK | Angiogenesis | C25H24N6O2 |
| CHIR-124 | Chk | Cell Cycle | C23H22ClN5O |
| Mardepodect (PF-2545920) | PDE | Metabolism | C25H20N4O |
| WAY-600 | mTOR | PI3K/Akt/mTOR | C28H30N8O |
| Nepicastat (SYN-117) HCl | Hydroxylase | Metabolism | C14H16ClF2N3S |
| RS-127445 | 5-HT Receptor | Neuronal Signaling | C17H16FN3 |
| CP-91149 | Phosphorylase | Metabolism | C21H22ClN3O3 |
| SB415286 | GSK-3 | PI3K/Akt/mTOR | C16H10ClN3O5 |
| GSK1070916 | Aurora Kinase | Cell Cycle | C30H33N7O |
| Niraparib (MK-4827) | PARP | DNA Damage | C19H20N4O |
| CHIR-98014 | GSK-3 | PI3K/Akt/mTOR | C20H17Cl2N9O2 |
| AMG-458 | c-Met | Protein Tyrosine Kinase | C30H29N5O5 |
| Tivantinib (ARQ 197) | c-Met | Protein Tyrosine Kinase | C23H19N3O2 |
| Canagliflozin | SGLT | GPCR & G Protein | C24H25FO5S |
| NVP-BVU972 | c-Met | Protein Tyrosine Kinase | C20H16N6 |
| MK-5108 (VX-689) | Aurora Kinase | Cell Cycle | $C_{22}H_{21}ClFN_3O_3S$ |
| SB705498 | TRPV | Others | C17H16BrF3N4O |
| Vistusertib (AZD2014) | mTOR | PI3K/Akt/mTOR | C25H30N6O3 |
| A-803467 | Sodium Channel | Transmembrane Transporters | C19H16ClNO4 |
| Sirtinol | Sirtuin | Epigenetics | C26H22N2O2 |
| Ipatasertib (GDC-0068) | Akt | PI3K/Akt/mTOR | C24H32ClN5O2 |
| Sapanisertib (INK 128, MLN0128) | mTOR | PI3K/Akt/mTOR | C15H15N7O |
| Tyrphostin AG 879 | HER2 | Protein Tyrosine Kinase | C18H24N2OS |
| JNJ-1661010 | FAAH | Metabolism | C19H19N5OS |
| CTEP (RO4956371) | GluR | Neuronal Signaling | C19H13ClF3N3O |

TABLE 2-continued

| Agent | Target | Pathway | Formula |
|---|---|---|---|
| Alogliptin (SYK-322) benzoate | DPP-4 | Proteases | C18H21N5O2 |
| T0070907 | PPAR | DNA Damage | C12H8ClN3O3 |
| GW441756 | Trk receptor | Protein Tyrosine Kinase | C17H13N3O |
| SB742457 | 5-HT Receptor | Neuronal Signaling | C19H19N3O2S |
| ZM 323881 HCl | VEGFR | Protein Tyrosine Kinase | C22H19ClFN3O2 |
| GNF-2 | Bcr-Abl | Angiogenesis | C18H13F3N4O2 |
| Lumiracoxib | COX | Neuronal Signaling | C15H13ClFNO2 |
| JNJ-7777120 | Histamine Receptor | Neuronal Signaling | C14H16ClN3O |
| IOX2 | HIF | Angiogenesis | C19H16N2O5 |
| PF-4981517 | P450 (e.g. CYP17) | Metabolism | C26H32N8 |
| CHIR-99021 (CT99021) HCl | GSK-3 | PI3K/Akt/mTOR | C22H19Cl3N8 |
| Rivaroxaban | Factor Xa | Metabolism | C19H18ClN3O5S |
| Linagliptin | DPP-4 | Proteases | C25H28N8O2 |
| Azilsartan Medoxomil | RAAS | Endocrinology & Hormones | C30H24N4O8 |
| Sulfaphenazole | P450 (e.g. CYP17) | Metabolism | C15H14N4O2S |
| Sitagliptin phosphate monohydrate | DPP-4 | Proteases | C16H20F6N5O6P |
| Avanafil | PDE | Metabolism | C23H26ClN7O3 |
| Eprosartan Mesylate | RAAS | Endocrinology & Hormones | C24H28N2O7S2 |
| Carprofen | COX | Neuronal Signaling | C15H12ClNO2 |
| Saxagliptin hydrate | DPP-4 | Proteases | C18H27N3O3 |
| Daminozide | Histone Demethylase | Epigenetics | C6H12N2O3 |
| Bedaquiline fumarate | Anti-infection | Microbiology | C36H35BrN2O6 |
| JZL184 | Lipase | Metabolism | C27H24N2O9 |
| SC-514 | IκB/IKK | NF-κB | C9H8N2OS2 |
| (R)-Nepicastat HCl | Hydroxylase | Metabolism | C14H16ClF2N3S |
| Asunaprevir | HCV Protease | Proteases | C35H46ClN5O9S |
| Trelagliptin succinate | DPP-4 | Proteases | C22H26FN5O6 |
| Dabrafenib Mesylate | Raf | MAPK | $C_{24}H_{24}F_3N_5O_5S_3$ |
| Argatroban Monohydrate | Thrombin | Others | C23H38N6O6S |
| Sitagliptin | DPP-4 | Proteases | C16H15F6N5O |
| Raltegravir potassium | Integrase, HIV Protease | Microbiology | C20H20FKN6O5 |
| Alogliptin | DPP-4 | Proteases | C18H21N5O2 |
| Dasabuvir(ABT-333) | HCV Protease | Proteases | C26H27N3O5S |
| Ertugliflozin | SGLT2 | Ion-Channel | C22H25ClO7 |
| Rolapitant | NK1-receptor | GPCR | C25H26F6N2O2 |
| Dapagliflozin propanediol monohydrate | SGLT | GPCR & G Protein | C24H35ClO9 |
| Bedaquiline | tuberculosis | Immunology | C32H31BrN2O2 |
| Fruquintinib | VEGFRs | VEGFR | C21H19N3O5 |
| JNJ0966 | Others | Others | C16H16N4O2S2 |
| acalisib (GS-9820) | PI3K | PI3K/Akt/mTOR | C21H16FN7O |
| BRL-50481 | PDE | Metabolism | C9H12N2O4S |
| Canagliflozin hemihydrate | SGLT | GPCR & G Protein | C48H52F2O11S2 |
| JANEX-1 | JAK | JAK/STAT | C16H15N3O3 |
| Anagliptin | DPP-4 | Proteases | C19H25N7O2 |
| GSK 5959 | Epigenetic Reader Do | Epigenetics | C22H26N4O3 |
| Pitolisant hydrochloride | Histamine Receptor | Neuronal Signaling | C17H27Cl2NO |
| K 858 | Kinesin | Cytoskeletal Signaling | C13H15N3O2S |
| BAY-61-3606 | Syk | Angiogenesis | C20H20Cl2N6O3 |
| Stattic | STAT | JAK/STAT | C8H5NO4S |
| GSK2656157 | PERK | Apoptosis | C23H21FN6O |
| XL388 | mTOR | PI3K/Akt/mTOR | C23H22FN3O4S |
| LY2090314 | GSK-3 | PI3K/Akt/mTOR | C28H25FN6O3 |
| MK-8745 | Aurora Kinase | Cell Cycle | C20H19ClFN5OS |
| Tepotinib (EMD 1214063) | c-Met | Protein Tyrosine Kinase | C29H28N6O2 |
| SGC 0946 | Histone Methyltransferase | Epigenetics | C28H40BrN7O4 |
| GSK2334470 | PDK | PI3K/Akt/mTOR | C25H34N8O |
| IPA-3 | PAR | Cytoskeletal Signaling | C20H14O2S2 |
| VE-822 | ATM/ATR | PI3K/Akt/mT0R | C24H25N5O3S |
| (+)-JQ1 | Epigenetic Reader Domain | Epigenetics | C23H25ClN4O2S |

TABLE 2-continued

| Agent | Target | Pathway | Formula |
|---|---|---|---|
| PYR-41 | E1 Activating | Ubiquitin | C17H13N3O7 |
| TCID | DUB | Ubiquitin | C9H2Cl4O2 |
| DMH1 | TGF-beta/Smad | TGF-beta/Smad | C24H20N4O |
| ML347 | TGF-beta/Smad, ALK | TGF-beta/Smad | C22H16N4O |
| UNC1999 | Histone Methyltransferase | Epigenetics | C33H43N7O2 |
| SSR128129E | FGFR | Angiogenesis | C18H15N2NaO4 |
| Spebrutinib (CC-292, AVL-292) | BTK | Angiogenesis | C22H22FN5O3 |
| SKI II | S1P Receptor | GPCR & G Protein | C15H11ClN2OS |
| PF-543 | S1P Receptor | GPCR & G Protein | C27H31NO4S |
| CID755673 | Serine/threonin kinase, CaMK | Apoptosis | C12H11NO3 |
| 1-Azakenpaullone | GSK-3 | PI3K/Akt/mTOR | C15H10BrN3O |
| CNX-2006 | EGFR | Protein Tyrosine Kinase | C26H27F4N7O2 |
| Bisindolylmaleimide I (GF109203X) | PKC | TGF-beta/Smad | C25H24N4O2 |
| Thiamet G | Others | Others | C9H16N2O4S |
| Alvelestat (AZD9668) | Serine Protease | Proteases | C24H20F3N5O4S |
| RGFP966 | HDAC | Epigenetics | C21H19FN4O |
| UNC0642 | Histone Methyltransferase | Epigenetics | C29H44F2N6O2 |
| NVP-TNKS656 | PARP | DNA Damage | C27H34N4O5 |
| AGI-6780 | Dehydrogenase | Metabolism | $C_{21}H_{18}F_3N_3O_3S_2$ |
| Ro3280 | PLK | Cell Cycle | C27H35F2N7O3 |
| NMS-P937 (NMS1286937) | PLK | Cell Cycle | C24H27F3N8O3 |
| CNX-774 | BTK | Angiogenesis | C26H22FN7O3 |
| AZD1981 | GPR | Endocrinology & Hormones | C19H17ClN2O3S |
| SRPIN340 | Others | Others | C18H18F3N3O |
| 4μ8C | Others | Others | C11H8O4 |
| NMS-E973 | HSP (e g. HSP90) | Cytoskeletal Signaling | C22H22N4O7 |
| PFI-2 HCl | Histone Methyltransferase | Epigenetics | C23H25F4N3O3S |
| GSK2606414 | PERK | Apoptosis | C24H20F3N5O |
| IPI-3063 | PI3K | PI3K/Akt/mTOR | C25H25N7O2 |
| Atglistatin | Lipase | Metabolism | C17H21N3O |
| CGP 57380 | MNK | MAPK | C11H9FN6 |
| SB-3CT | MMP | Proteases | C15H14O3S2 |
| AR-A014418 | GSK-3 | PI3K/Akt/mTOR | C12H12N4O4S |
| NH125 | CaMK | Neuronal Signaling | C27H45IN2 |
| XEN445 | Lipase | Metabolism | C18H17F3N2O3R |
| LDC000067 | CDK | Cell Cycle | C18H18N4O3S |
| PI-1840 | Proteasome | Proteases | C22H26N4O3 |
| FTI 277 HCl | Transferase | Metabolism | $C_{22}H_{30}C_iN_3O_3S_2$ |
| Nexturastat A | HDAC | DNA Damage | C19H23N3O3 |
| ESI-09 | cAMP | GPCR & G Protein | C16H15ClN4O2 |
| HJC0350 | cAMP | GPCR & G Protein | C15H19NO2S |
| HO-3867 | STAT | JAK/STAT | C28H30F2N2O2 |
| JNK Inhibitor IX | JNK | MAPK | C20H16N2OS |
| Trelagliptin | DPP-4 | Proteases | C18H20FN5O2 |
| XMD8-92 | ERK | MAPK | C26H30N6O3 |
| A-366 | Histone Methyltransferase | Epigenetics | C19H27N3O2 |
| GSK-LSD1 2HCl | Histone Demethylase | Epigenetics | C14H22Cl2N2 |
| LLY-507 | Histone Methyltransferase | Epigenetics | C36H42N6O |
| Santacruzamate A (CAY10683) | HDAC | DNA Damage | C15H22N2O3 |
| CAY10603 | HDAC | DNA Damage | C22H30N4O6 |
| GSK1324726A (I-BET726) | Epigenetic Reader Domain | Epigenetics | C25H23ClN2O3 |
| SD-208 | TGF-beta/Smad | TGF-beta/Smad | C17H10ClFN6 |
| TH588 | MTH1 | DNA Damage | C13H12Cl2N4 |
| SB225002 | CXCR | GPCR & G Protein | C13H10BrN3O4 |
| CPI-360 | Histone Methyltransferase | Epigenetics | C25H31N3O4 |
| Picropodophyllin (PPP) | IGF-1R | Protein Tyrosine Kinase | C22H22O8 |

TABLE 2-continued

| Agent | Target | Pathway | Formula |
|---|---|---|---|
| Savolitinib (AZD6094, HMPL-504) | c-Met | Protein Tyrosine Kinase | C17H15N9 |
| SP2509 | Histone Demethylase | Epigenetics | C19H20ClN3O5S |
| VX-11e | ERK | MAPK | $C_{24}H_{20}C_{12}FN_5O_2$ |
| SBE 13 HCl | PLK | Cell Cycle | C24H28Cl2N2O4 |
| BLZ945 | CSF-1R | Protein Tyrosine Kinase | C20H22N4O3S |
| LFM-A13 | BTK | Angiogenesis | C11H8Br2N2O2 |
| EPZ015666(GSK3235025) | Histone Methyltransferase | Epigenetics | C20H25N5O3 |
| VER155008 | HSP (e.g. HSP90) | Cytoskeletal Signaling | C25H23Cl2N7O4 |
| BPTES | Glutaminase | Proteases | C24H24N6O2S3 |
| AZ6102 | PPAR | DNA Damage | C25H28N6O |
| Erlotinib | EGFR | Protein Tyrosine Kinase | C22H23N3O4 |
| ORY-1001 (RG-6016) 2HCl | Histone Demethylase | Epigenetics | C15H24Cl2N2 |
| EPZ020411 2HCl | Histone Methyltransferase | Epigenetics | C25H40Cl2N4O3 |
| I-BRD9 | Epigenetic Reader Domain | Epigenetics | $C_{22}H_{22}F_3N_3O_3S_2$ |
| SirReal2 | Sirtuin | Epigenetics | C22H20N4OS2 |
| BDA-366 | Bcl-2 | Apoptosis | C24H29N3O4 |
| NVP-CGM097 | Mdm2 | Apoptosis | C38H47ClN4O4 |
| CC-223 | mTOR | PI3K/Akt/mTOR | C21H27N5O3 |
| PFI-4 | Epigenetic Reader Domain | Epigenetics | C21H24N4O3 |
| BIO-acetoxime | GSK-3 | PI3K/Akt/mTOR | C18H12BrN3O3 |
| GSK2292767 | PI3K | PI3K/Akt/mTOR | C24H28N6O5S |
| SIS3 HCl | TGF-beta/Smad | TGF-beta/Smad | C28H28ClN3O3 |
| Larotrectinib (LOXO-101) sulfate | Trk receptor | Protein Tyrosine Kinase | C21H24F2N6O6S |
| PLX7904 | Raf | MAPK | C24H22F2N6O3S |
| VPS34-IN1 | PI3K | PI3K/Akt/mTOR | C21H24ClN7O |
| A-196 | Histone Methyltransferase | Epigenetics | C18H16Cl2N4 |
| LDC4297 (LDC044297) | CDK | Cell Cycle | C23H28N8O |
| SMI-4a | Pim | JAK/STAT | C11H6F3NO2S |
| Empagliflozin (BI 10773) | SGLT | GPCR & G Protein | C23H27ClO7 |
| TCS 359 | FLT3 | Angiogenesis | C18H20N2O4S |
| NSC 23766 | Rho | Cell Cycle | C24H38Cl3N7 |
| GDC-0349 | mTOR | PI3K/Akt/mTOR | C24H32N6O3 |
| Cobimetinib (GDC-0973, RG7420) | MEK | MAPK | C21H21F3IN3O2 |
| GW2580 | CSF-1R | Protein Tyrosine Kinase | C20H22N4O3 |
| BMS-345541 | IκB/IKK | NF-κB | C14H17N5 |
| Dynasore | Dynamin | Cytoskeletal Signaling | C18H14N2O4 |
| Venetoclax (ABT-199, GDC-0199) | Bcl-2 | Apoptosis | C45H50ClN7O7S |
| ICI-118551 Hydrochloride | Adrenergic Receptor | GPCR & G Protein | C17H28ClNO2 |
| AMG 337 | c-Met | Protein Tyrosine Kinase | C23H22FN7O3 |
| PF-CBP1 HCl | Epigenetic Reader Domain | Epigenetics | C29H37ClN4O3 |
| CPI-637 | Epigenetic Reader Domain | Epigenetics | C22H22N6O |
| BI-78D3 | JNK | MAPK | C13H9N5O5S2 |
| SB366791 | TRPV | Transmembrane Transporters | C16H14ClNO2 |
| Thiomyristoyl | Sirtuin | DNA Damage | C34H51N3O3S |
| CCT245737 | Chk | Cell Cycle | C16H16F3N7O |
| GSK6853 | Epigenetic Reader Domain | Epigenetics | C22H27N5O3 |
| SHP099 dihydrochloride | phosphatase | Others | C16H21Cl4N5 |
| Selonsertib (GS-4997) | ASK | Apoptosis | C24H24FN7O |
| KYA1797K | Wnt/bleta-catenin | Stem Cells & Wnt | C17H11KN2O6S2 |
| IPI-549 | PI3K | PI3K/Akt/mTOR | C30H24N8O2 |
| SGC2085 | Histone Methyltransferase | Epigenetics | C19H24N2O2 |
| Irbinitinib (ARRY-380, ONT-380) | HER2 | Protein Tyrosine Kinase | C26H24N8O2 |
| NMS-P118 | PARP | DNA Damage | C20H24F3N3O2 |
| BAY-876 | GLUT | Metabolism | C24H16F4N6O2 |

TABLE 2-continued

| Agent | Target | Pathway | Formula |
|---|---|---|---|
| VPS34 inhibitor 1 (Compound 19, PIK-III analogue) | PI3K | PI3K/Akt/mTOR | C21H25N7O |
| UK-371804 HCl | Serine Protease | Proteases | $C_{14}H_{17}Cl_2N_5O_4S$ |
| GSK'872 (GSK2399872A) | Serine/threonin kinase | Apoptosis | C19H17N3O2S2 |
| LLY-283 | Histone Methyltransferase | Epigenetics | C17H18N4O4 |
| GSK180736A (GSK180736) | ROCK | Cell Cycle | C19H16FN5O2 |
| PD-166866 (PD166866) | FGFR | Angiogenesis | C20H24N6O3 |
| BLU-554 (BLU554) | FGFR | Angiogenesis | C24H24Cl2N4O4 |
| LY3214996 | ERK | MAPK | C22H27N7O2S |
| PF-06651600 | JAK | JAK/STAT | C15H19N5O |
| FM-381 | JAK | JAK/STAT | C24H24N6O2 |
| AZ31 | ATM/ATR | DNA Damage | C24H28N4O3 |
| Tofogliflozin(CSG 452) | SGLT | GPCR & G Protein | C22H28O7 |
| Omarigliptin (MK-3102) | DPP-4 | Proteases | C17H20F2N4O3S |
| Serabelisib (INK-1117, MLN-1117, TAK-117) | PI3K | PI3K/Akt/mTOR | C19H17N5O3 |
| FX1 | Bcl-6 | Apoptosis | C14H9ClN2O4S2 |
| Pamiparib (BGB-290) | PARP | DNA Damage | C16H15FN4O |
| NCT-503 | Dehydrogenase | Metabolism | C20H23F3N4S |
| Chk2 Inhibitor II (BML-277) | Chk | Cell Cycle | C20H14ClN3O2 |
| Ipragliflozin (ASP1941) | SGLT | GPCR & G Protein | C21H21FO5S |
| Nec-1s (7-Cl—O—Nec1) | TNF-alpha | Apoptosis | C13H12ClN3O2 |
| GSK'963 | NF-κB, TNF-alpha | NF-κB | C14H18N2O |
| GNF-6231 | Wnt/beta-catenin | Stem Cells & Wnt | C24H25FN6O2 |
| Skp2 inhibitor C1 (SKPin C1) | CDK | Cell Cycle | $C_{18}H_{13}BrN_2O_4S_2$ |
| PF-06840003 | IDO | Metabolism | C12H9FN2O2 |
| GI254023X | Immunology & Inflammation related | Immunology & Inflammation | C21H33N3O4 |
| BAY 1895344 (BAY-1895344) | ATM/ATR | DNA Damage | C20H22ClN7O |
| Tenalisib (RP6530) | PI3K | PI3K/Akt/mTOR | C23H18FN5O2 |
| H3B-6527 | FGFR | Protein Tyrosine Kinase | C29H34Cl2N8O4 |
| Cu-CPT22 | TLR | Immunology & Inflammation | C19H22O7 |
| AZD1390 | ATM/ATR | PI3K/Akt/mTOR | C27H32FN5O2 |
| Atuveciclib (BAY-1143572) | CDK | Cell Cycle | C18H18FN5O2S |
| LXH254 | Raf | MAPK | C25H25F3N4O2 |
| WM-1119 | Histone Acetyltransf | Epigenetics | C18H13F2N3O3S |
| Evobrutinib | BTK | Protein Tyrosine Kinase | C25H27N5O2 |
| LIT-927 | CXCR | Immunology & Inflammation | C17H13ClN2O3 |
| 4-Hydroxyquinazoline | Others | antiplatelet | C8H6N2O |
| Valbenazine tosylate | VMAT2 | Others | C38H54N2O10S2 |
| SAR125844 | c-Met | Protein Tyrosine Kinase | C25H23FN8O2S2 |
| dBET1 | Epigenetic Reader Do | Epigenetics | C38H37ClN8O7S |
| GSK'547 | TNF-alpha | Apoptosis | C20H18F2N6O |
| Palbociclib (PD-0332991) HCl | CDK | Cell Cycle | C24H30ClN7O2 |
| Palbociclib (PD0332991) Isethionate | CDK | Cell Cycle | C26H35N7O6S |
| LDN-193189 2HCl | TGF-beta/Smad | TGF-beta/Smad | C25H23ClN6 |
| MCC950(CP-456773) | Immunology & Inflammation related | Immunology & Inflammation | C20H23N2NaO5S |
| bpV (HOpic) | PTEN | Others | C6H4K2NO8V |
| Erlotinib HCl (OSI-744) | Autophagy, EGFR | Protein Tyrosine Kinase | C22H24ClN3O4 |
| SGX-523 | c-Met | Protein Tyrosine Kinase | C18H13N7S |
| (−)-Huperzine A (HupA) | GluR, AChR | Neuronal Signaling | C15H18N2O |
| GSK256066 | PDE | Metabolism | C27H26N4O5S |
| CCT137690 | Aurora Kinase | Cell Cycle | C26H31BrN8O |
| Capmatinib (INCB28060) | c-Met | Protein Tyrosine Kinase | C23H17FN6O |
| EPZ005687 | Histone Methyltransferase | Epigenetics | C32H37N5O3 |
| GSK126 | Histone Methyltransferase | Epigenetics | C31H38N6O2 |

TABLE 2-continued

| Agent | Target | Pathway | Formula |
|---|---|---|---|
| Tazemetostat (EPZ-6438) | Histone Methyltransferase | Epigenetics | C34H44N4O4 |
| ISRIB (trans-isomer) | PERK | Apoptosis | C22H24Cl2N2O4 |
| A-1210477 | Bcl-2 | Apoptosis | C46H55N7O7S |
| Otenabant (CP-945598) HCl | Cannabinoid Receptor | GPCR & G Protein | C25H26Cl3N7O |
| FGF401 | FGFR | Protein Tyrosine Kinase | $C_{25}H_{30}N_8O_4$ |
| Lazertinib (YH25448, GNS-1480) | EGFR | Protein Tyrosine Kinase | $C_{30}H_{34}N_8O_3$ |

In some embodiments, different concentrations of the therapeutic agent are applied to the TOs in each partition or a group of replicate partitions (e.g., 2, 3, 4, 5, 6, 7, 8, 9 or 10 or more partitions). In certain embodiments, different therapeutic agents or combination of therapeutic agents are applied to the TOs in each partition or a group of replicate partitions. In certain embodiments, tumor organoids derived from different subjects are assessed.

In some embodiments, the tumor organoids of the method are divided in plurality of tumor organoid subsets, wherein the plurality of subsets includes at least 10, 20, 30, 40, 50 60, 70, 80, 90, 100, 200, 300, 400, 500, 600, 700, 800, 900, or $1\times10^3$, $1\times10^4$, $1\times10^5$, or $1\times10^6$ subsets of tumor organoids. In some embodiments, each of the subsets include at least 10, 20, 30, 40, 50 60, 70, 80, 90, 100, 200, 300, 400, 500, 600, 700, 800, 900, or $1\times10^3$, $1\times10^4$ tumor organoids.

In some embodiments, tumor organoid profiles are acquired from at least about 60, 70, 80, 90, 100, 200, 300, 400, 500, 600, 700, 800, 900, or $1\times10^3$, $1\times10^4$, $1\times10^5$, or $1\times10^6$ individual tumor organoids per condition (e.g., a particular therapeutic dosage). In exemplary embodiments, wherein the tumor organoids of the method are divided in plurality of tumor organoid subsets that each receive a different therapeutic agent or dosage of a therapeutic agent, a tumor organoid profile is acquired for at least about 2, 3, 4, 5, 10, 15, 20, 25, 30, 35, 40, 45, 50, 60, 70, 80, 90, 100, 200, 300, 400, 500, 600, 700, 800, 900, or $1\times10^3$, $1\times10^4$, $1\times10^5$, or $1\times10^6$ individual tumor organoids in each of the subsets. In some embodiments, tumor organoid profiles are obtained for about 5-10, 10-20, 20-30, 30-40, 40-50, 50-60, 60-70, 70-80, 80-90, 90-100, 100-200, 200-300, 300-400, 400-500, 500-600, 600-700, 700-800 or 800-900, 10-50, 50-100, 100-500, 500-1,000, 1,000-1,500, or 1,500-2,000 tumor organoids for each subset. In exemplary embodiments, the tumor organoid profile includes a cell viability value for at least 10, 15, 20, 25, 30, 35, 40, 45, 50, 60, 70, 75, 80, 85, 90, 95, 99 or 100% of the tumor organoids for each subset.

The high number of measurements recorded per condition (e.g., dose) allows the use of more complex statistical methods that would otherwise be unable to be used with a low-throughput dose response assay. In some embodiments, the tumor organoid profiles obtained are adjusted for one or more confounding technical effect. Use of a linear model allows for inclusion of covariates to adjust for potential confounding technical effects including initial TO viability, differences in growth rates between TOs derived from different patients, and different cancer types, and leverages all of the TO data to gain better statistical power. In some embodiments, a linear model is applied to determine differences between patients, or between drugs, at equivalent therapeutic concentrations (or doses).

In particular embodiments, a tumor organoid profile includes a cell viability value, wherein the cell viability value is the percentage of viable cells in a particular tumor organoid. In certain embodiments, the cell viability value is determined by visual detection techniques including, for example, methods that use fluorescent light microscopy and/or compound light microscopy (i.e., brightfield microscopy) techniques. As disclosed herein, fluorescent light microscopy techniques include those that use fluorescent dyes to visualize dead/apoptotic cells and/or total cells. In some embodiments, wherein compound light microscopy techniques are used, artificial fluorescent images are derived from brightfield images using a trained model and cell viability values are determined based on the brightfield images, as disclosed herein.

In certain embodiments, the tumor organoid profiles are acquired at different time points. In some embodiments, the tumor organoid profiles acquired are used to generate a dose-response curve (see, e.g., Example 2 and FIG. 2, below). In particular embodiments, a particular therapeutic dosage is assigned to a patient based on the dose-response curve. Also provided herein are methods for treating a patient having a cancer with a therapeutic agent based on a dosage derived using the subject method provided herein.

Concurrently with or following the application of the therapeutic agent(s) to the TOs in the partitions, the TOs are contacted with one or more detection agents to assess for changes in morphological features or cell viability of individual cells in the TOs. In exemplary embodiments, the detection agents include fluorescent markers that can be visualized by fluorescent confocal imaging analysis. In particular embodiments, the markers include two or more markers for dead/apoptotic cells. Markers and assays useful for assessing dead apoptotic cells include, but are not limited to, IncuCyte® Caspase-3/7 Green Apoptosis Assay Reagent (Essen Biosciences cat #4440), and TO-PRO™-3 Iodide (642/661) (Fisher Scientific cat #T3605) and Annexin V assay (Abcam, ab14085).

In some embodiments, an additional detection agent is used to identify total cells in the tumor organoid sample. In some examples, all cells per organoid are measured by Hoechst 33342 staining, apoptotic cells per organoid are measured by Caspase 3/7 staining and dead/dying cells may are by TO-PRO-3 staining. Utilizing fluorescent markers for all cells and two markers for dead/apoptotic cells permits analysis of TOs at the single cell level and also permits generation of an absolute number of live and dead cells per organoid. This TO by TO analysis may provide more information than simply calculating a relative value of viable cells from an entire well. Maintaining TO heterogeneity allows for determination of whether all cells are dying at a constant rate or if there is a mix of susceptible and resistant cells to a given treatment based on the distribution of viable cells per organoid. The aspects, such as the number of partitions (e.g., wells), types of plates, and types of cultures disclosed here, are exemplary in nature. Other aspects known in the art may be used instead or in combination with those aspects disclosed herein.

Following contact with the detection agents, the TOs are imaged and a tumor organoid profile is obtained from each image. In particular embodiments, the tumor organoid profile includes the number of TOs per image, the total number of cells (live and dead) present in each TO, the number of dead and dying cells present, and/or a cell viability value indicating the percentage of viable cells/tumor organoid. In some embodiments, the TOs are imaged on an inverted confocal microscope using the light microscopy and multiple fluorescent channels with varying wave-length excitation sources (e.g. laser or LED) and emission filters. In exemplary embodiments, an analysis module in a computer system is used to derive the tumor organoid profile from the images.

In some embodiments, a brightfield image of the TO sample is obtained for each sample in addition to the cell death/viability data. In particular embodiments, tumor organoid profiles that include cell viability data (e.g., the percentage of viable cells in TO) and corresponding brightfield images for each TO sample at particular conditions (e.g., drug dosage conditions) are inputted into a classified trainer. In exemplary embodiments, an artificial fluorescent image is developed from the brightfield image. In particular embodiments, the trainer is used to predict morphological changes (e.g., cell death or apoptosis) in a tumor organoid sample in response to a particular condition (e.g., dose of a therapeutic agent) based on a brightfield image of the sample (see Example 2 and FIG. 3).

In another aspect, provided herein are computer systems for carrying out the subject methods for assessing the effects of an agent (e.g., a therapeutic agent) on tumor organoids (TOs). In some embodiments, the computer system includes at least one processor and a memory storing at least one program for execution by the at least one processor, the at least one program includes instructions for carrying out one or more steps of the subject methods.

In some embodiments, the disclosure provides methods and systems for evaluating an effect of a cancer therapeutic agent. In some embodiments, the method includes providing a plurality of tumor organoids cultured in a tumor organoid culture medium, where the plurality of tumor organoids is divided into a plurality of tumor organoid subsets. The method then includes contacting each subset in the plurality of tumor organoid subsets with a cancer therapeutic agent. The method also includes contacting each subset in the plurality of tumor organoid subsets with one or more cell death detection agents and a total cell detection agent. The method then includes obtaining a tumor organoid profile (e.g., cell viability value) for each subset in the plurality of subset. In exemplary embodiments, the tumor organoid profile is obtained for at least 10, 15, 20, 25, 30, 35, 40, 45, 50, 60, 70, 75, 80, 85, 90, 95, 100, 150, 200, 500 or, 1,000 individual tumor organoids for each subset. In some embodiments, the tumor organoid profile includes a cell viability value for every tumor organoid in the subset. In exemplary embodiments, the tumor organoid profile includes a cell viability value for at least 10, 15, 20, 25, 30, 35, 40, 45, 50, 60, 70, 75, 80, 85, 90, 95, 100, 150, 200, 500 or, 1,000 individual tumor organoids for each subset. In exemplary embodiments, the tumor organoid profile includes a cell viability value for at least 10, 15, 20, 25, 30, 35, 40, 45, 50, 60, 70, 75, 80, 85, 90, 95, 99 or 100% of the tumor organoids for each subset. The method then includes assessing the effect of the cancer therapeutic agent based on the tumor organoid profiles.

In some embodiments, the disclosure provides methods and systems for assigning a treatment dosage of a cancer therapeutic agent for a subject in need thereof. In some embodiments, the method includes providing a plurality of tumor organoids cultured in a tumor organoid culture medium, where the tumor organoids are derived from a subject, and where the plurality of tumor organoids is divided into a plurality of tumor organoid subsets. The method then includes contacting each subset in the plurality of tumor organoid subsets with a different dosage of a cancer therapeutic agent. The method also includes contacting each subset in the plurality of tumor organoid subsets with one or more cell death detection agents and a total cell detection agent. The method then includes obtaining a tumor organoid profile for each subset in the plurality of subset, where the tumor organoid profile includes a cell viability value for every tumor organoid in the subset. The method then includes determining a therapeutic agent dosage curve from the tumor organoid profiles. The method then includes assigning a treatment dosage of the cancer therapeutic agent to the subject based on the therapeutic agent dosage curve.

In some embodiments, a tumor's resistance to a particular therapeutic agent at a particular dosage is determined based on the proportion of tumor organoids derived from the tumor that have a 1% or greater viability value when exposed to the particular therapeutic agent at the dosage. In some embodiments, the tumor is determined to be likely resistant to the therapeutic agent composition at a particular concentration if 50%, 55%, 60%, 65%, 70%, 75%, 80%, 85%, 90%, or 99% or more of the tumor organoids for a subset contacted with the therapeutic agent at the particular concentration exhibit 50%, 55%, 60%, 65%, 70%, 75%, 80%, 85%, 90%, or 99% or more cell viability. In some embodiments, the tumor is determined to be likely resistant to the therapeutic agent composition at a particular concentration if 50% or more of the tumor organoids for a subset contacted with the therapeutic agent at the particular concentration exhibit 50% or more cell viability. In some embodiments, the tumor determined to be likely to be resistant to the therapeutic agent composition at a particular concentration if 1% more of the tumor organoids for a subset contacted with the therapeutic agent at the particular concentration exhibit 100% cell viability.

In some embodiments, wherein a patient's tumor is designated as likely to be resistant to a particular therapeutic agent or agents, a monitoring frequency that is more frequent than the standard monitoring frequency is recommended to the patient. wherein a patient's tumor is not designated as likely to be resistant to a particular therapeutic agent or agents, a standard monitoring frequency is recommended to the subject.

In exemplary embodiments, a plurality of tumor organoids from a tumor organoid subset that is designated as likely to be resistant to a therapeutic agent is isolated and analyzed for one or more genetic variants associated with resistance to the therapeutic agent, e.g., a genetic variant that is present in at least 50%, 55%, 60%, 65%, 70%, 75%, 80%, 85%, 90%, or 99% or more of the resistant tumor organoid. In exemplary embodiments, a plurality of tumor organoids from a tumor organoid subset that is designated as likely to be susceptible to a therapeutic agent (e.g., 0% cell viability) is isolated and analyzed for one or more genetic variants associated with susceptibility to the therapeutic agent e.g., a genetic variant that is present in at least 50%, 55%, 60%, 65%, 70%, 75%, 80%, 85%, 90%, or 99% or more of the susceptible tumor organoids.

O. Therapeutic Agents

Any suitable therapeutic agent can be used using the subject methods described herein. In some embodiments the therapeutic agent is a single therapeutic agent. In other embodiments, the therapeutic agent includes 2, 3, 4, 5, 6, 7, 8, 9, or 10 therapeutic agents.

Suitable therapeutic agents include, but are not limited to, molecular inhibitors, antibodies, recombinant nucleic acids (e.g., antisense oligonucleotides) and engineered immune cells (e.g., CAR T-cells and NK cells). Exemplary therapeutic agents include, but are not limited to, Paclitaxel, Gemcitabine, Cisplatin, Carboplatin, Oxaliplatin, Capecitabine, SN-38 (CPT-11), 5-FU, MTX (methotrexate), Docetaxel, Bortezomib, Everolimus, Ulixertinib, Dasatinib, Vinblastine, Nelarabine, Epirubicin, Afatinib, Lapatinib, Cytarabine, Cladribine, Doxorubicin, Azacitidine, and Staurosporine. Other examples include classes of drugs including but not limited to: taxanes, platinating agents, vinca alkaloids, alkylating agents, and anthracyclines. One or more molecular inhibitors may be applied to the TOs in the well plates. Molecular inhibitors may be selected by name, target, pathway, formula, or other known characterizations.

In some embodiments, the one or more therapeutic agents include one or more of the following: an inhibitor of SUV4-20 (SUV420H1 or SUV420H2), a tyrosine kinase inhibitor, a retinoid-like compound, a wee1 kinase inhibitor, an anaplastic lymphoma kinase inhibitor, an aurora A kinase inhibitor, an aurora B kinase inhibitor, a reversible inhibitor of eukaryotic nuclear DNA replication, an antimetabolite antineoplastic agent, an ataxia telangiectasia and Rad3-related protein (ATR) kinase inhibitor, an ATM kinase inhibitor, a checkpoint kinase inhibitor, a GSK-3a/b inhibitor, a proteasome inhibitor, an AXL or RET inhibitor, a c-Met or VEGFR2 inhibitor, an alkylating antineoplastic agent, a DNA-PK and/or mTOR inhibitor, an inhibitor of mammalian target of rapamycin (mTOR), a checkpoint kinase 1 (CHK1) inhibitor, a retinoic acid receptor β (RARβ) or RARγ antagonist, a retinoic acid receptor (RAR) γ-selective agonist, RARγ-selective retinoid, inducer of apoptosis, CDK2 a RAR agonist, a chemotherapy, a tyrosine kinase inhibitor antineoplastic agent, an antimicrotubular antineoplastic agent, a topoisomerase inhibitor antineoplastic agent, a sodium-glucose cotransporter-2/SGLT2 inhibitor, an inhibitor of the tropomyosin receptor kinases A, B and C, C-ros oncogene 1 and anaplastic lymphoma kinase, a topoisomerase inhibitor antineoplastic agent, an inhibitor of mTOR, an inhibitor of phosphatidylinositol 3-kinase (PI3K), an inhibitor of RIP3K, an analog of cyclophosphamide, an SGLT2 inhibitor, aWnt/β-catenin inhibitor, a tyrosine kinase inhibitor that interrupts the HER2/neu and epidermal growth factor receptor/EGFR pathways, an inhibitor of tropomyosin kinase receptors TrkA, TrkB, and TrkC, a cyclin-dependent kinase (CDK) inhibitor, a CDK7 inhibitor, an inhibitor of VEGFR1, VEGFR2 and VEGFR3 kinases, a DNA-PK/PI3K/mTOR inhibitor, a poly ADP ribose polymerase (PARP) inhibitor, an inhibitor of Rac GTPase, a taxane, a Bromodomain And PHD Finger Containing 1 (BRPF1) bromodomain inhibitor, a mitogen-activated protein kinase-activated protein kinase 2 (MAPK2) inhibitor, a RAF inhibitor, a histone deacetylase (HDAC) inhibitor, a CDK1 inhibitor, aTGF-beta/Smad inhibitor, a Pim kinase inhibitor, a DNA topoisomerase I inhibitor, active metabolite of CPT-11/Irinotecan, an atypical retinoid, apoptosis inducer, a multi-kinase inhibitor, a fms-like tyrosine kinase-3 (FLT3) inhibitor, a MEK inhibitor, an inhibitor of extracellular signal-regulated kinase (ERK) 1 and/or 2, or a DNA-dependent protein kinase/DNA-PK inhibitor.

In some embodiments, the one or more therapeutic agents include one or more for the following: A-196 (inhibitor of SUV4-20 or SUV420H1 and SUV420H2), Afatinib (tyrosine kinase inhibitor), Adapalene (retinoid-like compound), Adavosertib (MK-1775, wee1 kinase inhibitor), Alectinib (CH5424802, anaplastic lymphoma kinase inhibitor), Alisertib (MLN8237, aurora A kinase inhibitor), Aphidicolin (reversible inhibitor of eukaryotic nuclear DNA replication, antimitotic), Azacitidine (an antimetabolite antineoplastic agent, a chemotherapy), AZ20 (ataxia telangiectasia and Rad3-related protein/ATR kinase inhibitor), AZ31 (ataxia-telangiectasia mutated/ATM kinase inhibitor), AZD6738 (ataxia telangiectasia and Rad3-related protein/ATR kinase inhibitor), AZD7762 (checkpoint kinase inhibitor), Barasertib (AZD1152-HQPA, aurora B kinase inhibitor), BAY-1895344 (ATR and ATM kinase inhibitor), Berzosertib (ATR and ATM kinase inhibitor), BIO-acetoxime (GSK-3a/b inhibitor), Bortezomib (proteasome inhibitor), Cabozantinib (kinase inhibitor, inhibitor of AXL, RET, and tyrosine kinases c-Met and VEGFR2), Capecitabine (an antimetabolite antineoplastic agent, a chemotherapy), Carboplatin (an alkylating antineoplastic agent, a chemotherapy), CC-115 (DNA-PK and mTOR inhibitor), CC-223 (inhibitor of mammalian target of rapamycin/mTOR), CCT-245737 (checkpoint kinase 1/CHK1 inhibitor), CD-2665 (retinoic acid receptor β (RARβ)/RARγ antagonist), CD-437 (retinoic acid receptor (RAR)γ-selective agonist, γ-selective retinoid; inducer of apoptosis), CDK2 inhibitor II, CH-55 (RAR agonist), Cisplatin (an alkylating antineoplastic agent, a chemotherapy), Cladribine (an antimetabolite antineoplastic agent, a chemotherapy), Cytarabine (an antimetabolite antineoplastic agent, a chemotherapy), Dasatinib (a tyrosine kinase inhibitor antineoplastic agent, a chemotherapy), Docetaxel (an antimicrotubular antineoplastic agent, a chemotherapy), Doxorubicin (Adriamycin, a topoisomerase inhibitor antineoplastic agent, a chemotherapy), Empagliflozin (BI 10773, a sodium-glucose cotransporter-2/SGLT2 inhibitor), Entrectinib (RXDX-101, tyrosine kinase inhibitor, inhibitor of the tropomyosin receptor kinases A, B and C, C-ros oncogene 1 and anaplastic lymphoma kinase), Epirubicin (a topoisomerase inhibitor antineoplastic agent, a chemotherapy), Etoposide (a topoisomerase inhibitor antineoplastic agent, a chemotherapy), Everolimus (inhibitor of mTOR), Fluorouracil/5-FU (an antimetabolite antineoplastic agent, a chemotherapy), GDC-0349 (inhibitor of mTOR), GDC-0575 (ARRY-575, CHK1 inhibitor), Gemcitabine (an antimetabolite antineoplastic agent, a chemotherapy), GSK2292767 (inhibitor of phosphatidylinositol 3-kinase/PI3K), GSK-872 (GSK2399872A, kinase inhibitor, inhibitor of RIP3K), Hesperadin (aurora kinase inhibitor), Hydroxyurea (an antimetabolite antineoplastic agent, a chemotherapy), Ifosfamide (an analog of cyclophosphamide, an alkylating antineoplastic agent, a chemotherapy), Ipragliflozin (ASP1941, an SGLT2 inhibitor), KYA1797K (Wnt/β-catenin inhibitor), Lapatinib (tyrosine kinase inhibitor that interrupts the HER2/neu and epidermal growth factor receptor/EGFR pathways, an antineoplastic agent, a chemotherapy), Larotrectinib (inhibitor of tropomyosin kinase receptors TrkA, TrkB, and TrkC), LDC 4297 (Cyclin-dependent kinase/CDK inhibitor, CDK7 inhibitor), Lenvatinib (multiple kinase inhibitor, inhibitor of VEGFR1, VEGFR2 and VEGFR3 kinases), LY3023414

(DNA-PK/PI3K/mTOR Inhibitor), Methotrexate (an antimetabolite antineoplastic agent, a chemotherapy), Nelarabine (an antimetabolite antineoplastic agent, a chemotherapy), Niraparib (MK-4827, a poly ADP ribose polymerase/PARP inhibitor), NSC 23766 (inhibitor of Rac GTPase), Olaparib (PARP inhibitor), Oxaliplatin (an alkylating antineoplastic agent, a chemotherapy), Paclitaxel (a taxane, an antimicrotubular antineoplastic agent, a chemotherapy), Pamiparib (BGB-290, PARP inhibitor), PFI-4 (Bromodomain And PHD Finger Containing 1/BRPF1 bromodomain inhibitor), PHA-767491 HCl (Mitogen-activated protein kinase-activated protein kinase 2/MK2 and CDK inhibitor), PLX7904 (RAF inhibitor), Pracinostat (histone deacetylase/HDAC inhibitor), Pralatrexate (an antimetabolite antineoplastic agent, a chemotherapy), Prexasertib HCl (checkpoint kinase 1/CHK1 inhibitor), RO-3306 (CDK1 inhibitor), Rucaparib (PARP inhibitor), Selpercatinib (LOXO-292, ARRY-192, a tyrosine kinase inhibitor), SIS3 HCl (TGF-beta/Smad inhibitor), SMI-4a (Pim kinase inhibitor), SN-38 (inhibitor of DNA topoisomerase I, active metabolite of CPT-11/Irinotecan), ST-1926 (Adarotene, atypical retinoid, apoptosis inducer), Staurosporine (multi-kinase inhibitor used as a positive control), Talazoparib (BMN-673, PARP inhibitor), TCS 359 (fms-like tyrosine kinase-3/FLT3 inhibitor), Tenalisib (RP6530, a PI3K δ/γ inhibitor), Tozasertib (VX-680, MK-0457, an Aurora Kinase inhibitor), Trametinib (GSK1120212, a MEK inhibitor), Ulixertinib (inhibitor of extracellular signal-regulated kinase/ERK 1 and 2, with potential antineoplastic activity), Veliparib (ABT-888, PARP inhibitor), Vinblastine (an antimicrotubular antineoplastic agent, a chemotherapy), or VX-984 (DNA-dependent protein kinase/DNA-PK inhibitor).

In some embodiments, the one or more therapeutic agents include one or the follow therapeutic agents or combination therapeutic: afatinib plus MET inhibitor (for example, tivantinib, cabozantinib, crizotinib, etc.), AZ31 plus SN-38, bevacizumab (anti-VEGF monoclonal IgG1 antibody), cetuximab (epidermal growth factor receptor/EGFR inhibitor), crizotinib (a tyrosine kinase inhibitor antineoplastic agent), cyclophosphamide (an alkylating antineoplastic agent), erlotinib (epidermal growth factor receptor inhibitor antineoplastic agent), FOLFIRI, bevacizumab plus FOLFIRI, FOLFOX, gefitinib (EGFR inhibitor), gemcitabine plus docetaxel, pemtrexed (an antimetabolite antineoplastic agent), ramucirumab (Vascular Endothelial Growth Factor Receptor 2/VEGFR2 Inhibitor), or topotecan (a topoisomerase inhibitor).

P. Artificial Fluorescent Imaging

In some embodiments, the methods disclosed herein use artificial fluorescent images derived from brightfield images using a trained model to assess the effects of a particular therapeutic agent or agents on a tumor organoid or tumor organoid population.

Typically, drug response is measured via cell viability assays using live/dead fluorescent stains, which have multiple drawbacks. For example, fluorescence microscopy can generate bottlenecks in the high-throughput screening process, stains can be costly for large scale screening, relatively long image acquisition times reduce throughput, and stain cytotoxicity often limits temporal profiling. In contrast, brightfield and transmitted light microscopy do not require staining, allow for shorter acquisition times, and enable temporal profiling by avoiding cytotoxicity. However, visualizing and quantifying live/dead cells from brightfield images alone is not easily accessible and is a significant obstacle towards more cost-efficient high-throughput screening of tumor organoids. Certain systems and methods described herein provide artificial fluorescent images that can be generated using only brightfield images.

Analysis of drug response data by target may identify important pathways/mutations. For drugs that cause cell death in organoids, the targets of those drugs may be important. Thus, it is desirable to discover and/or develop additional drugs that modulate these targets. The cellular pathways and/or mutations that are important may be specific to the cancer type of the organoid. For example, if CDK inhibitors specifically kill colorectal cancer (CRC) tumor organoid cells, CDK may be especially important in CRC.

Figure 33:
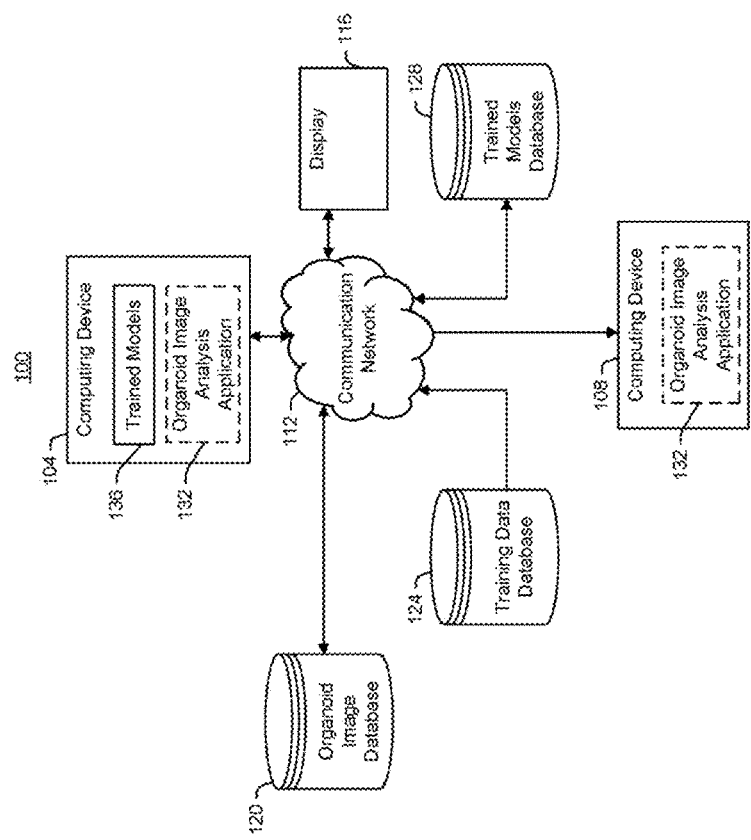
FIG. 33 shows an example of a system for automatically analyzing tumor organoid images.

FIG. 33 shows an example of a system 100 for automatically analyzing tumor organoid images. In some embodiments, the system 100 can include a computing device 104, a secondary computing device 108, and/or a display 116. In some embodiments, the system 100 can include an organoid image database 120, a training data database 124, and/or a trained models database 128. In some embodiments, the trained models database 128 can include one or more trained machine learning models such as artificial neural networks. In some embodiments, the computing device 104 can be in communication with the secondary computing device 108, the display 116, the organoid image database 120, the training data database 124, and/or the trained models database 128 over a communication network 112. As shown in FIG. 33, the computing device 104 can receive tumor organoid images, such as brightfield images of tumor organoids, and generate artificial fluorescent stain images of the tumor organoids. In some embodiments, the computing device 104 can execute at least a portion of an organoid image analysis application 132 to automatically generate the artificial fluorescent stain images.

The organoid image analysis application 132 can be included in the secondary computing device 108 that can be included in the system 100 and/or on the computing device 104. The computing device 104 can be in communication with the secondary computing device 108. The computing device 104 and/or the secondary computing device 108 may also be in communication with a display 116 that can be included in the system 100 over the communication network 112.

The communication network 112 can facilitate communication between the computing device 104 and the secondary computing device 108. In some embodiments, communication network 112 can be any suitable communication network or combination of communication networks. For example, communication network 112 can include a Wi-Fi network (which can include one or more wireless routers, one or more switches, etc.), a peer-to-peer network (e.g., a Bluetooth network), a cellular network (e.g., a 3G network, a 4G network, a 5G network, etc., complying with any suitable standard, such as CDMA, GSM, LTE, LTE Advanced, WiMAX, etc.), a wired network, etc. In some embodiments, communication network 112 can be a local area network, a wide area network, a public network (e.g., the Internet), a private or semi-private network (e.g., a corporate or university intranet), any other suitable type of network, or any suitable combination of networks. Communications links shown in FIG. 33 can each be any suitable communications link or combination of communications links, such as wired links, fiber optic links, Wi-Fi links, Bluetooth links, cellular links, etc.

The organoid image database 120 can include a number of raw tumor organoid images, such as brightfield images. In some embodiments, the brightfield images can be generated using a brightfield microscopy imaging modality. Exemplary brightfield images are described below. In some embodiments, the organoid image database 120 can include artificial fluorescent stain images generated by the organoid image analysis application 132.

The training data database 124 can include a number of images for training a model to generate artificial fluorescent stain images. In some embodiments, the training data image database 124 can include raw brightfield images and corresponding three channel fluorescent stain images. The trained models database 128 can include a number of trained models that can receive raw brightfield images of tumor organoids and output artificial fluorescent stain images. In some embodiments, trained models 136 can be stored in the computing device 104.

For an example of a system 100 for automatically analyzing tumor organoid images, see PCT/US20/63619, titled "Systems and Methods for High Throughput Drug Screening", filed on Dec. 7, 2020, and incorporated herein by reference in its entirety and for all purposes.

Figure 34:
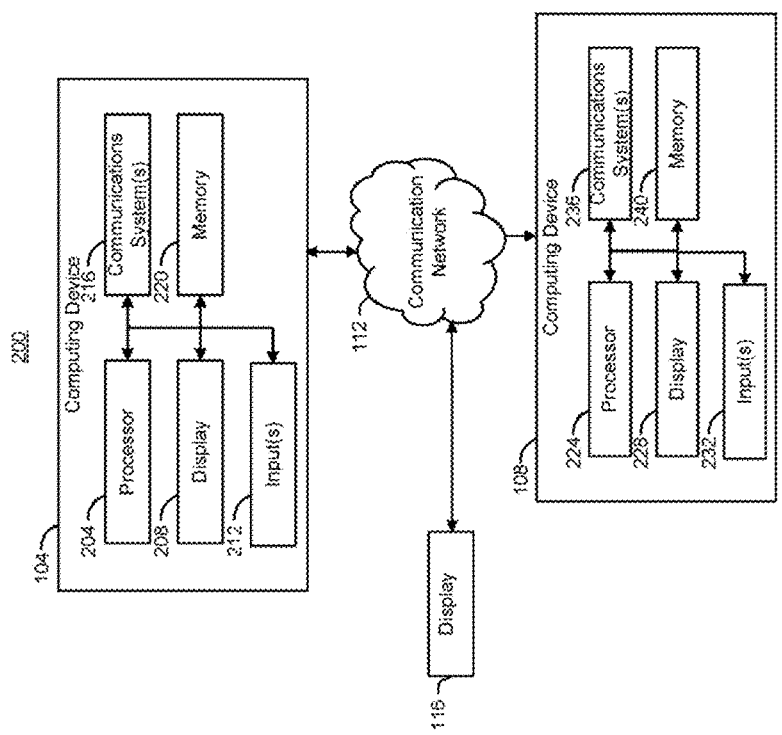
FIG. 34 shows an example of hardware that can be used in some embodiments of the system.

FIG. 34 shows an example 200 of hardware that can be used in some embodiments of the system 100. The computing device 104 can include a processor 204, a display 208, an input 212, a communication system 216, and a memory 220. The processor 204 can be any suitable hardware processor or combination of processors, such as a central processing unit ("CPU"), a graphics processing unit ("GPU"), etc., which can execute a program, which can include the processes described below.

In some embodiments, the display 208 can present a graphical user interface. In some embodiments, the display 208 can be implemented using any suitable display devices, such as a computer monitor, a touchscreen, a television, etc. In some embodiments, the inputs 212 of the computing device 104 can include indicators, sensors, actuatable buttons, a keyboard, a mouse, a graphical user interface, a touch-screen display, etc.

In some embodiments, the communication system 216 can include any suitable hardware, firmware, and/or software for communicating with the other systems, over any suitable communication networks. For example, the communication system 216 can include one or more transceivers, one or more communication chips and/or chip sets, etc. In a more particular example, communication system 216 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 216 allows the computing device 104 to communicate with the secondary computing device 108.

In some embodiments, the memory 220 can include any suitable storage device or devices that can be used to store instructions, values, etc., that can be used, for example, by the processor 204 to present content using display 208, to communicate with the secondary computing device 108 via communications system(s) 216, etc. The memory 220 can include any suitable volatile memory, non-volatile memory, storage, or any suitable combination thereof. For example, the memory 220 can include RAM, ROM, EEPROM, one or more flash drives, one or more hard disks, one or more solid state drives, one or more optical drives, etc. In some embodiments, the memory 220 can have encoded thereon a computer program for controlling operation of computing device 104 (or secondary computing device 108). In such embodiments, the processor 204 can execute at least a portion of the computer program to present content (e.g., user interfaces, images, graphics, tables, reports, etc.), receive content from the secondary computing device 108, transmit information to the secondary computing device 108, etc.

The secondary computing device 108 can include a processor 224, a display 228, an input 232, a communication system 236, and a memory 240. The processor 224 can be any suitable hardware processor or combination of processors, such as a central processing unit ("CPU"), a graphics processing unit ("GPU"), etc., which can execute a program, which can include the processes described below.

In some embodiments, the display 228 can present a graphical user interface. In some embodiments, the display 228 can be implemented using any suitable display devices, such as a computer monitor, a touchscreen, a television, etc. In some embodiments, the inputs 232 of the secondary computing device 108 can include indicators, sensors, actuatable buttons, a keyboard, a mouse, a graphical user interface, a touch-screen display, etc.

In some embodiments, the communication system 236 can include any suitable hardware, firmware, and/or software for communicating with the other systems, over any suitable communication networks. For example, the communication system 236 can include one or more transceivers, one or more communication chips and/or chip sets, etc. In a more particular example, communication system 236 can include hardware, firmware, and/or software that can be used to establish a coaxial connection, a fiber optic connection, an Ethernet connection, a USB connection, a Wi-Fi connection, a Bluetooth connection, a cellular connection, etc. In some embodiments, the communication system 236 allows the secondary computing device 108 to communicate with the computing device 104.

In some embodiments, the memory 240 can include any suitable storage device or devices that can be used to store instructions, values, etc., that can be used, for example, by the processor 224 to present content using display 228, to communicate with the computing device 104 via communications system(s) 236, etc. The memory 240 can include any suitable volatile memory, non-volatile memory, storage, or any suitable combination thereof. For example, the memory 240 can include RAM, ROM, EEPROM, one or more flash drives, one or more hard disks, one or more solid state drives, one or more optical drives, etc. In some embodiments, the memory 240 can have encoded thereon a computer program for controlling operation of secondary computing device 108 (or computing device 104). In such embodiments, the processor 224 can execute at least a portion of the computer program to present content (e.g., user interfaces, images, graphics, tables, reports, etc.), receive content from the computing device 104, transmit information to the computing device 104, etc.

The display 116 can be a computer display, a television monitor, a projector, or other suitable displays.

Figure 35:
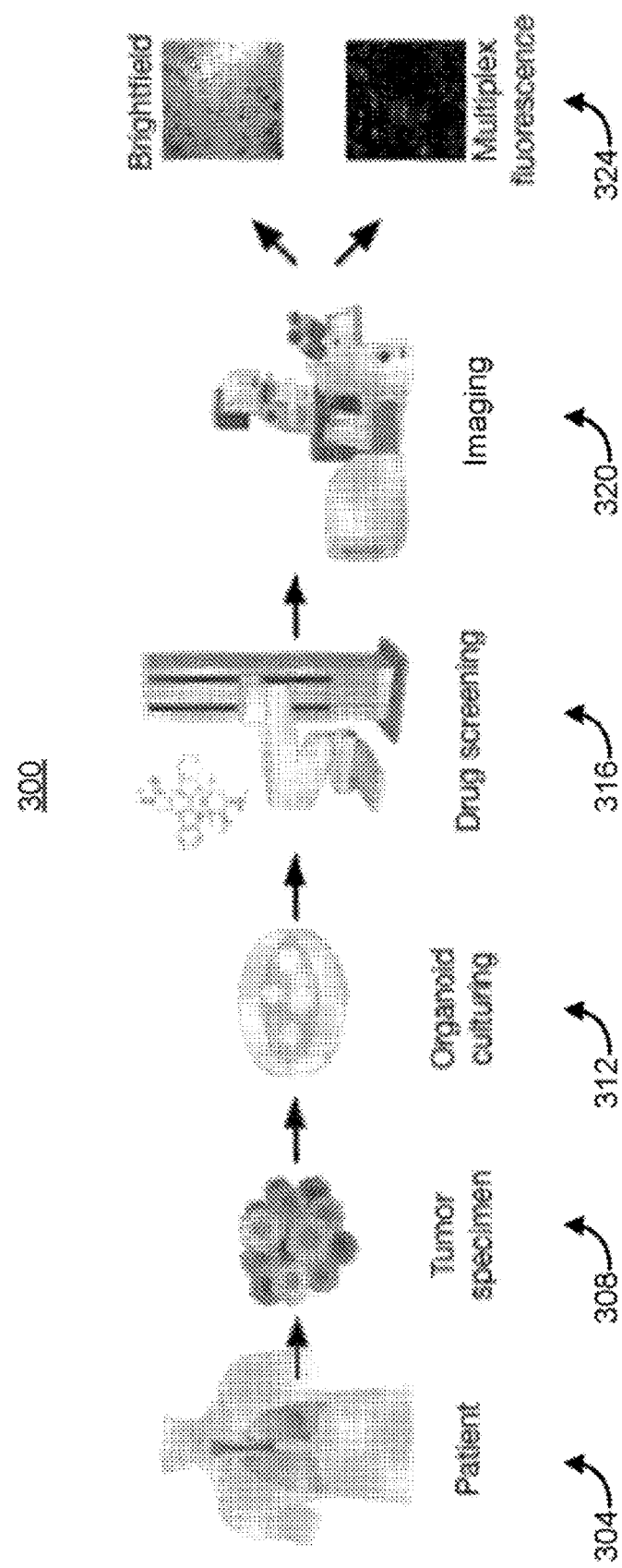
FIG. 35 shows an exemplary flow that can generate brightfield images and/or fluorescent images, as well as live/dead assays readouts, using patient derived organoids grown from tumor specimens.

FIG. 35 shows an exemplary flow 300 that can generate brightfield images and/or fluorescent images, as well as live/dead assays readouts, using patient derived organoids grown from tumor specimens. In some embodiments, the live/dead assays readouts can be produced using brightfield and multiplexed fluorescence imaging. Drug response can be measured via cell viability assays using live/dead fluorescent stains. In some embodiments, the flow 300 can be included in a high throughput drug screening system.

The flow 300 can include harvesting a tumor specimen 308 from a human patient 304, culturing organoids 312 using the tumor specimen 308, drug screening 316 the organoids, imaging the organoids 320, and outputting brightfield and fluorescence images 324 of the organoids. After the organoids are cultured, cells from the organoids can be plated into an assay plate (e.g. a 96-well assay plate, a 384-well assay plate, etc.). The assay plate may also be referred to as a plate. The drug screening 316 can include plating the cells and treating the cells with a number of different drugs and/or concentrations. For example, a 384-well plate can include fourteen drugs at seven different concentrations. As another example, a 96-well plate can include six drugs at five different concentrations. The imaging 320 can include brightfield imaging the treated cells, as well as applying fluorescent stains to at least a portion of the cells and fluorescent imaging the cells. In some embodiments, the fluorescent imaging can include producing three channels of data for each cell. The three channels of data can include a blue/all nuclei channel, a green/apoptotic channel, and a red/pink/dead channel. Each channel can be used to form a fluorescent image. Additionally, the imaging 320 can produce combined 3-channel fluorescent images that include the blue/all nuclei channel, the green/apoptotic channel, and the red/pink/dead channel. In some embodiments, the imaging 320 can include generating brightfield images of the cells using a bright-field microscope and generating fluorescent images of the cells using a confocal microscope such as a confocal laser scanning microscope. In some embodiments, instead of using traditional fluorescent staining to generate the fluorescent images, the imaging 320 can include generating brightfield images for at least a portion of the cells and generating artificial brightfield images for the portion of the cells based on the brightfield images using a process described below (e.g., the process of FIG. 41).

In some embodiments, brightfield images (for example a 2D brightfield projection) depicting a cell culture well during a drug screening assay can be generated using a 10× objective on a microscope. In some embodiments, the microscope can be an ImageXPRESS microscope available from Molecular Devices. In some embodiments, the cells can be cancer cell lines or cancer tumor organoids derived from patient specimens.

FIG. 36 shows an exemplary flow 400 for training a generator 408 to generate an artificial fluorescent image 412 based on an input brightfield image 404 of organoid cells. In some embodiments, the generator 408 can include a U-Net convolutional neural network. In some embodiments, the generator 408 can include a pix2pix model. In some embodiments, the generator 408 can be a generative adversarial network (GAN). An exemplary neural network that can be included in the generator 408 is described below in conjunction with FIG. 38. In some embodiments, the generator can include a neural network that can receive the brightfield image 404 and output a single three-channel fluorescent image (e.g., a 256×256×3 image). In some embodiments, the generator can include three neural networks that can each receive the brightfield image 404 and output a one-channel fluorescent image (e.g., a 256×256×1 image). Generators that include three neural networks that can each receive the brightfield image 404 and output a one-channel fluorescent image may be referred to as three-model generators. Each of the neural networks can be trained to output a specific channel of fluorescence. For example, a first neural network can output a blue/all nuclei channel image, a second neural network can output a green/apoptotic channel image, and a third neural network can output a red/dead channel image. The flow 400 can include combining the blue/all nuclei channel image, the green/apoptotic channel image, and the red/dead channel image into a single three-channel fluorescent image (e.g., a 256×256×3 image, a 1024×1024×3 image, etc.).

The flow can include providing the brightfield image 404, the artificial fluorescent image 412, and a ground truth fluorescent image associated with brightfield image to a discriminator 416 that can predict whether or not an image is real or generated by the generator 408 (e.g., the artificial fluorescent image 412). In some embodiments, the generator 408 can receive an image and output a label ranging from 0 to 1, with 0 indicating that image is generated by the generator 408 and 1 indicating that the image is real (e.g., the ground truth fluorescent image associated with the brightfield image 404). In some embodiments, the discriminator 416 can be a PatchGAN discriminator, such as a 1×1 PatchGAN discriminator. An exemplary discriminator is described below in conjunction with FIG. 39.

The flow 400 can include an objective function value calculation 420. The objective function value calculation 420 can include calculating an objective function value based on labels output by the discriminator 416 and/or by other metrics calculated based on the brightfield image 404, the artificial fluorescent image 412, and the ground truth fluorescent image. The objective function value can capture multiple loss functions (e.g., a weighted sum of multiple loss functions). In this way, the objective function value can act as a total loss value for the generator 408 and the discriminator 416. The flow 400 can include transmitting the objective function value and/or other information from the discriminator 416 to the generator 408 and the discriminator 416 in order to update both the generator 408 and the discriminator 416. A number of different suitable objective functions can be used to calculate the objective function value. However, in testing, a sum of GANLoss+0.83SSIM+0.17L1 was shown to outperform other tested loss functions such as GANLoss+L1 as used by the generator 408. GANLoss can be used to determine whether an image is real or generated. The L1 loss can be used as an additional objective to be minimized to ensure that the generated and real image have the least mean absolute error in addition to GANLoss. Structural Similarity Index (SSIM) can be used to improve performance across multiple performance metrics as well as reduce artifacts. The objective function value calculation 420 will be described below.

The flow 400 can include receiving a number of pairs of a brightfield image and a corresponding ground truth fluorescence image, and iteratively training the generator 408 using each pair of images.

In some embodiments, the flow 400 can include pre-processing the brightfield image 404 and the ground truth fluorescent image. Raw brightfield and fluorescent images may have minimal contrast and require enhancement before being used to train the generator 408. For example, in testing, the pixel intensities for the individual channels of the fluorescent image were generally skewed to zero, which may have been because most of the image is black (i.e., background), except for regions containing organoids and/or cells.

In some embodiments, the artificial fluorescent image 412 can be used to provide a count of live/dead cells. In order to enhance the contrast of the artificial fluorescent image 412 and improve the ability to count live/dead cells from the artificial fluorescent image 412, both the brightfield image 404 and the corresponding ground truth image can undergo contrast enhancement to brighten and sharpen organoids/cells.

In some embodiments, multiple brightfield images and multiple ground truth fluorescent images can be generated per well. For example, for a 96-well plate, there can be about 9-16 sites per well that get imaged.

In some embodiments, the raw brightfield and ground truth fluorescent images can have pixel intensities ranging from $[0, 2^{16}]$. First, a contrast enhancement process, which can be included in the organoid image analysis application 132, can convert each image to an unsigned byte format, with values ranging from [0, 255]. Next, the contrast enhancement process can stretch and clip each pixel intensity to a desired output range.

In some embodiments, the desired intensity range of the input to be stretched can be decided on a per image basis as follows: For the three pixel intensities corresponding to the three fluorophores used to generate the fluorescent image, the input range can be re-scaled using the mode of the pixel intensity distribution as the lower bound value and ⅒th the maximum pixel intensity as the upper bound. The contrast enhancement process can choose the upper bound in order to avoid oversaturated pixels and focus on cell signal. The contrast enhancement process can normalize each pixel intensity based on the lower bound and the upper bound, which function as a min/max range, using a min-max norm, and then each pixel can be multiplied by the output range [0,255]. For the brightfield image 404, the contrast enhancement process can determine an input range by uniformly stretching the 2nd and 98th percentile of pixel intensities to the output range [0,255].

For images with low signal, background noise may be included in the output range. To minimize any remaining back-ground noise, the contrast enhancement process can clip the minimum pixel value by two integer values for the red and green channels, and by three integer values for the blue channel, where the intensity range is wider on average. The maximum pixel values can be increased accordingly to preserve intensity range per image.

In some embodiments, the discriminator 416 can output a predicted label (e.g., a "0" or a "1") to the objective function calculation 420. The predicted label can indicate if the artificial fluorescent image 412 is fake or real. In some embodiments, the objective function can be calculated as a weighted sum of GANLoss, SSIM, and L1. In some embodiments, the GANLoss can be calculated based on the predicted label output by the discriminator. The GANLoss can be used to determine whether the artificial fluorescent image 412 is real or generated. In some embodiments, the L1 loss can be calculated based on the artificial fluorescent image 412 and the corresponding ground truth image. The L1 loss can be used as an additional objective to be minimized to ensure that the artificial fluorescent image 412 and the corresponding ground truth image have the least mean absolute error in addition to GANLoss.

Certain machine learning models, such as the pix2pix model, may only use GANLoss and L1 loss in training a generator. As mentioned above, the objective function calculation 420 can include an SSIM metric in addition to the GANLoss and the L1 loss, which can improve the performance of the generator 408 in comparison to a generator trained using only GANLoss and L1 loss.

In some embodiments, the objective function implemented in the objective function calculation can be defined as:

$$G^* = \arg\min_G \max_D \mathcal{L}_{GAN}(G, D) + \lambda \mathcal{L}_{L1}(G) + \beta(1 - \mathcal{L}_{SSIM}(G)) \quad (1)$$

where $\lambda + \beta = 1$, $L_{L1}$ is the mean absolute error loss, and $1 - L_{SSIM}(G)$ is the structural similarity index loss between the generated image G (e.g., the fluorescent image 412) and the corresponding ground truth image. In some embodiments, $\lambda$ can be 0.17 and $\beta$ can be 0.83. In some embodiments, $\lambda$ can be selected from 0.1 to 0.3, and $\beta$ can be selected from 0.7 to 0.9.

In some embodiments, SSIM can take into account the luminance (l), contrast (c), and structure (s) of two images and computes a metric between 0 and 1, where 1 indicates a perfect match between the two images:

$$l(x, y) = \frac{2\mu_x \mu_y + C_1}{\mu_x^2 + \mu_y^2 + C_1} \quad (2)$$

$$c(x, y) = \frac{2\sigma_x \sigma_y + C_2}{\sigma_x^2 + \sigma_y^2 + C_2} \quad (3)$$

$$s(x, y) = \frac{\sigma_{xy} + C_3}{\sigma_x \sigma_y + C_3} \quad (4)$$

$C_1$, $C_2$ and $C_3$ are small constants defined by:

$$C_1 = (K_1 L)^2, C_2 = (K_2 L)^2 \text{ and } C_3 = C_2/2 \quad (5)$$

where $K_1$, $K_2$ are two scalar constants whose values are less than 1, and L is the dynamic range of the pixel intensities (i.e. 256). SSIM can then be calculated as:

$$SSIM(x, y) = [l(x, y)]^\alpha \cdot [c(x, y)]^\beta \cdot [s(x, y)]^\gamma \quad (6)$$

$$SSIM(x, y) = \frac{(2\mu_x \mu_y + C_1)(2\sigma_{xy} + C_2)}{(\mu_x^2 + \mu_y^2 + C_1)(\sigma_x^2 + \sigma_y^2 + C2)} \quad (7)$$

where l, c, and s are computed using the mean, variance and covariance respectively of two images of the same size using a fixed window size. $\alpha$, $\beta$, and $\gamma$ are constants set to 1. In addition to structural similarity, we also evaluated model prediction using root mean square error, which is the sum of the squared difference of pixel intensities.

In some embodiments, once a dye is added to a cell culture well, the cells in that well cannot continue to be used for the experiment, such that it is difficult or impossible to measure cell death in that well at a subsequent point in time. In some embodiments, the flow 400 can include generating artificial fluorescent images, which can reduce time requirements for imaging by a factor of ten in comparison to utilizing dyes to generate the fluorescent images. Standard fluorescent imaging may take up to an hour to perform. In some embodiments, the flow 400 can be used in conjunction with a drug screening platform that uniquely interprets tumor organoids (TOs) which have limited biomass and intra-tumoral clonal heterogeneity by incorporating Patient Derived Tumor Organoids. The platform couples high content fluorescent confocal imaging analysis with a robust statistical analytical approach to measure hundreds of discrete data points of TO viability from as few as 10^3 cells.

Figure 37:
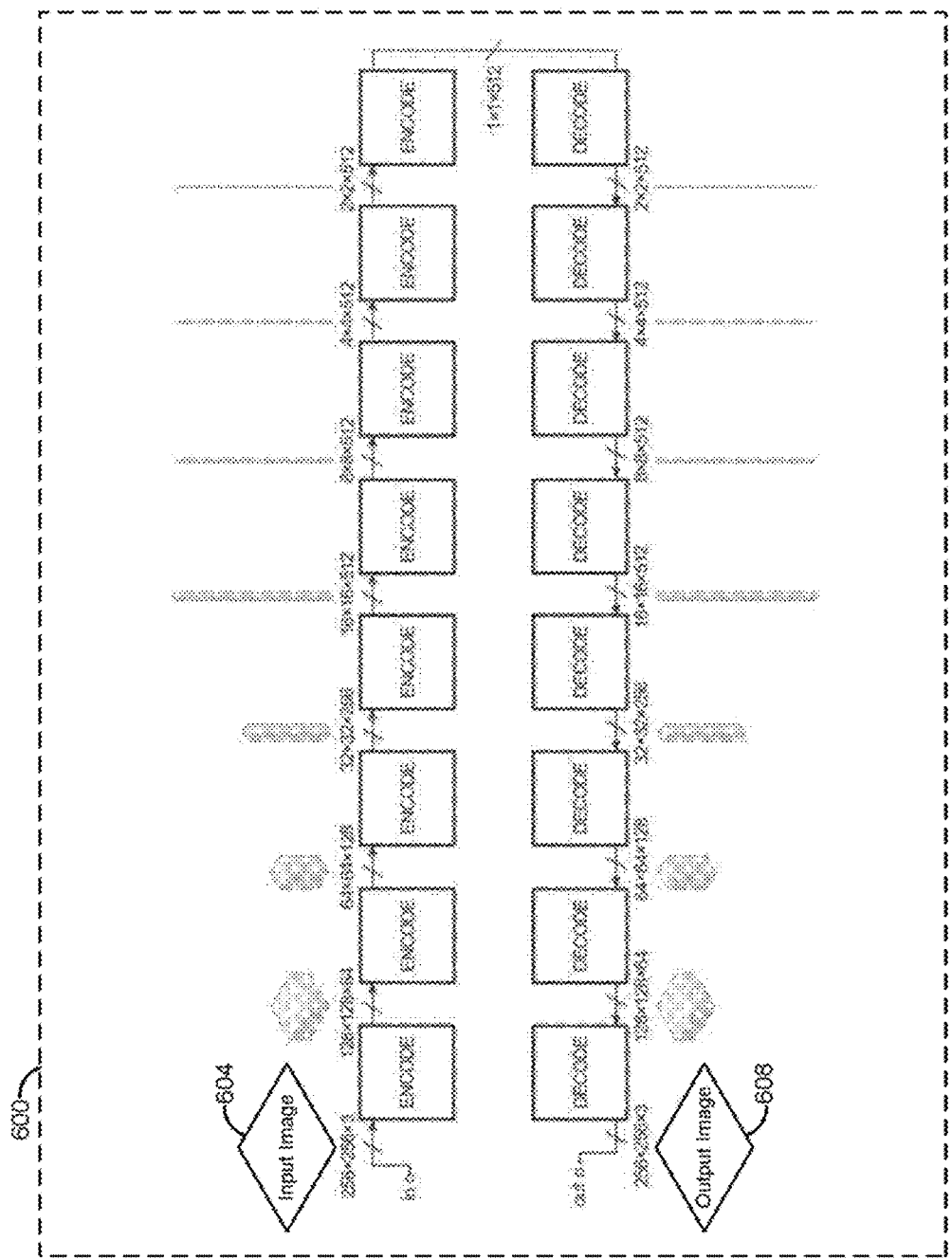
FIG. 37 shows an exemplary flow for generating an artificial fluorescent image.

Referring to FIG. 36 as well as FIG. 37, an exemplary flow 500 for generating an artificial fluorescent image 512 is shown. The flow 500 can include providing an input brightfield image 504 of plated cells to a trained model 508. The trained model 508 can include the generator 408, which can be trained using the flow 400. The trained model 508 can output an artificial fluorescent image 512. The fluorescent image 512 can be used to generate a live/dead assays readout and/or analyze the effectiveness of different drugs and/or dosages on cancer cells in tissue organoids.

Notably, the flow 500 can produce the fluorescent image 512 without the use of fluorescent dyes, which provides several advantages over traditional fluorescent imaging processes that require the use of fluorescent dyes. Some dyes have cytotoxicity and must be added a certain amount of time before imaging. Additionally, once certain dyes are added to a cell culture well, the cells in that well cannot continue to be used for reimaging because of the difficulty in measuring cell death in that well at a subsequent point in time. Thus, the flow 500 can improve the ease of generating the fluorescent images because the flow 500 may only require brightfield imaging, which is not time-dependent like the traditional fluorescent imaging. Additionally, the flow 500 can increase the speed at which the fluorescent images are obtained, because fluorescent dyes do not need to be applied to the cells, and because the flow 500 does not have to wait for the fluorescent dyes to diffuse before imaging the cells. As another example, the flow 500 can allow multiple fluorescent images to be generated for each cell well at a number of different time points. The fluorescent dyes used in traditional fluorescent imaging can damage the cells enough to prevent reimaging. In contrast, the flow 500 can be used to produce multiple fluorescent images over a time period of days, weeks, months, etc. Thus, the flow 500 can provide more data points per cell well than traditional fluorescent imaging.

Figure 38:
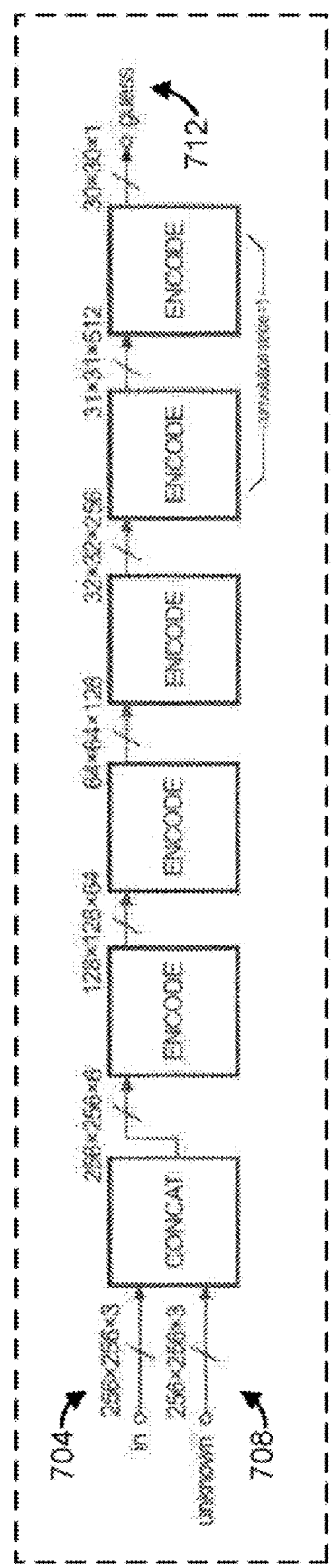
FIG. 38 shows an exemplary neural network.

FIG. 38 shows an exemplary neural network 600. The neural network 600 can be trained to receive an input image 604 and generate an artificial fluorescent image 608 based on the input image 604. In some embodiments, the input image 604 can be a raw brightfield image that has been processed to enhance contrast and/or modify other characteristics in order to enhance the raw brightfield image and potentially produce a better artificial fluorescent image (e.g., the fluorescent image 608).

In some embodiments, the neural network 600 can include a Unet architecture. In some embodiments, the Unet architecture can be sized to receive a 256×256×3 input image. The 256×256×3 input image can be a brightfield image. In some embodiments, the generator 408 in FIG. 36 and/or the trained model 508 in FIG. 37 can include the neural network 600.

Figure 39:
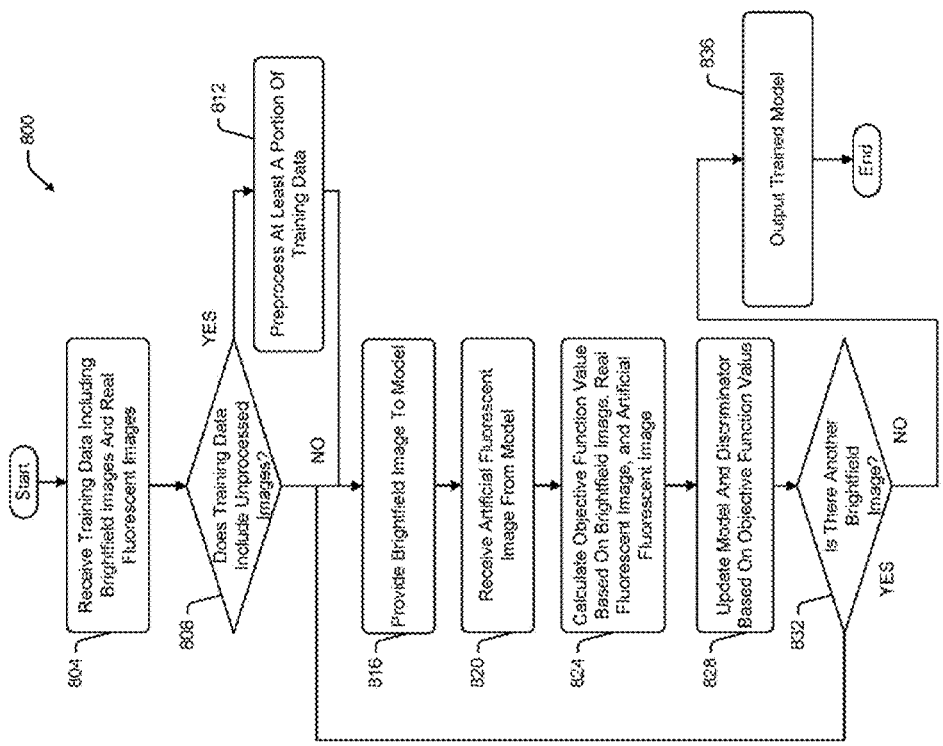
FIG. 39 shows an exemplary discriminator.

FIG. 39 shows an exemplary discriminator 700. In some embodiments, the discriminator 700 in FIG. 39 can be included as the discriminator 416 in the flow 400 shown in FIG. 36. In some embodiments, the discriminator 700 can be a 1×1 PatchGAN. In some embodiments, the discriminator 700 can receive a brightfield image 704 and a fluorescent image 708. The fluorescent image can be an artificial fluorescent image (e.g., the fluorescent image 608 in FIG. 38) or a ground truth fluorescent image. In some embodiments, each of the brightfield image 704 and the fluorescent image 708 can be 256×256×3 input images. In some embodiments, the brightfield image 704 and the fluorescent image 708 can be concatenated. In some embodiments, the concatenated image can be a 256×256×6 input image.

In some embodiments, the discriminator 700 can receive the brightfield image 704 and a fluorescent image 708 and generate a predicted label 712 indicative of whether or not the fluorescent image 708 is real or fake. In some embodiments, the predicted label 712 can be a "0" to indicate the fluorescent image 708 is fake, and "1" to indicate the fluorescent image 708 is real. In some embodiments, the discriminator 700 can include a neural network Referring to FIGS. 36-39, in some embodiments, the flow 400, the flow 500, the neural network 600, and the discriminator 700 can be implemented using Pytorch version 1.0.0. In some embodiments, the flow 400 can be used to train the generator 408 to generate artificial fluorescent images for a colon cancer organoid line. In some embodiments, the flow 400 can be used to train the generator 408 to generate artificial fluorescent images for a gastric cancer organoid line.

Figure 40:
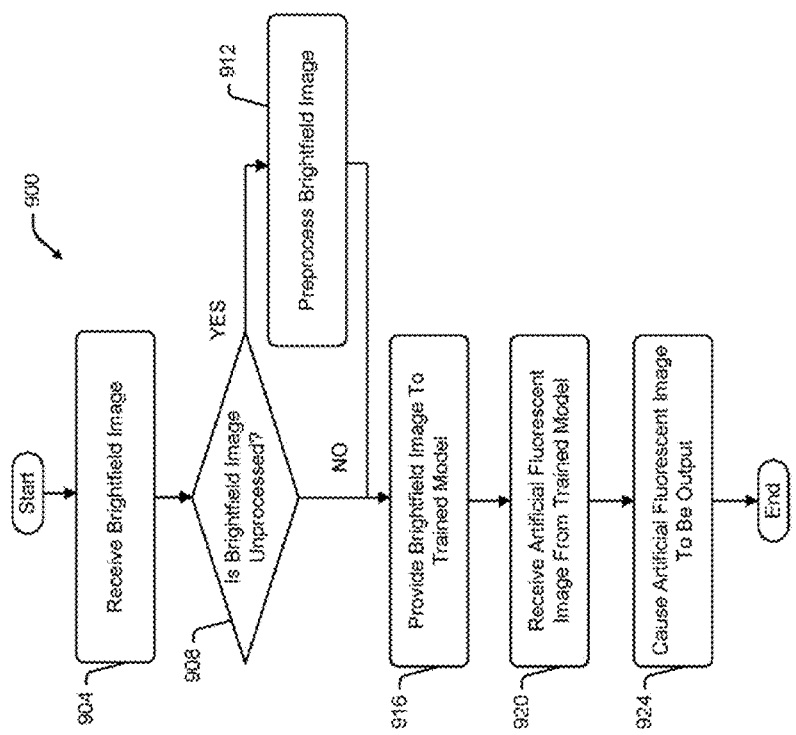
FIG. 40 shows an exemplary process that can train a model to generate an artificial fluorescent stain image of one or more organoids based on an input brightfield image.

FIG. 40 shows an exemplary process 800 that can train a model to generate an artificial fluorescent stain image of one or more organoids based on an input brightfield image. In some embodiments, the model can be the generator 408 in FIG. 36, and/or the neural network 600. In some embodiments, the model can include a neural network that can receive the input brightfield image and output a single three-channel fluorescent image (e.g., a 256×256×3 image). In some embodiments, the model can include three neural networks that can each receive the brightfield image and output a one-channel fluorescent image (e.g., a 256×256×1 image). The one-channel images can then be combined into a single three-channel fluorescent image.

In some embodiments, the process 800 can be used to train a model to output artificial fluorescent images of objects other than tumor organoids using a number of non-fluorescent images (e.g., brightfield images) and fluorescent stain images (which may have more or less than three channels) as training data.

The process 800 can be implemented as computer readable instructions on one or more memories or other non-transitory computer readable media, and executed by one or more processors in communication with the one or more memories or other media. In some embodiments, the process 800 can be implemented as computer readable instructions on the memory 220 and/or the memory 240 and executed by the processor 204 and/or the processor 224.

At 804, the process 800 can receive training data. In some embodiments, the training data can include a number of brightfield images and a number of associated real fluorescent images of organoids. In some embodiments, the organoids can be from a single tumor organoid line. In some embodiments, the brightfield images and the real fluorescent images can be preprocessed in order to enhance contrast as described above. In some embodiments, the brightfield images and the real fluorescent images can be raw images that have not undergone any preprocessing such as contrast enhancement.

At 808, if the training data includes raw brightfield images and/or raw real fluorescent images (i.e., "YES" at 808), the process 800 can proceed to 812. If the training data does not include any raw brightfield images or raw real fluorescent images (i.e., "NO" at 808), the process 800 can proceed to 816.

At 812, the process 800 can preprocess at least a portion of the brightfield images and/or real fluorescent images. In some embodiments, at 812, the process 800 can enhance the contrast of any raw brightfield images and/or real fluorescent images included in the training data. In some embodiments, the raw brightfield and ground truth fluorescent images can have pixel intensities ranging from $[0, 2^{16}]$. In some embodiments, the process 800 can convert each image to an unsigned byte format, with values ranging from $[0, 255]$. The process 800 can then stretch and clip each pixel intensity to a desired output range.

In some embodiments, the process 800 can stretch the desired intensity range of the input on a per image basis. For the three pixel intensities corresponding to the three fluorophores used to generate a real fluorescent image, the process 800 can re-scale the input range using the mode of the pixel intensity distribution as the lower bound value and 1/10th the maximum pixel intensity as the upper bound. The process 800 can determine the upper bound in order to avoid oversaturated pixels and focus on cell signal. The process 800 can normalize each pixel intensity based on the lower bound and the upper bound, which function as a min/max range, using a min-max norm, and then each pixel can be multiplied by the output range [0,255]. For each brightfield image included in the training data, the process 800 can determine an input range by uniformly stretching the 2nd and 98th percentile of pixel intensities to the output range [0,255].

For images with low signal, background noise may be included in the output range. In some embodiments, to minimize any remaining background noise, the process 800 can clip the minimum pixel value by two integer values for the red and green channels, and by three integer values for the blue channel, where the intensity range is wider on average. In some embodiments, the process 800 can increase maximum pixel values accordingly to preserve intensity range per image.

At 816, the process 800 can provide a brightfield image to the model. As described above, in some embodiments, the model can be the generator 408 in FIG. 36 and/or the neural network 600 in FIG. 38. In some embodiments, the model can include three neural networks, and each neural network can receive a copy of the brightfield image and output a different channel (e.g., red, green, or blue) of an artificial fluorescent image.

At 820, the process 800 can receive an artificial fluorescent image from the model. The model can generate the artificial fluorescent image (e.g., the artificial fluorescent image 412) based on the brightfield image (e.g., the brightfield image 404) provided to the model. In some embodiments, the process 800 can receive three one-channel images from three neural networks included in the model and combine the one-channel images into a single three-channel artificial fluorescent image.

At 824, the process 800 can calculate an objective function value based on the brightfield image, the real fluorescent image associated with the brightfield image, and the artificial fluorescent image. In some embodiments, the process 800 can determine a predicted label indicative of whether or not the artificial fluorescent image is real or not by providing the artificial fluorescent image and the real fluorescent image to a discriminator (e.g., the discriminator 416). In some embodiments, the objective function value can be calculated using equation (1) above, where $\lambda$ is 0.17 and $\beta$ is 0.83. In some embodiments, $\lambda$ can be selected from 0.1 to 0.3, and $\beta$ can be selected from 0.7 to 0.9. In some embodiments, the learning rate can fixed at 0.0002 for a first number of epochs (e.g., fifteen epochs) of training, and then linearly decayed to zero over a second number of epochs (e.g., ten epochs).

At 828, the process 800 can update the model (e.g., the generator 408) and the discriminator (e.g., the discriminator 416) based on the objective function value. In some embodiments, the model and the discriminator can each include a neural network. In some embodiments, the process 800 can update weights of layers included in neural networks included in the model and the discriminator based on the objective function value.

At 832, the process 800 can determine whether or not there is a brightfield image included in the training data that has not been provided to the model. If there is a brightfield image included in the training data that has not been provided to the model (e.g., "YES" at 832), the process can proceed to 816 in order to provide the brightfield image to the model. If there are no brightfield images included in the training data that has not been provided to the model (e.g., "NO" at 832), the process can proceed to 836.

At 836, the process 800 can cause the model to be output. At 836, the model has been trained, and can be referred to as a trained model. In some embodiments, the process 800 can cause the trained model to be output to at least one of a memory (e.g., the memory 220 and/or the memory 240) and/or a database (e.g., the trained models database 128). The trained model may be accessed and used in certain processes, such as the processes in FIGS. 41 and 45. The process 800 can then end.

Figure 41:
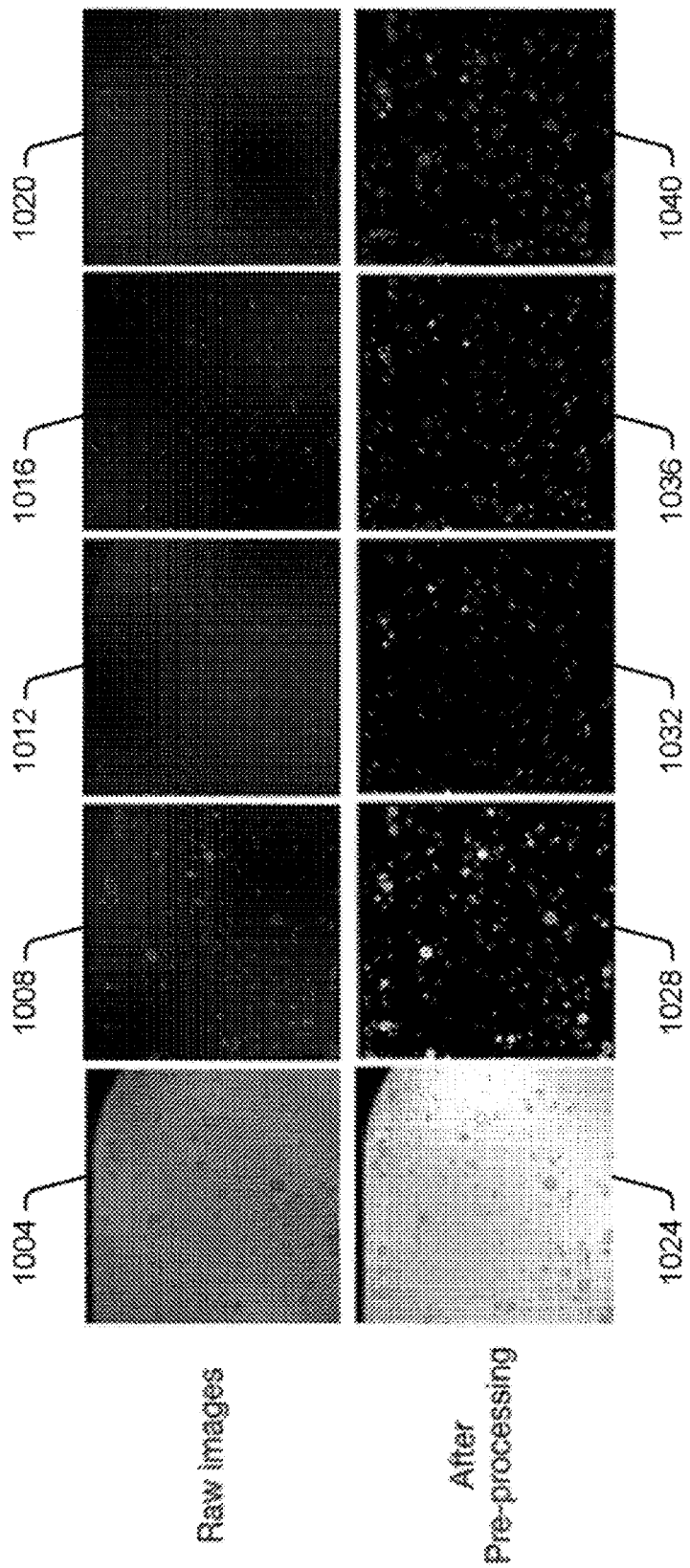
FIG. 41 shows an exemplary process that can generate an artificial fluorescent image of one or more organoids based on a brightfield image.

FIG. 41 shows an exemplary process 900 that can generate an artificial fluorescent image of one or more organoids based on a brightfield image. More specifically, the process 900 can generate the artificial fluorescent image using a trained model. In some embodiments, the model can be the generator 408 in FIG. 36, the trained model 508, and/or the neural network 600 in FIG. 38 trained using the process 800. In some embodiments, the model can include a neural network that can receive the input brightfield image and output a single three-channel fluorescent image (e.g., a 256×256×3 image). In some embodiments, the model can include three neural networks that can each receive the brightfield image and output a one-channel fluorescent image (e.g., a 256×256×1 image). The one-channel images can then be combined into a single three-channel fluorescent image.

In some embodiments, the process 900 can be used to generate artificial fluorescent images (which can have one channel, two channels, three channels, etc.) of objects other than tumor organoids using a non-fluorescent image (e.g., a brightfield image). In this way, objects other than tumor organoids that require fluorescent staining to be properly imaged can be artificially generated without the use of and/or drawbacks of fluorescent dyes.

The process 900 can be implemented as computer readable instructions on one or more memories or other non-transitory computer readable media, and executed by one or more processors in communication with the one or more memories or other media. In some embodiments, the process 900 can be implemented as computer readable instructions on the memory 220 and/or the memory 240 and executed by the processor 204 and/or the processor 224.

At 904, the process 900 can receive a brightfield image (e.g., the brightfield image 404 in FIG. 36 and/or the brightfield image 504 in FIG. 37) of one or more organoids. In some embodiments, the brightfield image can be preprocessed in order to enhance contrast as described above. In some embodiments, the brightfield image can be a raw image that has not undergone any preprocessing such as contrast enhancement.

At 908, the process 900 can determine if the brightfield image is unprocessed (i.e., raw). If the brightfield image is unprocessed (i.e., "YES" at 908), the process 900 can proceed to 912. If the brightfield image is not unprocessed (i.e., "NO" at 908), the process 900 can proceed to 916.

At 912, the process 900 can preprocess the brightfield image. In some embodiments, the brightfield image can have pixel intensities ranging from $[0, 2^{16}]$. In some embodiments, the process 900 can convert the brightfield image to an unsigned byte format, with values ranging from [0, 255]. In some embodiments, the process 900 can convert the brightfield image to another format with less bits than the original pixel intensity. The process 900 can then stretch and clip each pixel intensity to a desired output range. In some embodiments, the process 900 can determine an input range for the brightfield image by uniformly stretching the 2nd and 98th percentile of pixel intensities in the brightfield image to an output range [0,255].

At 916, the process 900 can provide the brightfield image to a trained model. In some embodiments, the model can include the generator 408 in FIG. 36 trained using the process 800 in FIG. 40, the trained model 508, and/or the neural network 600 trained using the process 800 in FIG. 40. In some embodiments, the trained model can include three neural networks, and each neural network can receive a copy of the brightfield image and output a different channel (e.g., red, green, or blue) of an artificial fluorescent image.

At 920, the process 900 can receive an artificial fluorescent image from the trained model. In some embodiments, the process 900 can receive three one-channel images from three neural networks included in the trained model and combine the one-channel images into a single three-channel artificial fluorescent image. The artificial fluorescent image can indicate whether cells included in the tumor organoids are alive or dead.

At 924, the process 900 can cause the artificial fluorescent image to be output. In some embodiments, the process 900 can cause the artificial fluorescent image to be output to at least one of a memory (e.g., the memory 220 and/or the memory 240) and/or a display (e.g., the display 116, the display 208, and/or the display 228). The artificial fluorescent image can be used to provide a live/dead count of cells in the organoids. In some embodiments, the process 900 can cause the artificial fluorescent image to be output to an automatic cell counting process in order to receive an accurate live/dead count of cells and/or a cell count report in the artificial fluorescent image. For example, the process 900 can cause the artificial fluorescent image to be output to the CellProfiler available at https://cellprofiler.org.

At 924, the process 900 can cause the artificial fluorescent image to be output. In some embodiments, the process 900 can cause the artificial fluorescent image to be output to at least one of a memory (e.g., the memory 220 and/or the memory 240) and/or a display (e.g., the display 116, the display 208, and/or the display 228). The artificial fluorescent image can be used to provide a live/dead count of cells in the organoids. In some embodiments, the process 900 can cause the artificial fluorescent image to be output to an automatic cell counting process in order to receive an accurate live/dead count of cells, a percentage of cells that are viable (alive) or dead, and/or a cell count report in the artificial fluorescent image. For example, the process 900 can cause the artificial fluorescent image to be output to the CellProfiler available at https://cellprofiler.org. In some embodiments, the process 900 can cause one or more channels of the artificial fluorescent image to be output to an automatic cell counting process in order to receive a cell count report, a percentage of cells that are viable (alive) or dead, and/or accurate live/dead count of cells in the artificial fluorescent image. In some embodiments, the process 900 can cause the brightfield image to be output to a trained model in order to receive a cell count report, a percentage of cells that are viable (alive) or dead, and/or accurate live/dead count of cells in the artificial fluorescent image. In some embodiments, the process 900 can cause a combination (e.g., image embeddings combined by concatenation) of the brightfield image and one, two, or three channels of the artificial fluorescent image to be output to an automatic cell counting process in order to receive a cell count report, a percentage of cells that are viable (alive) or dead, and/or an accurate live/dead count of cells in the artificial fluorescent image.

In some embodiments, at 924, the process 900 can identify cells in the artificial fluorescent image by converting each of the channels to grayscale, enhancing and suppressing certain features such as speckles, ring shapes, neurites, dark holes, identifying primary objects belonging to the all cell channel where the typical diameters of these objects (in pixel units) is set anywhere between 2 and 20 with a minimum cross entropy thresholding method at a smoothing scale of 1.3488, and identifying primary objects again belonging to the dead cells channel where typical diameter is anywhere between 5 and 20 in pixel units. In this way, the process 900 can generate a cell count report. In some embodiments, the process 924 can determine if a drug and/or dosage is effective in killing tumor organoid cells based on the live/dead count of cells. In some embodiments, at 924, the process 900 can extrapolate dose response from a distribution of organoid viability at a single concentration.

In some embodiments, the cell count report may be analyzed to quantify the efficacy of the drug in killing a particular line of tumor organoid cells. For example, if a concentration of a drug causes a lower number of live cells and/or greater number of dead cells, the drug may be rated as more effective in killing a particular line of tumor organoid cells. For each line of tumor organoid cells, characteristics of the tumor organoid cells (for example, molecular data including detected mutations, RNA expression profiles measured in the tumor organoid cells etc. and/or clinical data associated with the patient from which the tumor organoid was derived) and the results (including the drug efficacy rating) of each drug dose may be saved in a database of drug assay results. These results may be used to match therapies to patients. For example, if a patient has a cancer with characteristics similar to a tumor organoid cell line, drugs rated as effective in killing those tumor organoid cells may be matched to the patient.

In some embodiments, the process 900 can generate a report based on the cell count, the cell count report, and/or the artificial fluorescent image. In some embodiments, the process 900 can cause the report to be output to at least one of a memory (e.g., the memory 220 and/or the memory 240) and/or a display (e.g., the display 116, the display 208, and/or the display 228). The process 900 can then end.

Figure 42:
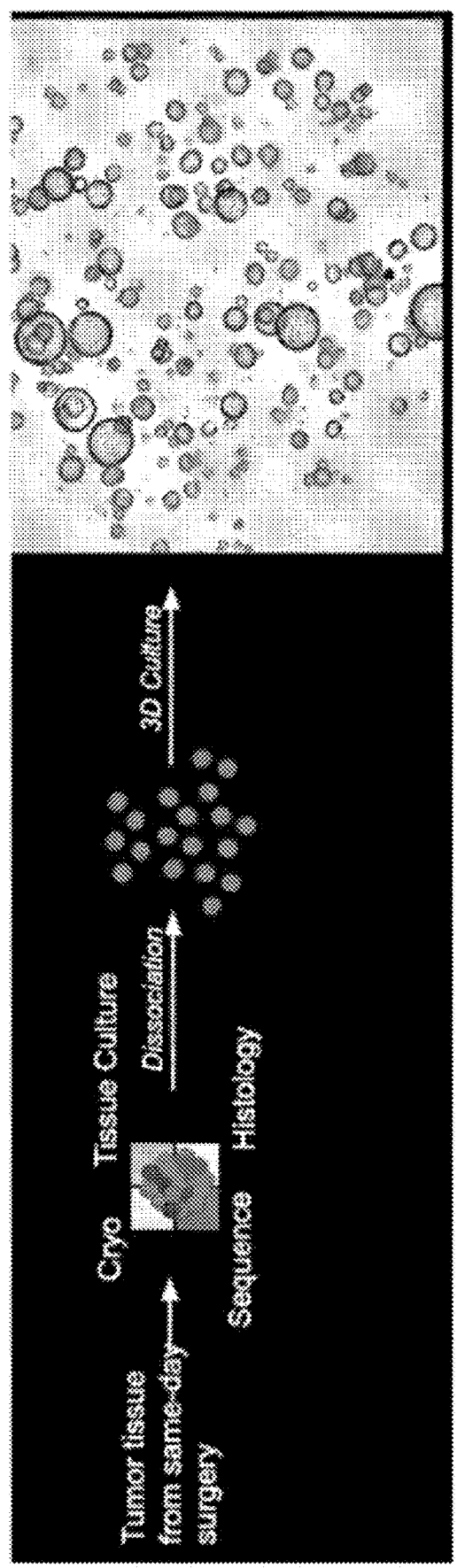
FIG. 42 shows exemplary raw images before preprocessing and after preprocessing.

FIG. 42 shows exemplary raw images before preprocessing and after preprocessing. The raw images before preprocessing include a brightfield image 1004, a blue/all nuclei channel fluorescent image 1008, a green/apoptotic channel fluorescent image 1012, red/pink/dead channel fluorescent image 1016, and a combined 3-channel fluorescent image 1020. The preprocessed images include a brightfield image 1024, a blue/all nuclei channel fluorescent image 1028, a green/apoptotic channel fluorescent image 1032, red/pink/dead channel fluorescent image 1036, and a combined 3-channel fluorescent image 1040. The organoids and cells are brighter and sharper in the preprocessed images. In some embodiments, the preprocessed images 1024-1040 can be generated at 812 in the process 800 in FIG. 40.

Figure 43:
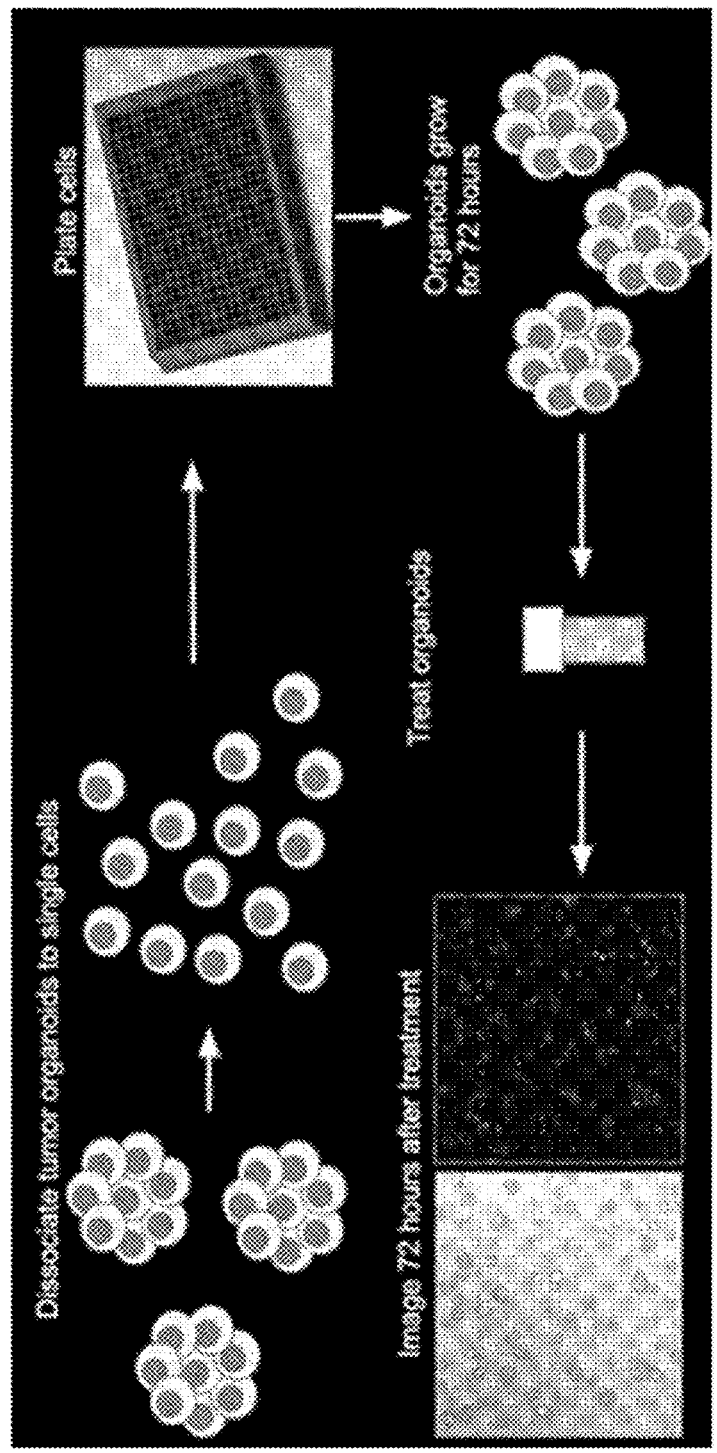
FIG. 43 shows an exemplary flow for culturing tumor organoids. Culture of patient derived tumor organoids.

FIG. 43 shows an exemplary flow 1100 for culturing tumor organoids. Culture of patient derived tumor organoids. The flow 100 can include obtaining tumor tissue from a same-day surgery, disassociating cells from the tumor tissue, and culturing the tumor organoids from the cells. An example of systems and methods for culturing tumor organoids may be found in U.S. patent application Ser. No. 16/693,117, titled "Tumor Organoid Culture Compositions, Systems, and Methods" and filed Nov. 22, 2019, which is incorporated by reference herein in its entirety. Tumor tissue sent from hospitals is cultured to form tumor organoids.

Figure 44:
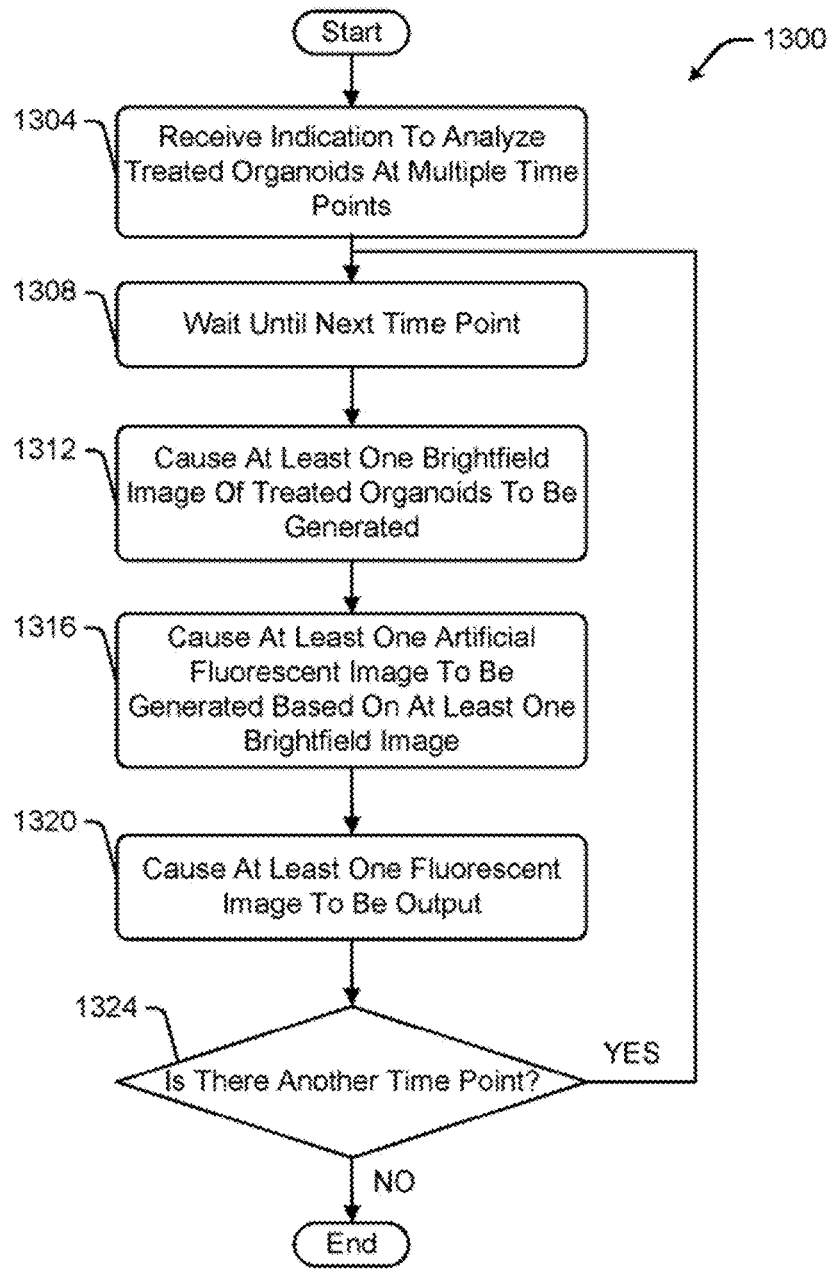
FIG. 44 shows an exemplary flow for conducting drug screens in accordance with systems and methods described herein.

FIG. 44 shows an exemplary flow 1200 for conducting drug screens in accordance with systems and methods described herein. In some embodiments, the flow 1200 can include disassociating tumor organoids into single cells, plating the cells (e.g., in a well plate such as a 96-well plate and/or a 384-well plate), growing the cells into organoids over a predetermined time period (e.g., seventy-two hours), treating the organoids with at least one therapeutic technique, and imaging the tumor organoids a predetermined amount of time (e.g., seventy-two hours) after the tumor organoids are treated. In some embodiments, only brightfield imaging may be performed on the tumor organoids, and any brightfield images generated can be used to generate artificial fluorescent images using the process 900 in FIG. 41. A live/dead count can then be generated based on the artificial fluorescent images. One example of systems and methods for using tumor organoids for drug screens may be found in PCT/US20/63619, titled "Systems and Methods for Predicting Therapeutic Sensitivity" and filed Oct. 22, 1920, which is incorporated by reference herein in its entirety.

Figure 45:
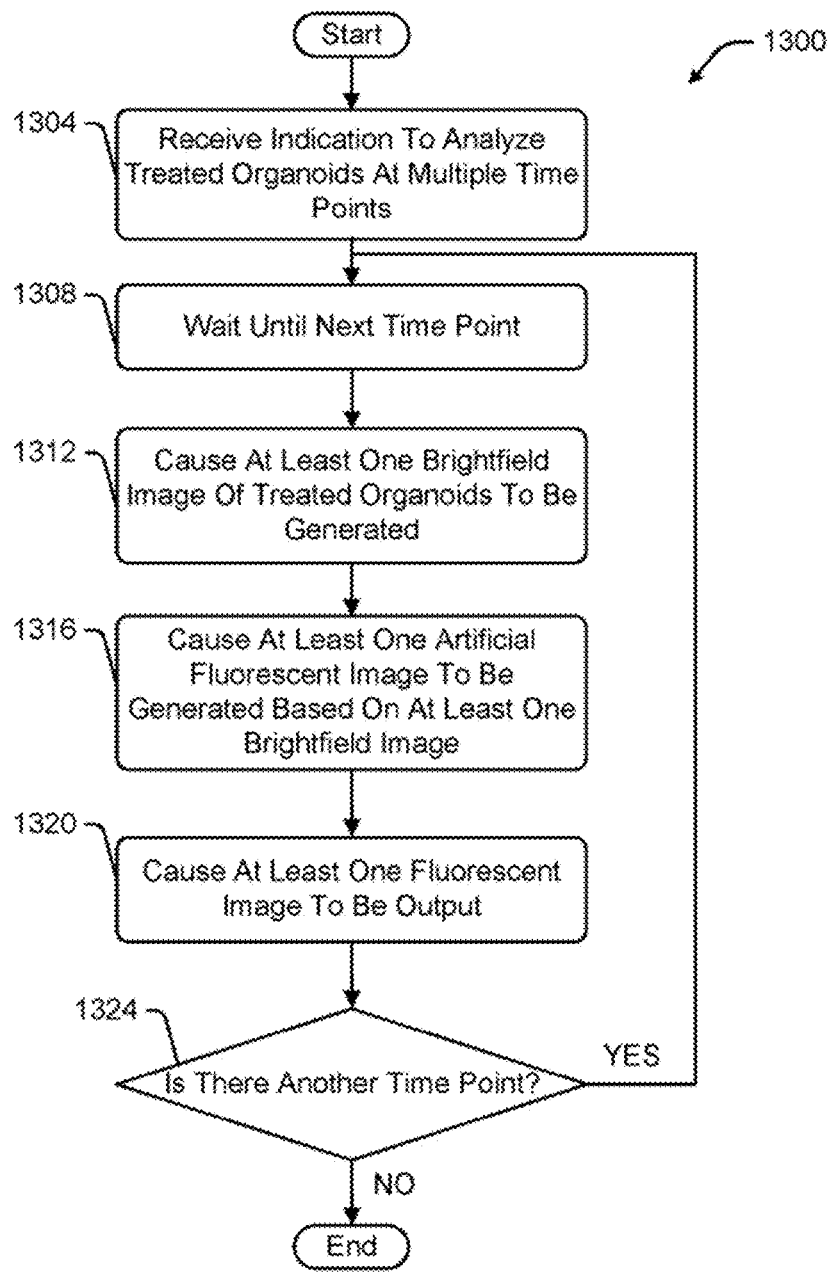
FIG. 45 shows an exemplary process that can generate artificial fluorescent images at multiple time points for at least one organoid.

FIG. 45 shows an exemplary process 1300 that can generate artificial fluorescent images at multiple time points for at least one organoid. Notably, the process 1300 can provide an advantage over standard fluorescent imaging techniques. As mentioned above, fluorescent dyes used to generate standard fluorescent images can damage the cells (e.g., killing the cells) in the organoids, and do not permit fluorescent images to be generated at different time points (e.g., every twelve hours, every twenty-four hours, every seventy-two hours, every week, etc.). In contrast, the process 1300 permits repeated fluorescent imaging of organoids because the process 1300 may only require brightfield images (which do not damage the organoids), and can generate artificial fluorescent images based on the brightfield images.

The process 1300 can be implemented as computer readable instructions on one or more memories or other non-transitory computer readable media, and executed by one or more processors in communication with the one or more memories or other media. In some embodiments, the process 1300 can be implemented as computer readable instructions on the memory 220 and/or the memory 240 and executed by the processor 204 and/or the processor 224.

At 1304, the process 1300 can receive an indication to analyze treated organoids at multiple time points. In some embodiments, the organoids can be plated (e.g., in a well plate such as a 96-well plate and/or a 384-well plate). In some embodiments, the organoids can be plated on multiple well plates. In some embodiments, the organoids can be plated on one or more petri dishes. In some embodiments, the organoids can be treated using a variety of different treatments, which can vary in drug type, drug concentration, and/or other parameters. In some embodiments, each well in a well plate can be associated with a different treatment.

In some embodiments, the multiple time points can represent a time after the organoids have been treated. For example, a twelve hour time point can be twelve hours after the time at which the organoids were treated. In some embodiments, the multiple time points can be spaced at regular intervals. For example, the multiple time points can occur every twelve hours, every twenty-four hours, every seventy-two hours, every week, etc. In some embodiments, the multiple time points can be irregularly spaced. For example, the time points can include a first time point at six hours, a second time point at twenty four-hours, a third time point at three days, a fourth time point at one week, and a fifth time point at twenty-eight days.

At 1308, the process 1300 can wait until the next time point included in the multiple time points. For example, if six hours has passed since the organoids have been treated, and the next time point is at twelve hours, the process 1300 can wait for six hours.

At 1312, the process 1300 can cause at least one bright-field image of the treated organoids to be generated. In some embodiments, process 1300 can generate the brightfield images of the treated organoids using a bright-field microscope and generating fluorescent images of the cells using a confocal microscope such as a confocal laser scanning microscope. In some embodiments, the process 1300 can preprocess the at least one brightfield image. For example, the process 1300 can, for each brightfield image, perform at least a portion of 912 in the process 900 in FIG. 41. In some embodiments, multiple brightfield images can be generated for each well. For example, for a 96-well plate, there can be about 9-16 sites per well that get imaged.

At 1316, the process 1300 can cause at least one artificial fluorescent image to be generated based on the at least one brightfield image. In some embodiments, the process 1300 can provide each brightfield image to a trained model, and receive an artificial fluorescent image associated with the brightfield image from the trained model. In some embodiments, the trained model can include the generator 408 in FIG. 36 trained using the process 800 in FIG. 36, the trained model 508, and/or the neural network 600 trained using the process 800 in FIG. 36. In some embodiments, the trained model can include a neural network that can receive the input brightfield image and output a single three-channel fluorescent image (e.g., a 256×256×3 image).

In some embodiments, the trained model can include three neural networks that can each receive the brightfield image and output a one-channel fluorescent image (e.g., a 256×256×1 image). The one-channel images can then be combined into a single three-channel fluorescent image. The at least one artificial fluorescent image can indicate whether cells included in the tumor organoids are alive or dead.

At 1320, the process 1300 can cause the at least one fluorescent image to be output. In some embodiments, the process 1300 can cause the at least one artificial fluorescent image to be output to at least one of a memory (e.g., the memory 220 and/or the memory 240) and/or a display (e.g., the display 116, the display 208, and/or the display 228). The at least artificial fluorescent image can be used to provide a live/dead count of cells in the organoids. In some embodiments, the process 900 can cause the artificial fluorescent image to be output to an automatic cell counting process in order to get an accurate live/dead count of cells in the artificial fluorescent image. For example, the process 900 can cause the artificial fluorescent image to be output to the CellProfiler available at https://cellprofiler.org. In this way, the process 1300 can automatically generate live/dead counts for multiple wells at multiple time points, which can make drug treatment experiments run faster and gather more data with the same number of wells as compared to standard fluorescent dye imaging techniques that kill cells.

In some embodiments, at 1320, the process 1300 can identify cells in the artificial fluorescent image by converting each of the channels to grayscale, enhancing and suppressing certain features such as speckles, ring shapes, neurites, dark holes, identifying primary objects belonging to the all cell channel where the typical diameters of these objects (in pixel units) is set anywhere between 2 and 20 with a minimum cross entropy thresholding method at a smoothing scale of 1.3488, and identifying primary objects again belonging to the dead cells channel where typical diameter is anywhere between 5 and 20 in pixel units. In this way, the process 1300 can generate a cell count report. In some embodiments, the process 1300 can generate a report based on the cell count, the cell count report, and/or the artificial fluorescent image. In some embodiments, the process 1300 can cause the report to be output to at least one of a memory (e.g., the memory 220 and/or the memory 240) and/or a display (e.g., the display 116, the display 208, and/or the display 228). The process 1300 can then end.

In some embodiments, the process 800 in FIG. 40, the process 900 in FIG. 41, and/or the process 1300 in FIG. 45 can be included in the organoids image analysis application 132 in FIG. 33.

EXAMPLES

A. Example 1—PARPi Sensitivity of BRCA1⁻/BRCA2⁻ Tumors

Tumor biopsies were collected from four individuals: UK1393, 10423-12001, 10524-12001, and 10941-12002. The tumors were genotyped and determined not carry BRCA1 or BRCA2 mutations. As such, according to conventional guidance, the tumors are not indicated for first-line therapy with a PARP inhibitor. In order to test whether these tumors may still be sensitive to PARP inhibitors, despite not carrying a BRCA1 or BRCA2 mutation, tumor organoids were cultured using cells from the biopsied material.

Briefly, cells within each of the biopsied tumor samples were dissociated and cultured to establish a tumor organoid culture line from the tumor of each individual. Single tumor organoids from the tumor organoid culture lines were collected and plated, individually, into wells of a multiwell plate with culture medium. A series of six concentrations of olaparib, in a 5-fold serial dilution, were established for the tumor organoids derived from each individual, as well as negative controls. After incubation with olaparib, a caspase 3/7 apoptosis assay was performed in each well, to determine the sensitivity of each tumor organoid to the respective concentration of olaparib. Results of the caspase dilution series experiments are plotted in FIG. 3.

Figure 3A:
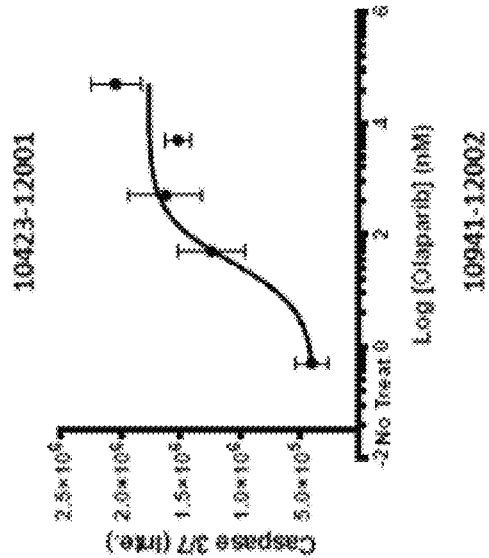
FIGS. 3A, 3B, 3C, and 3D illustrate dose response curves for the treatment of four patient-derived tumor organoid cell lines with olaparib, in accordance with some embodiments of the present disclosure.
Figure 3B:
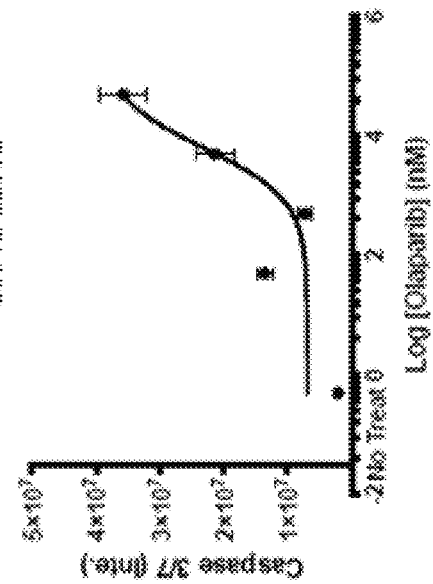
Figure 3C:
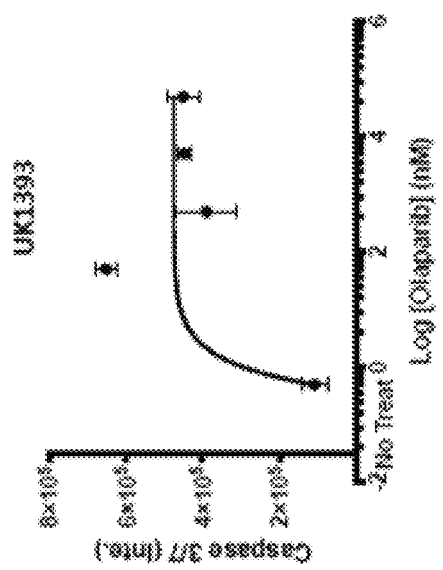
Figure 3D:
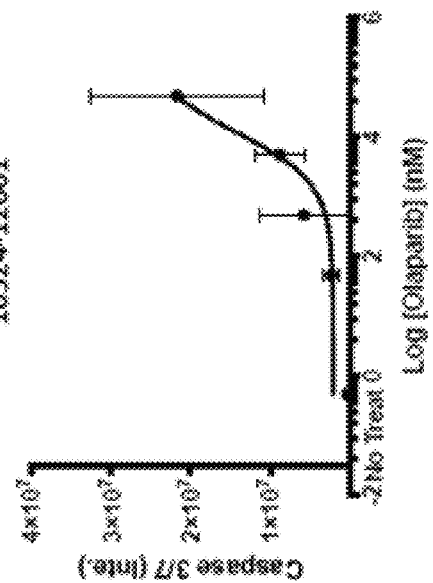

As expected, since the tumors did not carry a BRCA1 or BRCA2 mutation, three of the tumor organoid culture lines were fairly insensitive to olaparib: 10423-12001 (FIG. 3B), 10524-12001 (FIG. 3C), and 10941-12002 (FIG. 3D). However, unexpectedly, tumor organoid culture line UK1393 was more than 100-fold more sensitive to olaparib, despite being derived from a tumor that did not carry a BRCA1 or BRCA2 mutation. These results suggest that the cancer in this individual may be effectively treated with a PARP inhibitor as a first-line therapy, despite not carrying a biomarker conventionally associated with PARP inhibitor efficacy.

B. Example 2—Drug Screening Platform

Patient derived Tumor Organoids (TOs) are emerging as patient-representative models that recapitulate clinical responses to candidate therapeutics. Yet standard methods of interpreting in vitro treatments of TOs have been developed from monoclonal, rapidly proliferating 2D cell lines that are not amenable for TOs which have limited biomass and intra-tumoral clonal heterogeneity. To address these challenges, a drug screening platform more applicable for the unique characteristics of TOs was developed and optimized. The platform couples high content fluorescent confocal imaging analysis with a robust statistical analytical approach to measure hundreds of discrete data points of TO viability from as few as $10^3$ cells. This approach was validated through evaluating responses to hundreds of small molecule inhibitors as well as a panel of chemotherapeutic agents in TO models derived from different patients.

The platform was highly reproducible with minimal intra- and inter-assay variance (well:well variance=ns, plate:plate variance=ns, by ANOVA). QC of TOs was performed to remove outlier TOs by size and remaining TOs were normalized by mean vehicle proportion survival. To compare differential therapeutic toxicity between TOs from different patients, a linear model was developed to evaluate differences in proportion of surviving cells across equivalent therapeutic concentrations, identifying highly significant differences ($P<10^{-12}$). Intriguingly, the linear model not only uncovered heterogeneity of responses between TOs derived from different patients, but also identified organoid clonal populations derived from the same patient with differential drug response offering a window into uncovering functional intratumoral heterogeneity.

Lastly, throughput was substantially increased by applying a machine learning algorithm to predict therapeutic response via TO morphological changes from light microscopy. Employing this algorithm eliminated the need for fluorescent labeling leading to increased assay throughput by 3-4 fold amounting to 96 and 384 well plate acquisitions in as little as 5 and 15 minutes respectively. As such provided herein is a high-throughput capable of measuring TO therapeutic response with high statistical confidence and exquisite inter-assay reproducibility. This approach can be utilized in research settings to elucidate heterogeneity of therapeutic responses within and among patients, and may be utilized in the clinical laboratory to potentially guide precision oncology treatments.

1. Cell Plating

A drug screening platform may be utilized to assess the effectiveness of drugs or other agents on tumor organoids (TOs). Single cell suspensions of tumor organoid cells are generated as described below.

1. Gently remove the medium from the tumor organoids (TOs) by pipetting out the medium. Do not use vacuum to aspirate the medium.
2. Add 500 mL of TrypLE Express to each well, attempting to disrupt the organoid containing Matrigel domes.
3. Scrape the remaining Matrigel off the bottom of the wells with 1 mL pipette.
4. Place the dissociated organoids into a 15 ml low-binding centrifuge tube.
5. Place the tube in the 37° C. water bath for 15 min.
6. Spin the cells at 200 g for 5 min. in a 4° C. centrifuge.
7. Carefully pipet out and discard the supernatant.
8. Add 1 ml of DPBS to the cell pellet.
9. Centrifuge the cell containing tube at 4° C. at 200 g for 5 min.
10. Pipet out the supernatant and add any medium/reagent required for your following procedure.

In one example, TOs from 24-well plate culture are dissociated to single cells and seeded in 384-well plates in a mix of 30% Matrigel and 70% media. This allows TOs to form from individual cells for the assay, maintaining TO heterogeneity in each well. The cells are seeded at 2,000 cells per well allowing a sufficient number of TOs to form while not overcrowding the plate so that TOs do not overlap or touch allowing for easy identification of individual TOs.

2. Drug and Detection Reagent Application

Caspase 3/7 Green Apoptosis Assay Reagent (Essen Biosciences cat #4440) is diluted in media to 2.5 µM. Drugs are diluted to 20 µM in media with Caspase 3/7 reagent and 10-fold serial dilutions are prepared in a separate 384-well plate. Diluted drugs are added to the 384-well assay plate by pipetting 20 µl of the diluted drug, media, Caspase 3/7 mix to the appropriate wells using an Integra Viaflo automated pipetting system.

In one example, one or more chemotherapeutic agents may be applied to the TOs in the well plates. Example agents include Paclitaxel, Gemcitabine, Cisplatin, Carboplatin, Oxaliplatin, Capecitabine, SN-38 (CPT-11), 5-FU, MTX (methotrexate), Docetaxel, Bortezomib, Everolimus, Ulixertinib, Dasatinib, Vinblastine, Nelarabine, Epirubicin, Afatinib, Lapatinib, Cytarabine, Cladribine, Doxorubicin, Azacitidine, and Staurosporine. Other examples include classes of drugs including but not limited to: taxanes, platinating agents, *vinca* alkaloids, alkylating agents, and anthracyclines.

C. Example 3—High Content Fluorescent Confocal Imaging Analysis

TOs may be stained using common vital dyes to measure cellular behaviors amenable for high content fluorescent confocal imaging analysis. In one example, TOs are stained with Hoechst 33342 (Fisher Scientific cat #H3570), IncuCyte® Caspase-3/7 Green Apoptosis Assay Reagent (Essen Biosciences cat #4440), and TO-PRO™-3 Iodide (642/661) (Fisher Scientific cat #T3605) in multi-well tissue culture plates (e.g. 24, 48, 96, 384, etc.). After staining, TOs are imaged on an inverted confocal microscope using the light microscopy and multiple fluorescent channels with varying wave-length excitation sources (e.g. laser or LED) and emission filters. Each channel (i.e. light microscopy, Hoechst nuclear stain, FITC, Cy5) is acquired through an objective lens, in one example a 10× objective lens is used to take images at two sites per well with a stack of images in the Z plane ranging from 1-100 heights in the Z-plane with increments ranging from submicron to as high as 15 micron per Z-plane height. Z-stack images are projected to 2D and analyzed using image analysis software with parameters to identify TOs based on the pixel intensities in the nuclear stain channel (i.e. Hoechst 33342 channel) and the size of the object by measurements in 2D space of the object as well as number of nuclei. All cell nuclei are identified by Hoechst 33342 staining. TOs are identified by clusters of nuclei identified by Hoechst 33342 staining. Apoptotic cells are identified by Caspase 3/7 staining and dead cells are identified by TO-PRO-3 staining overlapping with Hoechst 33342 staining. The analysis module is used to enumerate TOs per image, how many cells (live and dead) are present in each TO, and how many dead and dying cells are present in each TO by Caspase 3/7 and TO-PRO-3 staining separately. The Caspase 3/7 and TO-PRO-3 stains provide two independent counts of dead and dying cells.

Utilizing fluorescent markers for all cells and two markers for dead/apoptotic cells permits analysis of TOs at the single cell level and also permits generation of an absolute number of live and dead cells per organoid. This TO by TO analysis provides more information than simply calculating a relative value of viable cells from an entire well. Maintaining TO heterogeneity allows for determination of whether all cells are dying at a constant rate or if there is a mix of susceptible and resistant cells to a given treatment based on the distribution of viable cells per organoid. The aspects, such as the number of wells, types of plates, and types of cultures disclosed here, are exemplary in nature. Other aspects known in the art may be used instead or in combination with those aspects disclosed herein.

Figure 4A:
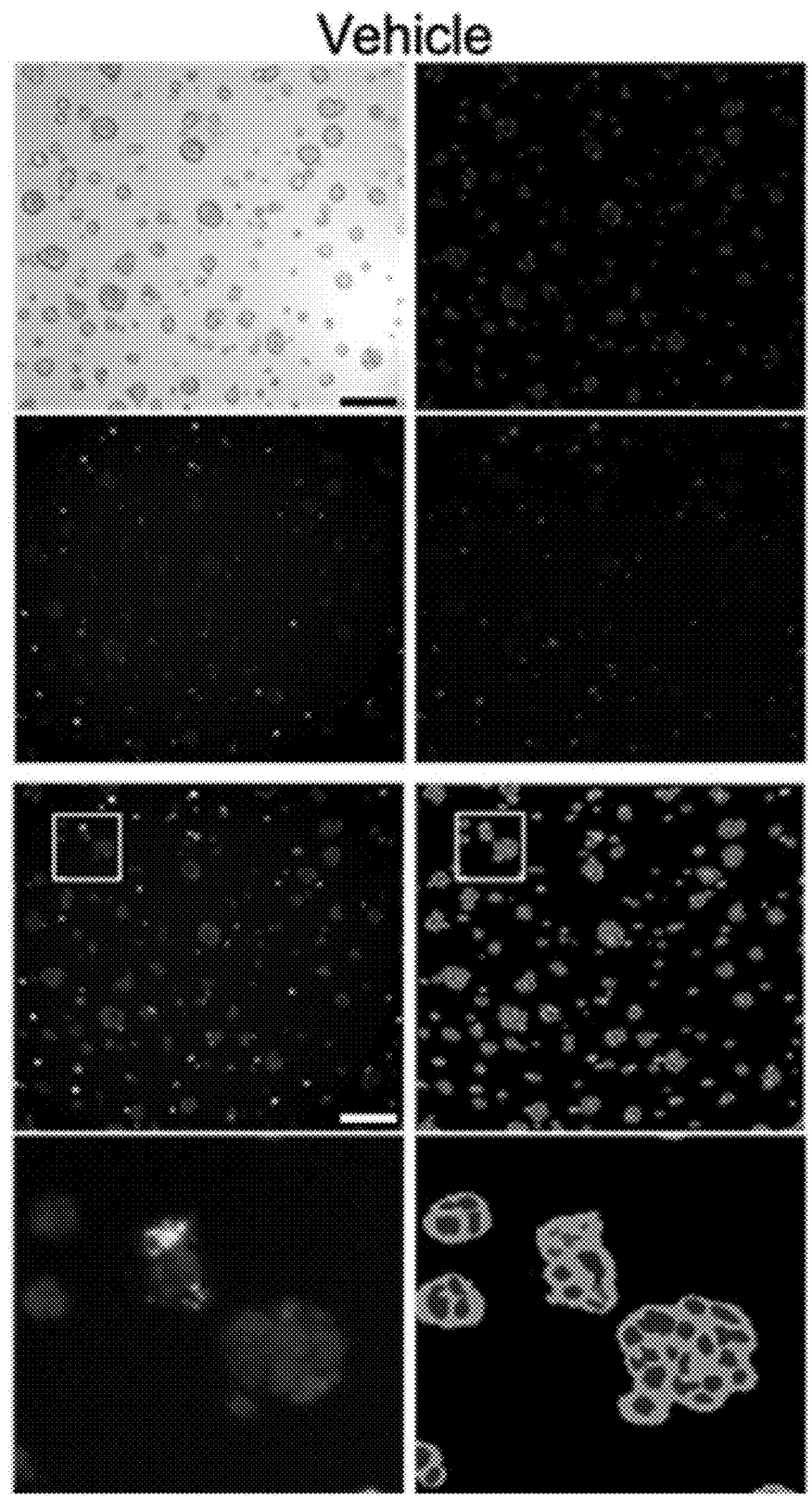
FIGS. 4A and 4B collectively show example image of high-content fluorescent confocal imaging analysis using the subject methods described herein. (Top panels) Brightfield (top left), Hoechst 33342 (top right), Caspase 3/7 (bottom left), and TO-PRO-3 (bottom right) staining is shown for vehicle control (FIG. 4A) and staurosporine treated (FIG. 4B) gastric cancer TOs. (Bottom panels) Overlays of the fluorescent channels and the result of image analysis are shown side by side. The outline of the larger objects in the right panels indicates the area of a given TO. Live and dead cells are shown in the image analysis panels. Scale bars represent 100 microns.
Figure 4B:
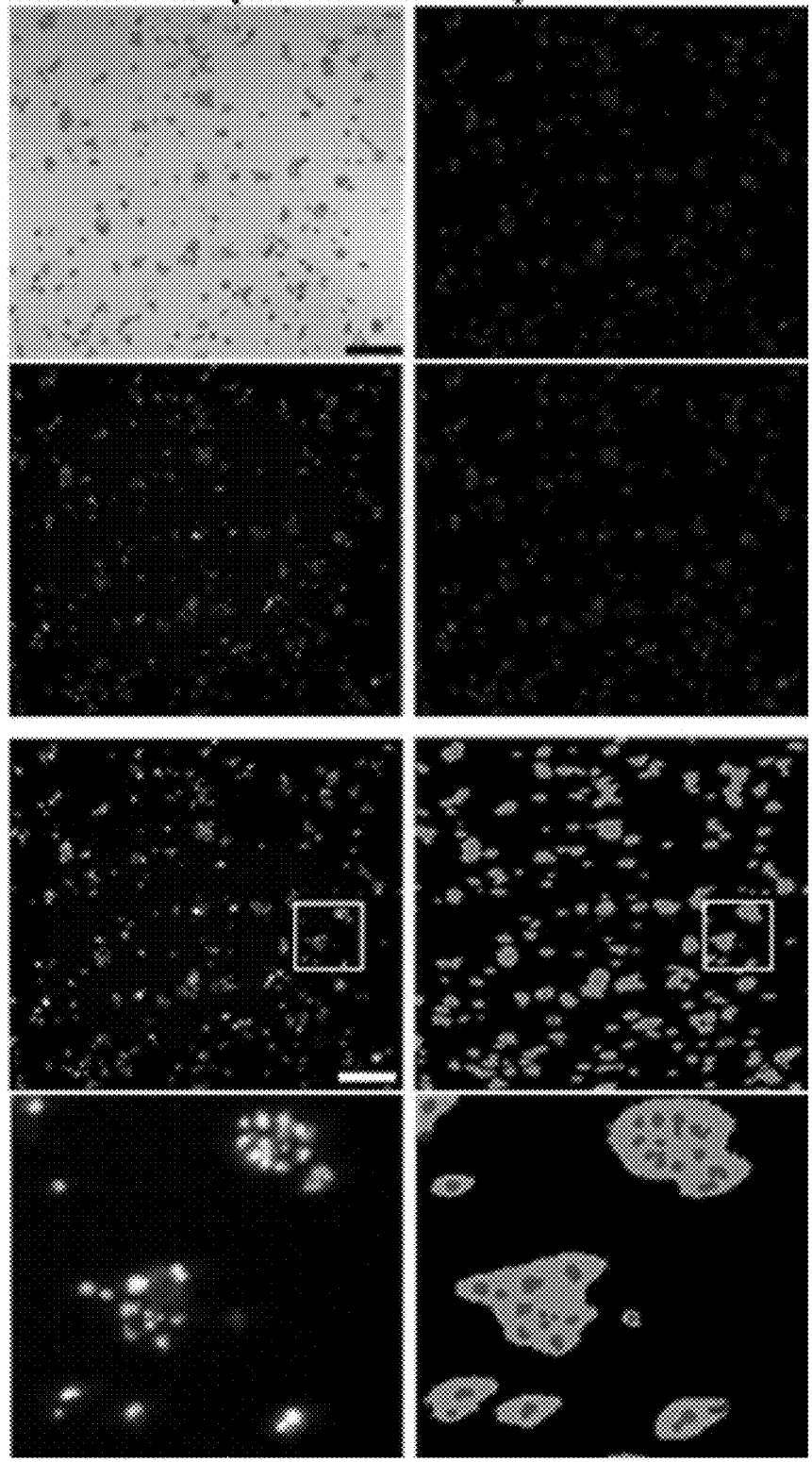

FIG. 4 shows an example image of high-content fluorescent confocal imaging analysis. (A-D) Brightfield (gray scale), Hoechst 33342 (blue), Caspase 3/7 (green), and TO-PRO-3 (red) staining is shown for vehicle control (A and B) and staurosporine treated (C and D) gastric cancer tumor organoids. (B and D) Overlays of the fluorescent channels and the result of image analysis are shown side by side. Light-blue coloring on the image analysis indicates the area of a given tumor organoid. Live (purple) and dead (red) cells are shown in the image analysis panels. Scale bars represent 100 microns.

D. Example 4—Statistical Approach

Since data are collected from hundreds of TOs per drug condition, hundreds of data points may be analyzed within an experimental replicate (usually a single culture well in a multiwell plate), rather than just collecting one data point from each experimental replicate well as is typically done in drug screens. The percent viable cells (which may be determined by a lack of Caspase 3/7 and/or TO-PRO-3 staining) is calculated for each individual TO. The percent viable cells per organoid from each technical replicate is then averaged together for the actual percent viable cells per drug concentration. These values are normalized to the percent viable cells per TO of the DMSO treated vehicle control and plotted to generate a dose-response curve.

Table 3 contains a small example of the data output. Each row of the table represents an individual organoid. The columns contain information for which well of the culture plate was imaged (Well Name), the size of the TO (TO area), the total number of cells in the organoid (All cells (TO-PRO-3) and All cells (Caspase 3/7)), the number of dead cells by positive TO-PRO-3 staining (Dead cells (TO-PRO-3)), the number of live cells by negative TO-PRO-3 staining (Live cells (TO-PRO-3)), the number of dead cells by positive Caspase 3/7 staining (Dead cells (Caspase 3/7)), and the number of live cells by negative Caspase 3/7 staining (Live cells (Caspase 3/7)).

TABLE 3

| Well Name | TO Area | All cells (TO-PRO-3) | Live cells (TO-PRO-3) | Dead cells (TO-PRO-3) | All cells (Caspase 3/7) | Live cells (Caspase 3/7) | Dead cells (Caspase 3/7) |
|---|---|---|---|---|---|---|---|
| O02 | 410.178223 | 2 | 1 | 1 | 2 | 2 | 0 |
| O02 | 152.455612 | 1 | 0 | 1 | 1 | 0 | 1 |
| O02 | 319.430817 | 1 | 0 | 1 | 1 | 0 | 1 |
| O02 | 3570.00244 | 0 | 0 | 0 | 0 | 0 | 0 |
| O02 | 212.348892 | 1 | 0 | 1 | 1 | 0 | 1 |
| O02 | 246.832901 | 1 | 0 | 1 | 1 | 0 | 1 |
| O02 | 348.469971 | 1 | 0 | 1 | 1 | 0 | 1 |
| O02 | 2268.68481 | 7 | 0 | 7 | 7 | 0 | 7 |
| O02 | 132.491196 | 1 | 0 | 1 | 1 | 0 | 1 |
| O02 | 1969.21838 | 7 | 1 | 6 | 7 | 0 | 7 |
| O02 | 1069.00427 | 4 | 1 | 3 | 4 | 1 | 3 |
| O02 | 373.879242 | 1 | 0 | 1 | 1 | 0 | 1 |
| O02 | 176.049942 | 1 | 0 | 1 | 1 | 0 | 1 |
| O02 | 1386.62012 | 4 | 0 | 4 | 4 | 0 | 4 |
| O02 | 214.163849 | 1 | 0 | 1 | 1 | 0 | 1 |
| O02 | 397.473572 | 1 | 0 | 1 | 1 | 0 | 1 |
| O02 | 343.025146 | 1 | 0 | 1 | 1 | 0 | 1 |
| O02 | 346.655029 | 1 | 0 | 1 | 1 | 0 | 1 |
| O02 | 840.320862 | 2 | 1 | 1 | 2 | 1 | 1 |

TABLE 3-continued

| Well Name | TO Area | All cells (TO-PRO-3) | Live cells (TO-PRO-3) | Dead cells (TO-PRO-3) | All cells (Caspase 3/7) | Live cells (Caspase 3/7) | Dead cells (Caspase 3/7) |
| --- | --- | --- | --- | --- | --- | --- | --- |
| O02 | 208.718994 | 1 | 0 | 1 | 1 | 0 | 1 |
| O02 | 264.982391 | 1 | 0 | 1 | 1 | 0 | 1 |
| O02 | 464.626648 | 1 | 0 | 1 | 1 | 0 | 1 |
| O02 | 947.402771 | 2 | 0 | 2 | 4 | 0 | 4 |
| O02 | 446.477173 | 1 | 0 | 1 | 1 | 0 | 1 |
| O02 | 568.078674 | 3 | 0 | 3 | 3 | 0 | 3 |
| O02 | 431.957581 | 2 | 0 | 2 | 2 | 0 | 2 |
| O02 | 713.274475 | 2 | 0 | 2 | 2 | 0 | 2 |
| O02 | 110.711815 | 1 | 0 | 1 | 1 | 0 | 1 |
| O02 | 980.071838 | 3 | 1 | 2 | 3 | 0 | 3 |

Figures 5A, 5B:
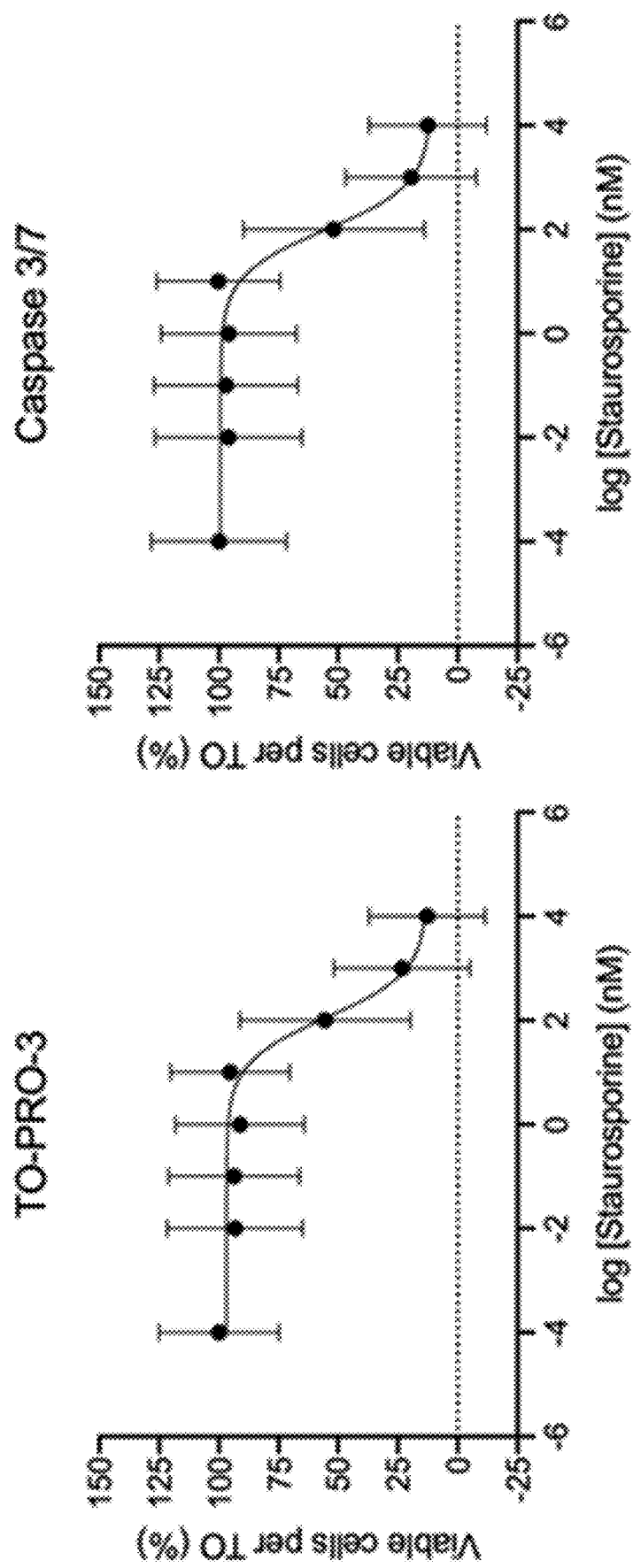
FIGS. 5A and 5B illustrate examples of dose-response curves determined from carbocyanine monomer nucleic acid staining (TO-PRO-3.

FIG. 5 shows an example dose-response curve for cell viability by TO-PRO-3 (left) and Caspase 3/7 (right) after treatment with staurosporine on tumor organoids derived from a gastric cancer. Each point represents the mean±SD from 450-1200 individual organoids.

Hundreds of discrete measurements of TO viability per drug concentration can be made, beginning with as few as $6 \times 10^5$ cells. These measurements may be performed for every cell of every organoid. There are hundreds of organoids per experimental condition such as incubation with a drug at a specific concentration with approximately between 3-15 cells per organoid.

Additionally, high reproducibility with minimal inter- and intra-assay variance can be achieved using the subject platform.

Due to the large number of TOs being measured per well, there is a high number of sampling occurring to identify the true mean. Just as one arrives at a high precision of 0.1666666 probability of rolling a six on a standard die if one rolls the die 600 times instead of just 6 times. The high accuracy of finding the true mean means that interwell reproducibility is high and inter assay reproducibility is also high.

To compare differential therapeutic toxicity between TOs from different patients, a linear model was developed to evaluate survival across equivalent therapeutic concentrations.

The high number of measurements recorded per dose allows the use of more complex statistical or non-statistical methods that would otherwise be unable to be used with a low-throughput dose response assay. Therefore, a linear model was used (Galton, 1886, "Regression Towards Mediocrity in Hereditary Stature," The Journal of the Anthropological Institute of Great Britain and Ireland 15: 246-263) to determine differences between patients, or between drugs, at equivalent therapeutic concentrations (or doses). Use of a linear model allows for inclusion of covariates to adjust for potential confounding technical effects including initial TO viability, differences in growth rates between TOs derived from different patients, and different cancer types, and leverages all of the TO data to gain better statistical power.

For example, to determine differences in viability to a 10 uM dose of staurosporine compared to a 10 uM dose of Olaparib that were run on different experiments (plates), we would run the following model and estimate the betas and corresponding p-values for each main effect ($x_{drug}$, and $x_{plate}$). Since we estimate both the drug and plate effect, we can control for potential experimental noise generated by the experiment being run on different plates.

$$Y_{normalized\ viability\ proportion} \sim \beta x_{drug} + \beta x_{plate} + \varepsilon$$

In a different example, differences in viability to a 1 nM dose of Dapagliflozin between TO cell lines that were run by different technicians is determined. Here, differences between TO lines (estimating the beta for)(canine) and determined, with control for experimental noise that might be due to different technicians running the assay:

$$Y_{normalized\ viability\ proportion} \sim \beta x_{cell\ line} + \beta x_{technician} + \varepsilon$$

Lastly, throughput was substantially increased by applying a deep learning algorithm to the high-dimensional dataset. The algorithm was adapted from the Generative Adversarial Network Pix2pix by Phillip Isola et al, 2018, "Image-to-Image Translation with Conditional Adversarial Networks," arXiv:1611.07004v3 [cs.CV] 26 Nov. 2018, which is hereby incorporated by reference. The GAN architecture makes use of a generator model that is trained to generate meaningful data (typically from noise), and a discriminator model that is trained to distinguish between what's real and what's been generated.

Pix2pix is a specific type of GAN designed for general purpose Image-to-Image translation involving the controlled conversion of a source image to target image. Here, pix2pix was employed to transfer the style of brightfield images to fluorescent images.

Figure 6:
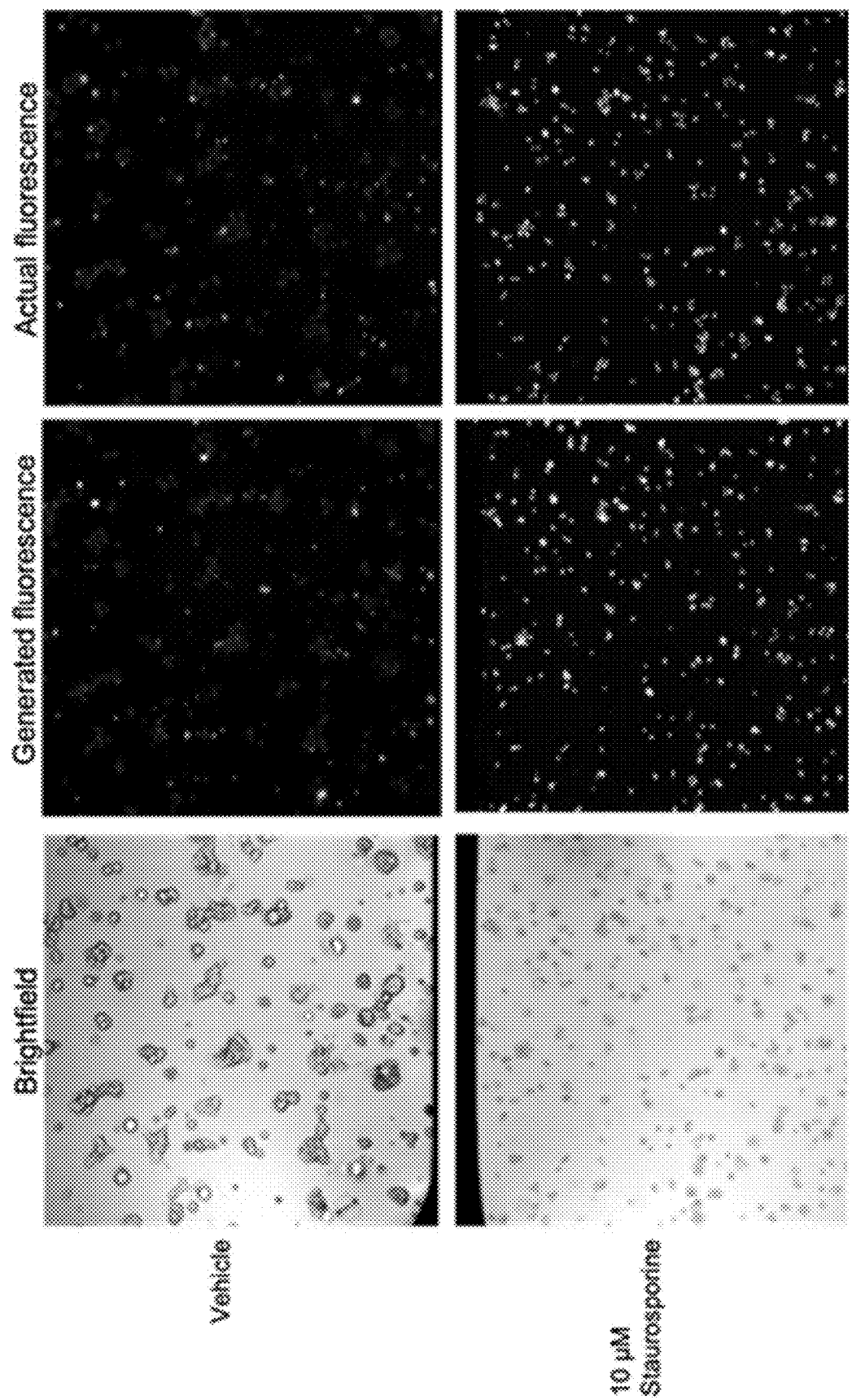
FIG. 6 shows a summary of a study, showing that a classifier trained using data sets obtained from the subject methods is capable of predicting morphological responses to pharmacological agents in a tumor organoid sample based on a brightfield image of the sample, in accordance with some embodiments of the present disclosure.

FIG. 6 shows two examples of predictions on a test set where the brightfield image is shown in the far left column, the model generated fluorescent image is shown in the middle column, and is the actual fluorescent image is shown in the far right column. As shown in FIG. 6, the trained model accurately predicted morphological responses to pharmacological agents based on brightfield images, thus potentially reducing a 384 well plate reading to as little as several minutes.

In summary, the systems and methods described here may measure therapeutic response in patient derived tumor organoids with high statistical confidence and technical reproducibility. The approach may be utilized in both research and clinical settings to better understand heterogeneity of therapeutic responses within and among patients, and further guide precision oncologic decision-making.

E. Example 5—Example PARP Inhibitor Drug Screen

A recent development in precision oncology is the use of poly (ADP-ribose) polymerase (PARP) inhibitors in patients whose tumors exhibit evidence of homologous recombination deficiency (HRD), especially in cases of somatic loss of BRCA1 or BRCA2, or LOH of functional BRCA1/2 alleles in patients with inherited non-functional BRCA1/2 alleles.

Figure 7A:
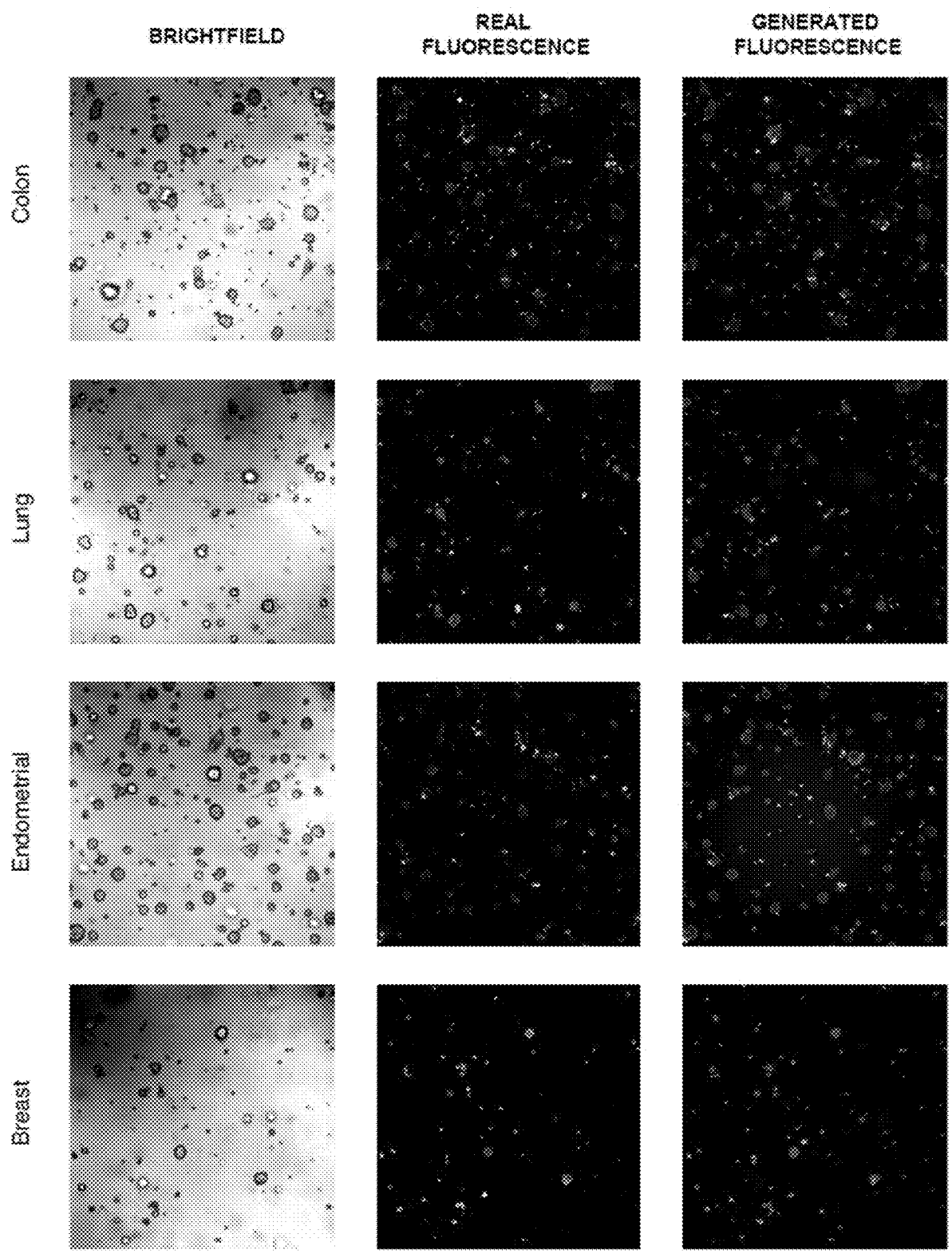
FIGS. 7A and 7B collectively illustrate a neural network-based model for predicting TO drug response.
Figure 7B:
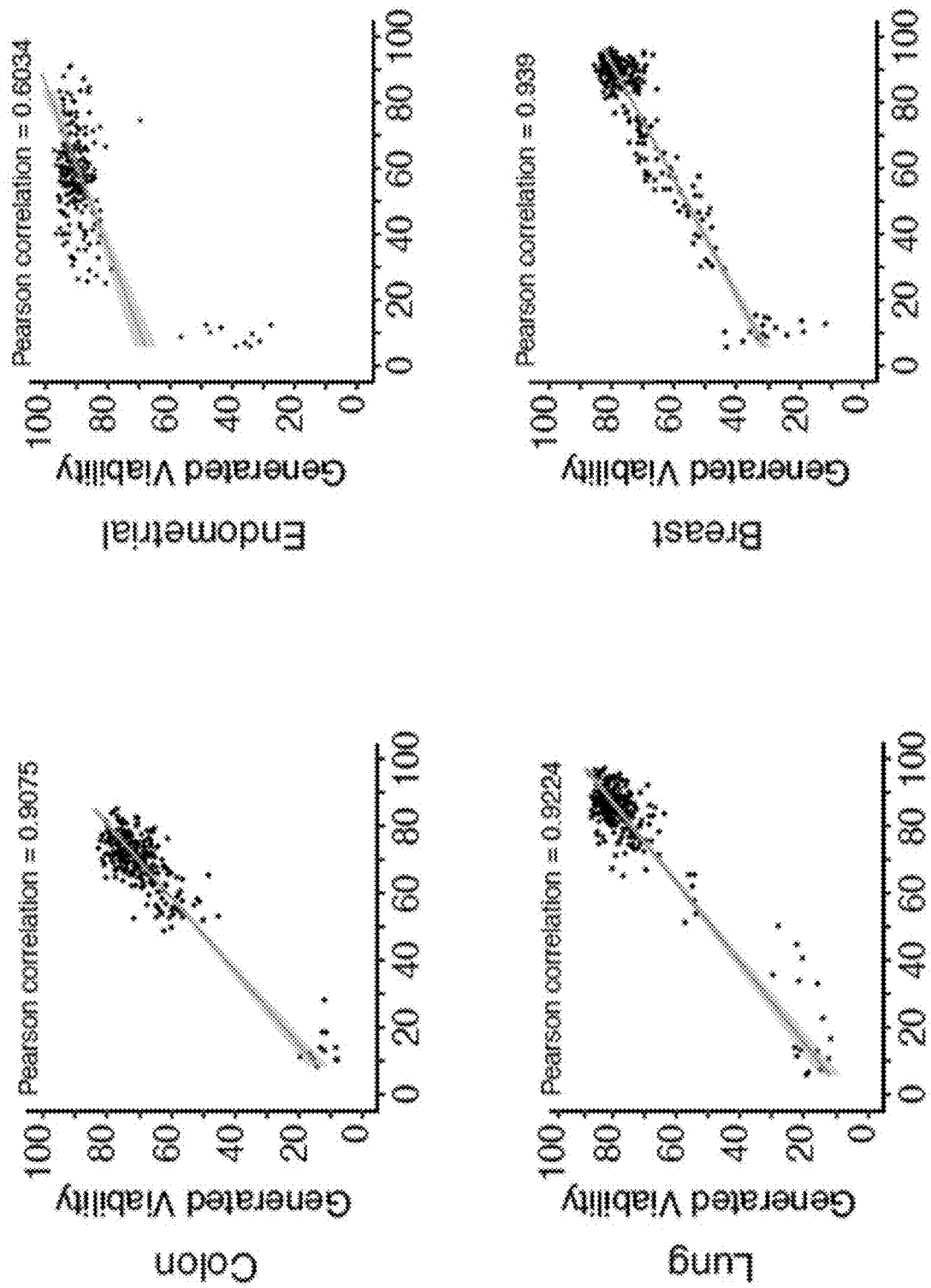
Figure 8:
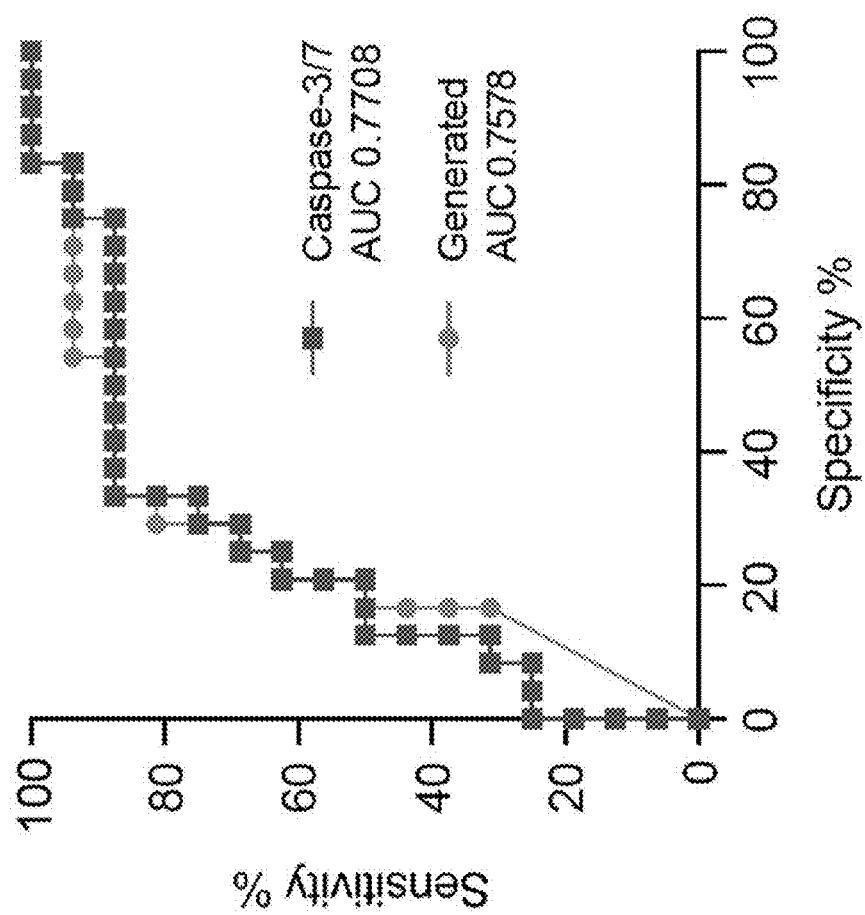
FIG. 8 illustrates AUC ROC curves between caspase and generated viabilities for the PARPi drug screen described in Example 5.

To advance TO utility for drug development and precision medicine, a universal label-free TO drug screening assay was developed. Without sacrificing throughput, this neural network prediction of drug response from light microscopy achieved high reproducibility compared to previously described metabolic-based assays (Tiriac et al., Cancer Discov 8, 1112-1129 (2018); Tiriac et al., Isolation and Characterization of Patient-derived Pancreatic Ductal Adenocarcinoma Organoid Models. J Vis Exp. (2020); Vlachogiannis et al., Science 359, 920-926 (2018)). Importantly, the network identified clinically relevant drug responses across a broad range of cancer-types including PARPi response from HRD-positive and -negative TOs. Notably, the PARPi responses in this small cohort of organoids were generally higher in HRD-positive TOs, with certain drugs exhibiting more potency in vitro than others. These observations confirm previous studies in patients (Coleman et al., Lancet 390, 1949-1961 (2017)) and short-term ovarian cancer organoid cultures (Hill et al., Cancer Discov 8, 1404-1421 (2018)). In addition, the RCA network identified response to afatinib associated with a high ERBB2 (HER2) amplification in the gastric TO. The distribution of response among the TO populations was demonstrative of functional intratumoral heterogeneity, as evidenced by a subset of the organoid population exhibiting resistance to afatinib. When correlated with the patient's clinical course, we found that the biopsy used to establish this TO line was obtained during disease progression on anti-ERBB2 therapy. Identifying heterogeneity in drug response has the potential to uncover mechanisms of primary resistance to novel therapeutics and may also provide predictive and prognostic information for treatment response in personalized clinical assays To provide proof-of-concept for this precision medicine approach, we evaluated ten TO lines (breast, endometrial, colon, ovarian, and NSCLC) based on HRD status. We assessed genome-wide LOH and categorized TOs as either HRD-positive or HRD-negative (Timms et al., Breast Cancer Research 16, 475 (2014); Yi et al., International Journal of Cancer 145, 1209-1220 (2019)). We then exposed TOs to a panel of FDA-approved PARP inhibitors and compared predicted drug responses, based on a trained neural network, to fluorescent-based readouts. We found the network predictions were strongly correlated with fluorescent-based drug responses across all cancer types (FIG. 7). Additionally, the classifier's measurement of PARPi response was able to discriminate between HRD-positive and HRD-negative organoids, comparable to fluorescent-based measurements (FIG. 8). Thus, the network-based assay accurately predicts clinically relevant drug responses.

1. Methodology

Tumor specimens were received from multiple institutions and processed for organoid culture at a CLIA-certified, CAP-accredited laboratory. All specimens were collected from consented patients under protocols monitored by the Institutional Review Board at each institution. The specimens were placed into iced RPMI (Lifetech) and processed the same day or after overnight storage at 4° C. The specimens were then digested to single-cell suspension with a GentleMACs instrument using the Miltenyi Tumor Dissociation kit (Miltenyi Biotec) according to the manufacturer's protocol.

2. Development and Culture of Tumor Organoids

Tumor organoids (TOs) were developed using an adapted epithelial cell-only submerged Matrigel culture technique (Sato et al., Nature 459, 262-265 (2009)). Briefly, cells were seeded at a density of 400 cells/μl in a 50 μl droplet of GFR Matrigel matrix (Corning) and grown in 24-well, flat-bottom tissue culture plates (Eppendorf). Growth medium was changed twice weekly and TOs were passaged every 1-2 weeks as needed. For passaging, growth media was removed, and Matrigel domes were disrupted mechanically by adding 500 μl TrypLE Express Enzyme (GIBCO) per well. TOs were transferred to 15-ml conical tubes and incubated in a 37° C. water bath for 10 minutes. Cells were then centrifuged at 200×g for 3 minutes and resuspended in 2 ml DPBS. Cells were resuspended in GFR Matrigel Matrix at 400 cells per microliter, and 50 μl domes were plated in pre-warmed, 24-well, flat-bottom plates and left to polymerize in a 37° C. incubator before the addition of 500 μl growth medium and 10 μM Y-27632 (Bio-techne) per well.

TO cultures were maintained in serum-free defined media conditions based on the consensus of previous reports for anticipated tumor types; namely, Advanced DMEM/F12 nutrient mix supplemented with B27, nicotinamide, n-acetylcysteine, recombinant growth factors EGF, Noggin, R-spondin1 (RSPO-1), Wnt-3A, FGF-2, 7, and 10, and small molecule inhibitors of p38 MAPK and TGF-beta.

3. Tumor Organoid Growth Analysis

Two independent observers determined organoid formation and serial passaging. Cells that demonstrated exponential increase in biomass on serial passage were deemed high proliferation and were cryopreserved in Recovery Cell Culture Freezing media (Gibco) when biomass reached >$10^6$ cells, following the manufacturer's protocol.

For quantitative organoid growth measurements, brightfield images of 24-well plates containing TOs were captured at a minimum of two different time points for the same passage using the ImageXpress Micro Confocal high-content imaging system (Molecular Devices, CA). The average total area sum of TOs was then plotted by time and the maximum growth rate was calculated by linear regression.

4. Pathologic Evaluation

Cultures were intermittently selected for formalin fixation and were prepared for H&E staining either via paraffin embedding or cyto-spin. H&E stains of organoid cultures from 320 patients were interpreted by a board-certified pathologist (GK) using histologic and cytologic features. Due to the use of growth factors, cultures displayed features of cellular proliferation including nuclear hyperchromasia with slight pleomorphism, increase in nuclear to cytoplasmic ratio and conspicuous nucleoli. Mitotic figures were frequent with few atypical forms. As such, the identification of malignant cells on the basis of cytologic features was obscured and was therefore based on the degree of these changes and the presence of marked loss of polarity and macronucleoli.

5. Sample Processing and Nucleic Acid Isolation

Organoids were dissociated using TrypLE Express Enzyme (GIBCO) and dissociated cells were immediately lysed in 350 μL of buffer RLT from the Allprep DNA/RNA Micro Kit (Qiagen) and stored at −80° C. Upon thawing, cell lysates were homogenized using QIAshredder spin columns (Qiagen). DNA and RNA were isolated using the Allprep DNA/RNA Micro Kit per manufacturer's instructions.

HLA-typed PBMC controls used for flow cytometry analysis were commercially procured as cryovials. PBMCs were thawed, washed, and resuspended in RPMI growth medium containing 10% FBS and 2 mM L-glutamine. Cells were left to recover for 1 hr at 37° C.

6. Next-Generation Sequencing

Next-generation sequencing was conducted as previously described (Beaubier et al., 2019a; Beaubier et al., 2019b). Briefly, nucleic acids were library prepped using a targeted gene panel as previously described, loaded on an Illumina HiSeq 4000 (Illumina), and DNA tumor libraries were sequenced to an average unique on-target depth of 500×. Similarly, RNA was prepared using an exome-capture RNA-Seq protocol and sequenced on the Illumina HiSeq 4000 platform. Variant calls and other molecular signatures, such as copy-number alterations, fusion events, and mRNA gene expression levels, were called and reported based on established guidelines.

7. Associations of Clinical and Molecular Features with Sustainable Growth

Clinical features including tissue site, T stage, N stage, M stage, race (caucasian, Asian, African-american, other), sex, neoadjuvant therapy treatment, and biospecimen features such as cell count and cold ischemia time (>12 hours) were structured as binary values and evaluated as a generalized linear model. Logistic regression was then applied to model high-proliferation organoid growth as a linear combination of clinical features using the stats R package (v3.5.2).

Analysis of single-nucleotide variants (SNV), copy-number alterations (CNA), and transcriptome profiling was performed using a NGS assay (Beaubier et al., Nat Biotechnol 37, 1351-1360 (2019); Beaubier et al., Oncotarget 10, 2384-2396 (2019)). The combined effect of pathogenic variants within a gene classified by the assay platform were then tested using a gene-based test as implemented in SKAT-o (Lee et al., American journal of human genetics 91, 224-237 (2012)). Gene-based tests were performed within each cancer and combined across cancers. Transcriptome analysis was performed as described below.

Copy-number calls were determined for paired probes by an internal algorithm that considered tumor purity and sequencing depth in a two-pass approach. First, segmentation of chromosomal regions was performed to define chromosomal regions with specific copy numbers using panel coverage data and transformed to provide probe-level copy-number values. Next, the segment data was used in a second algorithm to approximate integer copy-number values for major (total observed copies at a given loci) and minor allele count as well as estimates for tumor purity, ploidy, and B-allele frequencies (BAF). Following segmentation, copy number and tumor purity were assessed using a grid search methodology. Starting from the initial estimate of the tumor purity lower bound, a copy-number state matrix was generated containing total/minor copy state combinations and their expected log ratios and log BAF given the initialized tumor purity. Each segment was projected into the matrix and the log probability that it belonged to each analyzed copy state was computed based on drawing from a normal probability density function defined by the expected log-ratio and the pre-computed log ratio standard deviation. The same process was applied for log BAF with a sliding-weight scale based on the number of heterozygous germline variants observed within the segment. This was done to account for noise in log BAF in the context of sparse observations.

8. Drug Screen and Image Analysis

A 320-drug panel was purchased from Selleckchem, which is detailed on their website (found online at selleckchem.com/screening/selective-library.html). Additional compounds are included in STAR methods.

TOs were dissociated as described above and resuspended in a 30:70% mix of GFR Matrigel:growth media at a concentration of 100 cells/μl. The solution was added to 384-well assay plates (Corning) at 20 μl per well for a final concentration of 2,000 cells per well. Assay plates were covered with a Breathe-Easy sealing membrane (Sigma Aldrich) to prevent evaporation. TOs were grown for 72 hours before drug addition. Drugs were prepared in growth media with 2.5 μM Caspase-3/7 Green Apoptosis Assay Reagent (Essen Bioscience). Serial dilutions of each molecule were prepared in 384-well polystyrene plates (Nunc). Diluted drug was added to the assay plate using an Integra Viaflo pipette (Integra) mounted on an Integra Assist Plus Pipetting Robot (Integra). Assay plates were again covered with a Breathe-Easy sealing membrane and TOs were exposed to drugs for another 72 hours before imaging.

Prior to imaging, TOs were incubated with 4 μM Hoechst 33342 (Fisher Scientific) and 300 nM TO-PRO-3 Iodide (642/661) (Invitrogen) for 1.5-2 hours. Assay plates were imaged using an ImageXpress Micro Confocal (Molecular Devices) at 10× magnification so that ~100-200 TOs were imaged per well. Images were acquired as 4×15 μm Z-stacks and the 2D projections were analyzed to assess cell viability. Confocal images were analyzed using the MetaXpress software (Molecular Devices) custom module editor feature to design an analysis module that identified TOs by clusters of Hoechst 33342 staining, individual cells by Hoechst 33342 staining, and dead/dying cells by either TO-PRO-3 or Caspase-3/7 staining. The result of this analysis module is a spreadsheet detailing the number of live and dead cells for every individual organoid.

The percentage of viable cells per organoid was calculated based on the image analysis described above. Organoids with fewer than three cells and larger than the top one percent by size were excluded from analysis. The mean viability for all organoids at a given drug concentration was used in dose-response curves to calculate AUC. AUC was calculated using the computeAUC function using settings for "actual" AUC of the R Package PharmacoGx (v1.17.1). Heatmaps of AUC values were generated using the Pheatmap package (v1.0.12) in R. Scatterplots of AUC values were generated using the ggplot2 package (v3.3.0) in R.

9. Response and Label-Free Prediction from Brightfield Images

The multiplexed fluorescence images were 1024×1024×3 RGB images, where red corresponds to dead cells (TO-PRO-3), green to apoptotic cells (Caspase-3/7), and blue to nuclei (Hoechst 33342). All wavelength channels underwent a simple intensity rescaling contrast enhancement technique to brighten and sharpen the TOs/cells as well as remove background noise. The mean viability for all organoids per site was obtained from the MetaXpress software readout.

F. Example 6—PARPi Sensitivity in Colorectal Cancer Tumor Organoids

In this example, PARPi sensitivity was measured for two colorectal tumor organoids (TOs). Each TO or source tissue associated with the TO (for example, a patient biopsy used to generate the TO) were genetically sequenced to determine whether the TO had variants (mutations) in homologous recombination proteins (including BRCA1 and BRCA2) and whether the TO was likely to have homologous recombination deficiency (HRD), according to an HRD engine.

None of the TOs had pathogenic single nucleotide variants (SNVs) in BRCA1 or BRCA2. None of the TOs had loss of heterozygosity (LOH) of BRCA1 or BRCA2. None of the TOs had bi-allelic loss of BRCA1 or BRCA2 (both a pathogenic SNV and LOH) and traditionally would not have been expected to have HRD or respond to PARPi therapy. BRCA mutation and LOH status was based on sequencing analysis of either the TO or the source tissue.

Regardless of the lack of bi-allelic BRCA loss, some of the TOs were analyzed by an HRD engine and predicted to have HRD based on other criteria.

The HRD engine is described in U.S. patent application Ser. No. 16/789,363, titled "An Integrated Machine-Learning Framework To Predict Homologous Recombination Deficiency", filed Feb. 12, 2020, the contents of which are incorporated by reference herein in their entirety for any and all purposes. In another embodiment, the HRD score or likelihood of PARPi sensitivity may be determined by the trained classifier disclosed herein.

One of the TOs had a low HRD score (unlikely to have HRD or be sensitive to PARPi) and one of the TOs had a high HRD score (likely to have HRD and be sensitive to PARPi).

All of the TOs were grown in culture wells and each well was exposed for 96 hours to either a negative control (1% DMSO) or one of multiple PARPi therapies (Rucaparib, Niraparib, Pamiparib, Talazoparib, Olaparib, or Veliparib) at one of three concentrations (1 nM, 100 nM, or 10,000 nM). Some of the organoids were exposed to additional concentrations as noted in the x-axis of the figures.

At 96 hours the cells were stained by either caspase 3/7 or TO-PRO-3 (caspase 3/7 stained dying, apoptic cells and TO-PRO-3 stained dead cells). For each PARPi therapy, efficacy was measured at each concentration by detecting the proportion of viable cells that were not stained and normalizing that proportion to the proportion of viable cells in the negative control well, where the proportion of negative control well cells that were viable was adjusted to 100% or 75% (indicated in the figure). This normalization resulted in some experimental wells having a proportion of viable cells that was greater than 100% (or 75%). A best fit curve was generated for the viability proportion at each concentration and an inverse AUC was calculated as the area between actual cell viability (the best fit curve) and 100% (or 75%) cell viability. The inverse AUC served as an additional measure of PARPi efficacy, where a higher inverse AUC indicated a higher drug efficacy.

The PARPi therapies were hypothesized to be more effective against TOs with a high HRD score than TOs with a low HRD score.

The viability data shown below indicate that the PARPi therapies were more effective against TOs with a high HRD score than TOs with a low HRD score.

For organoids that were PARPi sensitive, PARPi therapies were effective against TOs that did not have BRCA1 or BRCA2 mutations or biallelic inactivation of BRCA1 or BRCA2.

Figure 9A:
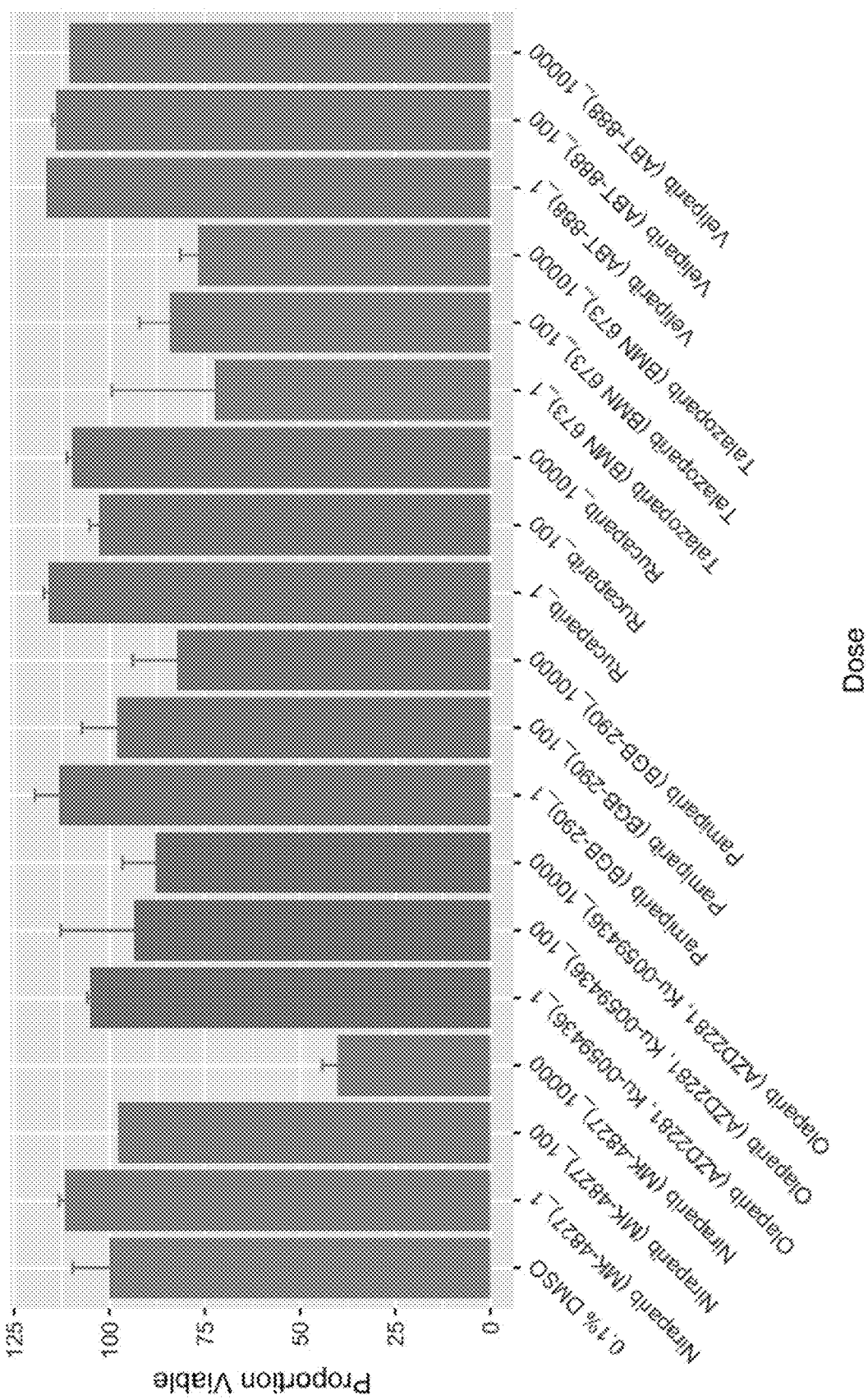
FIGS. 9A and 9B illustrate viability data for a tumor organoid having a low HRD score, a pathogenic BRCA1 mutation, no BRCA2 mutations and no BRCA1 or BRCA2 LOH. The x-axis label indicates the PARP-i therapy and dose. The y-axis indicates the percent of cells in the well that were viable, normalized to the DMSO mock condition (negative control).
Figure 9B:
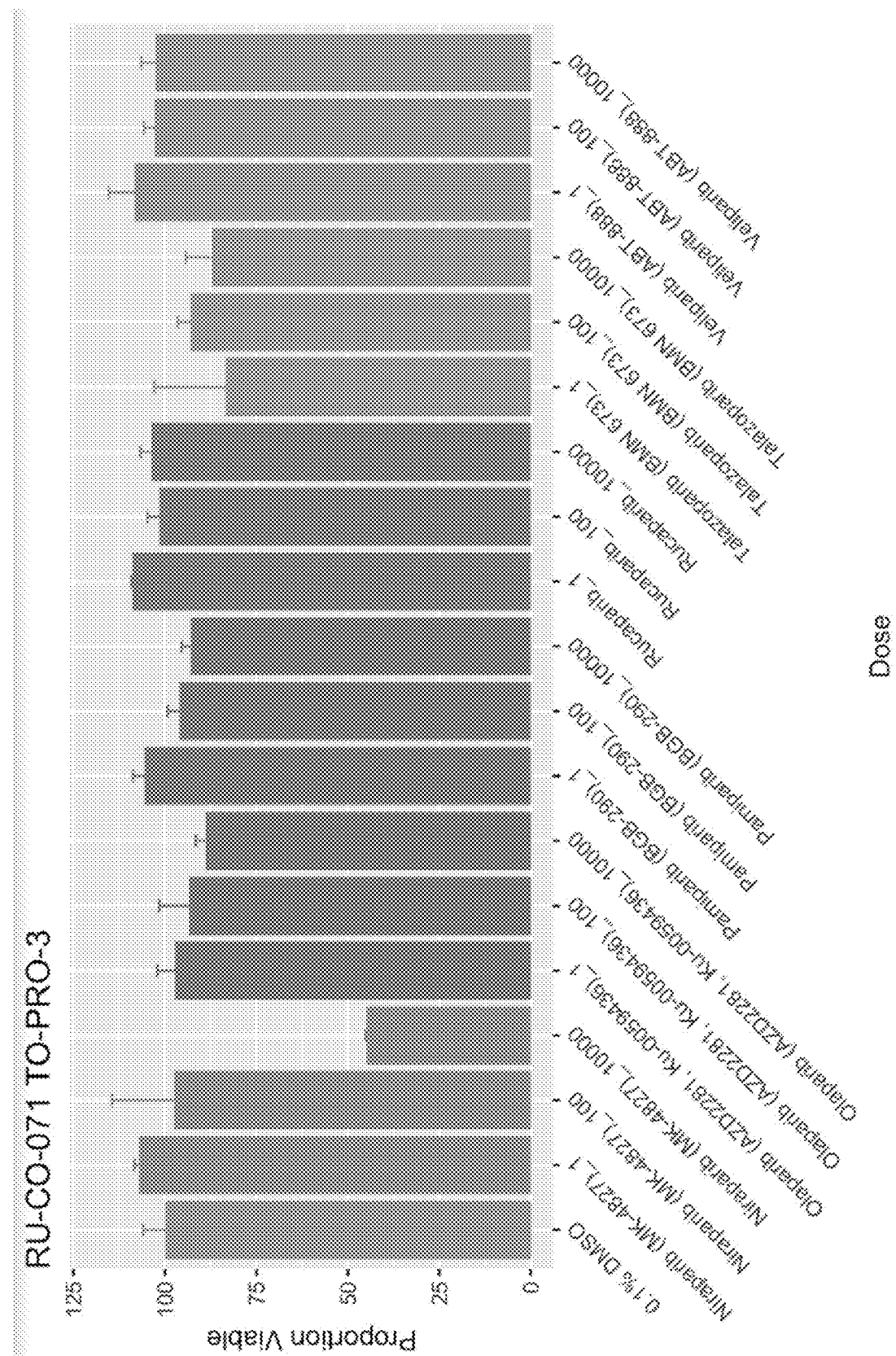

FIGS. 9A and 9B illustrate viability data for a tumor organoid having a low HRD score, a pathogenic BRCA1 mutation, no BRCA2 mutations and no BRCA1 or BRCA2 LOH. The x-axis label indicates the PARP-i therapy and dose. The γ-axis indicates the percent of cells in the well that were viable, normalized to the DMSO mock condition (negative control).

Figure 10A:
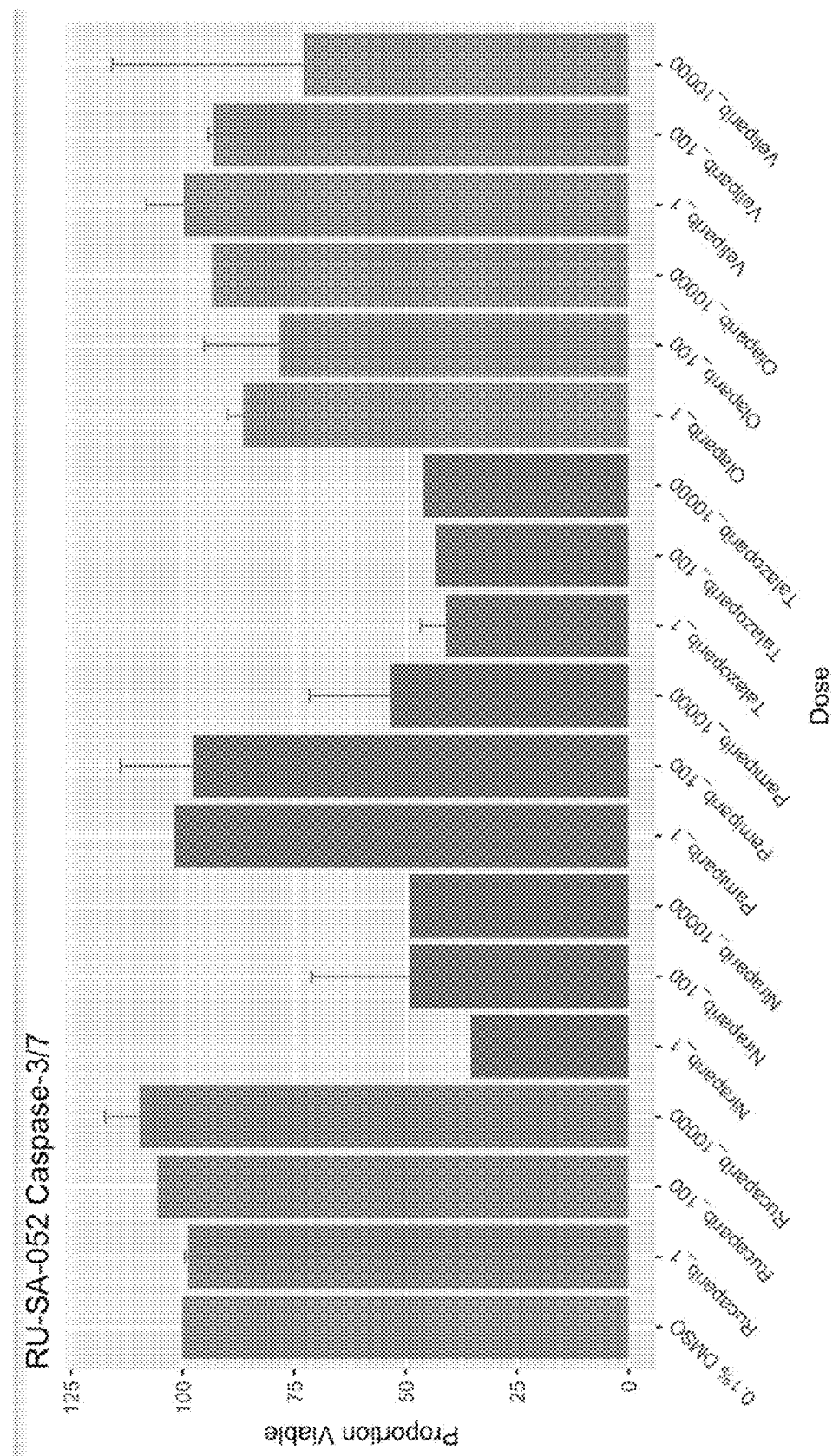
FIGS. 10A and 10B illustrate viability data for a colorectal tumor organoid having a high HRD score, no BRCA1 or BRCA2 mutations and no BRCA1 or BRCA2 LOH. The x-axis label indicates the PARP-i therapy and dose. The y-axis indicates the percent of cells in the well that were viable, normalized to the DMSO mock condition (negative control).
Figure 10B:
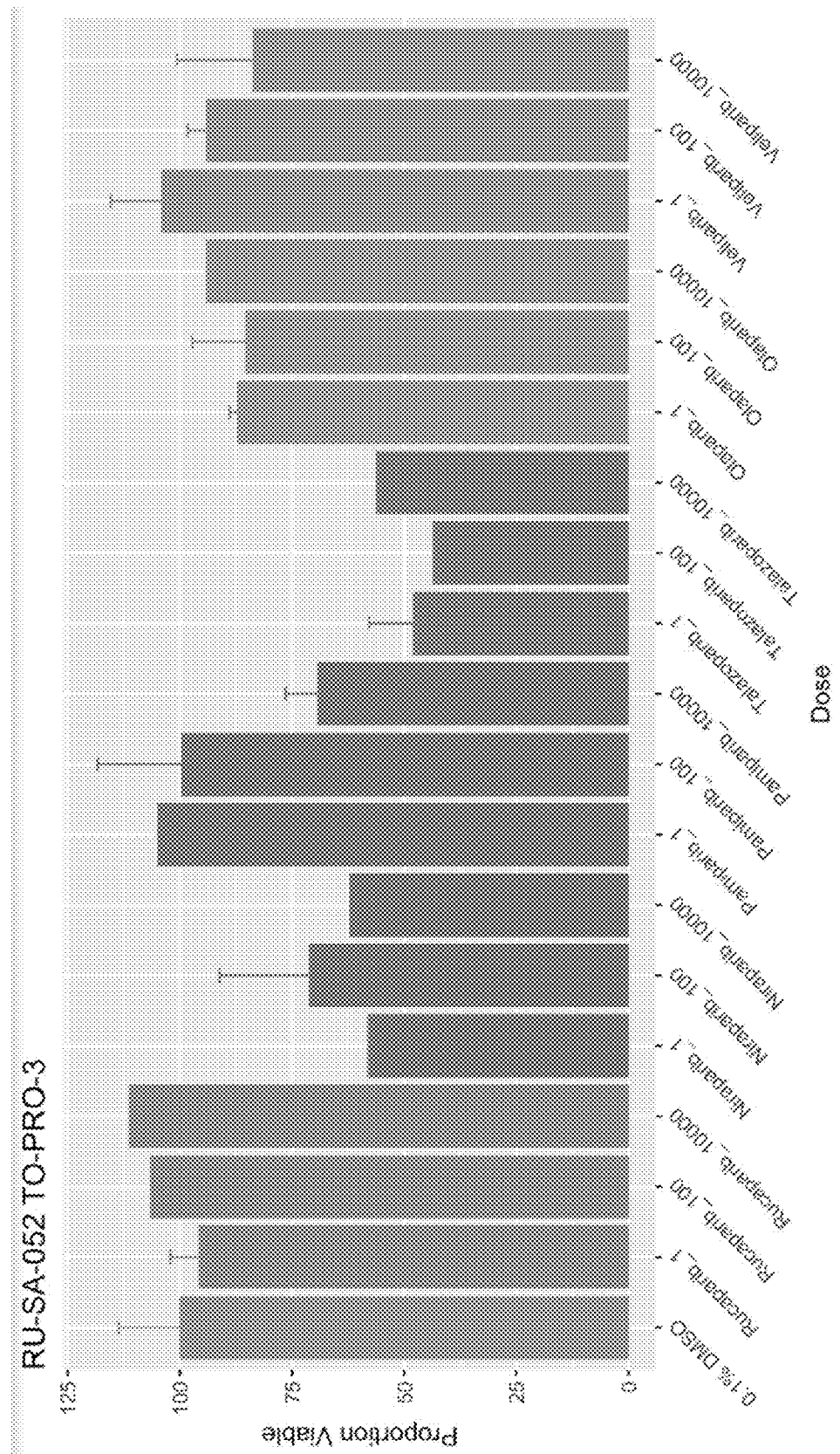

FIGS. 10A and 10B illustrate viability data for a colorectal tumor organoid having a high HRD score, no BRCA1 or BRCA2 mutations and no BRCA1 or BRCA2 LOH. The x-axis label indicates the PARP-i therapy and dose. The γ-axis indicates the percent of cells in the well that were viable, normalized to the DMSO mock condition (negative control).

G. Example 7—PARPi Sensitivity in Breast Cancer Tumor Organoids

In this example, PARPi sensitivity was measured for three tumor organoids (TOs). Each TO or source tissue associated with the TO (for example, a patient biopsy used to generate the TO) were genetically sequenced to determine whether the TO had variants (mutations) in homologous recombination proteins (including BRCA1 and BRCA2) and whether the TO was likely to have homologous recombination deficiency (HRD), according to an HRD engine.

None of the TOs had pathogenic single nucleotide variants (SNVs) in BRCA1 or BRCA2. None of the TOs had loss of heterozygosity (LOH) of BRCA1 or BRCA2. None of the TOs had bi-allelic loss of BRCA1 or BRCA2 (both a pathogenic SNV and LOH) and traditionally would not have been expected to have HRD or respond to PARPi therapy. BRCA mutation and LOH status was based on sequencing analysis of either the TO or the source tissue.

Regardless of the lack of bi-allelic BRCA loss, some of the TOs were analyzed by an HRD engine and predicted to have HRD based on other criteria.

The HRD engine is described in U.S. patent application Ser. No. 16/789,363, titled "An Integrated Machine-Learning Framework To Predict Homologous Recombination Deficiency", filed Feb. 12, 2020, the contents of which are incorporated by reference herein in their entirety for any and all purposes. In another embodiment, the HRD score or likelihood of PARPi sensitivity may be determined by the trained classifier disclosed herein.

Two of the TOs had a low HRD score (unlikely to have HRD or be sensitive to PARPi) and one of the TOs had a high HRD score (likely to have HRD and be sensitive to PARPi).

All of the TOs were grown in culture wells and each well was exposed for 96 hours to either a negative control (1% DMSO) or one of multiple PARPi therapies (Rucaparib, Niraparib, Pamiparib, Talazoparib, Olaparib, or Veliparib) at one of three concentrations (1 nM, 100 nM, or 10,000 nM). Some of the organoids were exposed to additional concentrations as noted in the x-axis of the figures.

At 96 hours the cells were stained by either caspase 3/7 or TO-PRO-3. Caspase 3/7 stained dying, apoptic cells and TO-PRO-3 stained dead cells. For each PARPi therapy, efficacy was measured at each concentration by detecting the proportion of viable cells that were not stained and normalizing that proportion to the proportion of viable cells in the negative control well, where the proportion of negative control well cells that were viable was adjusted to 100% or 75% (indicated in the figure). This normalization resulted in some experimental wells having a proportion of viable cells that was greater than 100% (or 75%). A best fit curve was generated for the viability proportion at each concentration and an inverse AUC was calculated as the area between actual cell viability (the best fit curve) and 100% (or 75%) cell viability. The inverse AUC served as an additional measure of PARPi efficacy, where a higher inverse AUC indicated a higher drug efficacy.

The PARPi therapies were hypothesized to be more effective against TOs with a high HRD score than TOs with a low HRD score.

The viability data shown below indicate that the PARPi therapies were more effective against TOs with a high HRD score than TOs with a low HRD score.

For organoids that were PARPi sensitive, PARPi therapies were effective against TOs that did not have BRCA1 or BRCA2 mutations or biallelic inactivation of BRCA1 or BRCA2.

Figure 11A:
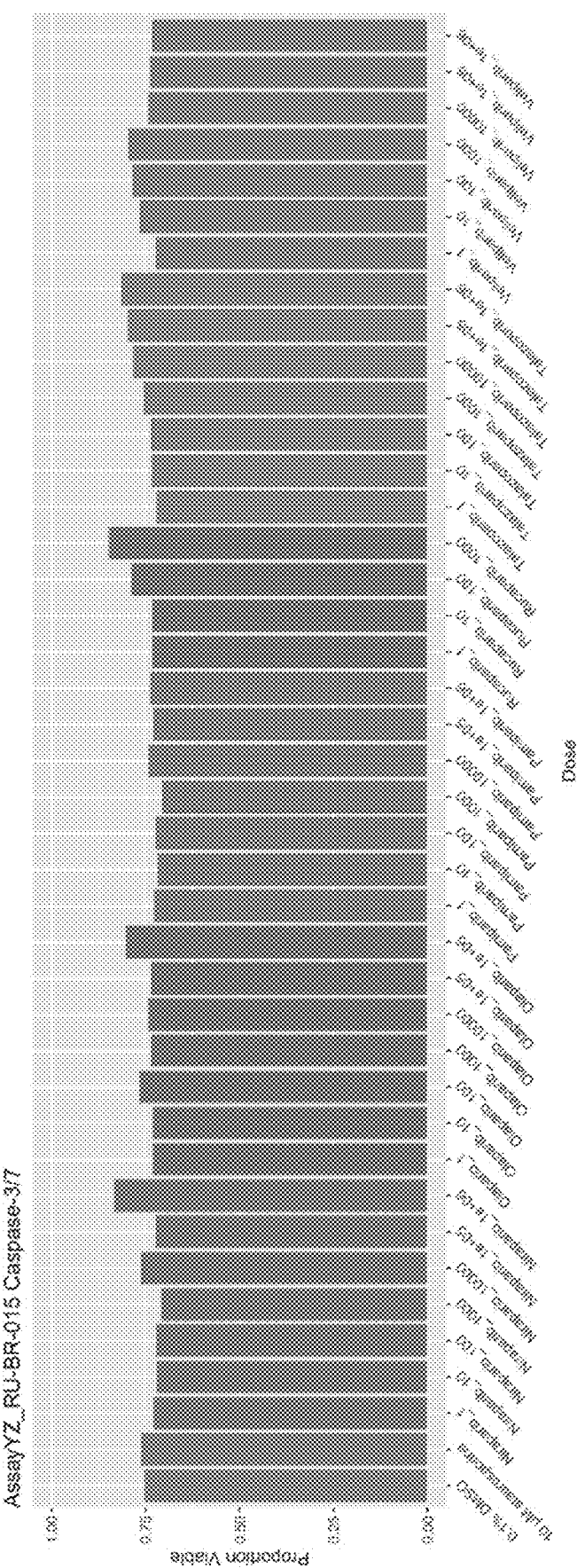
FIGS. 11A and 11B illustrate viability data for a tumor organoid having a low HRD score, no BRCA1 or BRCA2 mutations and no BRCA1 or BRCA2 LOH. The x-axis label indicates the PARP-i therapy and dose. The y-axis indicates the percent of cells in the well that were viable, normalized to the DMSO mock condition (negative control).
Figure 11B:
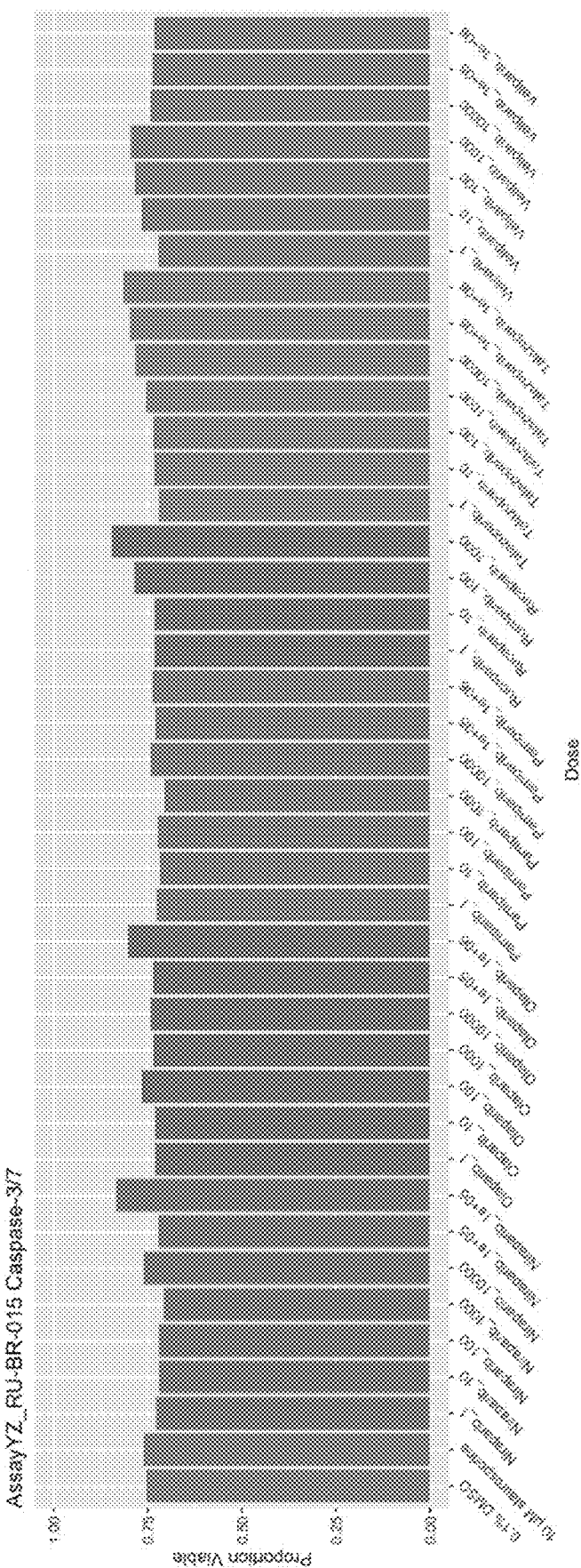

FIGS. 11A and 11B illustrate viability data for a tumor organoid having a low HRD score, no BRCA1 or BRCA2 mutations and no BRCA1 or BRCA2 LOH. The x-axis label indicates the PARP-i therapy and dose. The γ-axis indicates the percent of cells in the well that were viable, normalized to the DMSO mock condition (negative control).

Figure 12A:
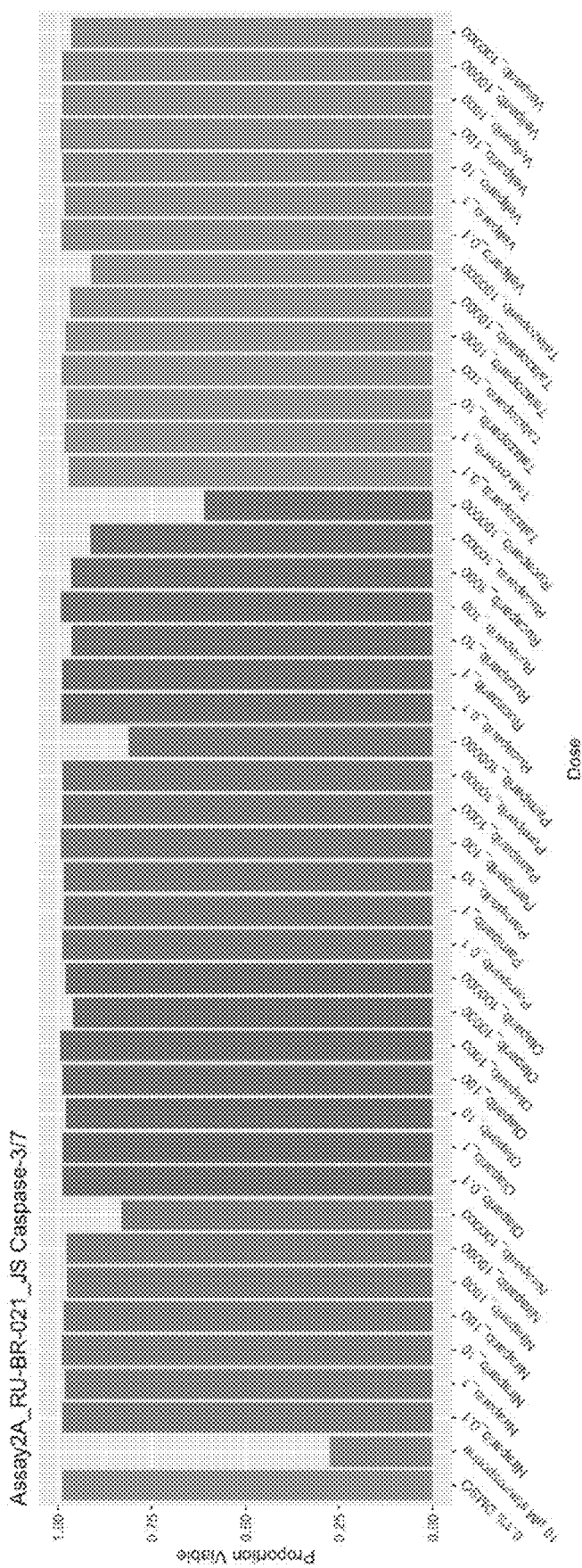
FIGS. 12A and 12B illustrate viability data for a tumor organoid having a low HRD score, no BRCA1 or BRCA2 mutations and no BRCA1 or BRCA2 LOH. The x-axis label indicates the PARP-i therapy and dose. The y-axis indicates the percent of cells in the well that were viable, normalized to the DMSO mock condition (negative control).
Figure 12B:
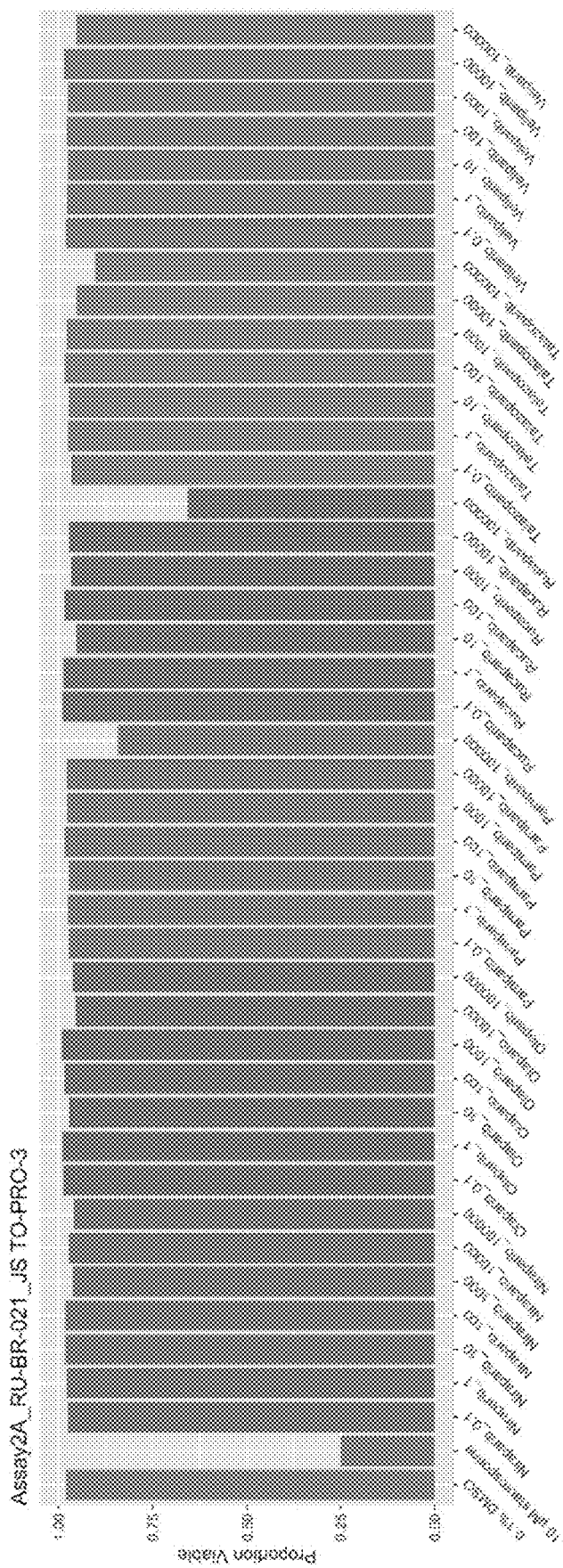

FIGS. 12A and 12B illustrate viability data for a tumor organoid having a low HRD score, no BRCA1 or BRCA2 mutations and no BRCA1 or BRCA2 LOH. The x-axis label indicates the PARP-i therapy and dose. The γ-axis indicates the percent of cells in the well that were viable, normalized to the DMSO mock condition (negative control).

Figure 13A:
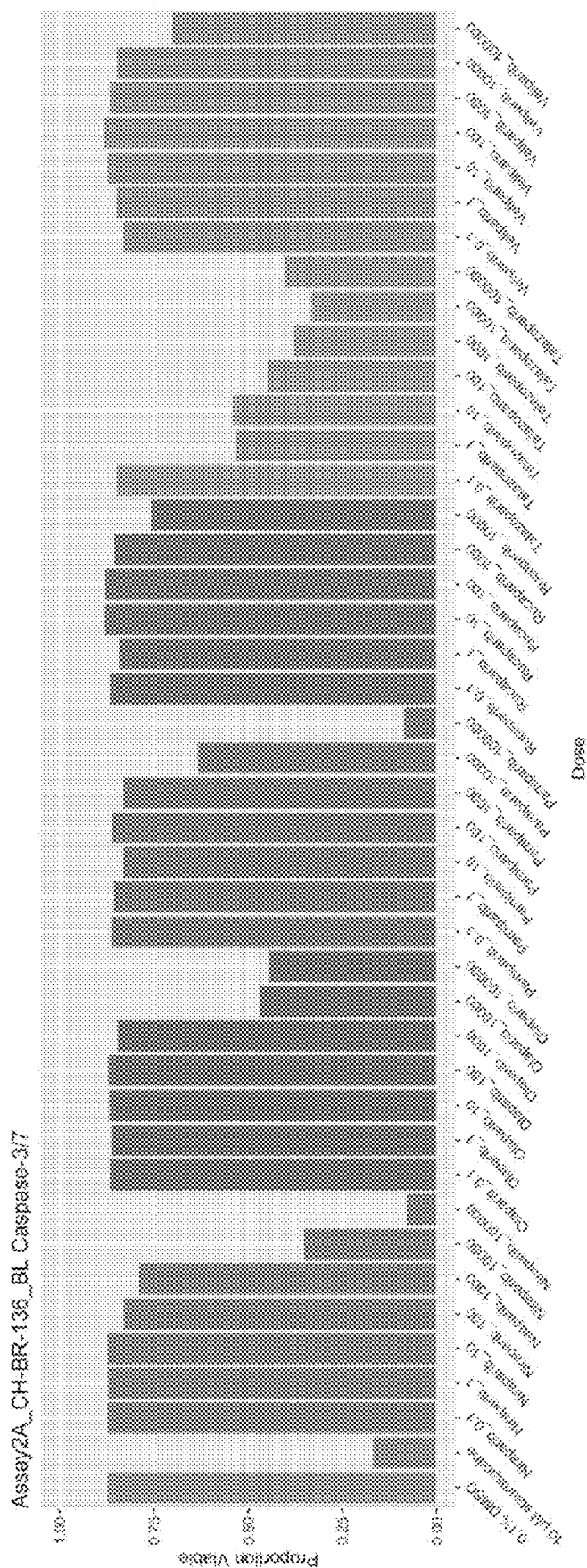
FIGS. 13A and 13B illustrate viability data for a tumor organoid having a high HRD score, no BRCA1 or BRCA2 mutations and no BRCA1 or BRCA2 LOH. The x-axis label indicates the PARP-i therapy and dose. The y-axis indicates the percent of cells in the well that were viable, normalized to the DMSO mock condition (negative control).
Figure 13B:
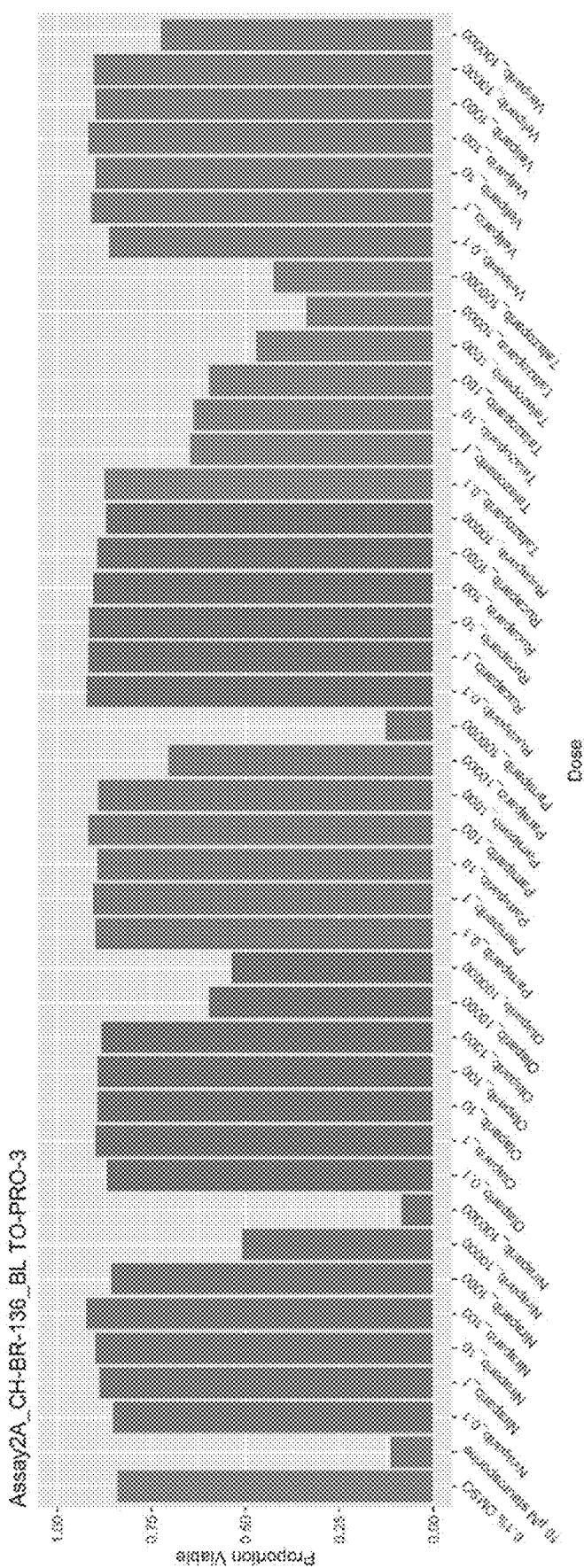

FIGS. 13A and 13B illustrate viability data for a tumor organoid having a high HRD score, no BRCA1 or BRCA2 mutations and no BRCA1 or BRCA2 LOH. The x-axis label indicates the PARP-i therapy and dose. The γ-axis indicates the percent of cells in the well that were viable, normalized to the DMSO mock condition (negative control).

H. Example 8—PARPi Sensitivity in Ovarian Cancer Tumor Organoids

In this example, PARPi sensitivity was measured for two ovarian cancer tumor organoids (TOs). Each TO or source tissue associated with the TO (for example, a patient biopsy used to generate the TO) were genetically sequenced to determine whether the TO had variants (mutations) in homologous recombination proteins (including BRCA1 and BRCA2) and whether the TO was likely to have homologous recombination deficiency (HRD), according to an HRD engine.

None of the TOs had pathogenic single nucleotide variants (SNVs) in BRCA1 or BRCA2. One of the TOs had loss of heterozygosity (LOH) of BRCA1 or BRCA2 and had only one functioning copy of the gene. None of the TOs had bi-allelic loss of BRCA1 or BRCA2 (both a pathogenic SNV and LOH) and traditionally would not have been expected to have HRD or respond to PARPi therapy. BRCA mutation and LOH status was based on sequencing analysis of either the TO or the source tissue.

Regardless of the lack of bi-allelic BRCA loss, some of the TOs were analyzed by an HRD engine and predicted to have HRD based on other criteria.

The HRD engine is described in U.S. patent application Ser. No. 16/789,363, titled "An Integrated Machine-Learning Framework To Predict Homologous Recombination Deficiency", filed Feb. 12, 2020, the contents of which are incorporated by reference herein in their entirety for any and all purposes. In another embodiment, the HRD score or likelihood of PARPi sensitivity may be determined by the trained classifier disclosed herein.

One of the TOs had a low HRD score (unlikely to have HRD or be sensitive to PARPi) and one of the TOs had a high HRD score (likely to have HRD and be sensitive to PARPi).

All of the TOs were grown in culture wells and each well was exposed for 96 hours to either a negative control (1% DMSO) or one of multiple PARPi therapies (Rucaparib, Niraparib, Pamiparib, Talazoparib, Olaparib, or Veliparib) at one of three concentrations (1 nM, 100 nM, or 10,000 nM). Some of the organoids were exposed to additional concentrations as noted in the x-axis of the figures.

At 96 hours the cells were stained by either caspase 3/7 or TO-PRO-3. Caspase 3/7 stained dying, apoptic cells and TO-PRO-3 stained dead cells. For each PARPi therapy, efficacy was measured at each concentration by detecting the proportion of viable cells that were not stained and normalizing that proportion to the proportion of viable cells in the negative control well, where the proportion of negative control well cells that were viable was adjusted to 100% or 75% (indicated in the figure). This normalization resulted in some experimental wells having a proportion of viable cells that was greater than 100% (or 75%). A best fit curve was generated for the viability proportion at each concentration and an inverse AUC was calculated as the area between actual cell viability (the best fit curve) and 100% (or 75%) cell viability. The inverse AUC served as an additional measure of PARPi efficacy, where a higher inverse AUC indicated a higher drug efficacy.

The PARPi therapies were hypothesized to be more effective against TOs with a high HRD score than TOs with a low HRD score.

The viability data shown below indicate that the PARPi therapies were more effective against TOs with a high HRD score than TOs with a low HRD score.

For organoids that were PARPi sensitive, PARPi therapies were effective against TOs that did not have BRCA1 or BRCA2 mutations or biallelic inactivation of BRCA1 or BRCA2.

Figure 14A:
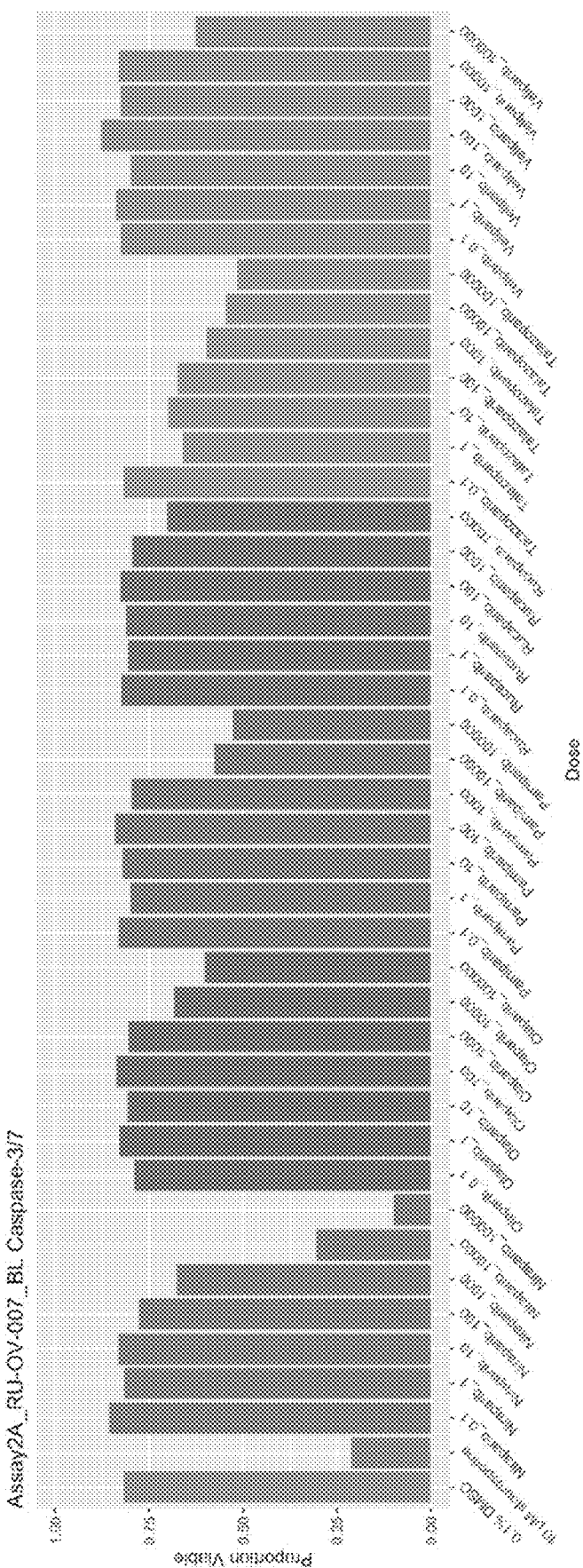
FIGS. 14A and 14B illustrate viability data for a tumor organoid having a low HRD score, no BRCA1 or BRCA2 mutations, BRCA1 LOH, and no BRCA2 LOH. The x-axis label indicates the PARP-i therapy and dose. The y-axis indicates the percent of cells in the well that were viable, normalized to the DMSO mock condition (negative control).
Figure 14B:
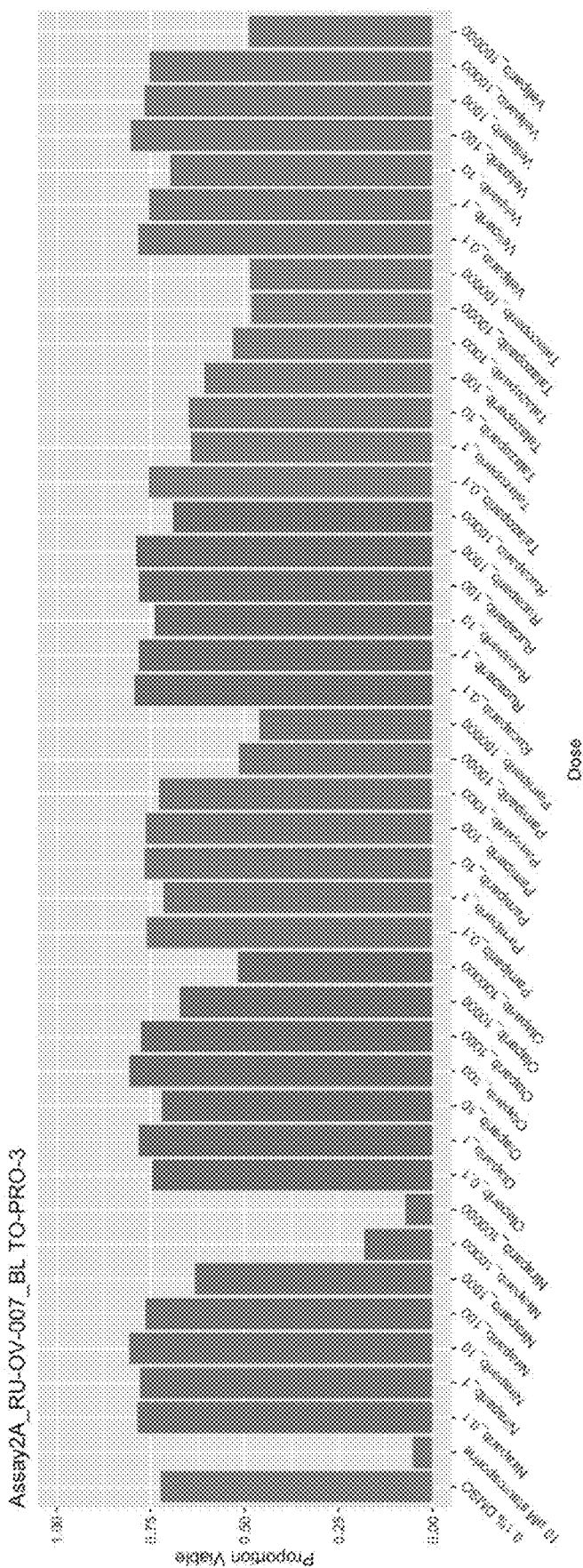

FIGS. 14A and 14B illustrate viability data for a tumor organoid having a low HRD score, no BRCA1 or BRCA2 mutations, BRCA1 LOH, and no BRCA2 LOH. The x-axis label indicates the PARP-i therapy and dose. The y-axis indicates the percent of cells in the well that were viable, normalized to the DMSO mock condition (negative control).

Figure 15A:
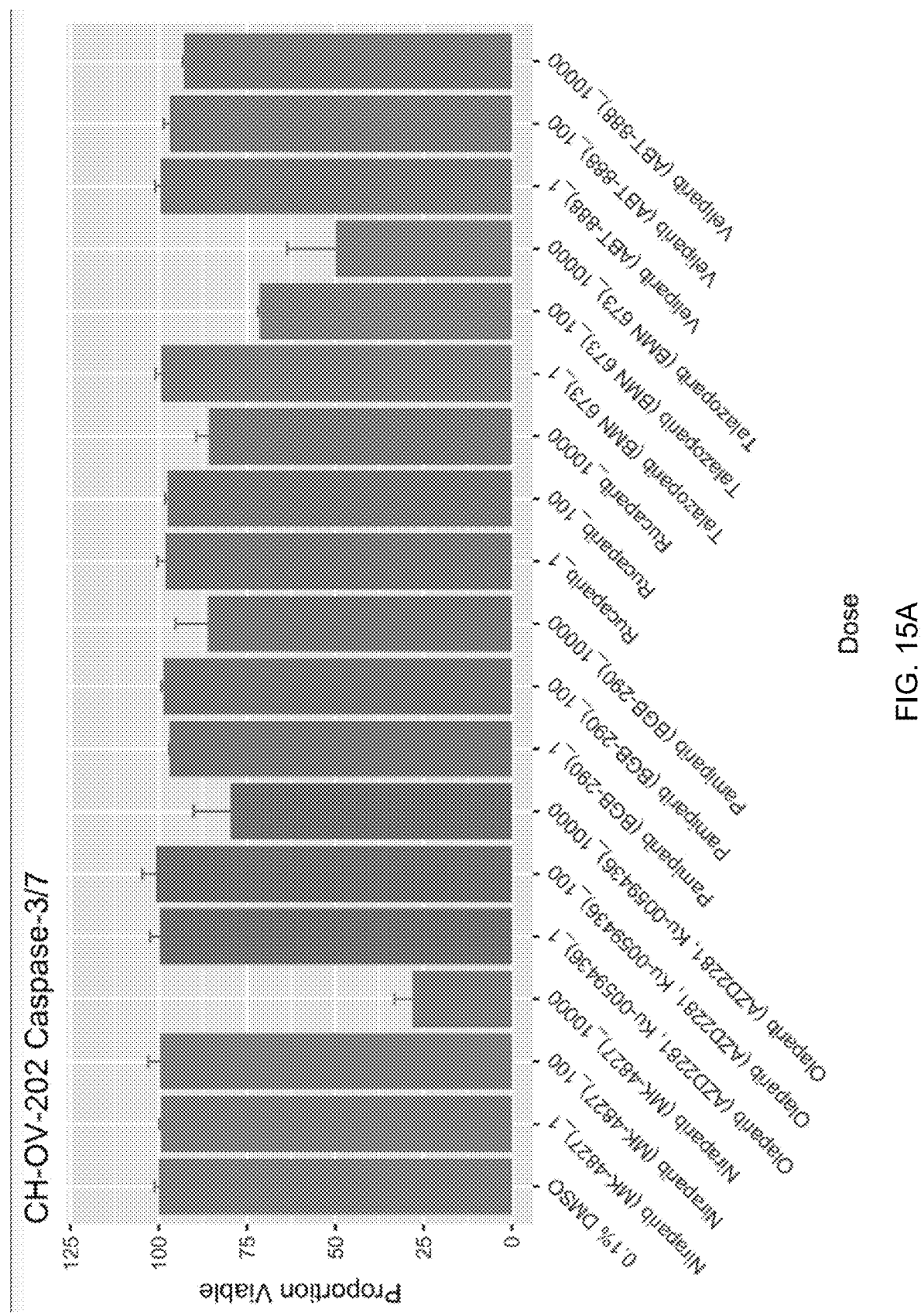
FIGS. 15A and 15B illustrate viability data for a tumor organoid having a high HRD score, no BRCA1 or BRCA2 mutations and no BRCA1 or BRCA2 LOH. The x-axis label indicates the PARP-i therapy and dose. The y-axis indicates the percent of cells in the well that were viable, normalized to the DMSO mock condition (negative control). Lower doses of PARPi were more effective for this organoid than the low HRD shown in the previous figures organoid.
Figure 15B:
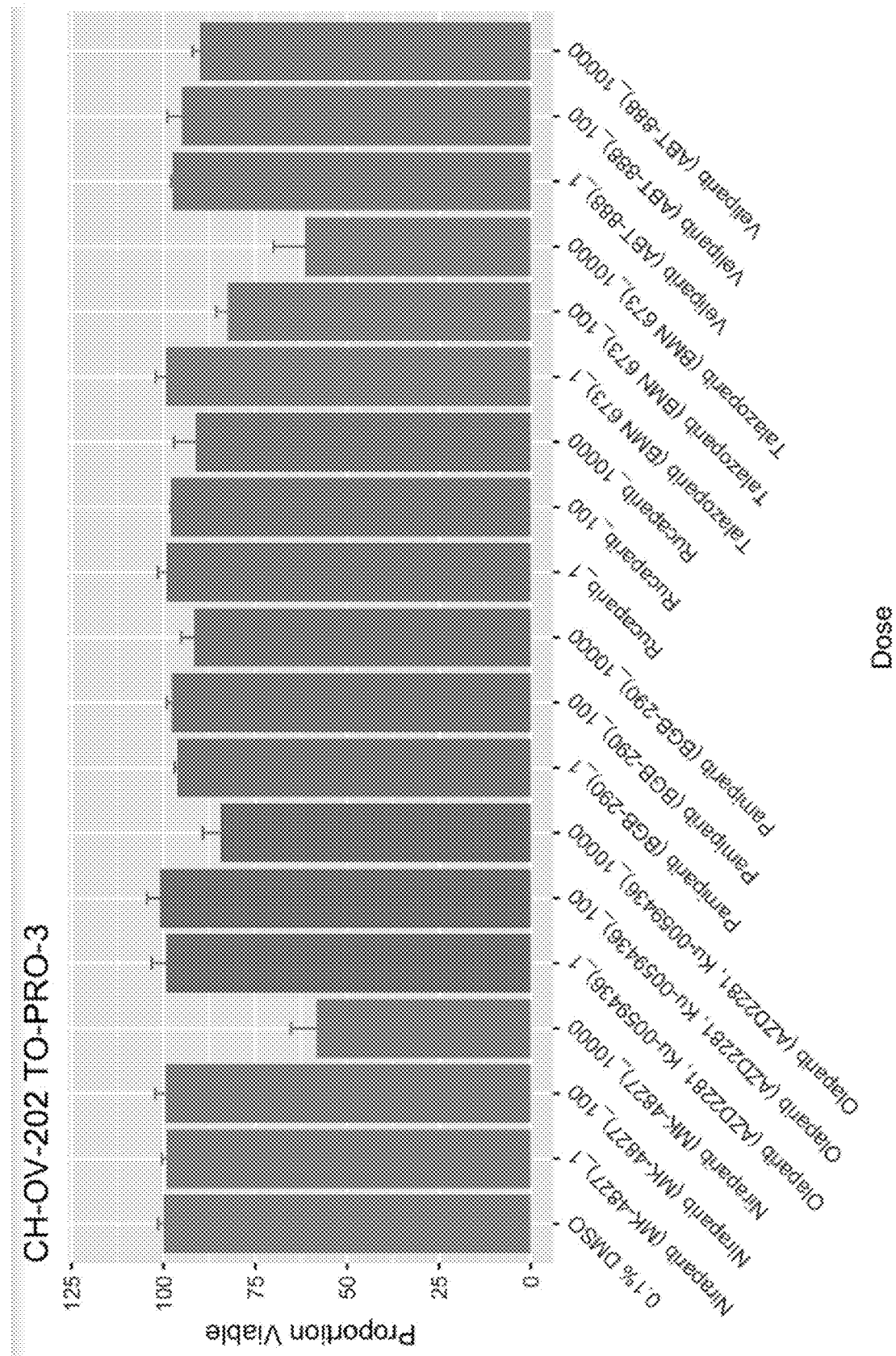

FIGS. 15A and 15B illustrate viability data for a tumor organoid having a high HRD score, no BRCA1 or BRCA2 mutations and no BRCA1 or BRCA2 LOH. The x-axis label indicates the PARP-i therapy and dose. The y-axis indicates the percent of cells in the well that were viable, normalized to the DMSO mock condition (negative control). Lower doses of PARPi were more effective for this organoid than the low HRD shown in the previous figures organoid.

I. Example 9—PARPi Sensitivity in Non-Small Cell Lung Cancer Cancer Tumor Organoids In this example, PARPi sensitivity was measured for two non-small cell lung cancer tumor organoids (TOs). Each TO or source tissue associated with the TO (for example, a patient biopsy used to generate the TO) were genetically sequenced to determine whether the TO had variants (mutations) in homologous recombination proteins (including BRCA1 and BRCA2) and whether the TO was likely to have homologous recombination deficiency (HRD), according to an HRD engine.

None of the TOs had pathogenic single nucleotide variants (SNVs) in BRCA1 or BRCA2. None of the TOs had loss of heterozygosity (LOH) of BRCA1 or BRCA2. None of the TOs had bi-allelic loss of BRCA1 or BRCA2 (both a pathogenic SNV and LOH) and traditionally would not have been expected to have HRD or respond to PARPi therapy. BRCA mutation and LOH status was based on sequencing analysis of either the TO or the source tissue.

Regardless of the lack of bi-allelic BRCA loss, some of the TOs were analyzed by an HRD engine and predicted to have HRD based on other criteria.

The HRD engine is described in U.S. patent application Ser. No. 16/789,363, titled "An Integrated Machine-Learning Framework To Predict Homologous Recombination Deficiency", filed Feb. 12, 2020, the contents of which are incorporated by reference herein in their entirety for any and all purposes. In another embodiment, the HRD score or likelihood of PARPi sensitivity may be determined by the trained classifier disclosed herein.

One of the TOs had a low HRD score (unlikely to have HRD or be sensitive to PARPi) and one of the TOs had a high HRD score (likely to have HRD and be sensitive to PARPi).

All of the TOs were grown in culture wells and each well was exposed for 96 hours to either a negative control (1% DMSO) or one of multiple PARPi therapies (Rucaparib, Niraparib, Pamiparib, Talazoparib, Olaparib, or Veliparib) at one of three concentrations (1 nM, 100 nM, or 10,000 nM). Some of the organoids were exposed to additional concentrations as noted in the x-axis of the figures.

At 96 hours the cells were stained by either caspase 3/7 or TO-PRO-3. Caspase 3/7 stained dying, apoptic cells and TO-PRO-3 stained dead cells. For each PARPi therapy, efficacy was measured at each concentration by detecting the proportion of viable cells that were not stained and normalizing that proportion to the proportion of viable cells in the negative control well, where the proportion of negative control well cells that were viable was adjusted to 100% or 75% (indicated in the figure). This normalization resulted in some experimental wells having a proportion of viable cells that was greater than 100% (or 75%). A best fit curve was generated for the viability proportion at each concentration and an inverse AUC was calculated as the area between actual cell viability (the best fit curve) and 100% (or 75%) cell viability. The inverse AUC served as an additional measure of PARPi efficacy, where a higher inverse AUC indicated a higher drug efficacy.

The PARPi therapies were hypothesized to be more effective against TOs with a high HRD score than TOs with a low HRD score.

The viability data shown below indicate that the PARPi therapies were more effective against TOs with a high HRD score than TOs with a low HRD score.

For organoids that were PARPi sensitive, PARPi therapies were effective against TOs that did not have BRCA1 or BRCA2 mutations or biallelic inactivation of BRCA1 or BRCA2.

Figure 16A:
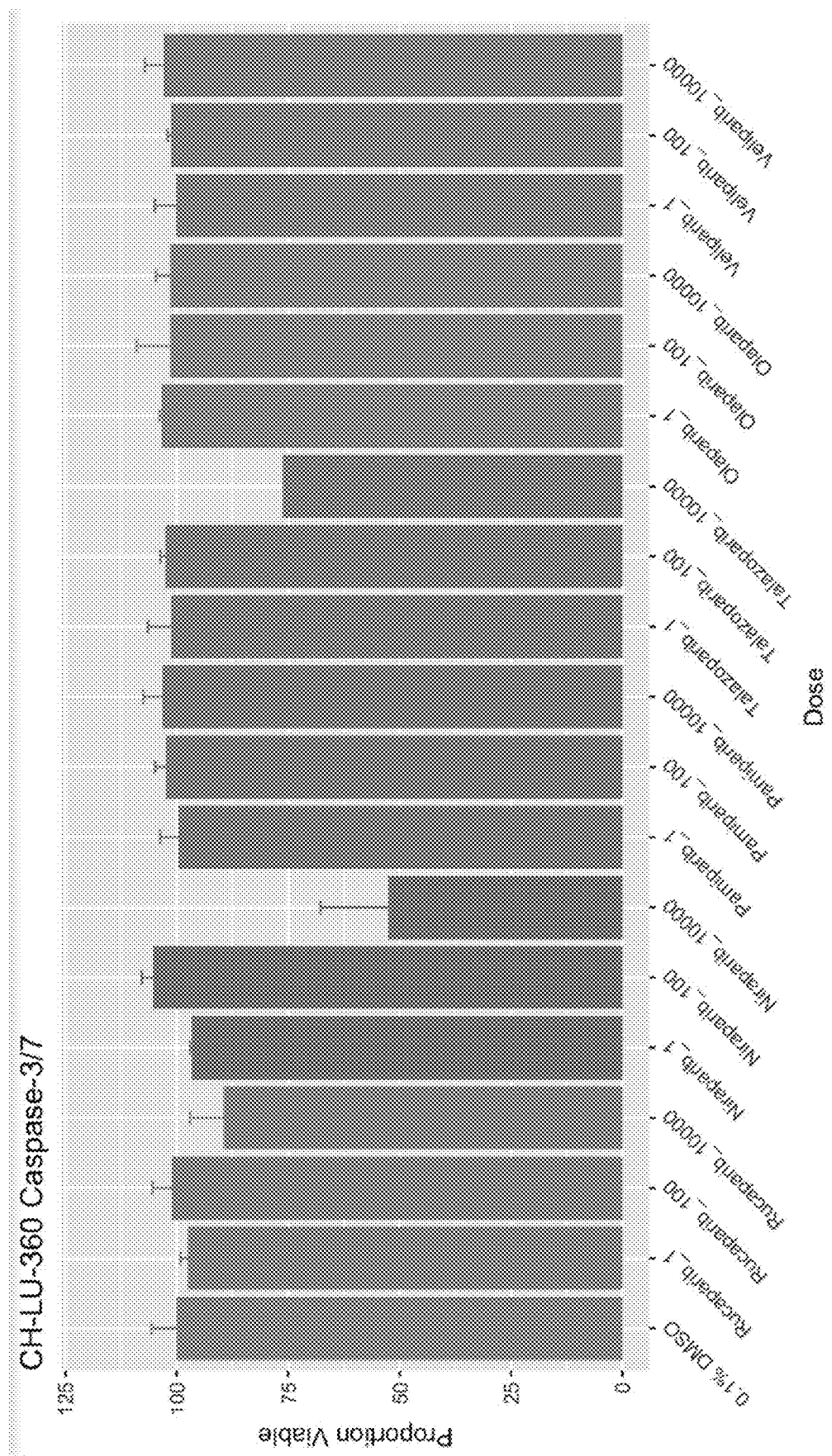
FIGS. 16A and 16B illustrate viability data for a tumor organoid having a low HRD score, no BRCA1 or BRCA2 mutations and no BRCA1 or BRCA2 LOH. The x-axis label indicates the PARP-i therapy and dose. The y-axis indicates the percent of cells in the well that were viable, normalized to the DMSO mock condition (negative control).
Figure 16B:
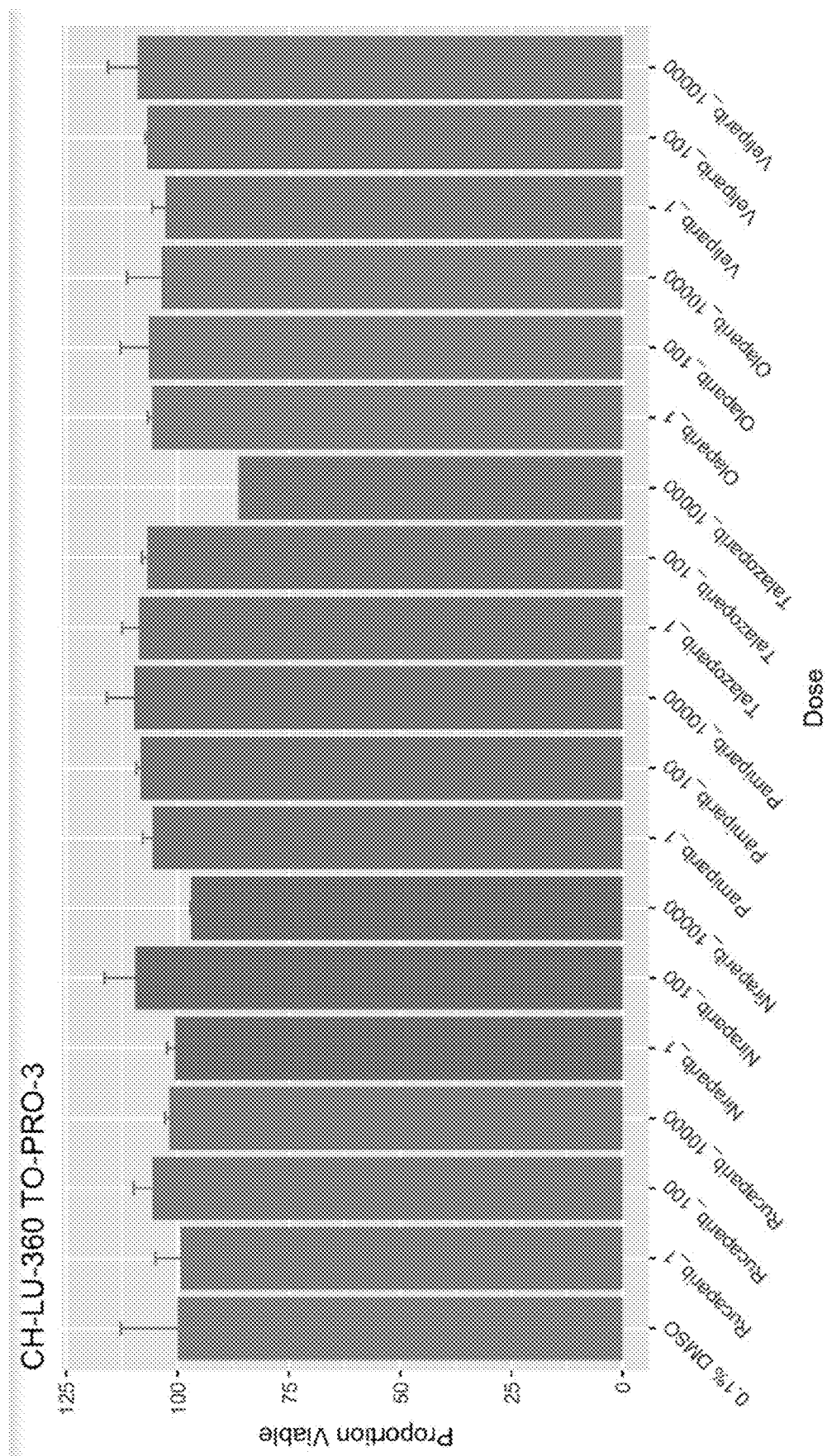

FIGS. 16A and 16B illustrate viability data for a tumor organoid having a low HRD score, no BRCA1 or BRCA2 mutations and no BRCA1 or BRCA2 LOH. The x-axis label indicates the PARP-i therapy and dose. The γ-axis indicates the percent of cells in the well that were viable, normalized to the DMSO mock condition (negative control).

Figure 17A:
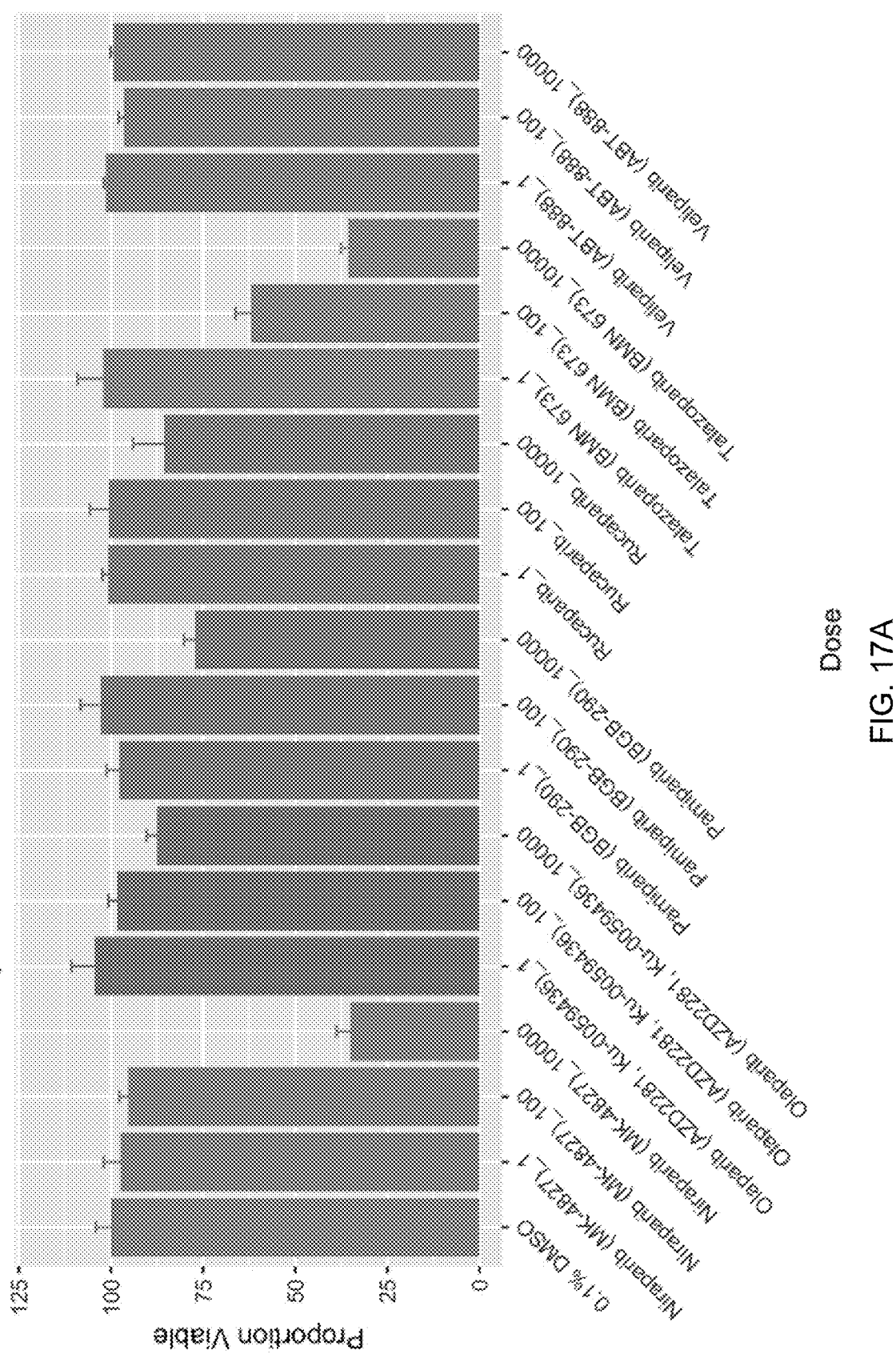
FIGS. 17A and 17B illustrate viability data for a tumor organoid having a high HRD score, no BRCA1 or BRCA2 mutations, no BRCA1 LOH and having BRCA2 LOH. The x-axis label indicates the PARP-i therapy and dose. The y-axis indicates the percent of cells in the well that were viable, normalized to the DMSO mock condition (negative control).
Figure 17B:
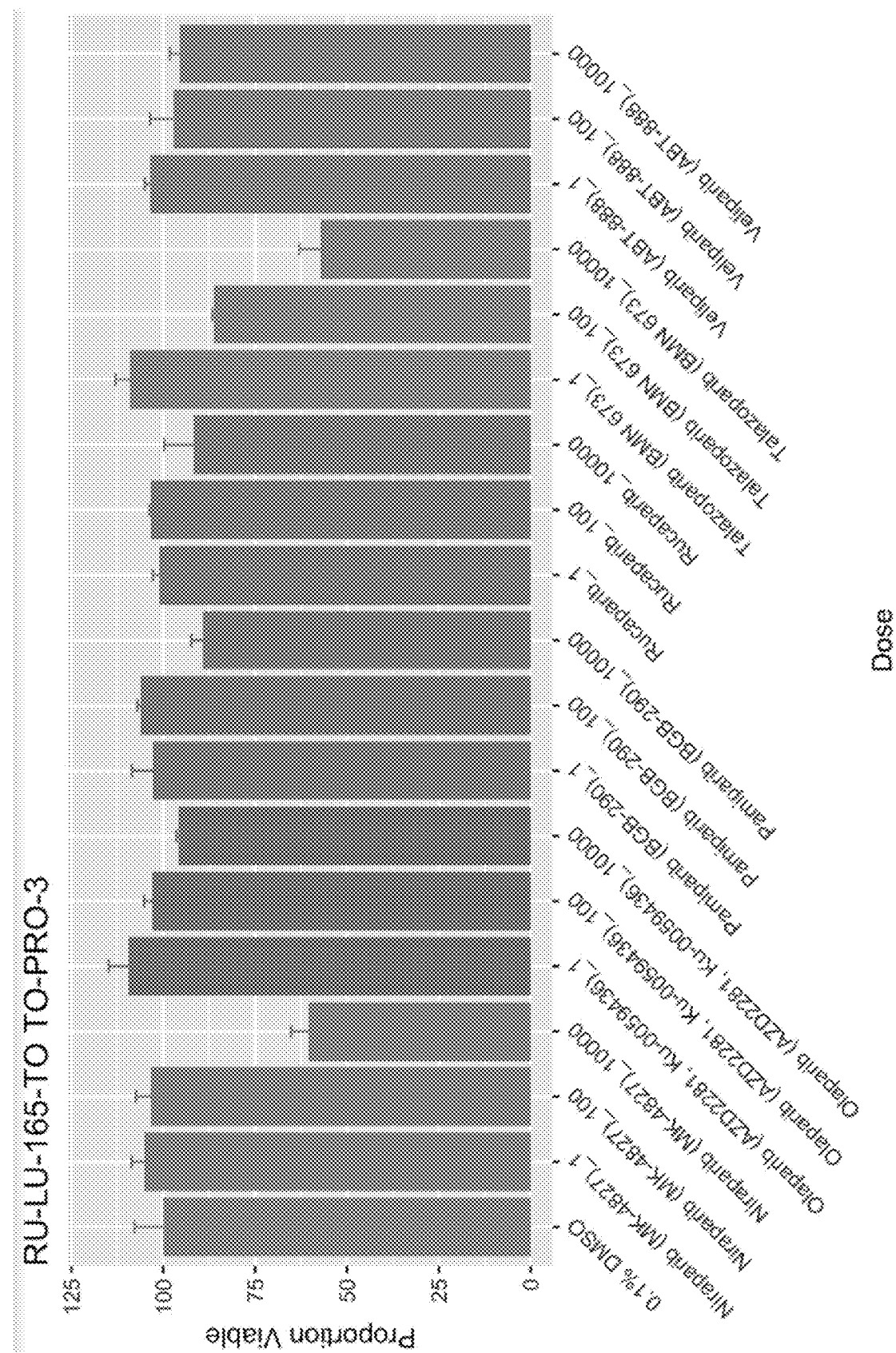

FIGS. 17A and 17B illustrate viability data for a tumor organoid having a high HRD score, no BRCA1 or BRCA2 mutations, no BRCA1 LOH and having BRCA2 LOH. The x-axis label indicates the PARP-i therapy and dose. The γ-axis indicates the percent of cells in the well that were viable, normalized to the DMSO mock condition (negative control).

J. Example 10—PARPi Sensitivity in Endometrial Tumor Organoids

In this example, PARPi sensitivity was measured for one endometrial tumor organoid (TOs). Each TO or source tissue associated with the TO (for example, a patient biopsy used to generate the TO) were genetically sequenced to determine whether the TO had variants (mutations) in homologous recombination proteins (including BRCA1 and BRCA2) and whether the TO was likely to have homologous recombination deficiency (HRD), according to an HRD engine.

None of the TOs had pathogenic single nucleotide variants (SNVs) in BRCA1 or BRCA2. None of the TOs had loss of heterozygosity (LOH) of BRCA1 or BRCA2. None of the TOs had bi-allelic loss of BRCA1 or BRCA2 (both a pathogenic SNV and LOH) and traditionally would not have been expected to have HRD or respond to PARPi therapy. BRCA mutation and LOH status was based on sequencing analysis of either the TO or the source tissue.

The TO was analyzed by an HRD engine and predicted not to have HRD.

The HRD engine is described in U.S. patent application Ser. No. 16/789,363, titled "An Integrated Machine-Learning Framework To Predict Homologous Recombination Deficiency", filed Feb. 12, 2020, the contents of which are incorporated by reference herein in their entirety for any and all purposes. In another embodiment, the HRD score or likelihood of PARPi sensitivity may be determined by the trained classifier disclosed herein.

One of the TOs had a low HRD score (unlikely to have HRD or be sensitive to PARPi).

All of the TOs were grown in culture wells and each well was exposed for 96 hours to either a negative control (1% DMSO) or one of multiple PARPi therapies (Rucaparib, Niraparib, Pamiparib, Talazoparib, Olaparib, or Veliparib) at one of three concentrations (1 nM, 100 nM, or 10,000 nM). Some of the organoids were exposed to additional concentrations as noted in the x-axis of the figures.

At 96 hours the cells were stained by either caspase 3/7 or TO-PRO-3. Caspase 3/7 stained dying, apoptic cells and TO-PRO-3 stained dead cells. For each PARPi therapy, efficacy was measured at each concentration by detecting the proportion of viable cells that were not stained and normalizing that proportion to the proportion of viable cells in the negative control well, where the proportion of negative control well cells that were viable was adjusted to 100% or 75% (indicated in the figure). This normalization resulted in some experimental wells having a proportion of viable cells that was greater than 100% (or 75%). A best fit curve was generated for the viability proportion at each concentration and an inverse AUC was calculated as the area between actual cell viability (the best fit curve) and 100% (or 75%) cell viability. The inverse AUC served as an additional measure of PARPi efficacy, where a higher inverse AUC indicated a higher drug efficacy.

The viability data shown below indicate that the PARPi therapies were not effective against a TO with a low HRD score.

Figure 18A:
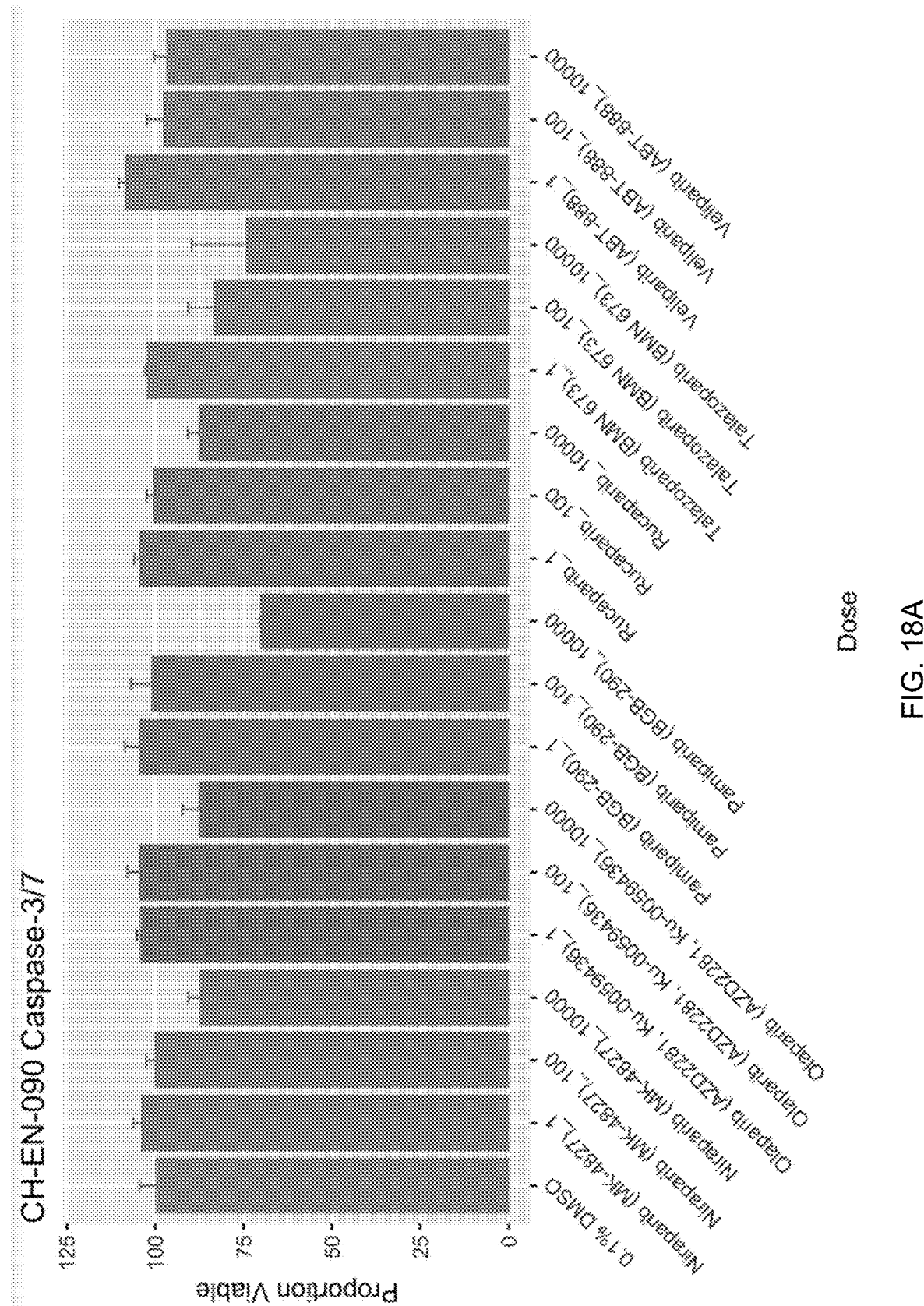
FIGS. 18A and 18B illustrate viability data for a tumor organoid having a low HRD score, no BRCA1 or BRCA2 mutations and no BRCA1 or BRCA2 LOH. The x-axis label indicates the PARP-i therapy and dose. The y-axis indicates the percent of cells in the well that were viable, normalized to the DMSO mock condition (negative control).
Figure 18B:
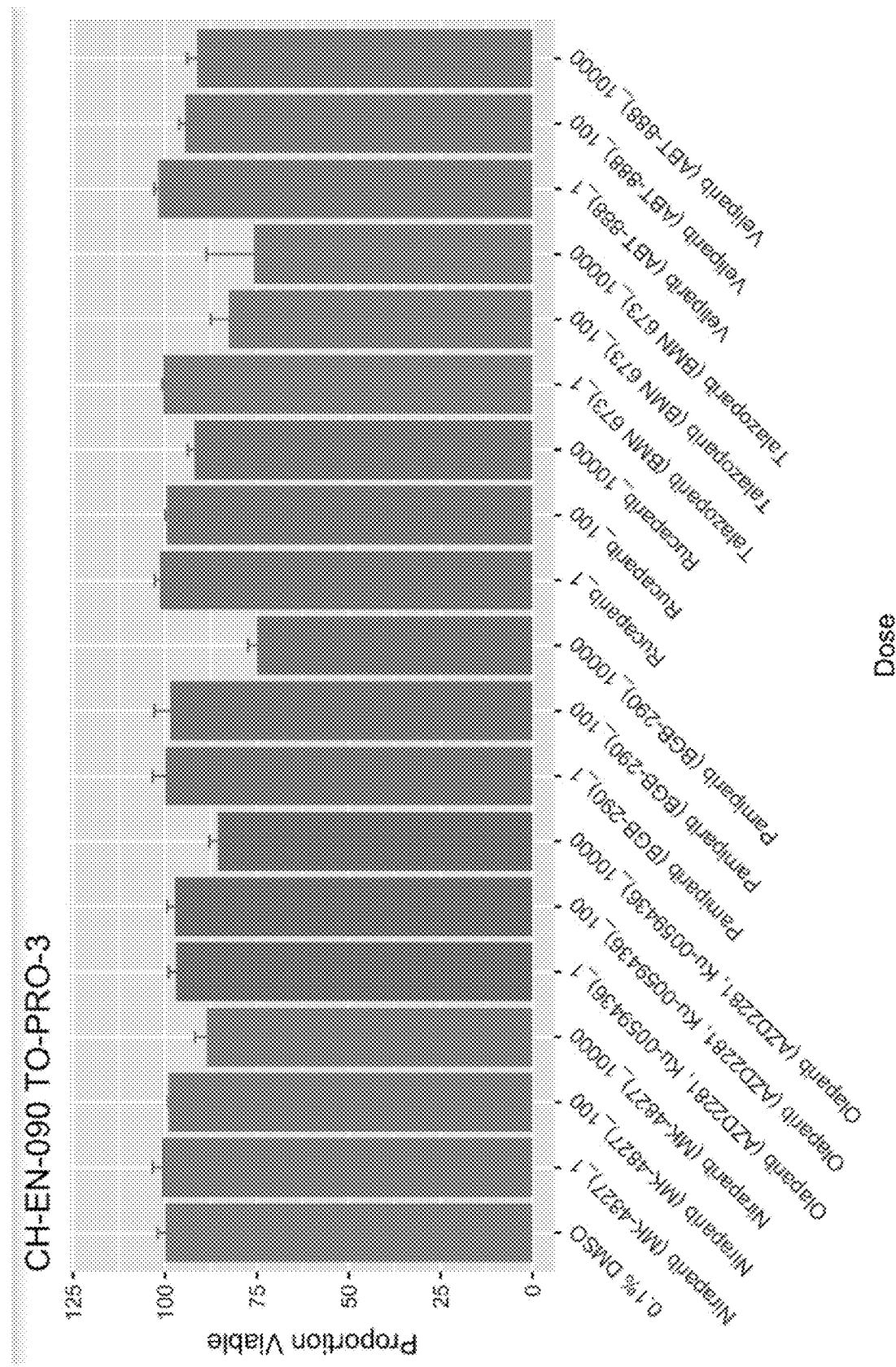

FIGS. 18A and 18B illustrate viability data for a tumor organoid having a low HRD score, no BRCA1 or BRCA2 mutations and no BRCA1 or BRCA2 LOH. The x-axis label indicates the PARP-i therapy and dose. The γ-axis indicates the percent of cells in the well that were viable, normalized to the DMSO mock condition (negative control).

K. Example 11—A Pan-Cancer Organoid Platform for Precision Medicine

1. Summary

Patient-derived tumor organoids are emerging as high-fidelity models to study cancer biology and develop novel precision medicine therapeutics. However, utilizing organoid technologies for systems biology-based approaches has been limited by a lack of scalable and reproducible methods to develop and profile these models. The generation of a robust pan-cancer organoid platform with chemically defined media was described and its evaluation in cultures from over one thousand patients. Crucially, tumor genetic and transcriptomic recapitulation was demonstrated utilizing this approach, and further optimize defined minimal media for organoid initiation and propagation. Additionally, a neural network-based approach for label-free, light microscopy based drug-assays capable of predicting patient-specific heterogeneity in drug responses and with universal applicability across solid cancers was developed. The pan-cancer platform, molecular data, and neural network-based drug assay serve as a resource to accelerate the broad implementation of organoid models for systems biology-based precision medicine research and guide the development of personalized therapeutic profiling programs.

2. Introduction

Over the past decade, oncology therapy has moved from "one-size-fits-all" to a more individualized treatment approach known as precision medicine. A core objective of precision medicine is the identification of therapies that target the unique biology of each patient's disease. For example, targeted therapies have been designed against multiple single molecular alterations, such as mutations in driver oncogenes (Bailey et al., 2018; Cancer Genome Atlas, 2012a, b; Cancer Genome Atlas Research, 2012) gene fusions (Seshagiri et al., 2012), and protein overexpression (Ancevski Hunter et al., 2018; Sanchez-Vega et al., 2019), and can elicit deep and durable responses. However, patients harboring clinically actionable alterations show varying responses to therapies targeting those alterations, potentially due to differential cellular states or genetic backgrounds. A critical barrier to the widespread adoption of precision medicine has been the lack of a robust and reproducible preclinical platform to connect molecular profiles of patient tumors with effective therapeutic treatments in a scalable manner suited for systems biology approaches Recently, patient-derived tumor organoid (TO) technologies have been used to create cellular models of diverse cancer types, including colon (Fujii et al., 2016; van de Wetering et al., 2015), breast (Sachs et al., 2018), pancreatic (Boj et al., 2015; Romero-Calvo et al., 2019; Tiriac et al., 2018), liver (Broutier et al., 2017), lung (Sachs et al., 2019), endometrial (Boretto et al., 2017; Turco et al., 2017), prostate (Gao et al., 2014), and esophagogastric (Kijima et al., 2019; Li et al., 2018; Nanki et al., 2018), among others. In addition to advancing fundamental research, TOs have recently been employed for drug development and precision medicine studies. For example, several groups have reported that patient-derived organoid cultures mimic patient responses to chemotherapies (de Witte et al., 2020; Driehuis et al., 2019; Ferguson et al., 2020; Narasimhan et al., 2020; Ooft et al., 2019) or chemoradiation (Ganesh et al., 2019; Yao et al., 2020). However, these protocols lack consistency within and between specific tumors and reproducibility is limited owing to utilization of undefined cell-line conditioned media and therapeutic profiling assays have not demonstrated pan-cancer generalizability.

Here, a pan-cancer platform was established for utilizing TOs in drug screening and modeling responses to cancer therapies in a large-scale production pipeline. This study included analysis of over 1,000 organoid cultures representing high-incidence cancers to assess clinical and molecular determinants of organoid culture success, molecular concordance between TOs and source tumors, minimal growth factor dependencies by tissue of origin, and development of a label-free neural network-based therapeutic profiling assay applicable across all cancer types. Taken together, the combination of these resources establishes robust and reproducible standards for the application of TOs for systems biology approaches to unlock new precision oncology strategies.

3. Results a. Surveying Tumor Organoid Production at Scale

Figures 19A, 19B:
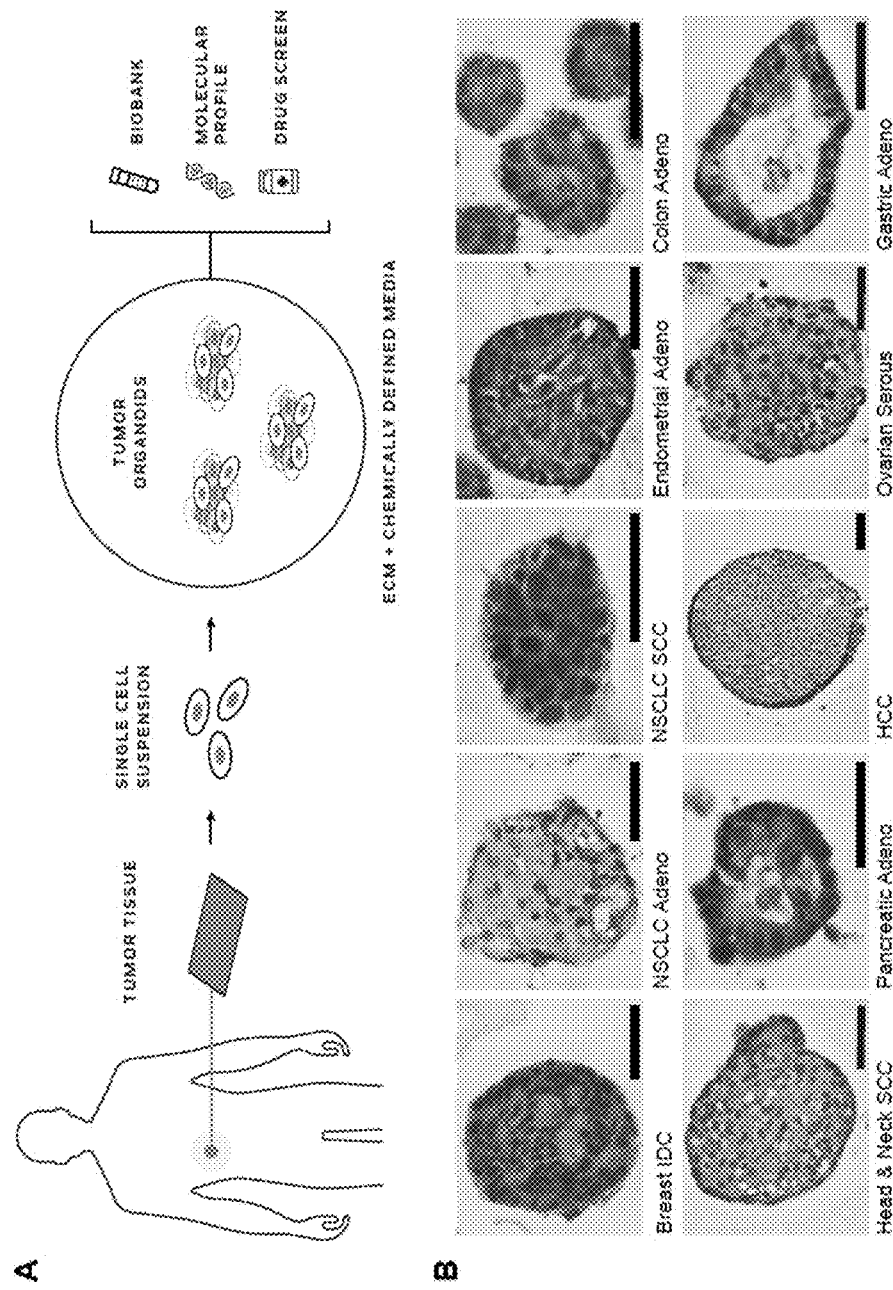

A patient-derived TOs was developed from a large variety of cancers for use in precision medicine and high-throughput translational research applications, including biobanking, molecular profiling, and drug screening (FIG. 19A). TO cultures from 1,298 patient tumors representing the major incidences of carcinoma in the US were initiated. To maximize consistency, organoids were cultured and passaged as single-cell suspensions in extracellular matrix (ECM, Matrigel) using chemically defined culture media representing a consensus of previous reports (FIG. 19E, STAR methods). Of the 1,298 cultures, 213 were excluded from this analysis due to atypical, benign or non-malignant diagnoses. Of the 1085 remaining TO cultures, 73% (792/1085) established organoids as visualized by light microscopy, which is consistent with previous reports (Boj et al., 2015; Boretto et al., 2019; Broutier et al., 2017; Fujii et al., 2016; Gao et al., 2014; Li et al., 2018; Nanki et al., 2018; Sachs et al., 2018; Sachs et al., 2019; Tiriac et al., 2018; Tiriac et al., 2020; Turco et al., 2017; van de Wetering et al., 2015). Intermittent histological evaluation (n=320, FIG. 19B) by a board-certified pathologist identified rare instances of benign epithelia in 5% (16/320) of cultures.

Figure 19C:
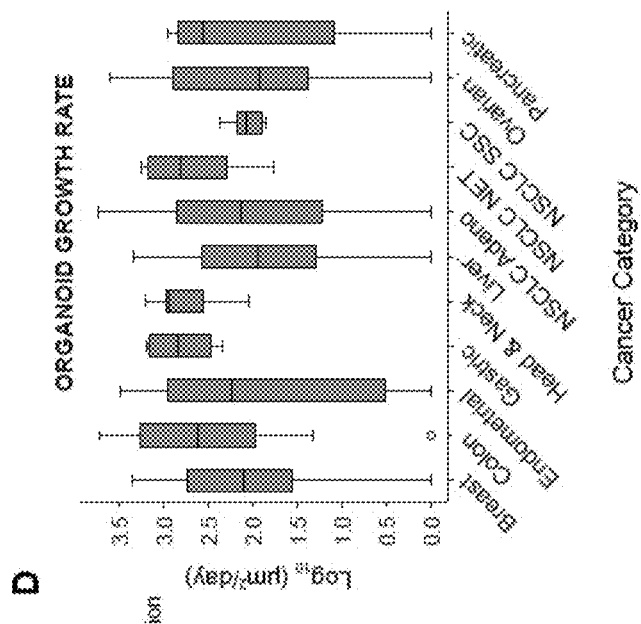
Figure 19D:
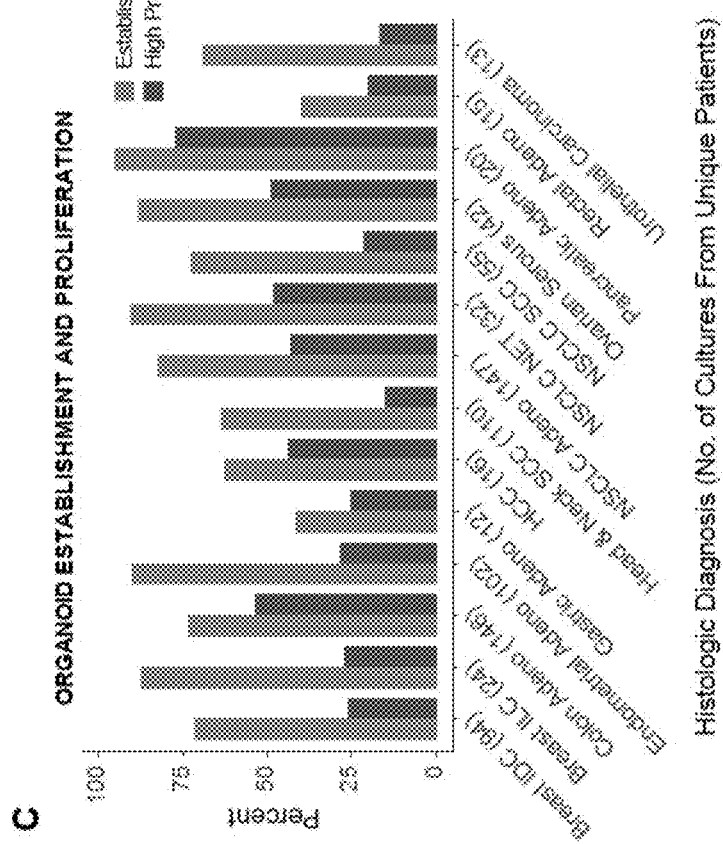

Growth in TOs generated was further evaluated from prevalent histologic tumor subtypes with at least 10 unique cultures (FIG. 19C). It was determined that 15-60% of TO cultures (depending on cancer type) exhibited a sustainable high proliferation phenotype. These high proliferation TO cultures were able to expand to $10^6$-$10^7$ cells upon serial passage, and were suitable for biobanking for future research studies (FIG. 19C). Additionally, time-lapse microscopy on a subset of TOs (n=165) revealed that cultures exhibited heterogeneity of growth within and between cancer types (FIG. 19D). The maximal observed growth rates were between 10 and 1,000 μm²/day (interquartile ranges), with colon and gastric adenocarcinomas exhibiting the largest proportion of rapidly growing TO types (FIG. 19D).

b. Clinical and Molecular Associations of Tumor Organoid Proliferation

The ability to predict which TO cultures will achieve high proliferation will enable researchers to quickly identify TOs that can be biobanked versus those that are more suitable for a single, patient-specific study. Clinical and molecular features enriched in high and low/no proliferation TOs were examined using a generalized linear model with histologic subtype as a covariate (FIG. 19E). Initial counts of >100,000 viable cells positively contributed to the high-proliferation phenotype (P=0.012), and within histologic subtypes was significant in NSCLC adenocarcinoma and breast invasive ductal carcinoma (IDC) (P=0.039 and P=0.0012, respectively; hypergeometric test). Interestingly, clinical features such as neoadjuvant treatment, lymph node metastasis, and tumor size were not associated with a proliferation phenotype, with the exception of gastric and rectal adenocarcinoma. In these cases, TOs developed from metastatic lesions were significantly associated with high proliferation (P=0.021 and P=0.026 respectively; hypergeometric test).

Figures 20A, 20B:
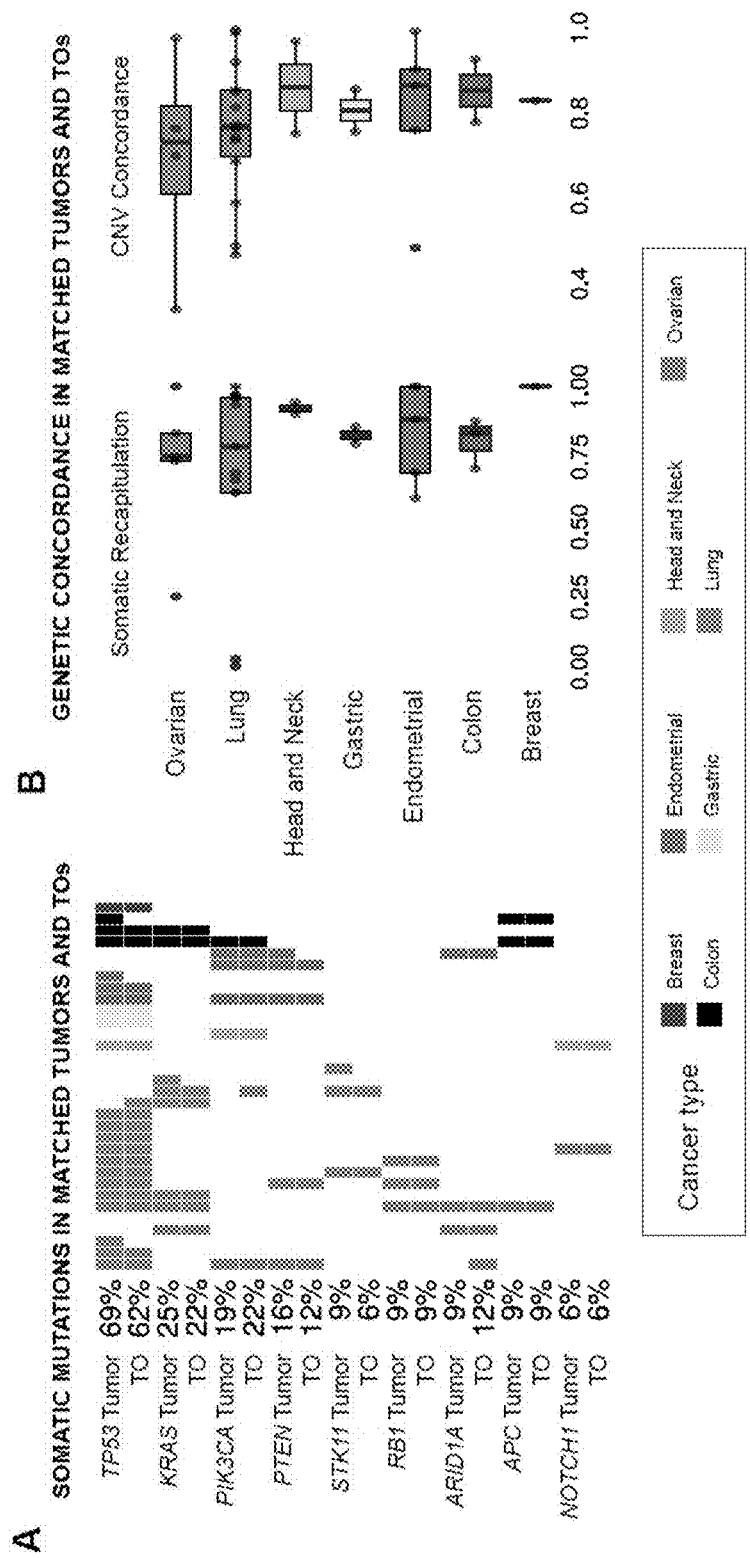
FIGS. 20A-20F show the genomic and transcriptomic concordance between TOs and source tumors. A: Somatic mutation landscape. Genes presented were the top 10 most frequently mutated genes. For each gene, the top row represents source tumor mutations and the bottom row represents TO mutations. B: Somatic recapitulation and CNV concordance across cancers. Note—x-axis range is from 0.4 to 1.0. C: VAF correlation of recapitulated variants. Tumor VAF was adjusted for tumor purity. Points are colored by cancer type. For A-C, variants included were classified as pathogenic, likely pathogenic or of unknown significance. D: Transcriptome correlation between source tumors and tumor organoids. Unpaired correlation represents all other pairwise comparisons between tumors and organoids. E: Representative copy-number plots depicting a colon cancer tumor and corresponding patient-derived TO. Major copy-number alterations >3 megabases (Mb) are depicted as blocks and copy-number alterations <3 Mb are depicted as points. Highlighted is a region on chromosome 6 that is depicted as having a normal copy number in the sequenced tumor, but a predicted loss of heterozygosity in the paired patient derived TO. F: (Top) Three paired panels of Tempus xT sequencing coverage in the HLA-A locus (by normal, source tumor, and patient-derived TO). (Bottom) positive control (non-patient paired, genotype-matched (HLA-A02 positive) PBMC; negative control (unrelated HLA-A02 negative) PBMC; and patient-derived TO) fluorescence-activated cell sorting (FACS) data by panMHC and HLA-A02 antibodies.
Figures 20C, 20D:
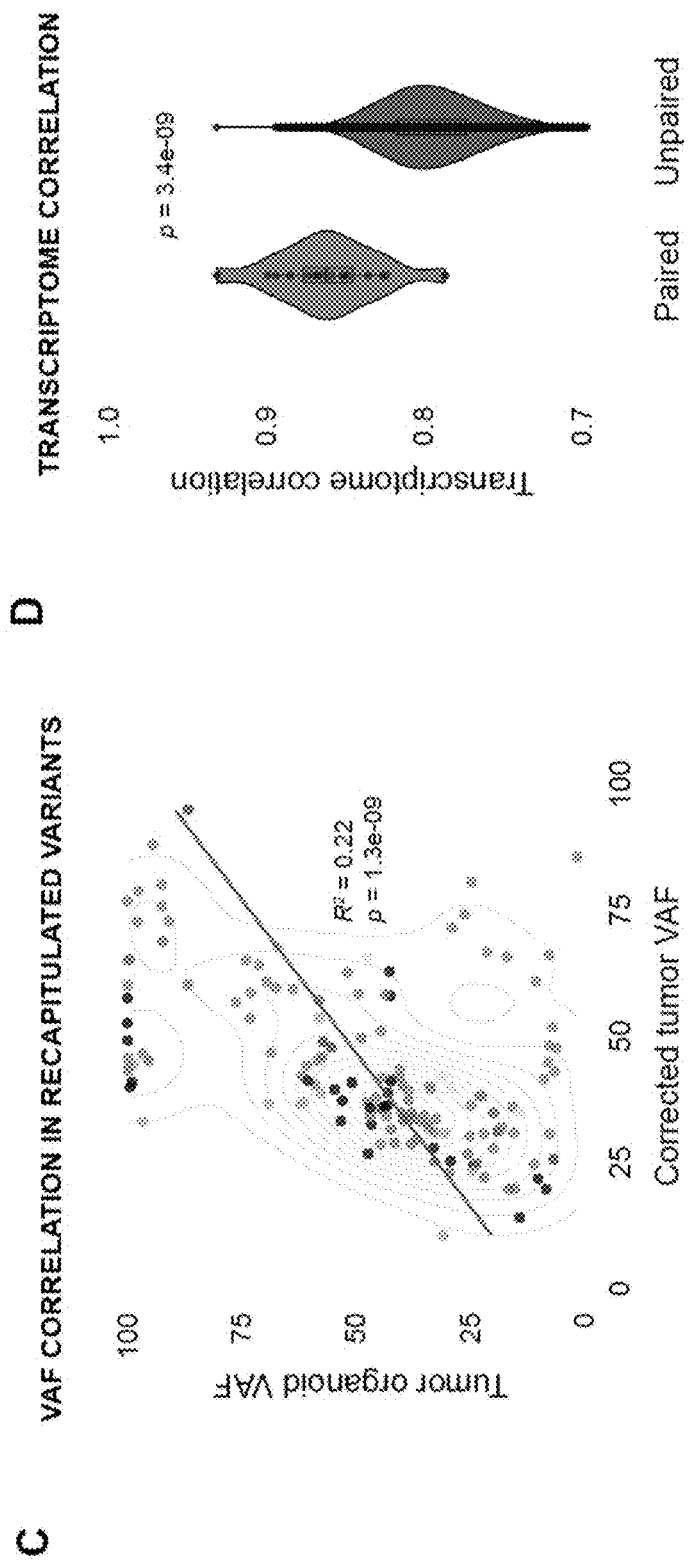

To test for molecular signatures in source tumors that predict high-proliferation TOs, 125 source tumors (74% with high proliferation) were identified with available data from the Tempus xT test, a targeted DNA sequencing panel of 596 oncogenes. Enrichment of pathogenic molecular alterations were tested for within each of the 596 genes sequenced with the Tempus xT panel (Beaubier et al., 2019a; Beaubier et al., 2019b), but found no significant single-gene mutation differences. Thus, based on these 125 examples, this result indicates no overt proliferation bias toward TOs with specific genetic drivers using the pan-cancer approach described herein.

c. Tumor Organoids Recapitulate Genomic and Transcriptomic Profiles of Source Tumors To verify whether TO cultures recapitulated patient molecular profiles, xT DNA sequencing and whole-transcriptome analysis were conducted on matched tumor-TO pairs. TOs were evaluated with available archival source tumor tissue for matched xT DNA sequencing and whole transcriptome analysis (n=32 with xT DNA; n=18 with RNA-Seq). To investigate the degree to which TOs and their source tumors exhibited similar genomic profiles, frequencies of somatic alterations classified as pathogenic, likely pathogenic, or variant of unknown significance (VUS) were first examined and confirmed consistent co-occurrence and mutual exclusivity patterns across groups (FIG. 20A). The rates of somatic variant recapitulation and CNV concordance (FIG. 20B) were then evaluated. On average, somatic recapitulation of source tumor variants (variant allele fraction [VAF]>10%) in the TOs had rates >76.9% (within cancer ranges 70%-92%) and CNV concordance was >77.6% (within cancer ranges 69%-86%). Three outlier organoid samples with low somatic recapitulation rates were identified: two derived from NSCLC and one from ovarian carcinoma. The ovarian source tumor was driven by a loss-of-function BRCA1 germline mutation plus loss of heterozygosity (LOH), both of which were recapitulated in the corresponding organoid. The remaining variants reflected passenger events from resultant genomic instability. For the two NSCLC outliers, one TO failed to recapitulate the source tumor's KRAS Q61H driver mutation and the other TO, its source tumor's STK11 mutation, suggesting outgrowth of either alternative clones from tumor heterogeneity or dysplastic epithelium from field effect. After adjusting for purity in the source tumor, VAF analysis of recapitulated pathogenic or likely pathogenic variants provided further support for overall genetic concordance ($R^2=0.22$) but also showed a set of TOs with somatic variants that expanded to high frequencies (FIG. 20C). Overall, these genetic concordance patterns indicate several events consistent with recapitulation of tumor heterogeneity and others demonstrating clonal selection.

Overall transcriptomic concordance was next assessed between TOs and their corresponding source tumors. Higher mean rank correlation between TOs and source tumor pairs (R=0.845 [0.690-0.935]) were observed when compared to randomly sampled sets of tumor and organoid pairs ($P=3.4 \times 10^{-9}$; R=0.797 [0.664-0.90]; FIG. 20D).

d. Human Leukocyte Antigen Loss of Heterozygosity in Tumor Organoids

Figure 20E:
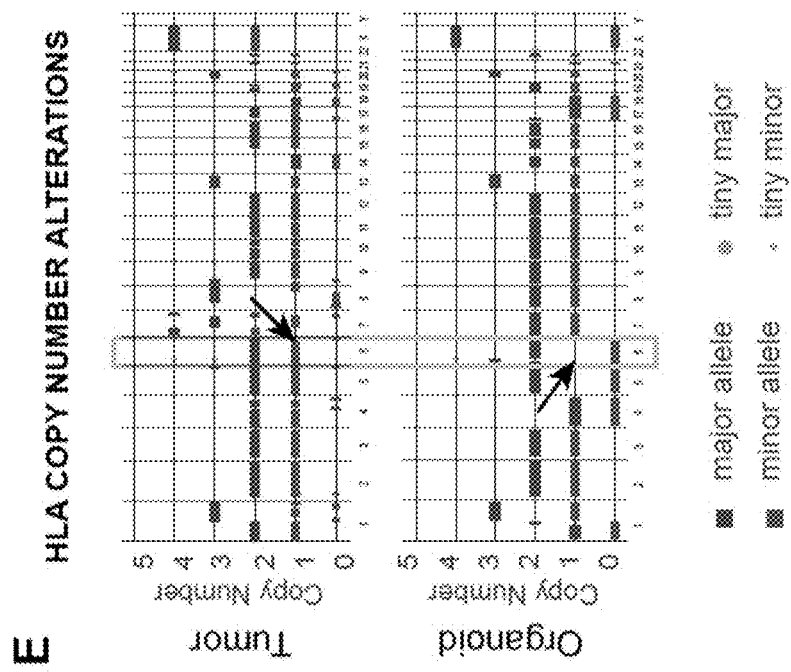
Figure 20F:
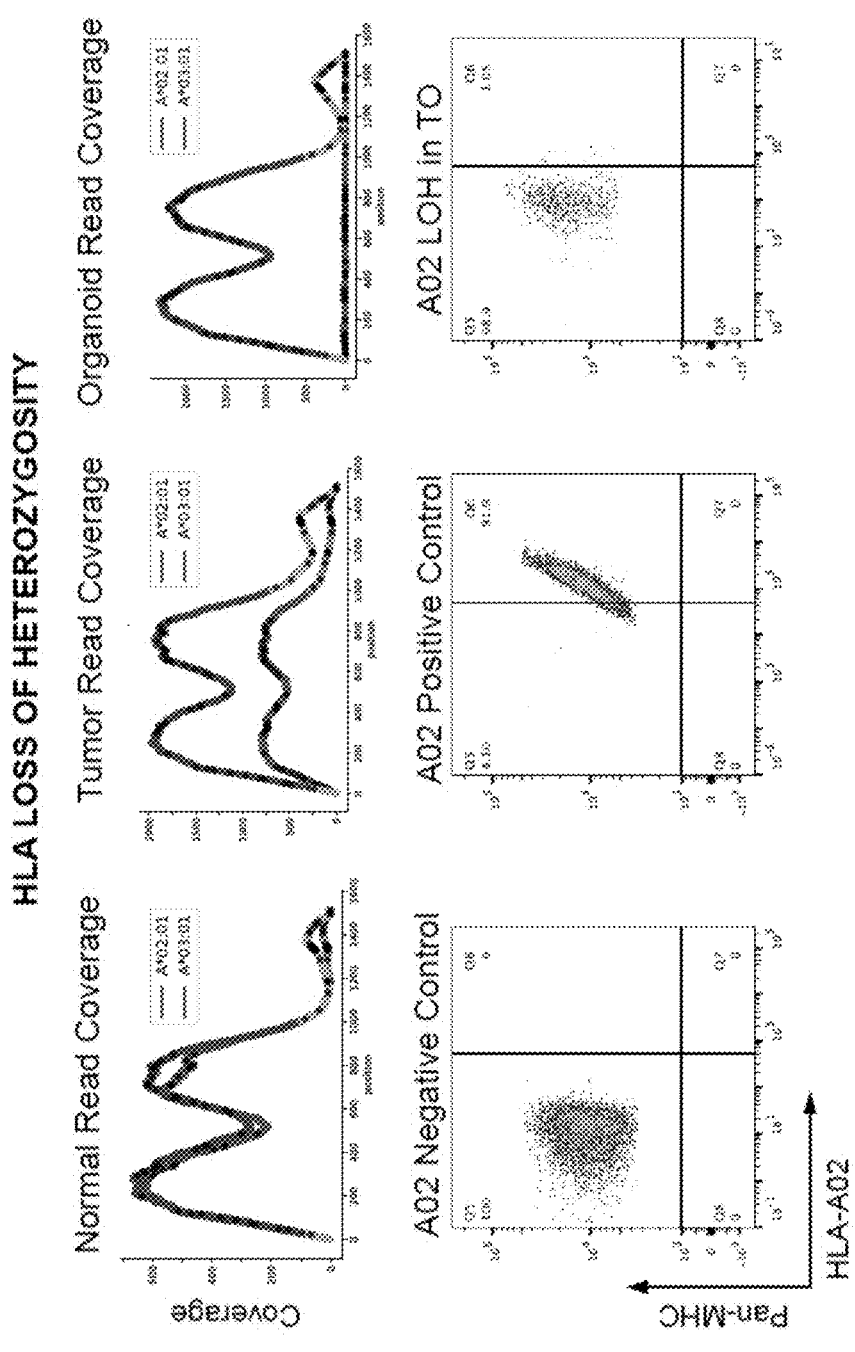

It was next sought to functionally validate recapitulation of a pan-cancer genetic alteration between TOs and source tumors. Loss of heterozygosity of the Human Leukocyte Antigen Class I (HLA LOH) was recently shown to be an important biomarker for immunotherapy response with major implications for the development of targeted immunotherapies (McGranahan et al., 2017; Chowell et al., 2016) across cancers. Therefore, the preservation of HLA LOH in TOs were investigated. Paired normal sequencing from normal tissue or plasma buffy coat for 22 samples were leveraged, and 5 (22.7%) tumor cases were identified where one of the HLA alleles demonstrated a comparative reduction in DNA coverage indicating LOH. For an example of identifying HLA LOH, see U.S. patent application Ser. No. 16/789,413, titled "Detection Of Human Leukocyte Antigen Class I Loss Of Heterozygosity In Solid Tumor Types By NGS DNA Sequencing" and filed Feb. 12, 2020, the contents of which are incorporated by reference herein in their entirety and for all purposes. One respective paired TO was selected for functional validation. DNA sequencing demonstrated a complete loss of the A*02:01 allele in this TO, purifying the heterogeneous signal in the parent tumor (FIG. 20E,F). This was confirmed with flow cytometry, which demonstrated the TO retained surface expression of the HLA allele that was predicted to be retained (A*03:01), and absence of the allele predicted to be lost (A*02:01) (FIG. 20F).

e. Tumor Organoids Maintain Oncogenic Signatures Representative of Each Cancer Type Having confirmed TO recapitulation of source tumors in this small cohort, a cohort level pan-cancer molecular characterization of TOs was carried out and a comparison was made to an independent cohort of representative cancer patients. An additional 200 sequentially established TO cultures for Tempus xT testing was targeted, including whole transcriptome analysis, yielding a total of 230 TOs with DNA and 177 with RNA data. TO's genomic and transcriptomic profiles were then compared to an independent cohort of 261 patient tumors with relevant cancer types previously profiled with the same assay as part of the xT500 cohort (Beaubier et al., 2019a) and also pooled the 32 patient tumors used in the tumor:TO concordance analysis. A gene-based test was employed to compare the frequency of mutations between TOs and tumors within each cancer type, using variants classified as pathogenic, likely pathogenic, or of unknown significance (data not shown). Statistically significant differences were not detected from any genes, indicating the TO cohort is largely comparable to other large-scale genomic sequencing cohorts of clinical specimens (Zehir et al., 2017).

Unsupervised RNA clustering of the 50 most variable MSigDB $C_6$ oncogenic signatures in TOs revealed clustering by cancer type, indicating in vitro maintenance of the disrupted transcriptional pathways that are associated with each cancer type (data not shown). For example, colon adenocarcinoma TOs clustered apart from other cancer types, with upregulated cell cycle- and Wnt-related pathways clustering together. Meanwhile, breast cancer organoids show clustering of upregulated HER2 and NOTCH pathways (data not shown).

f. Differentially Activated Pathways Between Tumors and Tumor Organoids

Figure 21A:
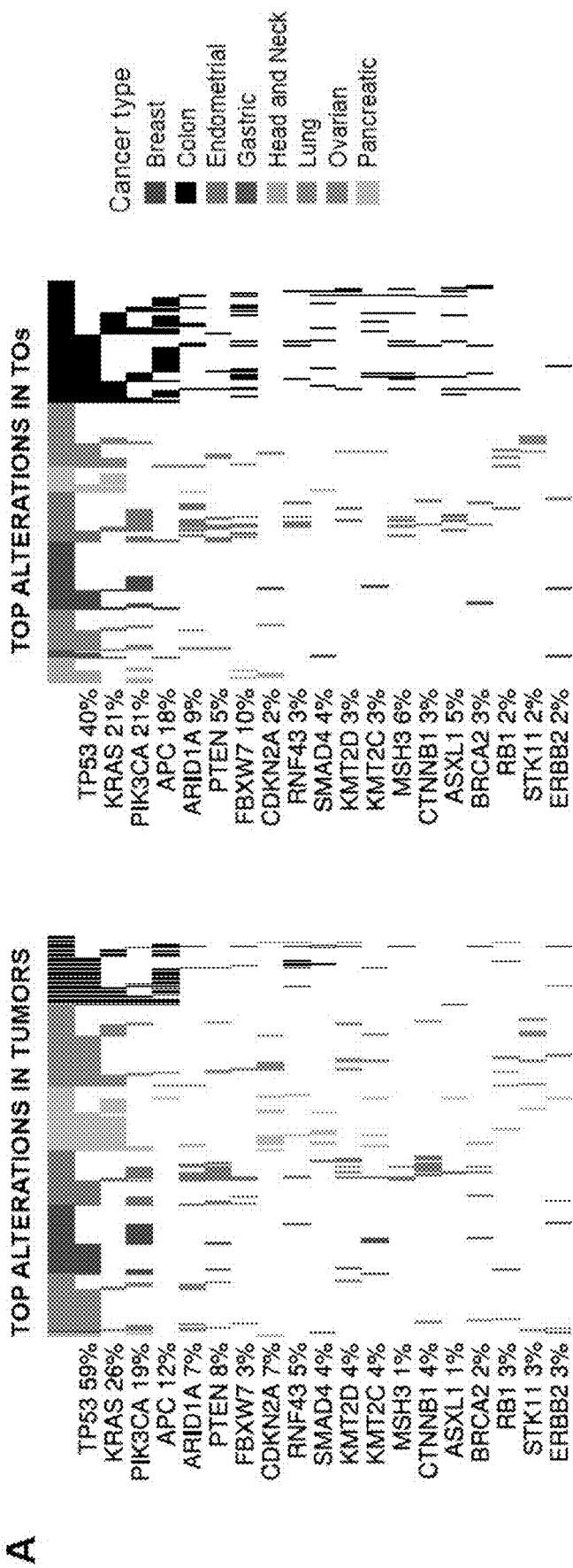
FIGS. 21A-21E show that tumor organoids recapitulate patient tumor molecular landscapes. A: Pan-cancer somatic mutational landscapes in Tempus xT-sequenced tumors (n=292) and TOs (n=230). The top 20 most altered genes (by row) are represented across cancer types (by color). Variants included were classified as pathogenic, likely pathogenic or of unknown significance. B: Transcriptome PCA of 177 TOs exhibits clustering by cancer type. C: Clustered heatmap of differentially activated hallmark ssGSEA pathways between tumors and TOs. Presented pathways were differentially activated (P<0.01) in at least one of the six most represented cancer types. Color scale indicates odds ratio (OR) of difference, with red color indicating higher activation in the tumor organoid and blue indicating lower activation. D: Concordance between presence of Wnt and P53 pathway-disrupting mutations and RNA-based pathway disruption in TOs. Plots represent ssGSEA scores for the relevant MSigDB hallmark pathway in TOs with and without pathogenic or likely pathogenic mutations in APC in (Wnt pathway) and TP53 (P53 signaling pathway). All cancer types are represented. E. Estrogen pathway activation based on ssGSEA score in indicated cancer/cancer group for MSigDB hallmark pathway Estrogen Response Early.
Figure 21B:
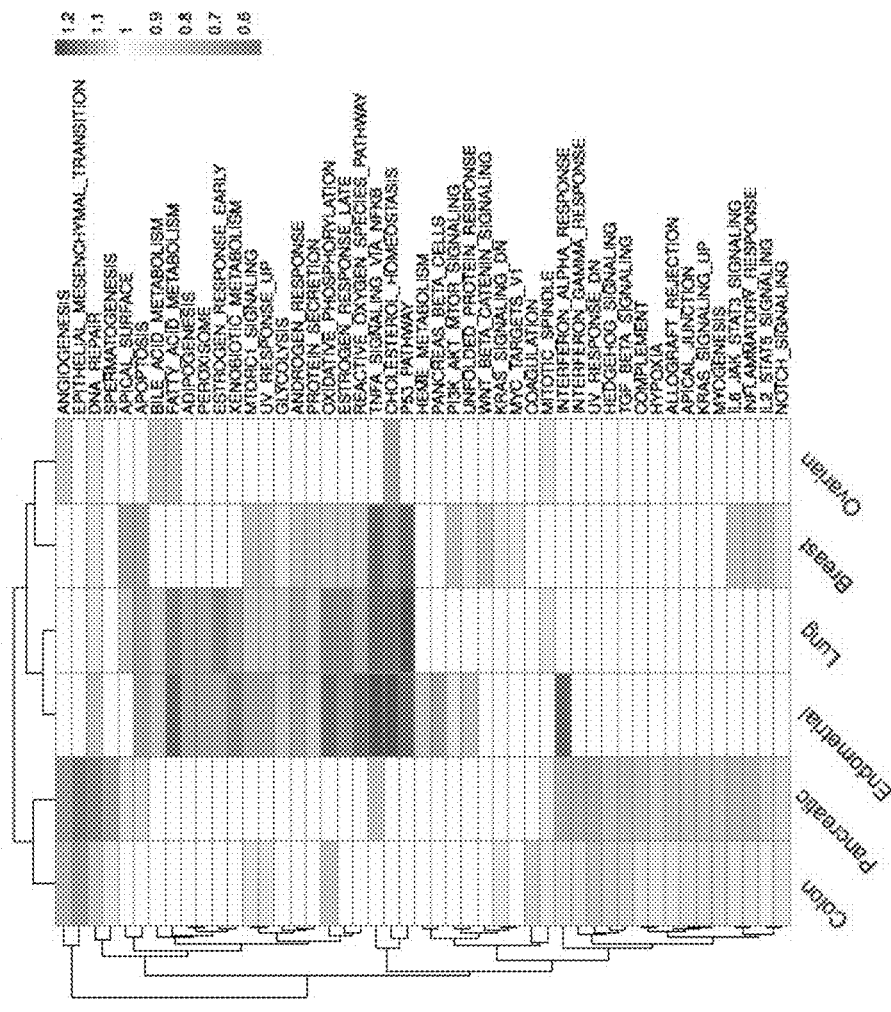
Figure 21C:
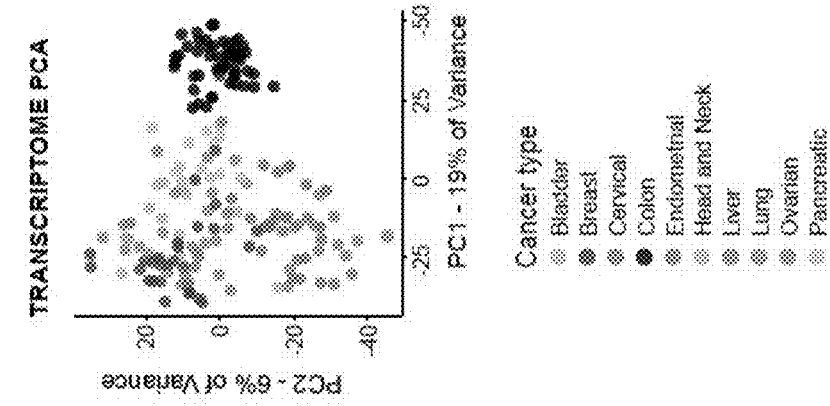

To characterize the biological differences between TOs and tumors, an evaluation of the differences in pathway disruption between all patient tumors and available TOs in cancer types with at least 10 unmatched Tos was performed. Single-sample GSEA (ssGSEA) scores were calculated for the 50 mSigDB Hallmark pathways (Liberzon et al., 2015) and tested for differences in pathway scores using a linear model with covariates applied to account for the 18 matched TO and source tumor pairs when applicable. As anticipated, expression variability was dominated by growth and immune pathways indicative of stromal elimination in TOs (data not shown). To control for this, a second analysis was performed, including tumor purity as a covariate. A substantial proportion of pathway activity was preserved across cancer types, with nearly half (24/50) of Hallmark pathways showing significant differences in two or fewer of the six considered cancer types. Several pathways that showed increased activation were growth- or metabolism-related, including PI3K, estrogen signaling, glycolysis, oxidative phosphorylation, xenobiotic metabolism, and fatty acid metabolism (FIG. 21C). It was presumed that these changes reflect intrinsic characteristics of in vitro culture (e.g., sustained exposure to growth factors). Notable exceptions to this pattern are colon and pancreatic cancer, which both exhibit many disparate pathways with decreased activation, including immune and growth pathways. The mechanisms underlying the bias towards decreased activation in these two cancers, as well as their notable similarity, are unclear and require further validation and study, although the genetic complexity of these cancer types may be a factor.

Figures 21D, 21E:
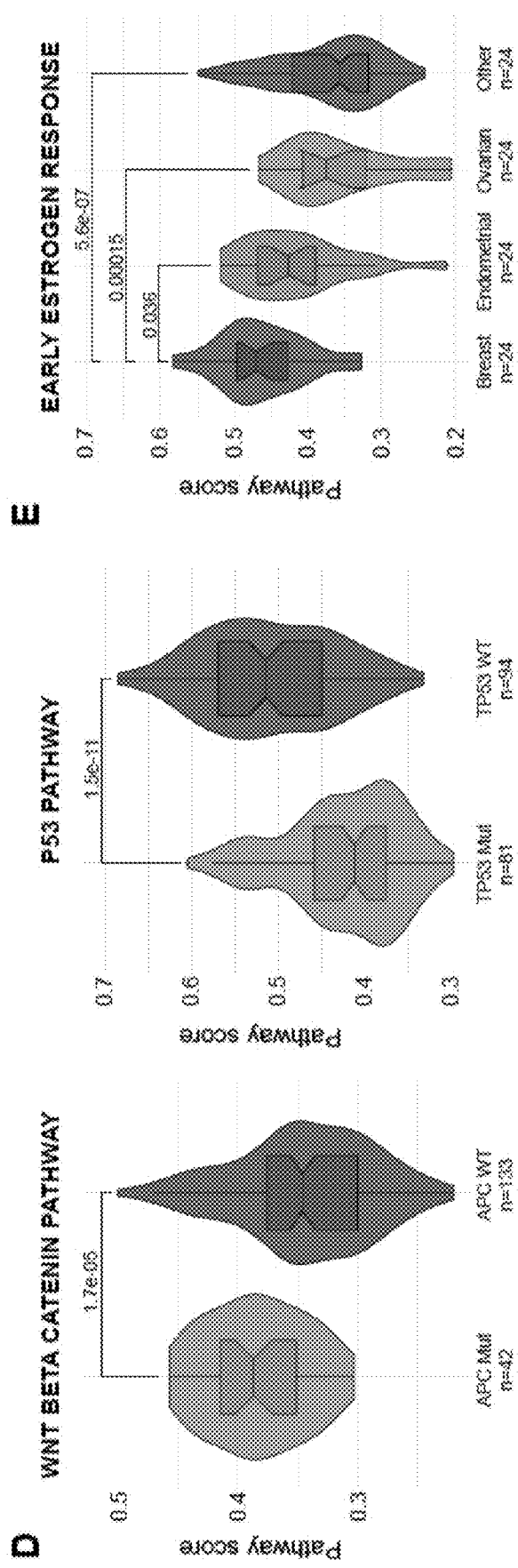

Mutation-driven oncogenic signaling pathway disruption is established as a primary contributor of oncogenesis and tumor maintenance (Sanchez-Vega et al., 2018). Therefore, to determine whether RNA-based pathway activation scores in mutated pathways were maintained within the organoids, the correspondence between mutation signatures and relevant ssGSEA Hallmark pathway disruption was tested for classical growth and apoptosis evasion pathways. As expected, Wnt disruption via pathogenic mutations in APC led to significantly higher Wnt pathway activity in a pan-cancer model ($P=1.7 \times 10^{-5}$), whereas P53 disruption significantly abrogated P53 signaling ($P=1.5 \times 10^{-11}$; FIG. 21D). A significant difference was also observed between KRAS mutant and KRAS WT samples for the upregulated KRAS signaling signature among colon cancer TOs ($P=1.7 \times 10^{-4}$) but not pan-cancer likely due to tonic EGFR activation from receptor ligands present in media, i.e. EGF (data not shown). In addition, the estrogen transcriptional response was compared across breast, endometrial, and ovarian cancer TOs, with breast cancer TOs consistently showing the highest levels compared to all other TOs in early response genes ($P=1.9\times10^{-6}$; FIG. 21E). These results show that commonly mutated genes drive transcriptional changes in oncogenic signaling pathways in TOs in a manner consistent with that observed in source tumors.

g. Growth Factor Requirements for Organoid Culture

Figures 22A, 22B, 22C:
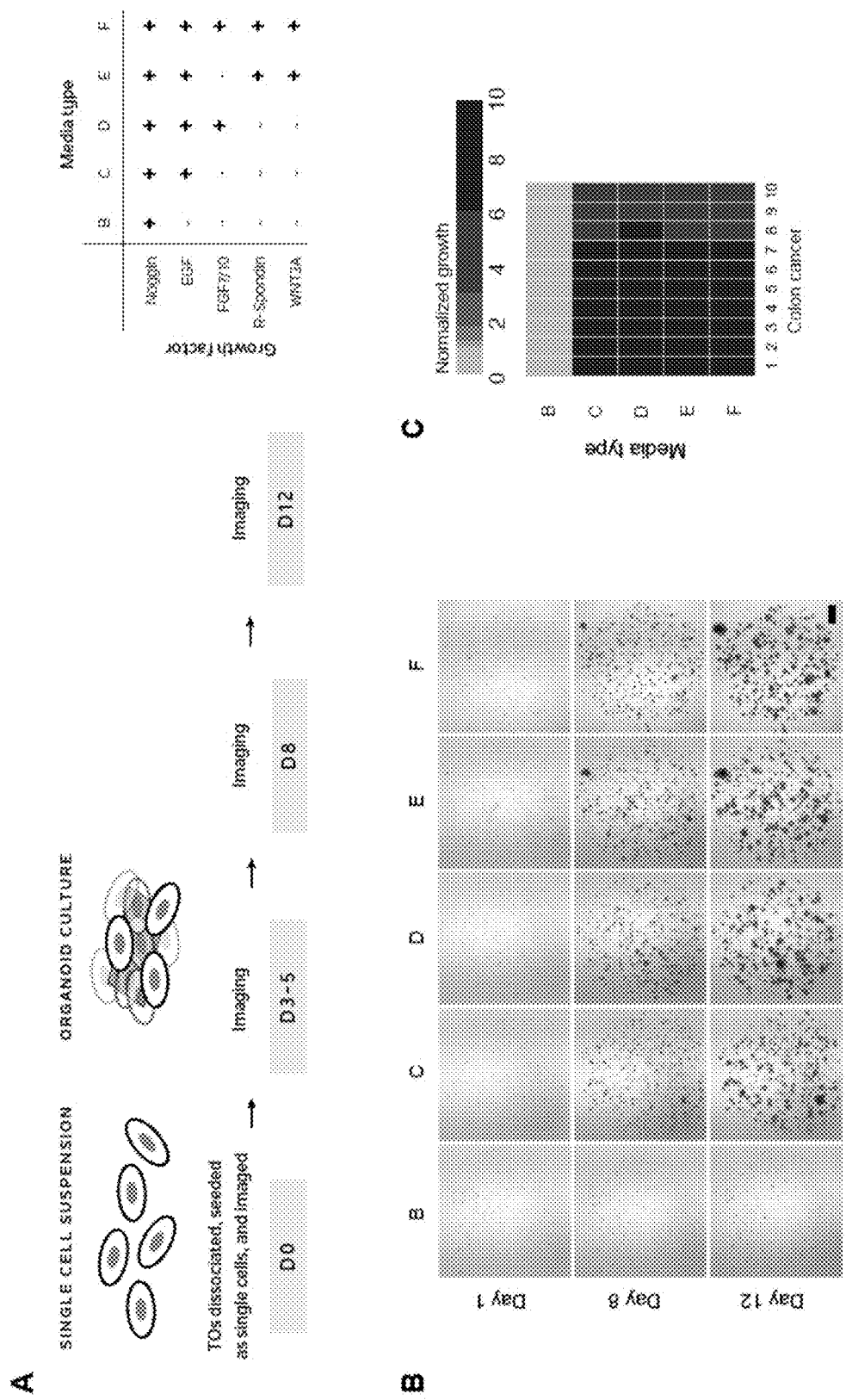
FIGS. 22A-22G summarize a study showing pan-cancer niche factor requirements in tumor organoid cultures. A: Workflow and timeline of TO niche factor profiling and media formulations. Bold plus signs indicate the presence of growth factors in each media type. B: Representative time-lapse images of colon TO growth in varying media formulations. Scale bar=70 μm. C: Heatmap of the growth of ten colon TO lines in varying media formulations. Data are represented as the maximum growth rate normalized to type B (mitogen free) media. D: Heatmap of the growth of 45 TO lines in varying media formulations. Data are represented as the maximum growth rate normalized to type B (mitogen free) media. *P<0.01 by ANOVA. E: Growth curve showing change of mean Pancreatic TO area over time in various media conditions. F: PCA of whole transcriptomes from 8 TO lines grown in various media conditions. G: Barplot of establishment of 100 sequential TO cultures in minimal vs. standard chemically defined media.

Previous reports suggest mutational profiles of TOs govern niche growth factor requirements in cancers (Fujii et al., 2016; Sato et al., 2011). Since transcriptional changes in oncogenic signaling pathways in TOs were observed, the extent to which these changes resulted in functional phenotypes that support TO growth in cancer subtypes was investigated. First, the quantified growth in colon cancer TOs (n=10) was quantified using combinations of peptide and protein growth factors in a manner similar to Fujii et al. (2016) (FIG. 22A). TO growth was measured using automated high-throughput brightfield imaging (FIG. 22B). Consistent with Fujii et al. 2016, colon cancer organoids propagated in the absence of Wnt-3A and R-spondin 1 (RSPO-1), attributable to APC inactivation (FIG. 22C).

Figures 22D, 22E, 22F, 22G:
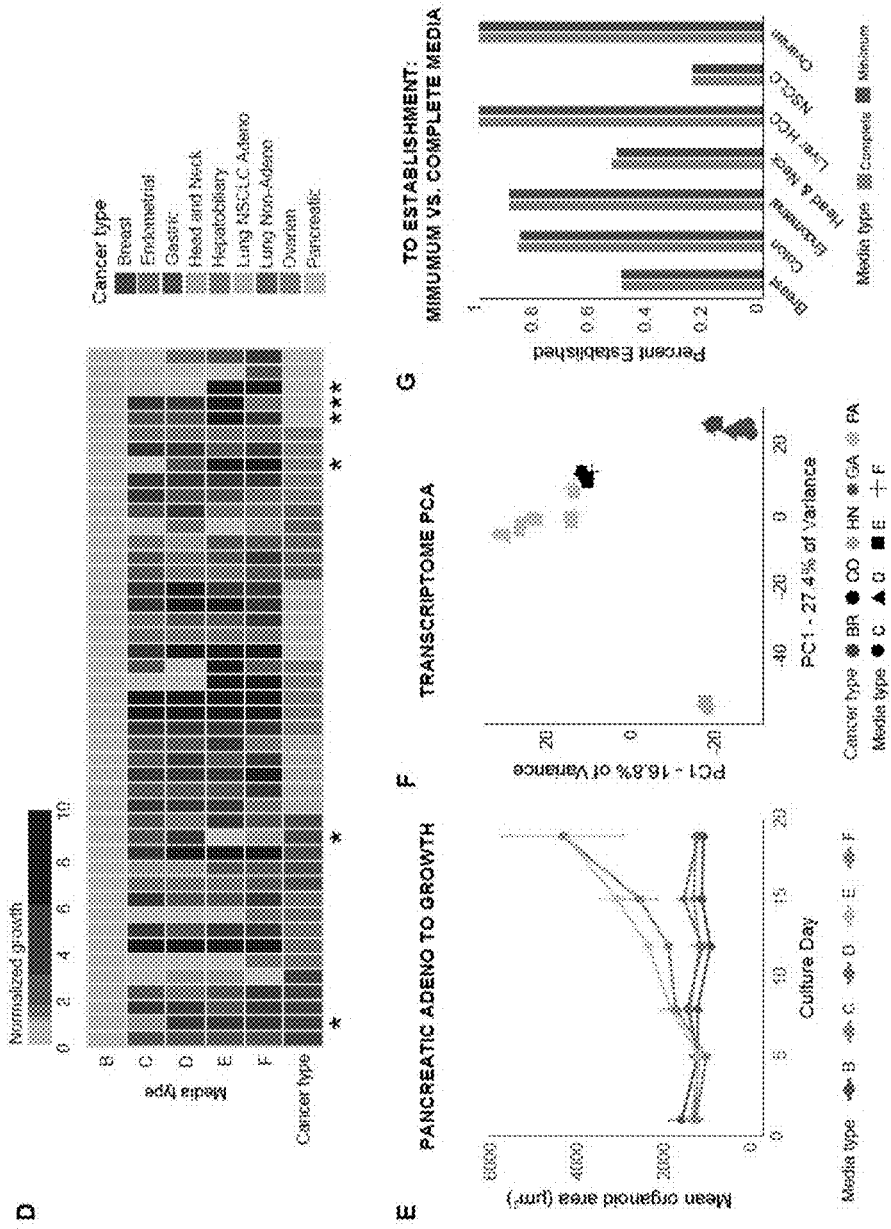

These experiments were then extended to an additional 40 TOs representing other prevalent histologies in the biobank (FIG. 22D). While epidermal growth factor (EGF) stimulated proliferation in all cultures, most TO lines exhibited no significant differences in growth between various media compositions (ANOVA $P<0.05$). However, in breast and ovarian cancer TO lines, fibroblast growth factors (FGFs) enhanced propagation in some cases (FIG. 22D), consistent with previous reports Hill et al., 2018; Sachs et al., 2018). Wnt-3A and RSPO-1 dependence in pancreatic cancer TO lines (FIG. 22E) was confirmed and also consistent with previous reports (Boj et al., 2015; Seino et al., 2018; Tiriac et al., 2018). Interestingly, some TOs did not appear to require any mitogen growth factors (FIG. 22D). Evaluation of the mutations in these TOs revealed a high degree of aneuploidy as compared to TOs that were EGF-dependent (data not shown).

It was then investigated how gene expression is affected by media conditions. Four pancreatic cancer lines were selected and one of each from breast, colon, head and neck (HNSCC), and lung cancer TO lines that were cultured in EGF-containing media with and without additional growth factors for RNA-Seq. PCA analysis demonstrated that the primary determinant of transcriptomic differences was cancer type (FIG. 22F). GSEA of this limited data set revealed upregulation of housekeeping and cell cycle genes within media containing Wnt-3A and RSPO-1 as compared to other media types, which is consistent with the phenotypic observations in pancreatic TOs (FIG. 22E). While these experiments did not illustrate a significant difference between growth factor requirements in the majority of cases, these findings could be due to TOs adapting to in vitro culture conditions and minimizing the dependence on specific niche factors. Next, organoid establishment upon initiation of TO cultures from 100 sequential non-pancreatic tumors grown in either minimal or complete media was evaluated. No significant differences between minimal (type B) and complete media (type F) in the proliferation and formation of TOs from primary tumor single cell suspensions were observed. (FIG. 22G).

h. Development of a Label-Free Universal Organoid Drug Screening Assay

It was next sought to develop a robust and reliable assay to profile therapeutics in vitro. Given the evidence of intratumoral clonal heterogeneity within the cultures (FIG. 20C), an assay was sought that could measure therapeutic response heterogeneity. It was reasoned that since organoids form via clonal outgrowths of single cells, with multiple organoids growing within each well, measuring drug response at single organoid resolution could be achieved via microscopy. Additionally, measuring response for each TO would increase the number of technical replicates to hundreds per well, providing highly accurate measurements of mean drug response as compared to previous reports that measure responses at the micro-well level using biochemical assays (Ooft et al., 2019; Tiriac et al., 2018; van de Wetering et al., 2015). It was also desired to ensure high throughput, low-cost, and scalability. Recent advances in computational prediction of fluorescent signals from unlabeled light microscopy (Christiansen et al., 2018; Ounkomol et al., 2018), as well as conditional generative adversarial networks (GANs), such as Pix2Pix (Isola et al., 2017) and CycleGAN (Zhu et al., 2017), have enabled realistic translation and prediction of images from one domain (i.e., black and white photographs) to another domain (i.e., color photographs). However, the application of GAN-based style-transfer to patient-derived TOs has not been described. A light microscopy-based assay was developed to eliminate the use of costly vital dyes, enable rapid image acquisition, and minimize phototoxicity in time-lapse imaging.

Figure 23A:
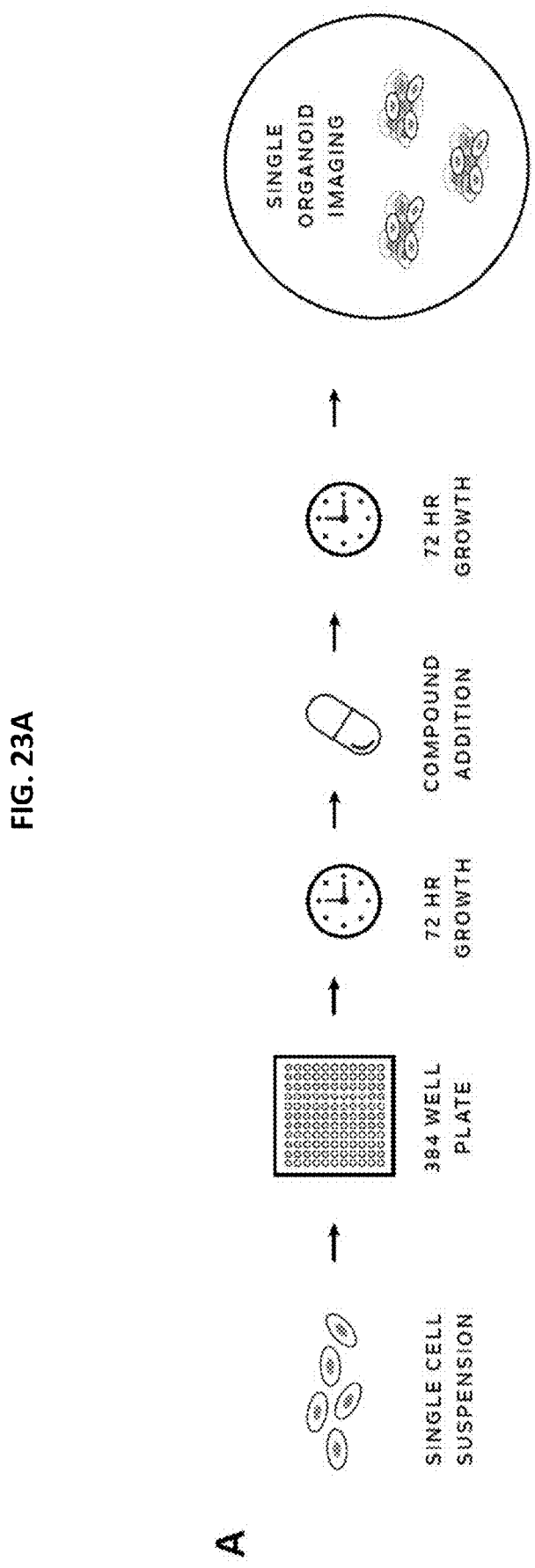
FIGS. 23A-23D provide a summary of a study for the development of a label-free universal organoid drug screening assay. A: Experimental design of the drug assays. B: Representative images from high-content imaging analysis of TOs treated with either vehicle (0.1% DMSO) or 10 μM Staurosporine. Fluorescent labeling (top row) was used to identify all cells (blue, Hoechst 33342), apoptotic cells (green, Caspase-3/7), and dead cells (red, TO-PRO-3). Scale bar=200 μm. C: Example dose-response curve for staurosporine for both the cystic TO (CRC) and solid TO (gastric) lines for TO viability calculated from TO-PRO-3, Caspase-3/7, and live cells per TO. The mean viability (or number of live cells per TO) was calculated for each well and normalized to the mean of the vehicle control. Points indicate mean±SD of technical triplicate wells. D: Heatmaps show the inverse AUC for all 351 compounds for both the gastric and CRC TOs for each readout. Dose-response curves were used to calculate the inverse AUC for each drug.

Since a robust ground truth readout of TO viability required, a high-content image analysis was first performed with standard inverted microscopy to measure viability and apoptosis (STAR methods, FIG. 23A,B). Binary classification of vital dye labeling of individual cells thus enabled us to acquire comprehensive measurements of TO viability, apoptosis and proliferation (by number of viable cells per TO) (FIG. 23A,B).

The drug screening assay was optimized for 384-well plates, with Z prime values ranging from 0.882 to 0.975, which is suitable for screening assays (Narasimhan et al., 2020; Zhang et al., 1999). The screening assay's reliability and reproducibility was benchmarked on two distinct TO lines that represented solid (gastric cancer) and cystic (colon cancer, CRC) organoid morphology. Two independent rounds of screening were performed with a library of 351 chemotherapeutics and small molecule inhibitors. To measure compound potency, the inverse area under the curve (AUC) of dose-response curves was calculated from normalized viability measurements. There was high correlation between the two rounds of experiments for proliferation, apoptosis, and viability, and all readouts outperformed metabolic assays performed in parallel (MTS assays).

Figures 23B, 23C:
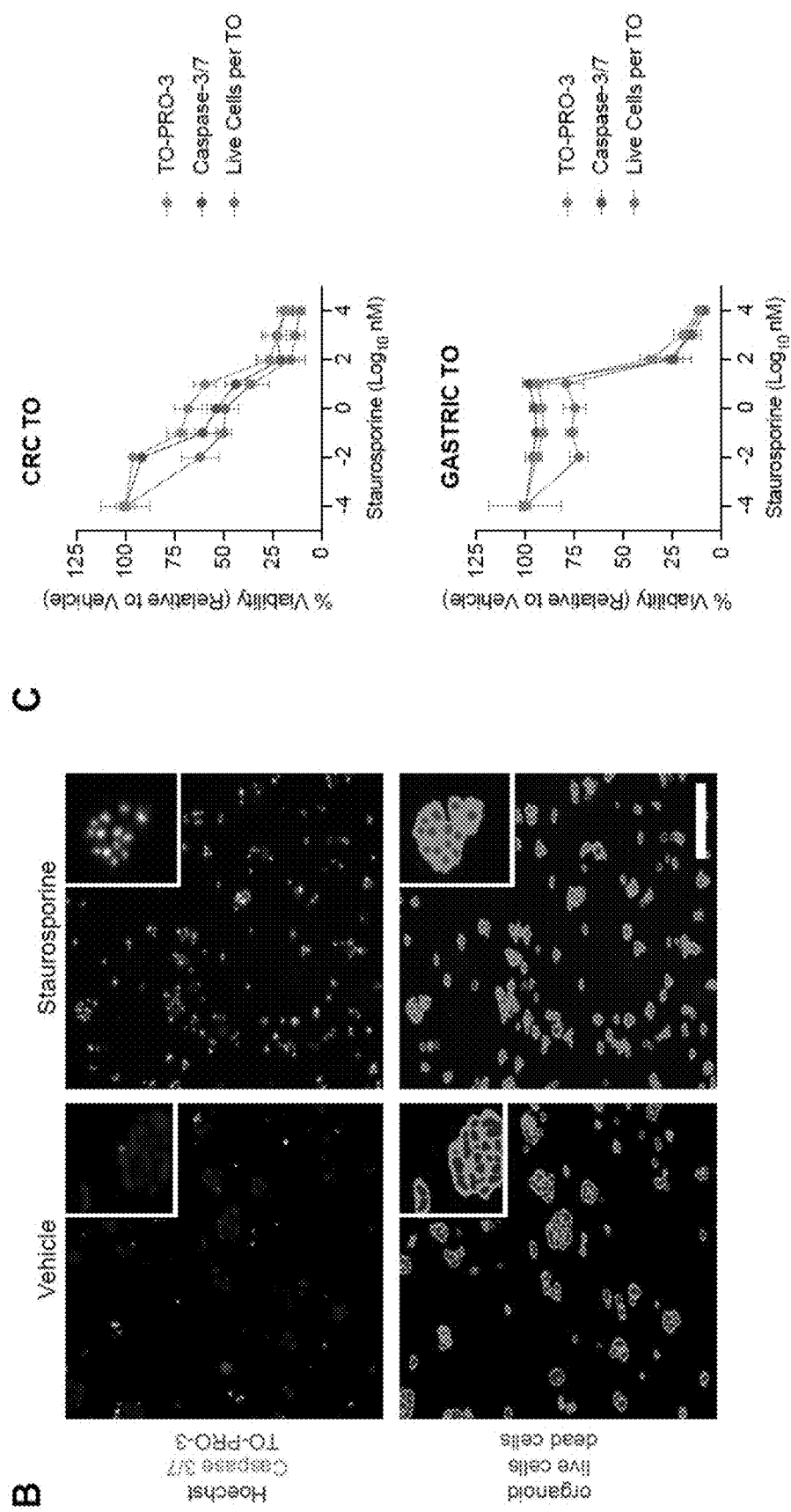
Figure 23D:
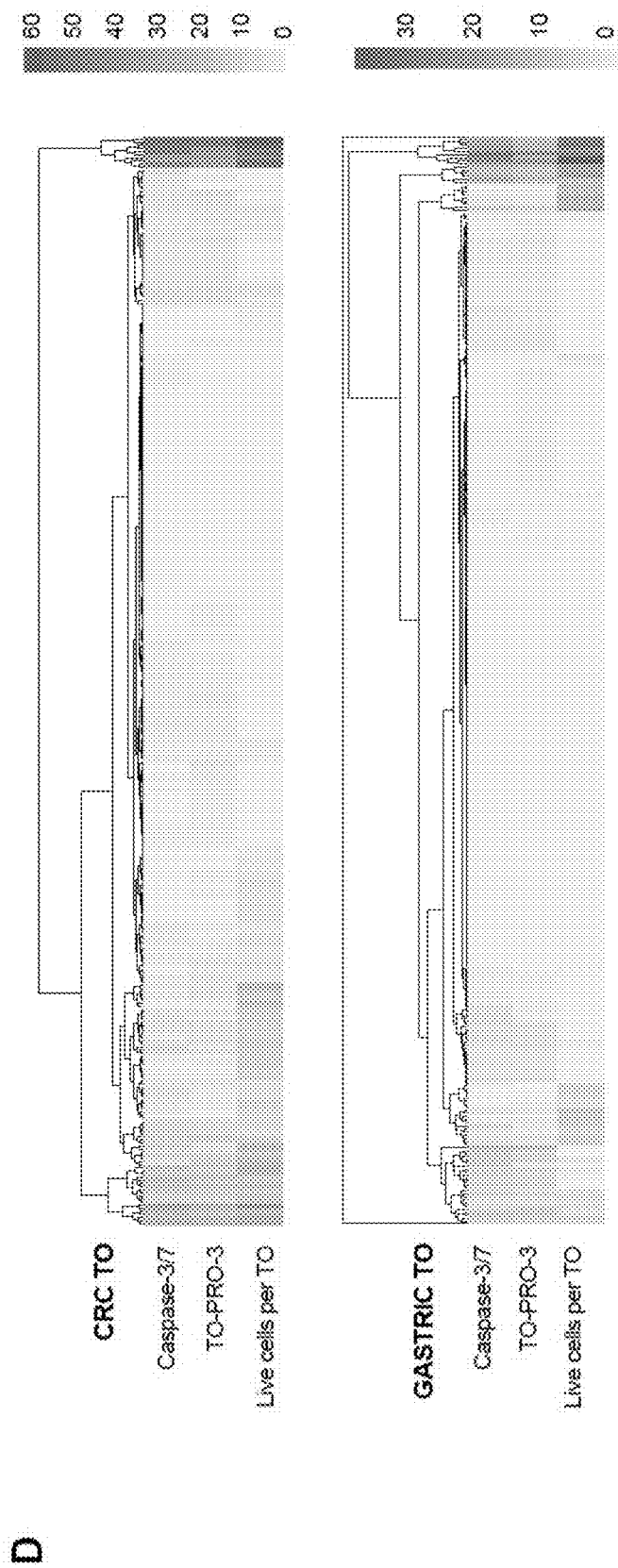

Next, the assay's suitability for high-throughput screening was determined. The sensitivity and specificity in a dose-response series was evaluated, with dosing based on TO viability at 10 µM. Using an inverse AUC cutoff of 5 to classify effective drugs, it was determined that the microscopy-based measurements outperformed MTS assays via receiver operating curve (ROC) analysis for both TO lines tested (ROC AUC values: gastric=0.906 cell death, 0.917 apoptosis, compared to MTS 0.801; CRC=0.923 cell death, 0.929 apoptosis, compared to MTS 0.843). Unsupervised hierarchical clustering of drug response was performed and it was found that measures of cell death and viability largely overlapped, but there were drugs that clustered by viability readout, representing agents with cytostatic, not cytotoxic effects (FIG. 23D). Extending these analyses across two TO lines showed that drug responses clustered by TO line and not by assay readout, confirming biologic specificity (data not shown). Finally, given that drug responses were measured at single TO resolution, individual TO response distributions were examined. Evidence of heterogeneity of TO drug response was found in some TOs, whereas others exhibited a more uniform drug response (data not shown).

i. Neural Network-Based Model for Predicting TO Drug Response

Figures 24A, 24B, 24C:
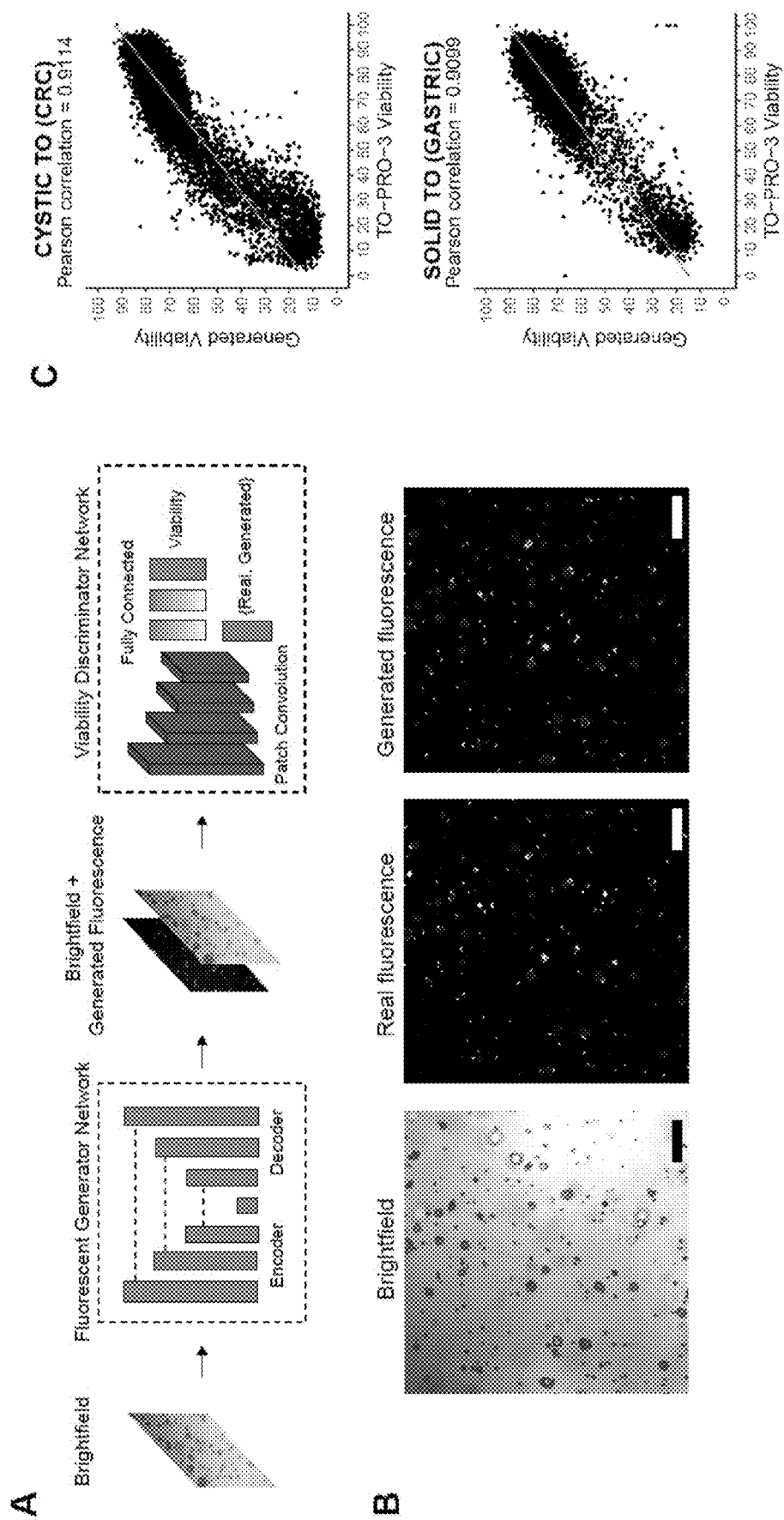
FIGS. 24A-24G depict a summary of a study for the development of a neural network-based model for predicting TO drug response. A: Schematic representation of Regularized Conditional Adversarial Network architecture showing dual predictive ability. Fluorescent Generator (Left) generates a fluorescence registered readout for every input brightfield image. Viability Discriminator (Right) predicts an overall TO viability for the paired brightfield and generated fluorescence readout. B: Representative images highlighting the brightfield, real fluorescence and generated fluorescence readouts from the CRC TO. Scale bar=200 μm. C: Scatter plots showing the relationship between ground truth (TO-PRO-3) and predictive average TO-PRO-3 viabilities on images belonging to CRC TO (not included in the training set) and Gastric TO. D and E: Compounds were grouped by their reported targets and are shown ranked by median inverse AUC values calculated from dose-response curves of RCA generated viability values for the CRC (D) and gastric (E) TOs. Dose-response curves for trametinib (D) and afatinib (E) highlighting the correlation between generated, TO-PRO-3 and Caspase-3/7 viabilities. F: Copy-number amplification plot for the Gastric TO exhibiting ERBB2 amplification (arrow). G: AUC ROC curves between fluorescent and generated viabilities to assess sensitivity and specificity of PARPi response to classify organoids as HRD positive or HRD negative as determined by genome-wide LOH proportion (Tempus HRD assay).

After the establishment of a ground-truth readout, a neural network-based model was developed to generate data from fluorescent readouts from light microscopy images alone. Moreover, owing to the flexibility of neural network architectures, recent work where GANs have been adapted to regression tasks as a framework for response prediction was drawn upon (Aggarwal et al., 2020; Olmschenk et al., 2019). It was reasoned that a single framework could enable both the prediction of fluorescent stain and response directly from brightfield images (FIG. 24A). To that end, a preliminary high-throughput drug screening model was developed and referred to as a Regularized Conditional Adversarial (RCA) network, which is an extension of Pix2pix (Isola et al. 2017), and includes an additional network to predict overall viability per brightfield image (FIG. 24A).

The RCA network was trained on 8,415 paired brightfield and 3-channel fluorescence images from the colon adenocarcinoma TO screening experiments (FIG. 23), each with associated calculated drug responses based on TO-PRO-3 viability. The RCA model combines the brightfield and generated fluorescence readout to predict an overall average viability using the Viability Discriminator Network (FIG. 24A, see STAR methods for details on training). The RCA network was benchmarked against the 351-compound screen from the colon adenocarcinoma TO and found that it demonstrated highly significant correlations between ground truth and predicted organoid response in this TO with cystic morphology (FIG. 24C). Extending this analysis to a gastric cancer TO line with a solid TO morphology again resulted in excellent correlation (Pearson correlation=0.91, FIG. 24C). Representative images of real versus generated fluorescence demonstrated nearly indistinguishable visual matching (FIG. 24B). These results were confirmed using two quantitative metrics: the structural similarity index (SSIM) as well as the root mean squared error (RMSE). The reported average SSIM and RMSE values across 1,526 samples of the colon adenocarcinoma TO used in the screening experiment were 0.90 and 0.13924 respectively. For the gastric TO line, the reported average SSIM and RMSE values across 9200 samples were 0.898 and 0.136, respectively.

Figure 24D:
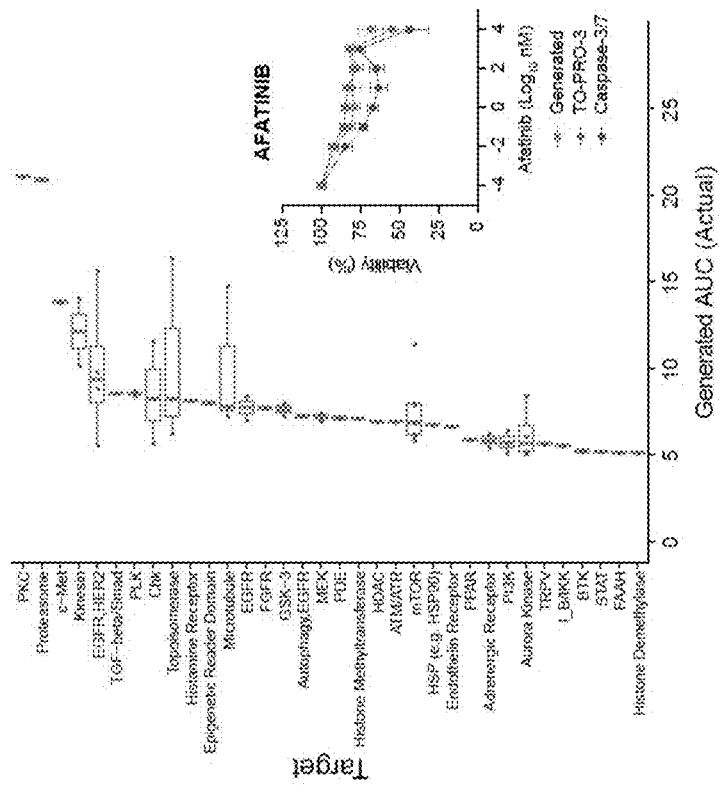
Figure 24E:
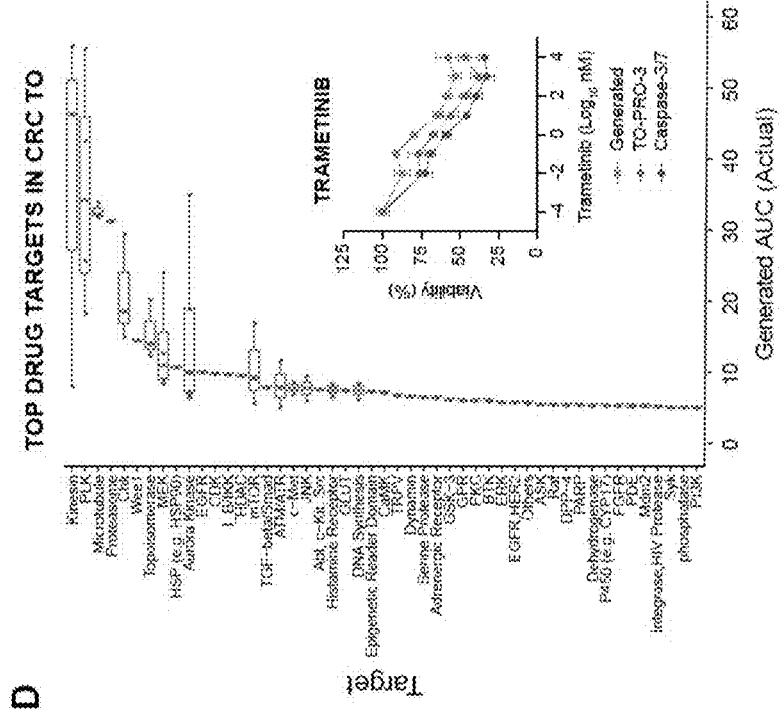
Figure 24F:
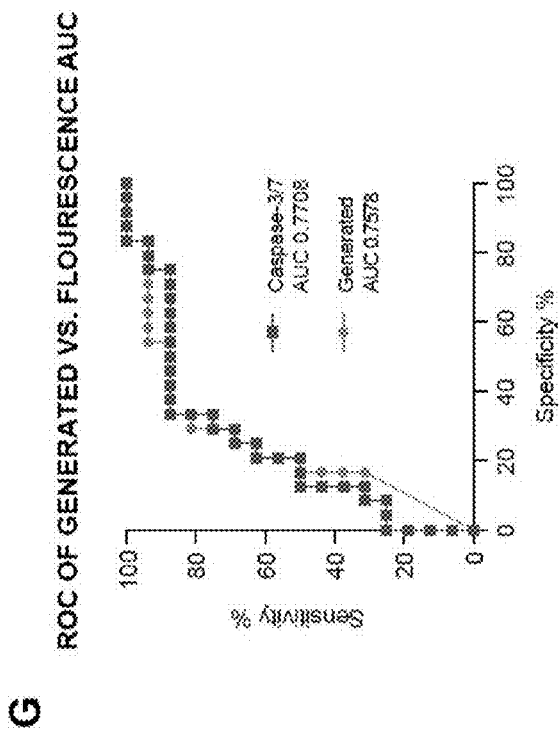

Next, the ability of the RCA network was investigated to discriminate clinically relevant drug responses. Differentially active compounds between the two TO lines as determined by the RCA network was first evaluated. In the colon TO line, sensitivity to drugs that inhibit MEK, a critical component of the mitogen-activated protein kinase (MAPK) pathway (FIG. 24D), was observed. The dose-response curve for trametinib, a potent MEK1 and MEK2 inhibitor, showed a similar response for TO viability measured by TO-PRO-3, Caspase-3/7, and predicted TO viability from the RCA (FIG. 24D). Analysis of the molecular profile of the colon TO revealed a KRAS G12V missense mutation as well as a copy-number amplification of BRAF, both of which are commonly associated with CRC and upregulate the MAPK pathway (Vaughn et al. 2011). In contrast, the gastric cancer TO line was enriched for compounds with purported activity against EGFR and ERBB2 (HER2) receptor tyrosine kinases (e.g. Afatinib) (FIG. 24E). Analyzing the genomic profile of this TO revealed a significant amplification of ERBB2 (copy number>20), suggesting the potency of these agents was due to a dependence of ERBB2 copy gain (FIG. 24F).

Figure 24G:
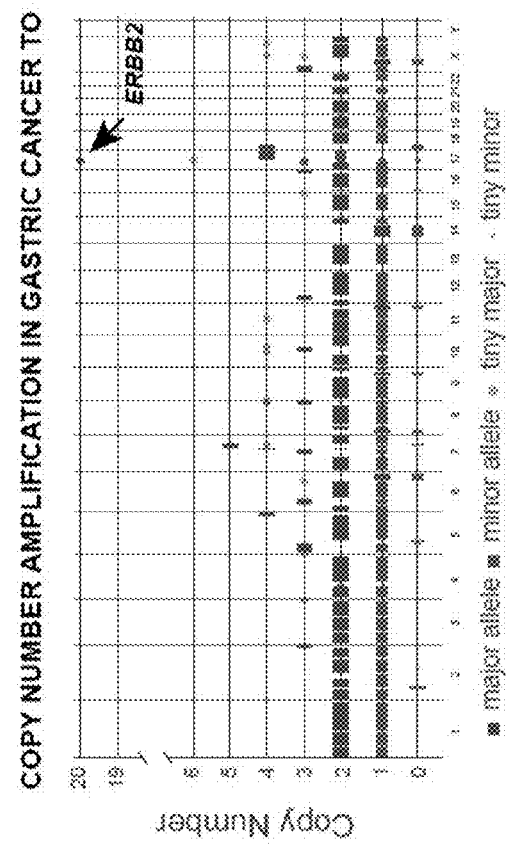

To further test the RCA network's generalizability, a precision medicine scenario generalizable across multiple cancer indications was sought. A recent development in precision oncology is the use of poly (ADP-ribose) polymerase (PARP) inhibitors in patients whose tumors exhibit evidence of homologous recombination deficiency (HRD), especially in cases of somatic loss of BRCA1 or BRCA2, or LOH of functional BRCA1/2 alleles in patients with inherited non-functional BRCA1/2 alleles. Ten additional TO lines (breast, endometrial, colon, ovarian, and NSCLC) were then evaluated for genome-wide LOH indicative of HRD, and categorized TOs as either HRD-positive or HRD-negative (Timms et al., 2014; Yi et al., 2019). TOs were then exposed to a panel of FDA-approved PARP inhibitors and compared RCA network-predicted drug responses to fluorescent-based readouts. It was determined that the RCA network predictions were strongly correlated with fluorescent-based drug responses across all cancer types (data not shown). Additionally, the RCA network's measurement of PARPi response was able to discriminate between HRD-positive and -negative organoids comparable to fluorescent-based measurements (FIG. 24G). Taken together, the RCA network-based assay accurately predicts clinically relevant drug responses in a universal label-free manner.

4. Discussion

A pan-cancer patient-derived TO platform is presented for precision medicine applications. The unprecedented scale of this study elucidated key insights in TO production, molecular characterization, and in vitro profiling that carry implications for the future of TO use in research and clinical settings. For example, the results from more than 1,000 cultures across multiple tumor types confirm that TO growth is unbiased in terms of clinical phenotypes. Moreover, best practices in TO development were informed, such as obtaining sufficiently sized biopsy or resection specimens in order to yield adequate cellular biomass for high-proliferation cultures. Crucially, the molecular landscape of this pan-cancer TO cohort represents those seen in previously sequenced patient cohort (Beaubier et al., 2019a) and mirrored previous TO cohorts of individual cancer types (Driehuis et al., 2019; Fujii et al., 2016; Hill et al., 2018; Sachs et al., 2018). It was also confirmed that TOs recapitulate structural genomic features of the tumor including the locus of HLA class I alleles. As HLA loss is an immune evasion mechanism (McGranahan et al., 2017), these findings suggest that HLA genotype and LOH should be considered when utilizing TOs in immuno-oncology research and drug discovery.

Transcriptomic analyses of TOs confirmed conservation of relevant tumor signaling pathways and led to the investigation of which growth factors were sufficient to initiate and propagate organoids. In contrast to several seminal studies on TO culture (Boj et al., 2015; Dijkstra et al., 2020; Sachs et al., 2018; Seino et al., 2018), it was found that EGF and Noggin were sufficient for the majority of organoids with the exception of certain gastric and pancreatic cancers as previously described (Fujii et al., 2016; Seino et al., 2018). Furthermore, drug screens under minimal media conditions uncovered clinically relevant therapeutic sensitivities. These findings suggest future organoid studies and biobanking efforts such as the Human Cancer Models Initiative (Gerhard et al., 2020) can be achieved with less complex media formulations, thus amounting to substantial reductions in time, cost, user error, and methodological variation. Comprehensive pan-cancer studies should be conducted to determine genotypes that require more bespoke media formulations, as accomplished in pancreatic cancer (Seino et al., 2018).

To advance TO utility for drug development and precision medicine, a universal label-free TO drug screening assay was also devised. Without sacrificing throughput, the RCA network prediction of drug response from light microscopy achieved high reproducibility compared to previously described metabolic-based assays (Tiriac et al., 2018; Tiriac et al., 2020; Vlachogiannis et al., 2018). Importantly, the RCA network identified clinically relevant drug responses across a broad range of cancer-types including PARPi response from HRD-positive and -negative TOs. Notably, the PARPi responses in this small cohort of organoids were generally higher in HRD-positive TOs, with certain drugs exhibiting more potency in vitro than others. These observations confirm previous studies in patients (Coleman et al., 2017) and short-term ovarian cancer organoid cultures (Hill et al., 2018). In addition, the RCA network identified response to afatinib associated with a high ERBB2 (HER2) amplification in the gastric TO. The distribution of response among the TO populations was demonstrative of functional intratumoral heterogeneity, as evidenced by a subset of the organoid population exhibiting resistance to afatinib. When correlated with the patient's clinical course, it was found that the biopsy used to establish this TO line was obtained during disease progression on anti-ERBB2 therapy. Identifying heterogeneity in drug response has the potential to uncover mechanisms of primary resistance to novel therapeutics and may also provide predictive and prognostic information for treatment response in personalized clinical assays.

Deep learning light microscopy-based assays are not only capable of determining drug sensitivities but may do so with far less biomass input, especially if longitudinal time-lapse imaging is used. As opposed to endpoint measurements, time-lapse reduces the number of conditions and replicates required to measure drug efficacy potentially overcoming significant barriers in personalized in vitro drug testing by decreasing the interval to expand TOs between biopsy and drug assays. In fact, a recent endpoint-based in vitro organoid drug assay performed in a CLIA-certified laboratory reported an average 8-week interval between initiation of organoid culture and drug profiling (Narasimhan et al., 2020). Based on these findings, it is believed that light microscopy-based deep learning holds the potential to provide actionable results in more clinically applicable timeframes.

The comprehensive data and robust methods described in this study will hopefully serve to advance the application of organoids in precision oncology research, especially systems biology approaches centered on connecting molecular features of these models to therapeutic response. In summary, it is believed that this pan-cancer organoid platform will be a valuable resource to cancer researchers especially those pursuing precision oncology.

L. Example 12—High Throughput Tumor Organoid Drug Screen

In this example, data for each therapy is presented as a histogram. For each range of viability percentages (for example, ~0-5%, ~5-10%, ~10-15%, ... ~95-100%, etc.) on the γ-axis, the histogram shows the number of organoids associated with that viability percentage range (along the x-axis). Viability was determined by the systems and methods disclosed above.

Each tumor organoid line in these examples was cultured individually in wells of a tissue culture plate, as described above.

Each well of tumor organoids was exposed to one of the following therapies: A-196 (inhibitor of SUV4-20 or SUV420H1 and SUV420H2), Afatinib (tyrosine kinase inhibitor), Adapalene (retinoid-like compound), Adavosertib (MK-1775, wee1 kinase inhibitor), Alectinib (CH5424802, anaplastic lymphoma kinase inhibitor), Alisertib (MLN8237, aurora A kinase inhibitor), Aphidicolin (reversible inhibitor of eukaryotic nuclear DNA replication, antimitotic), Azacitidine (an antimetabolite antineoplastic agent, a chemotherapy), AZ20 (ataxia telangiectasia and Rad3-related protein/ATR kinase inhibitor), AZ31 (ataxia-telangiectasia mutated/ATM kinase inhibitor), AZD6738 (ataxia telangiectasia and Rad3-related protein/ATR kinase inhibitor), AZD7762 (checkpoint kinase inhibitor), Barasertib (AZD1152-HQPA, aurora B kinase inhibitor), BAY-1895344 (ATR and ATM kinase inhibitor), Berzosertib (ATR and ATM kinase inhibitor), BIO-acetoxime (GSK-3a/b inhibitor), Bortezomib (proteasome inhibitor), Cabozantinib (kinase inhibitor, inhibitor of AXL, RET, and tyrosine kinases c-Met and VEGFR2), Capecitabine (an antimetabolite antineoplastic agent, a chemotherapy), Carboplatin (an alkylating antineoplastic agent, a chemotherapy), CC-115 (DNA-PK and mTOR inhibitor), CC-223 (inhibitor of mammalian target of rapamycin/mTOR), CCT-245737 (checkpoint kinase 1/CHK1 inhibitor), CD-2665 (retinoic acid receptor β (RARβ)/RARγ antagonist), CD-437 (retinoic acid receptor (RAR)γ-selective agonist, γ-selective retinoid; inducer of apoptosis), CDK2 inhibitor II, CH-55 (RAR agonist), Cisplatin (an alkylating antineoplastic agent, a chemotherapy), Cladribine (an antimetabolite antineoplastic agent, a chemotherapy), Cytarabine (an antimetabolite antineoplastic agent, a chemotherapy), Dasatinib (a tyrosine kinase inhibitor antineoplastic agent, a chemotherapy), Docetaxel (an antimicrotubular antineoplastic agent, a chemotherapy), Doxorubicin (Adriamycin, a topoisomerase inhibitor antineoplastic agent, a chemotherapy), Empagliflozin (BI 10773, a sodium-glucose cotransporter-2/SGLT2 inhibitor), Entrectinib (RXDX-101, tyrosine kinase inhibitor, inhibitor of the tropomyosin receptor kinases A, B and C, C-ros oncogene 1 and anaplastic lymphoma kinase), Epirubicin (a topoisomerase inhibitor antineoplastic agent, a chemotherapy), Etoposide (a topoisomerase inhibitor antineoplastic agent, a chemotherapy), Everolimus (inhibitor of mTOR), Fluorouracil/5-FU (an antimetabolite antineoplastic agent, a chemotherapy), GDC-0349 (inhibitor of mTOR), GDC-0575 (ARRY-575, CHK1 inhibitor), Gemcitabine (an antimetabolite antineoplastic agent, a chemotherapy), GSK2292767 (inhibitor of phosphatidylinositol 3-kinase/PI3K), GSK-872 (GSK2399872A, kinase inhibitor, inhibitor of RIP3K), Hesperadin (aurora kinase inhibitor), Hydroxyurea (an antimetabolite antineoplastic agent, a chemotherapy), Ifosfamide (an analog of cyclophosphamide, an alkylating antineoplastic agent, a chemotherapy), Ipragliflozin (ASP1941, an SGLT2 inhibitor), KYA1797K (Wnt/β-catenin inhibitor), Lapatinib (tyrosine kinase inhibitor that interrupts the HER2/neu and epidermal growth factor receptor/EGFR pathways, an antineoplastic agent, a chemotherapy), Larotrectinib (inhibitor of tropomyosin kinase receptors TrkA, TrkB, and TrkC), LDC 4297 (Cyclin-dependent kinase/CDK inhibitor, CDK7 inhibitor), Lenvatinib (multiple kinase inhibitor, inhibitor of VEGFR1, VEGFR2 and VEGFR3 kinases), LY3023414 (DNA-PK/PI3K/mTOR Inhibitor), Methotrexate (an antimetabolite antineoplastic agent, a chemotherapy), Nelarabine (an antimetabolite antineoplastic agent, a chemotherapy), Niraparib (MK-4827, a poly ADP ribose polymerase/PARP inhibitor), NSC 23766 (inhibitor of Rac GTPase), Olaparib (PARP inhibitor), Oxaliplatin (an alkylating antineoplastic agent, a chemotherapy), Paclitaxel (a taxane, an antimicrotubular antineoplastic agent, a chemotherapy), Pamiparib (BGB-290, PARP inhibitor), PFI-4 (Bromodomain And PHD Finger Containing 1/BRPF1 bromodomain inhibitor), PHA-767491 HCl (Mitogen-activated protein kinase-activated protein kinase 2/MK2 and CDK inhibitor), PLX7904 (RAF inhibitor), Pracinostat (histone deacetylase/HDAC inhibitor), Pralatrexate (an antimetabolite antineoplastic agent, a chemotherapy), Prexasertib HCl (checkpoint kinase 1/CHK1 inhibitor), RO-3306 (CDK1 inhibitor), Rucaparib (PARP inhibitor), Selpercatinib (LOXO-292, ARRY-192, a tyrosine kinase inhibitor), SIS3 HCl (TGF-beta/Smad inhibitor), SMI-4a (Pim kinase inhibitor), SN-38 (inhibitor of DNA topoisomerase I, active metabolite of CPT-11/Irinotecan), ST-1926 (Adarotene, atypical retinoid, apoptosis inducer), Staurosporine (multikinase inhibitor used as a positive control), Talazoparib (BMN-673, PARP inhibitor), TCS 359 (fms-like tyrosine kinase-3/FLT3 inhibitor), Tenalisib (RP6530, a PI3K δ/γ inhibitor), Tozasertib (VX-680, MK-0457, an Aurora Kinase inhibitor), Trametinib (GSK1120212, a MEK inhibitor), Ulixertinib (inhibitor of extracellular signal-regulated kinase/ERK 1 and 2, with potential antineoplastic activity), Veliparib (ABT-888, PARP inhibitor), Vinblastine (an antimicrotubular antineoplastic agent, a chemotherapy), or VX-984 (DNA-dependent protein kinase/DNA-PK inhibitor).

In another example, a well of tumor organoids may be exposed to one of the following therapies or combination therapies: afatinib plus MET inhibitor (for example, tivantinib, cabozantinib, crizotinib, etc.), AZ31 plus SN-38, bevacizumab (anti-VEGF monoclonal IgG1 antibody), cetuximab (epidermal growth factor receptor/EGFR inhibitor), crizotinib (a tyrosine kinase inhibitor antineoplastic agent), cyclophosphamide (an alkylating antineoplastic agent), erlotinib (epidermal growth factor receptor inhibitor antineoplastic agent), FOLFIRI, bevacizumab plus FOLFIRI, FOLFOX, gefitinib (EGFR inhibitor), gemcitabine plus docetaxel, pemtrexed (an antimetabolite antineoplastic agent), ramucirumab (Vascular Endothelial Growth Factor Receptor 2/VEGFR2 Inhibitor), or topotecan (a topoisomerase inhibitor).

1. Gastric Cancer

In this example, tissue culture wells containing a gastric cancer tumor organoid line were each exposed to one of the therapies listed above. In this example, an ERBB2 variant (mutation) was detected when the tumor organoids were genetically sequenced.

Figures 25A, 25B, 25C:
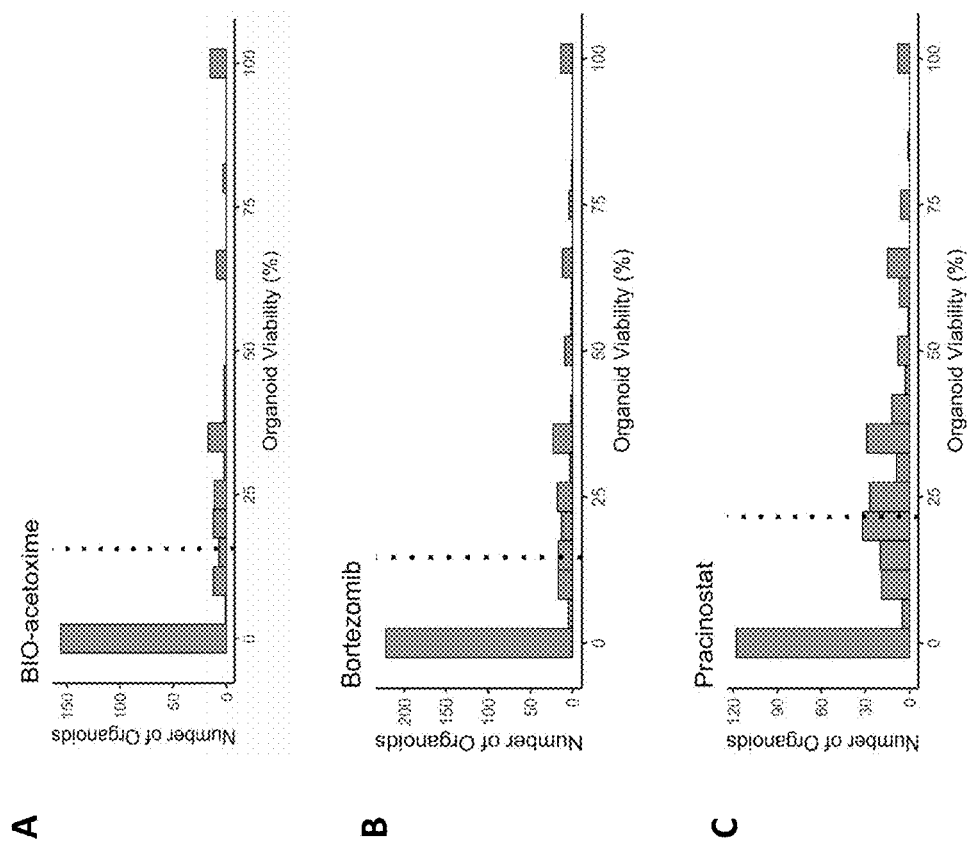
FIG. 25A-25C are histograms summarizing a therapeutic agent screen for a gastric cancer tumor organoid line according to the methods described herein.

FIG. 25A is a histogram summarizing the caspase 3/7 readout results for GSK inhibitor BIO-axetocime (10,000 nM dose). Approximately 150 organoids had 0% viability and were susceptible to the drug. Approximately 20 organoids had 100% viability and were resistant to the drug. The black dotted line indicates that the mean viability for all organoids in the plot is approximately 15%. This histogram indicates the general absence of organoids associated with this gastric cancer organoid line that are resistant to BIO-acetoxime.

FIG. 25B is a histogram summarizing the caspase 3/7 readout results for proteasome inhibitor Bortezomib (10,000 nM dose). Approximately 225 organoids had 0% viability and were susceptible to the drug. Approximately 15 organoids had 100% viability and were resistant to the drug. The black dotted line indicates that the mean viability for all organoids in the plot is approximately 15%. This histogram indicates the general absence of organoids associated with this gastric cancer organoid line that are resistant to Bortezomib.

FIG. 25C is a histogram summarizing the caspase 3/7 readout results for HDAC inhibitor pracinostat (10,000 nM dose). Approximately 120 organoids had 0% viability and were susceptible to the drug. Approximately 10 organoids had 100% viability and were resistant to the drug. The black dotted line indicates that the mean viability for all organoids in the plot is approximately 20%. This histogram indicates the general absence of organoids associated with this gastric cancer organoid line that are resistant to pracinostat.

2. Lung Cancer 1

In this example, tissue culture wells containing a first lung cancer tumor organoid line were each exposed to one of the therapies listed above.

Figures 26A, 26B, 26C, 26D:
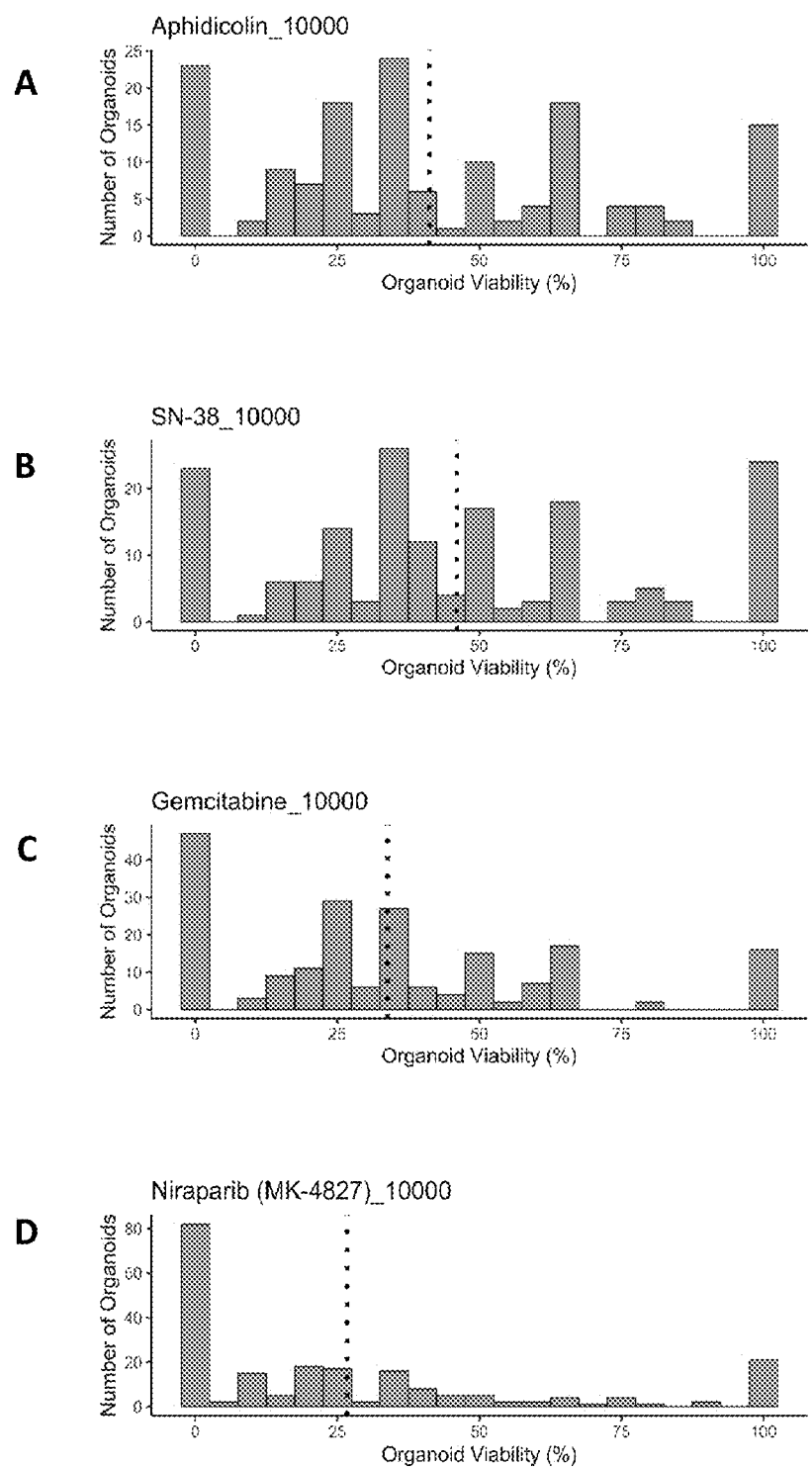
FIG. 26A-26D are histograms summarizing a therapeutic agent screen for a lung cancer tumor organoid line according to the methods described herein.

FIG. 26A is a histogram summarizing the caspase 3/7 readout results for antimetabolite chemotherapy gemcitabine (10,000 nM dose). Approximately 50 organoids had 0% viability and were susceptible to the drug. Approximately 15 organoids had 100% viability and were resistant to the drug. The black dotted line indicates that the mean viability for all organoids in the plot is approximately 35%. This histogram indicates the presence of a small proportion of organoids associated with this lung cancer organoid line that are resistant to gemcitabine.

FIG. 26B is a histogram summarizing the caspase 3/7 readout results for topoisomerase inhibitor SN-38 (10,000 nM dose). Approximately 20 organoids had 0% viability and were susceptible to the drug. Approximately 20 organoids had 100% viability and were resistant to the drug. The black dotted line indicates that the mean viability for all organoids in the plot is approximately 45%. This histogram indicates the presence of organoids associated with this lung cancer organoid line that are resistant to SN-38.

FIG. 26C is a histogram summarizing the caspase 3/7 readout results for antimetabolite chemotherapy gemcitabine (10,000 nM dose). Approximately 23 organoids had 0% viability and were susceptible to the drug. Approximately 15 organoids had 100% viability and were resistant to the drug. The black dotted line indicates that the mean viability for all organoids in the plot is approximately 40%. This histogram indicates the presence of organoids associated with this lung cancer organoid line that are resistant to aphidicolin.

FIG. 26D is a histogram summarizing the caspase 3/7 readout results for PARP inhibitor Niraparib (10,000 nM dose). Approximately 80 organoids had 0% viability and were susceptible to the drug. Approximately 20 organoids had 100% viability and were resistant to the drug. The black dotted line indicates that the mean viability for all organoids in the plot is approximately 25%. This histogram indicates the presence of a small proportion of organoids associated with this lung cancer organoid line that are resistant to Niraparib.

3. Lung Cancer 2

In this example, tissue culture wells containing a second lung cancer tumor organoid line were each exposed to one of the therapies listed above.

Figures 27A, 27B, 27C, 27D:
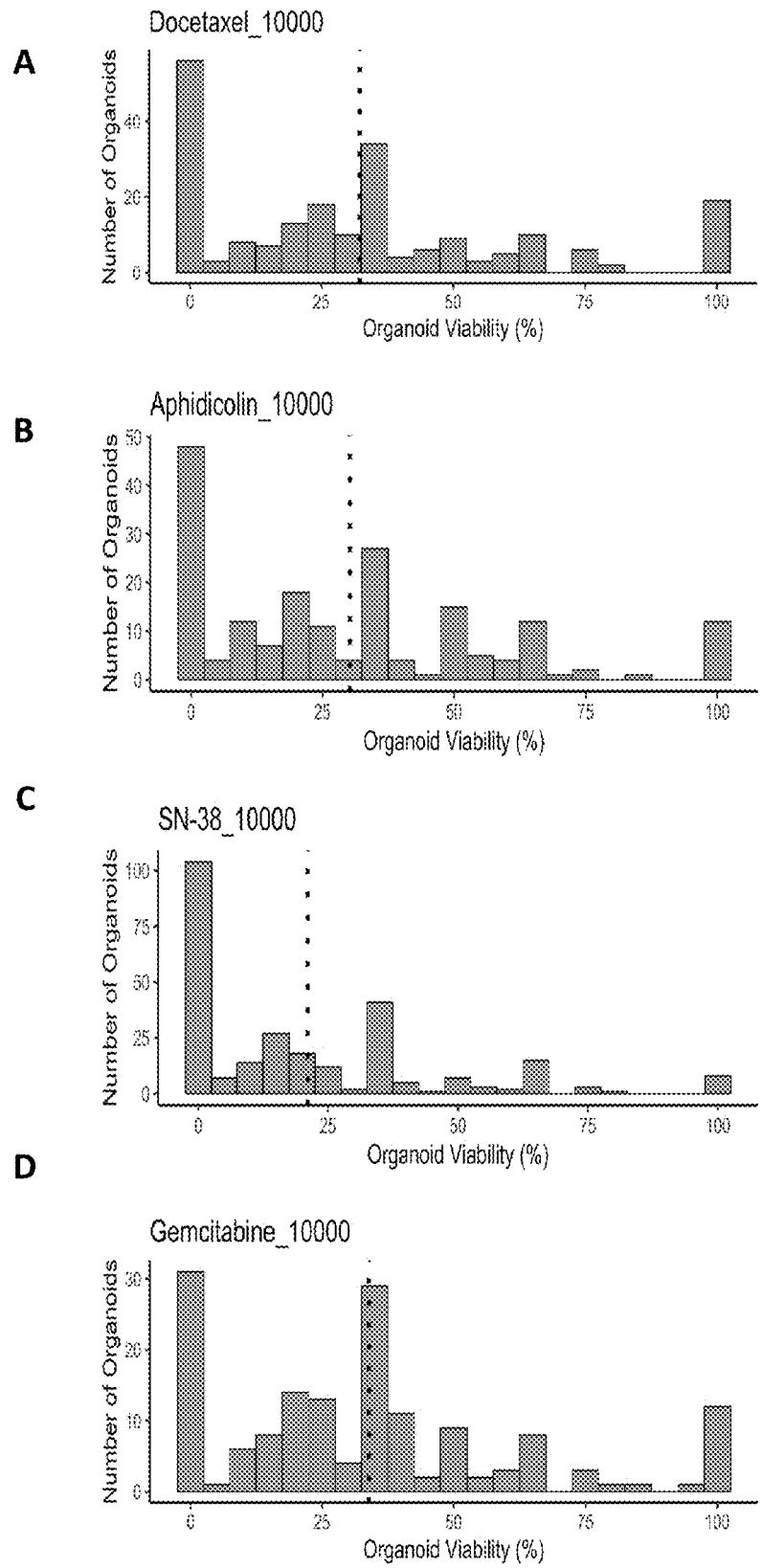
FIG. 27A-27D are histograms summarizing a therapeutic agent screen for a lung cancer tumor organoid line according to the methods described herein.

FIG. 27A is a histogram summarizing the caspase 3/7 readout results for antimicrotubular chemotherapy docetaxel (10,000 nM dose). Approximately 50 organoids had 0% viability and were susceptible to the drug. Approximately 20 organoids had 100% viability and were resistant to the drug. The black dotted line indicates that the mean viability for all organoids in the plot is approximately 30%. This histogram indicates the presence of a small proportion of organoids associated with this lung cancer organoid line that are resistant to docetaxel.

FIG. 27B is a histogram summarizing the caspase 3/7 readout results for antimitotic chemotherapy aphidicolin (10,000 nM dose). Approximately 50 organoids had 0% viability and were susceptible to the drug. Approximately 15 organoids had 100% viability and were resistant to the drug. The black dotted line indicates that the mean viability for all organoids in the plot is approximately 30%. This histogram indicates the presence of a small proportion of organoids associated with this lung cancer organoid line that are resistant to aphidicolin, which is a smaller resistant proportion than was detected in the first lung tumor organoid line.

FIG. 27C is a histogram summarizing the caspase 3/7 readout results for topoisomerase inhibitor SN-38 (10,000 nM dose). Approximately 100 organoids had 0% viability and were susceptible to the drug. Approximately 5 organoids had 100% viability and were resistant to the drug. The black dotted line indicates that the mean viability for all organoids in the plot is approximately 20%. This histogram indicates the general absence of organoids associated with this lung cancer organoid line that are resistant to SN-38, unlike the resistant proportion seen in the first lung tumor organoid line.

FIG. 27D is a histogram summarizing the caspase 3/7 readout results for antimetabolite chemotherapy gemcitabine (10,000 nM dose). Approximately 30 organoids had 0% viability and were susceptible to the drug. Approximately 10 organoids had 100% viability and were resistant to the drug. The black dotted line indicates that the mean viability for all organoids in the plot is approximately 35%. This histogram indicates the presence of a small proportion of organoids associated with this lung cancer organoid line that are resistant to gemcitabine.

4. Head and Neck Cancer

In this example, tissue culture wells containing a head and neck cancer tumor organoid line were each exposed to one of the therapies listed above.

Figures 28A, 28B:
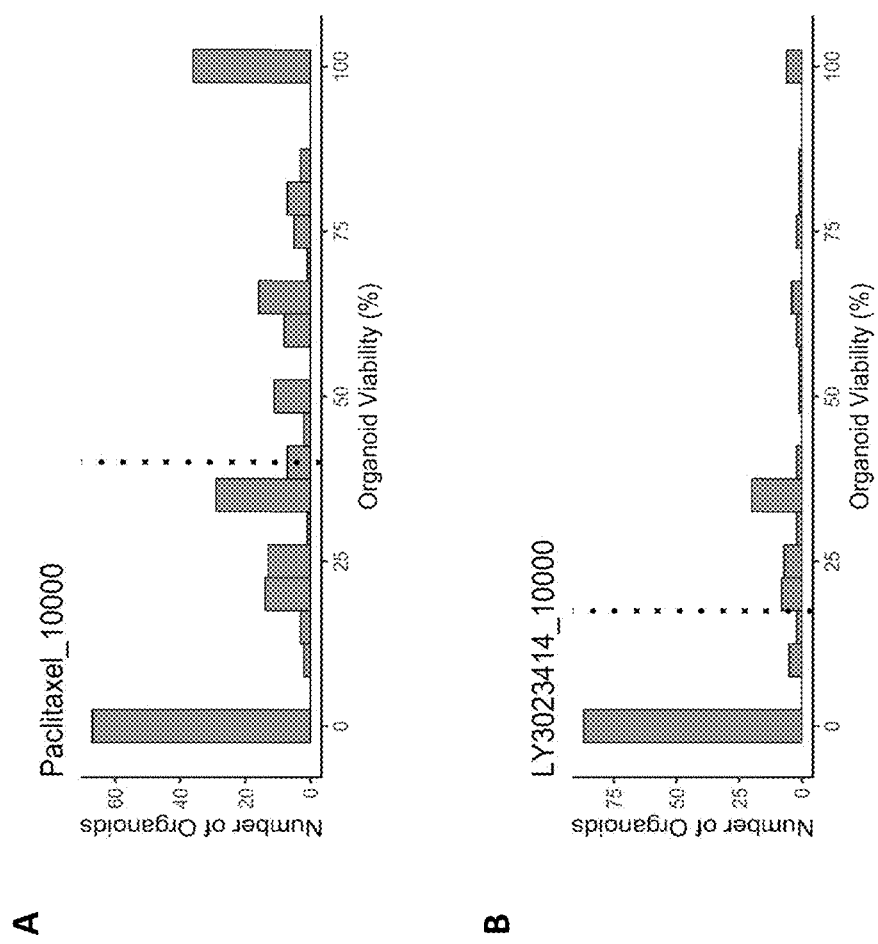
FIG. 28A-28B are histograms summarizing a therapeutic agent screen for a head and neck cancer tumor organoid line according to the methods described herein.

FIG. 28A is a histogram summarizing the caspase 3/7 readout results for antimicrotubular chemotherapy paclitaxel (10,000 nM dose). Approximately 65 organoids had 0% viability and were susceptible to the drug. Approximately 35 organoids had 100% viability and were resistant to the drug. The black dotted line indicates that the mean viability for all organoids in the plot is approximately 40%. This histogram indicates the presence of a small proportion of organoids associated with this head and neck cancer organoid line that are resistant to paclitaxel.

FIG. 28B is a histogram summarizing the caspase 3/7 readout results for kinase inhibitor LY3023414 (10,000 nM dose). Approximately 80 organoids had 0% viability and were susceptible to the drug. Approximately 5 organoids had 100% viability and were resistant to the drug. The black dotted line indicates that the mean viability for all organoids in the plot is approximately 15%. This histogram indicates the general absence of organoids associated with this head and neck cancer organoid line that are resistant to LY3023414.

5. Endometrial Cancer 1

In this example, tissue culture wells containing a first endometrial cancer tumor organoid line were each exposed to one of the therapies listed above.

Figures 29A, 29B, 29C:
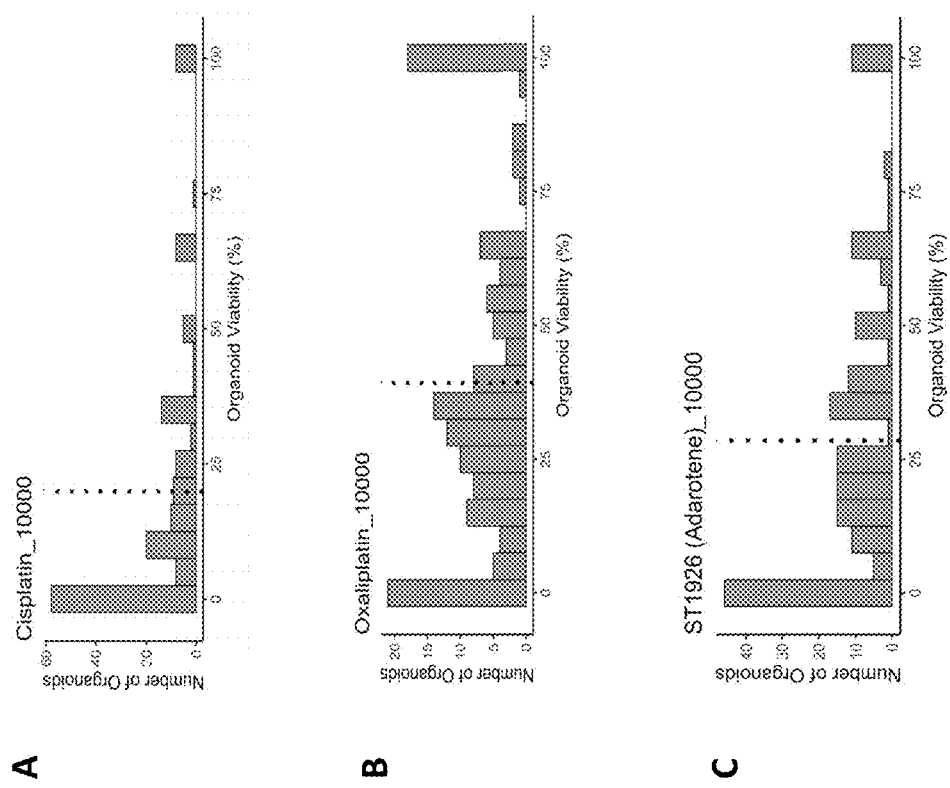
FIG. 29A-29C are histograms summarizing a therapeutic agent screen for an endometrial cancer tumor organoid line according to the methods described herein.

FIG. 29A is a histogram summarizing the caspase 3/7 readout results for alkylating chemotherapy cisplatin (10,000 nM dose). Approximately 60 organoids had 0% viability and were susceptible to the drug. Approximately 5 organoids had 100% viability and were resistant to the drug. The black dotted line indicates that the mean viability for all organoids in the plot is approximately 20%. This histogram indicates the general absence of organoids associated with this endometrial cancer organoid line that are resistant to cisplatin.

FIG. 29B is a histogram summarizing the caspase 3/7 readout results for alkylating chemotherapy oxaliplatin (10,000 nM dose). Approximately 20 organoids had 0% viability and were susceptible to the drug. Approximately 18 organoids had 100% viability and were resistant to the drug. The black dotted line indicates that the mean viability for all organoids in the plot is approximately 40%. This histogram indicates the presence of organoids associated with this endometrial cancer organoid line that are resistant to oxaliplatin, unlike the cisplatin. In light of these results, a report may indicate that cisplatin is ranked higher than oxaliplatin as a therapy that is likely to be effective.

FIG. 29C is a histogram summarizing the caspase 3/7 readout results for apoptosis inducer ST-1926 (10,000 nM dose). Approximately 45 organoids had 0% viability and were susceptible to the drug. Approximately 10 organoids had 100% viability and were resistant to the drug. The black dotted line indicates that the mean viability for all organoids in the plot is approximately 30%. This histogram indicates the general absence of organoids associated with this endometrial cancer organoid line that are resistant to ST-1926.

6. Endometrial Cancer 2

In this example, tissue culture wells containing a second endometrial cancer tumor organoid line were each exposed to one of the therapies listed above.

Figures 30A, 30B, 30C:
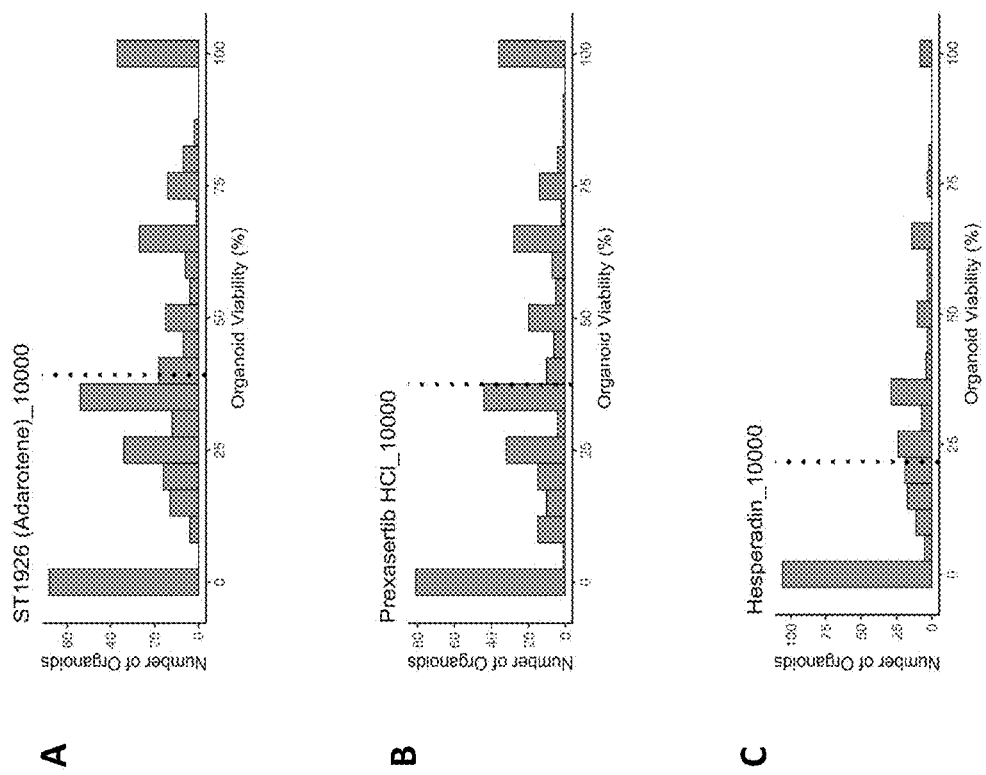
FIG. 30A-30C are histograms summarizing a therapeutic agent screen for an endometrial cancer tumor organoid line according to the methods described herein.

FIG. 30A is a histogram summarizing the caspase 3/7 readout results for apoptosis inducer ST-1926 (10,000 nM dose). Approximately 65 organoids had 0% viability and were susceptible to the drug. Approximately 40 organoids had 100% viability and were resistant to the drug. The black dotted line indicates that the mean viability for all organoids in the plot is approximately 40%. This histogram indicates the presence of a small proportion of organoids associated with this endometrial cancer organoid line that are resistant to ST-1926, and may indicate that this organoid line is more resistant to ST1926 than the endometrial cancer organoid line in the example above.

FIG. 30B is a histogram summarizing the caspase 3/7 readout results for kinase inhibitor Prexasertib (10,000 nM dose). Approximately 80 organoids had 0% viability and were susceptible to the drug. Approximately 35 organoids had 100% viability and were resistant to the drug. The black dotted line indicates that the mean viability for all organoids in the plot is approximately 40%. This histogram indicates the presence of a small proportion of organoids associated with this endometrial cancer organoid line that are resistant to Prexasertib.

FIG. 30C is a histogram summarizing the caspase 3/7 readout results for kinase inhibitor hesperadin (10,000 nM dose). Approximately 100 organoids had 0% viability and were susceptible to the drug. Approximately 5 organoids had 100% viability and were resistant to the drug. The black dotted line indicates that the mean viability for all organoids in the plot is approximately 20%. This histogram indicates the general absence of organoids associated with this endometrial cancer organoid line that are resistant to hesperadin.

7. Colon Cancer

In this example, tissue culture wells containing a colon cancer tumor organoid line were each exposed to one of the therapies listed above.

Figures 31A, 31B, 31C:
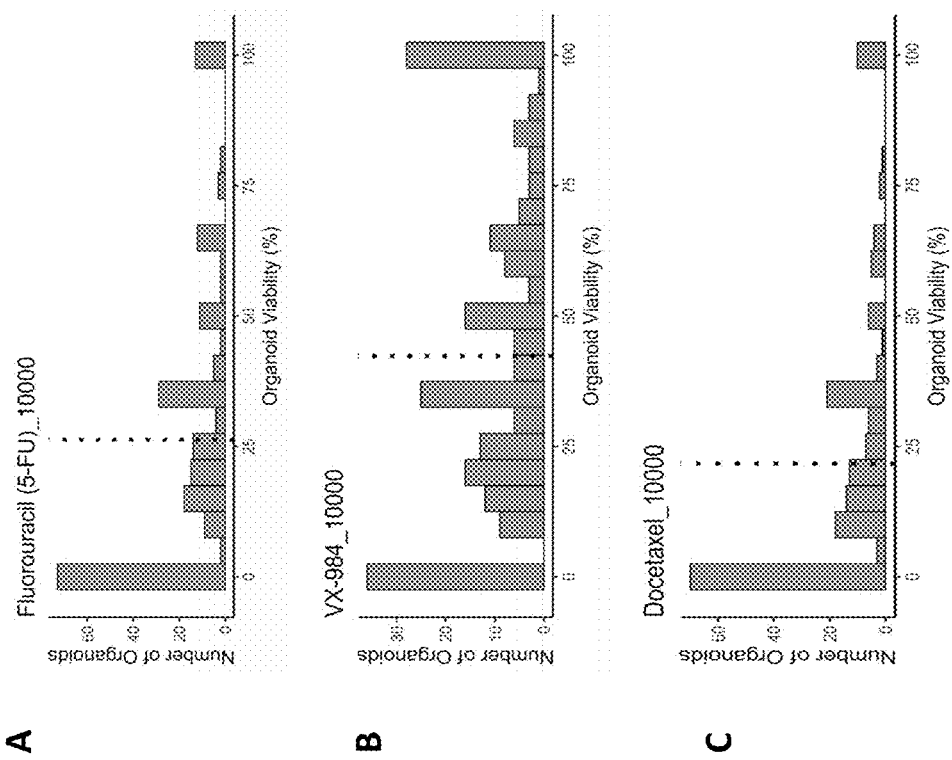
FIG. 31A-31C are histograms summarizing a therapeutic agent screen for a colon cancer tumor organoid line according to the methods described herein.

FIG. 31A is a histogram summarizing the caspase 3/7 readout results for antimetabolite chemotherapy Fluorouracil (10,000 nM dose). Approximately 70 organoids had 0% viability and were susceptible to the drug. Approximately 10 organoids had 100% viability and were resistant to the drug. The black dotted line indicates that the mean viability for all organoids in the plot is approximately 25%. This histogram indicates the general absence of organoids associated with this colon cancer organoid line that are resistant to Fluorouracil.

FIG. 31B is a histogram summarizing the caspase 3/7 readout results for kinase inhibitor VX-984 (10,000 nM dose). Approximately 35 organoids had 0% viability and were susceptible to the drug. Approximately 25 organoids had 100% viability and were resistant to the drug. The black dotted line indicates that the mean viability for all organoids in the plot is approximately 40%. This histogram indicates the presence of organoids associated with this colon cancer organoid line that are resistant to VX-984.

FIG. 31C is a histogram summarizing the caspase 3/7 readout results for antimicrotubular chemotherapy Docetaxel (10,000 nM dose). Approximately 70 organoids had 0% viability and were susceptible to the drug. Approximately 15 organoids had 100% viability and were resistant to the drug. The black dotted line indicates that the mean viability for all organoids in the plot is approximately 20%. This histogram indicates the general absence of organoids associated with this colon cancer organoid line that are resistant to Docetaxel.

8. Colorectal Cancer

In this example, tissue culture wells containing a colorectal cancer tumor organoid line were each exposed to one of the therapies listed above.

Figures 32A, 32B:
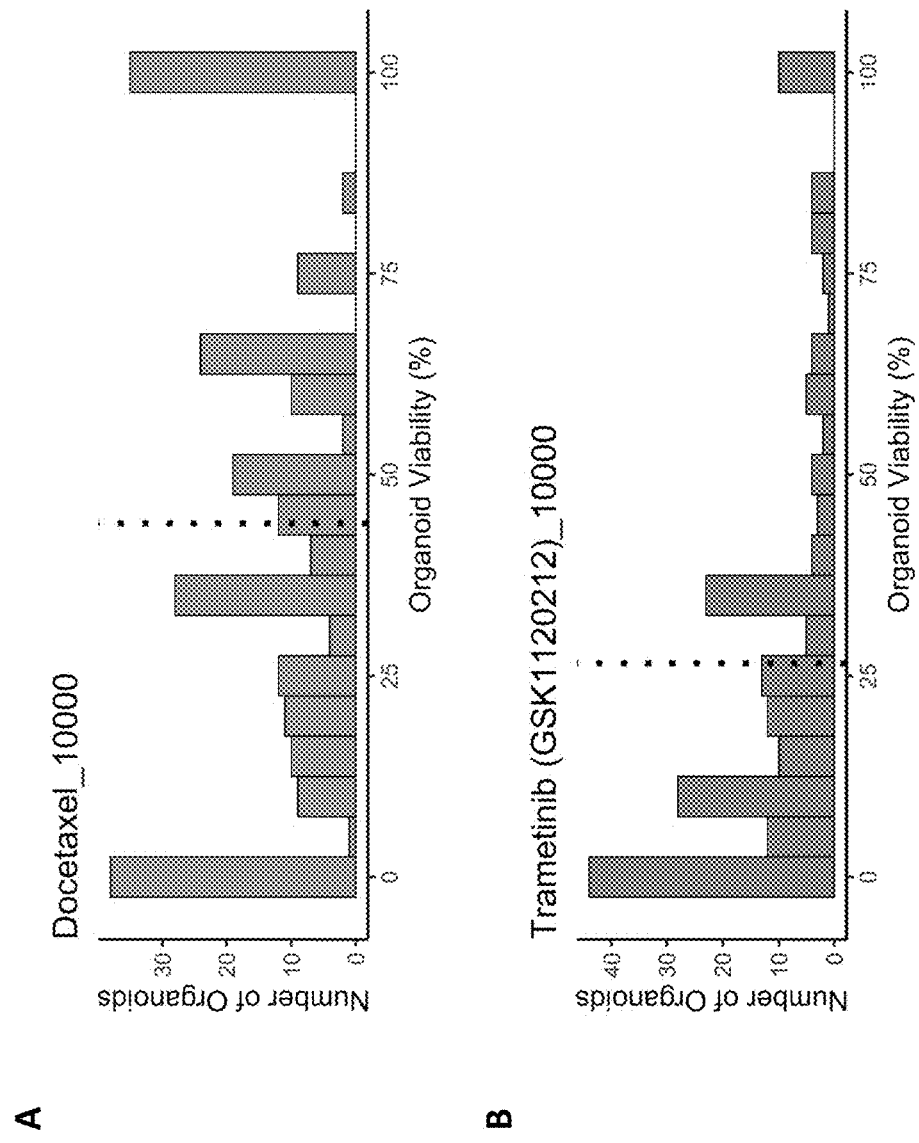
FIG. 32A-32B are histograms summarizing a therapeutic agent screen for a colorectal cancer tumor organoid line according to the methods described herein.

FIG. 32A is a histogram summarizing the caspase 3/7 readout results for antimicrotubular chemotherapy Docetaxel (10,000 nM dose). Approximately 35 organoids had 0% viability and were susceptible to the drug. Approximately 30 organoids had 100% viability and were resistant to the drug. The black dotted line indicates that the mean viability for all organoids in the plot is approximately 45%. This histogram indicates the presence of organoids associated with this colorectal cancer organoid line that are resistant to Docetaxel, and may indicate that this colorectal cancer organoid line is more resistant than the colon cancer organoid line in the example above.

FIG. 32B is a histogram summarizing the caspase 3/7 readout results for kinase inhibitor trametinib (10,000 nM dose). Approximately 50 organoids had 0% viability and were susceptible to the drug. Approximately 10 organoids had 100% viability and were resistant to the drug. The black dotted line indicates that the mean viability for all organoids in the plot is approximately 25%. This histogram indicates the presence of a small proportion of organoids associated with this colorectal cancer organoid line that are resistant to trametinib.

In this colon TO line, sensitivity to drugs that inhibit MEK, a critical component of the mitogen-activated protein kinase (MAPK) pathway was found. The dose-response curve for trametinib, a potent MEK1 and MEK2 inhibitor, showed a similar response for TO viability measured by TO-PRO-3, Caspase-3/7, and predicted TO viability from the RCA. Analysis of the molecular profile of the colon TO revealed a KRAS G12V missense mutation as well as a copy-number amplification of BRAF, both of which are commonly associated with CRC and upregulate the MAPK pathway (Vaughn et al. 2011).

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a non-transitory computer readable storage medium. For instance, the computer program product could contain the program modules shown in any combination in FIG. 1 and/or as described elsewhere within the application. These program modules can be stored on a CD-ROM, DVD, magnetic disk storage product, USB key, or any other non-transitory computer readable data or program storage product.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

Many modifications and variations of this disclosure can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The disclosure is to be limited only by the terms of the appended claims, along with the full scope of equivalents to which such claims are entitled.

What is claimed is:

1. A method of evaluating an effect of a therapeutic agent composition for a subject, the method comprising:
   A) exposing a plurality of tumor organoid subsets with a therapeutic agent composition comprising one or more therapeutic agents, wherein each of the tumor organoid subsets comprises at least five tumor organoids,
      wherein each tumor organoid subset in the plurality of tumor organoid subsets is in a different well in one or more multi-well plates;
      wherein each tumor organoid subset in the plurality of tumor organoid subsets comprises a plurality of tumor organoids that are derived from one or more cells of a tumor biopsy from the subject, and
      wherein each of the tumor organoid subsets in the plurality of tumor organoid subsets is exposed to a particular concentration of the therapeutic agent composition;
   B) exposing each respective tumor organoid subset in the plurality of tumor organoid subsets to one or more fluorescent markers;

C) imaging the plurality of tumor organoid subsets thereby forming a plurality of two-dimensional pixelated digital fluorescent images;

D) obtaining, using a computer system, for each respective tumor organoid subset in the plurality of tumor organoid subsets, a corresponding tumor organoid profile using numeric values for individual pixels within one or more corresponding two-dimensional pixelated digital fluorescent images in the plurality of two-dimensional pixelated digital fluorescent images, thereby obtaining a plurality of tumor organoid profiles, wherein each respective tumor organoid profile in the plurality of tumor organoid profiles comprises a separate numeric cell viability value for each of the at least five tumor organoids in the respective tumor organoid subset that corresponds to the respective tumor organoid profile; and E) assessing the effect of the therapeutic agent composition on each of the tumor organoids of the at least five tumor organoids in each of the tumor organoid subsets in the plurality of tumor organoid subsets based on the separate numeric cell viability value for each tumor organoid in each tumor organoid subset in the plurality of tumor organoid subsets.

2. The method of claim 1, wherein the one or more fluorescent markers comprises one or more cell death detection agents and a total cell detection agent.

3. The method of claim 1, wherein the obtaining step D) comprises determining the proportion of numeric cell viability values of a given tumor organoid subset that have greater than 1% cell viability after contact with the therapeutic agent composition.

4. The method of claim 3, wherein the assessing step E) comprises determining a probability or a likelihood that the subject's tumor is resistant to the therapeutic agent composition at a particular concentration based on the proportion of numeric cell viability values of a given tumor organoid subset in the plurality of tumor organoid subsets that have greater than 1% cell viability after contact with the therapeutic agent composition at the particular concentration.

5. The method of claim 4, wherein the subject's tumor is determined to be likely resistant to the therapeutic agent composition at a particular concentration when 50% or more of the numeric cell viability values for a tumor organoid subset in the plurality of tumor organoid subsets contacted with the therapeutic agent composition at the particular concentration are 50% or more viable.

6. The method of claim 4, wherein the subject's tumor is determined to be likely to be resistant to the therapeutic agent composition at a particular concentration when 1% or more of the numeric cell viability values for a tumor organoid subset in the plurality of tumor organoid subsets is contacted with the therapeutic agent composition at the particular concentration are 100% or more viable.

7. The method of claim 4, wherein the subject's tumor is designated as likely to be resistant to the therapeutic agent composition and the method further comprises recommending to the subject a monitoring frequency that is more frequent than a standard monitoring frequency.

8. The method of claim 4, wherein the subject's tumor is not designated as likely to be resistant to the therapeutic agent composition and the method further comprises recommending to the subject a standard monitoring frequency.

9. The method of claim 4, the method further comprising isolating a plurality of tumor organoids from a tumor organoid subset that is designated as likely to be resistant to the therapeutic agent composition and analyzing the plurality of tumor organoids for one or more genetic variants associated with resistance to the therapeutic agent composition.

10. The method of-claim 4, the method further comprising the step of isolating a set of tumor organoids within the plurality of tumor organoid subsets having 0% cell viability and genetically sequencing the isolated set of tumor organoids to detect one or more genetic variants associated with at least 50% of the isolated tumor organoids, wherein one or more genetic variants associated with at least 50% of the isolated set of tumor organoids is determined to be associated with susceptibility to the therapeutic agent composition.

11. The method of claim 9, wherein the isolating is performed using Ficoll-Paque isolation.

12. The method of claim 1, wherein the tumor organoid profile comprises a separate numeric cell viability value for each of at least 10, 20, 30, 40, 50, 60, 70, 80, 90, 100, 200, 300, 400, 500, 600, 700, 800, 900, or $1 \times 10^3$, $1 \times 10^4$, $1 \times 10^5$, or $1 \times 10^6$ tumor organoids in each of the tumor organoid subsets.

13. The method of claim 1, wherein the plurality of tumor organoid subsets comprises at least 10, 15, 20, 25, 30, 35, 40, 50, 55, 60, 70, 80, 90, 100, 200, 300, 400, 500, 600, 700, 800, 900, $1 \times 10^3$, $1 \times 10^4$, $1 \times 10^5$, or $1 \times 10^6$ tumor organoid subsets.

14. The method of claim 1, wherein each of at least two of the tumor organoid subsets is exposed to a unique concentration of the therapeutic agent composition.

15. The method of claim 1, wherein the therapeutic agent composition comprises two or more therapeutic agents.

16. The method of claim 1, wherein the subject has a basal cell skin cancer, a squamous cancer, a breast cancer, a bladder cancer, a cervical cancer, a colon cancer, an endometrial cancer, a head and neck cancer, a hepatobiliary cancer, a kidney cancer, a gastric cancer, a lung cancer, a mesothelial cancer of the pleural cavity, a mesothelial cancer of the peritoneal cavity, an ovarian cancer, prostate cancer, or a rectal cancer.

17. The method of claim 1, wherein the method further comprises:

F) exposing one or more tumor organoid subsets in the plurality of tumor organoid subsets that are designated as likely to be resistant to the therapeutic agent composition to a second therapeutic agent composition;

G) obtaining a second tumor organoid profile for each of the one or more tumor organoid subsets in step F), wherein each of the second tumor organoid profiles comprises a separate numeric cell viability value for at least five tumor organoids in the subset; and H) assessing an effect of the second therapeutic agent composition based on the second tumor organoid profiles.

18. The method of claim 17, wherein the method further comprises assigning a treatment regimen to the subject based on step H).

19. The method of claim 1, further comprising administering a therapy to the subject based on step E).

20. The method of claim 1, wherein the therapeutic agent composition consists of one of the following:

a DNA damage response modulator, a cell cycle inhibitor, a metabolic inhibitor, a DNA synthesis inhibitor, an RNA synthesis inhibitor, a chemotherapy, an antimetabolite antineoplastic agent, an antimicrotubular antineoplastic agent, an antimetabolite antineoplastic agent, an antimitotic antineoplastic agent, an alkylating antineoplastic agent, a topoisomerase inhibitor, an apoptosis inducer inducers, a kinase inhibitor, a proteasome inhibitor, a PARP inhibitor, a MEK inhibitor, an Akt inhibitor, an ATM/ATR inhibitor, a TGF-beta/Smad inhibitor, a HDAC inhibitor, or a retinoic acid receptor antagonist or agonist.

21. The method of claim 1, wherein the assessing step E) comprises determining a sensitivity of the plurality of tumor organoids subsets to the therapeutic agent composition, and wherein the method further comprises:

F) administering the therapeutic agent composition to the subject when the therapeutic agent composition satisfies a sensitivity threshold, and administering a therapy that is not the therapeutic agent composition when the therapeutic agent composition does not satisfy the sensitivity threshold, wherein the therapeutic agent composition comprises a PARP inhibitor.

22. The method of claim 1, wherein each pixel in each pixelated digital fluorescent image in the plurality of two-dimensional pixelated digital fluorescent images has a value between 0 and $2^{16}$.

23. The method of claim 1, wherein the imaging C) comprises (i) taking a set of two or more two-dimensional pixelated digital fluorescent images of a first tumor organoid subset in the plurality of tumor organoid subsets in the different well, wherein each respective image in the set of two-dimensional pixelated digital fluorescent images of the first tumor organoid subset is at a different Z-plane in a plurality of Z-planes, and (ii) projecting the set of two-dimensional pixelated digital fluorescent images into a single two-dimensional pixelated digital fluorescent image for the obtaining D) step.

24. The method of claim 23 wherein each Z-plane is associated with a different submicron to 15 micron portion of a height in the different well.

25. The method of claim 1, wherein the one or more fluorescent markers is a plurality of fluorescent markers and wherein each two-dimensional pixelated digital fluorescent image in the plurality of two-dimensional pixelated digital fluorescent images is a multichannel image.

26. The method of claim 25, wherein the exposing B) exposes each respective tumor organoid subset in the plurality of tumor organoid subsets with a first fluorescent marker, a second fluorescent marker, and a third fluorescent marker, wherein the first fluorescent marker is Hoechst 33342, the second fluorescent marker is Caspase 3/7, and the third fluorescent marker is TO-PRO-3, and wherein the multichannel image comprises a first channel for Hoechst 33342 fluorescence, a second channel for Caspase 3/7 fluorescence, and a third channel for TO-PRO-3 fluorescence.

27. The method of claim 25, wherein the exposing B) exposes each respective tumor organoid subset in the plurality of tumor organoid subsets to a first fluorescent marker, a second fluorescent marker, and a third fluorescent marker and wherein the multichannel image comprises a first channel for blue fluorescence, a second channel for green fluorescence, and a third channel for red fluorescence.

* * * * *